(12) United States Patent
Sugiyama et al.

(10) Patent No.: US 9,715,885 B2
(45) Date of Patent: Jul. 25, 2017

(54) SIGNAL PROCESSING APPARATUS, SIGNAL PROCESSING METHOD, AND SIGNAL PROCESSING PROGRAM

(71) Applicant: NEC Corporation, Tokyo (JP)

(72) Inventors: Akihiko Sugiyama, Tokyo (JP); Ryoji Miyahara, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 14/773,273

(22) PCT Filed: Feb. 26, 2014

(86) PCT No.: PCT/JP2014/054634
§ 371 (c)(1),
(2) Date: Sep. 4, 2015

(87) PCT Pub. No.: WO2014/136629
PCT Pub. Date: Sep. 12, 2014

(65) Prior Publication Data
US 2016/0019914 A1    Jan. 21, 2016

(30) Foreign Application Priority Data

Mar. 5, 2013 (JP) ................................ 2013-042448
Mar. 5, 2013 (JP) ................................ 2013-042449
(Continued)

(51) Int. Cl.
*G10L 25/51* (2013.01)
*G10L 21/0232* (2013.01)
(Continued)

(52) U.S. Cl.
CPC .............. *G10L 25/51* (2013.01); *A61B 5/024* (2013.01); *G10L 21/0232* (2013.01); *A61B 5/0402* (2013.01); *G10L 25/18* (2013.01)

(58) Field of Classification Search
CPC ...... G10L 25/51; G10L 21/0232; A61B 5/024
(Continued)

(56) References Cited

U.S. PATENT DOCUMENTS 5,479,168 A * 12/1995 Johnson .................... G06J 1/00
                                                341/110
6,420,989 B1 * 7/2002 Herbold .................... H03L 7/16
                                                341/155
(Continued)

FOREIGN PATENT DOCUMENTS

JP    3-6600      1/1991
JP    8-54897     2/1996
(Continued)

OTHER PUBLICATIONS

M. Kato et al., "Noise Suppression with High Speech Quality Based on Weighted Noise Estimation and MMSE STSA", IEICE Trans. Fundamentals (Japanese Edition), vol. J87-A, No. 7, pp. 851-860, Jul. 2004.
(Continued)

*Primary Examiner* — Gerald Gauthier
(74) *Attorney, Agent, or Firm* — Finnegan, Henderson, Farabow, Garrett & Dunner, L.L.P.

(57) ABSTRACT

This invention provides a signal processing apparatus for effectively detecting an abrupt change in an input signal. The signal processing apparatus includes a converter that converts an input signal into a phase component signal and an amplitude component signal in a frequency domain. The signal processing apparatus further includes a calculator that calculates feature amounts of the phase component signal and the amplitude component signal derived by the converter. The signal processing apparatus further includes a
(Continued)

determiner that determines presence probability of an abrupt change in the input signal based on the feature amounts calculated by the calculator.

30 Claims, 69 Drawing Sheets

(30) Foreign Application Priority Data

Mar. 5, 2013 (JP) ................................ 2013-042450
Mar. 5, 2013 (JP) ................................ 2013-042451

(51) Int. Cl.
*A61B 5/024* (2006.01)
*G10L 25/18* (2013.01)
*A61B 5/0402* (2006.01)

(58) Field of Classification Search
USPC .................... 73/584; 341/110, 155; 342/175;
375/260, 308, 346, 371; 381/56, 94.1;
455/422.1; 708/300
See application file for complete search history.

(56) References Cited

U.S. PATENT DOCUMENTS

| | | | |
|---|---|---|---|
| 2003/0223524 A1* | 12/2003 | Mennenga | H04L 27/0014 375/371 |
| 2005/0114128 A1 | 5/2005 | Hetherington et al. | |
| 2005/0199064 A1* | 9/2005 | Wen | G01H 1/00 73/584 |
| 2006/0023800 A1* | 2/2006 | Okada | H04L 27/2647 375/260 |
| 2006/0271356 A1 | 11/2006 | Vos | |
| 2006/0277038 A1 | 12/2006 | Vos et al. | |
| 2006/0277039 A1 | 12/2006 | Vos et al. | |
| 2006/0277042 A1 | 12/2006 | Vos et al. | |
| 2006/0282262 A1 | 12/2006 | Vos et al. | |
| 2006/0282263 A1 | 12/2006 | Vos et al. | |
| 2007/0088541 A1 | 4/2007 | Vos et al. | |
| 2007/0088542 A1 | 4/2007 | Vos et al. | |
| 2007/0088558 A1 | 4/2007 | Vos et al. | |
| 2008/0126086 A1 | 5/2008 | Vos et al. | |
| 2011/0112670 A1 | 5/2011 | Disch et al. | |
| 2011/0250879 A1* | 10/2011 | Miyahara | H04B 7/2606 455/422.1 |
| 2012/0224718 A1* | 9/2012 | Sugiyama | G10L 21/0208 381/94.1 |
| 2012/0294388 A1* | 11/2012 | Choi | H04L 27/362 375/308 |
| 2013/0077802 A1* | 3/2013 | Sugiyama | H04B 15/00 381/94.1 |
| 2013/0088383 A1* | 4/2013 | Forstner | H01Q 1/3233 342/175 |
| 2013/0251079 A1* | 9/2013 | Miyahara | H04B 1/10 375/346 |
| 2013/0332500 A1* | 12/2013 | Sugiyama | G10L 21/0208 708/300 |
| 2016/0019913 A1* | 1/2016 | Sugiyama | G10L 25/51 381/56 |
| 2016/0019914 A1* | 1/2016 | Sugiyama | A61B 5/024 381/56 |
| 2016/0210987 A1* | 7/2016 | Sugiyama | G10L 21/0232 |
| 2016/0217803 A1* | 7/2016 | Sugiyama | G10L 21/0232 |
| 2016/0254008 A1* | 9/2016 | Sugiyama | H04N 1/42 |
| 2016/0315601 A1* | 10/2016 | Gu | G01R 31/31709 |

FOREIGN PATENT DOCUMENTS

| | | |
|---|---|---|
| JP | 2006-163417 | 6/2006 |
| JP | 2007-251908 | 9/2007 |
| JP | 2010-237703 | 10/2010 |
| JP | 2011-514987 | 5/2011 |
| JP | 2011-199808 | 10/2011 |
| JP | 2011-254122 | 12/2011 |
| TW | 200703240 A | 1/2007 |
| TW | I330828 | 9/2010 |
| WO | WO 2008/111462 A1 | 9/2008 |
| WO | WO 2009/112141 A1 | 9/2009 |

OTHER PUBLICATIONS

R. Martin, "Spectral Subtraction Based on Minimum Statistics", EUSPICO-94, pp. 1182-1185, Sep. 1994.

"1.5-Mbit/s encoding of video signal and additional audio signal for digital storage media—section 3, audio", JIS X 4323, p. 99, Nov. 1996.

A. de Cheveigne et al., "YIN, a fundamental frequency estimator for speech and music", J. Acoustic Soc. Amer.., vol. 111, No. 4, pp. 1917-1930, Apr. 2002.

J. Flanagan et al., "Speech Coding", IEEE Transactions on Communications, vol. 27, No. 4, pp. 710-737, Apr. 1979.

A. Subramanya et al., "Automatic Removal of Typed Keystrokes From Speech Signals", IEEE Signal Processing Letters, vol. 14, No. 5, pp. 363-366, May 2007.

J. Murphy et al., "Joint Bayesian Removal of Impulse and Background Noise", IEEE Proceedings of ICASSP, pp. 261-264, May 2011.

R. Talmon et al., "Transient Noise Reduction Using Nonlocal Diffusion Filters", IEEE Transactions on Audio, Speech, and Language Processing, vol. 19, No. 6, pp. 1584-1599, Jun. 2011.

International Search Report and Written Opinion mailed Apr. 22, 2014 in corresponding PCT International Application.

Office Action mailed on Feb. 15, 2016, by the Taiwanese Patent Office in counterpart Taiwanese Patent Application No. 103106690.

* cited by examiner

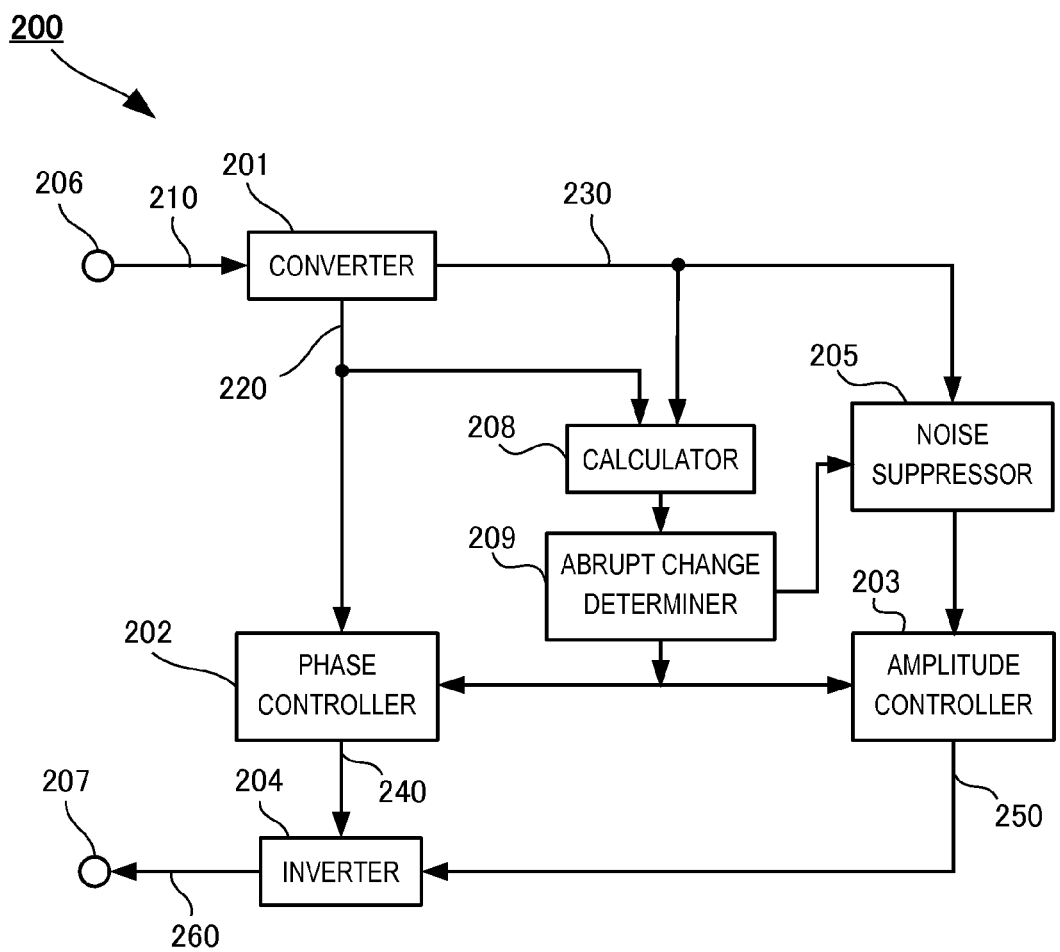
F I G. 2

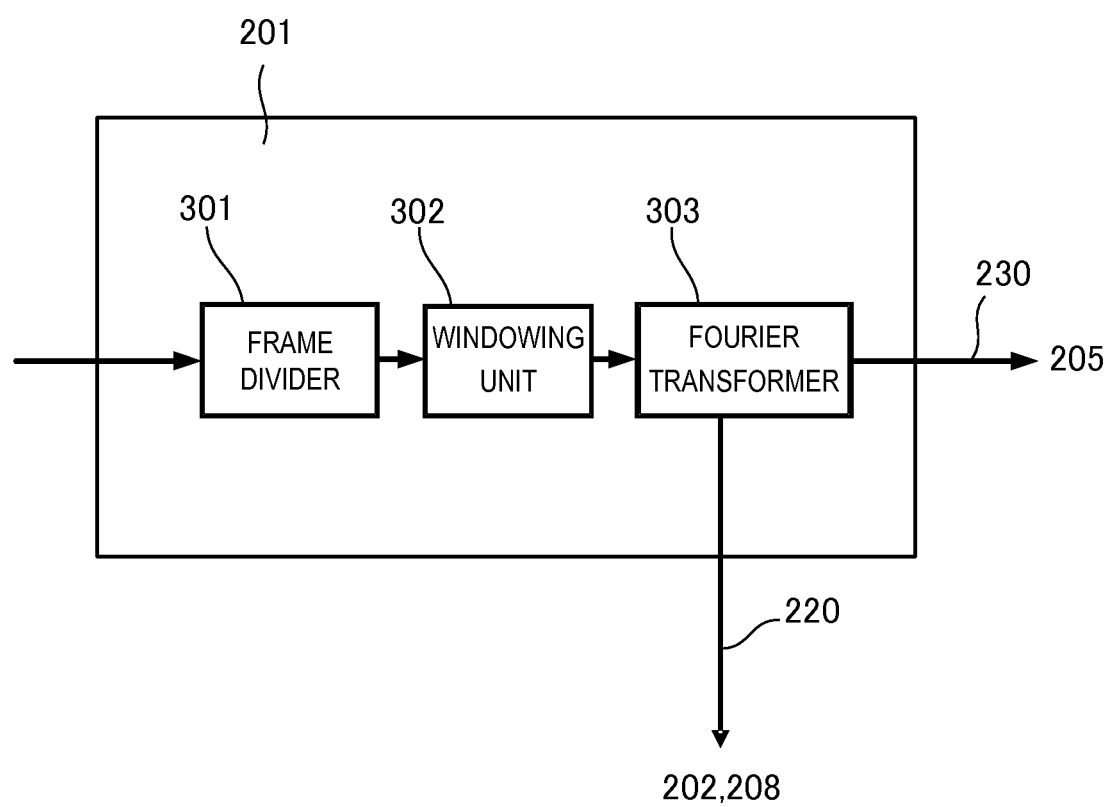
F I G. 3

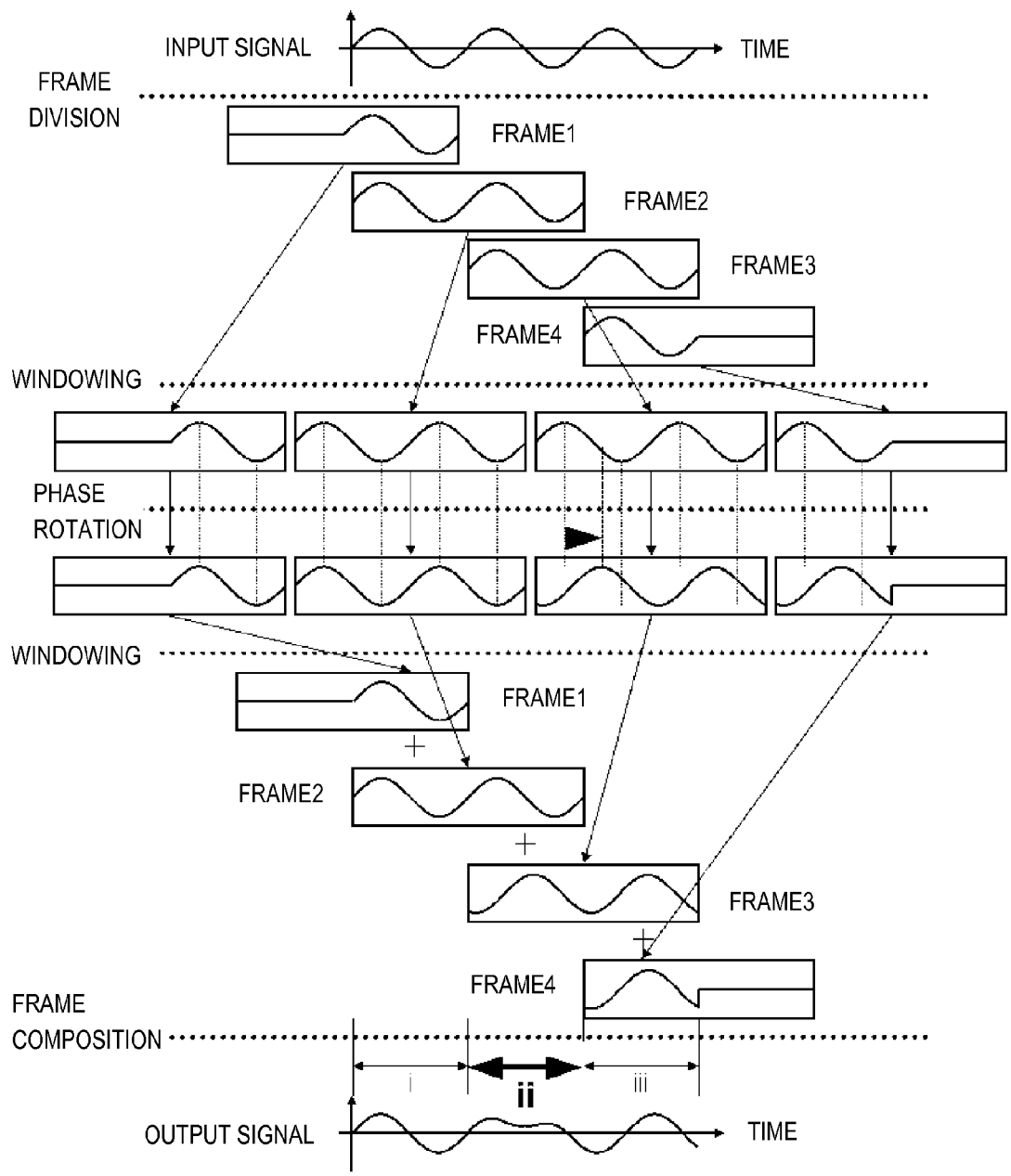
F I G. 7

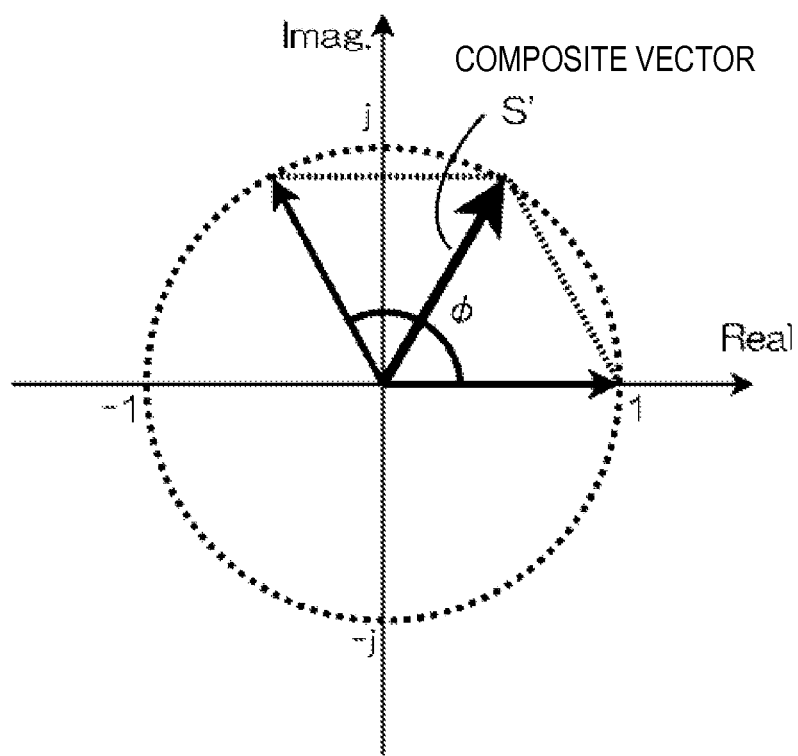
F I G. 10

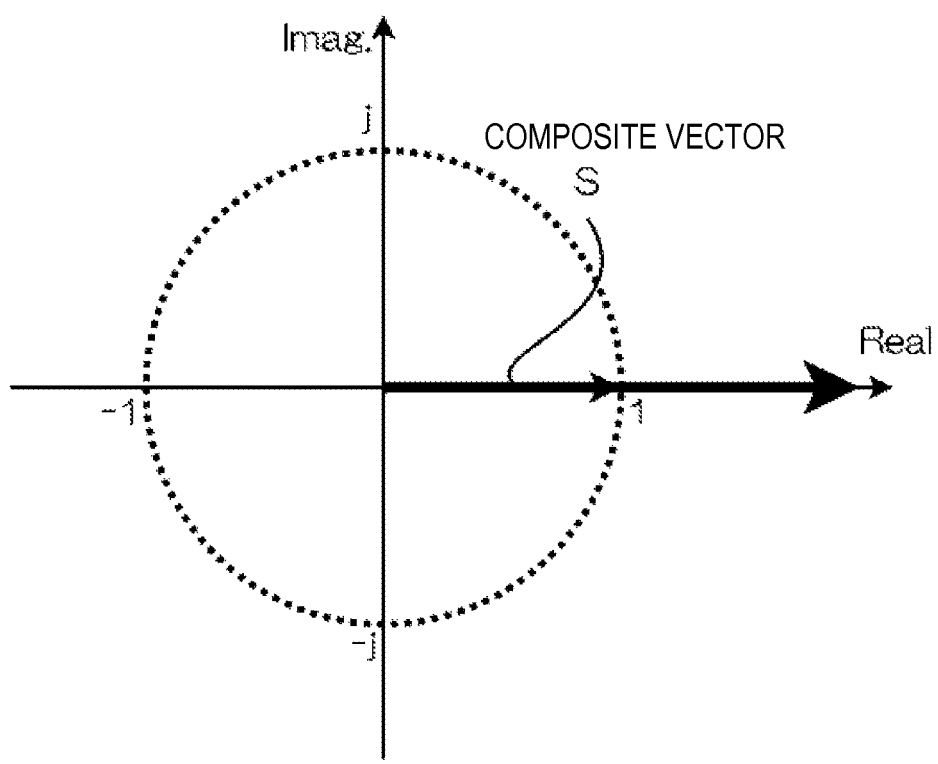
F I G. 11

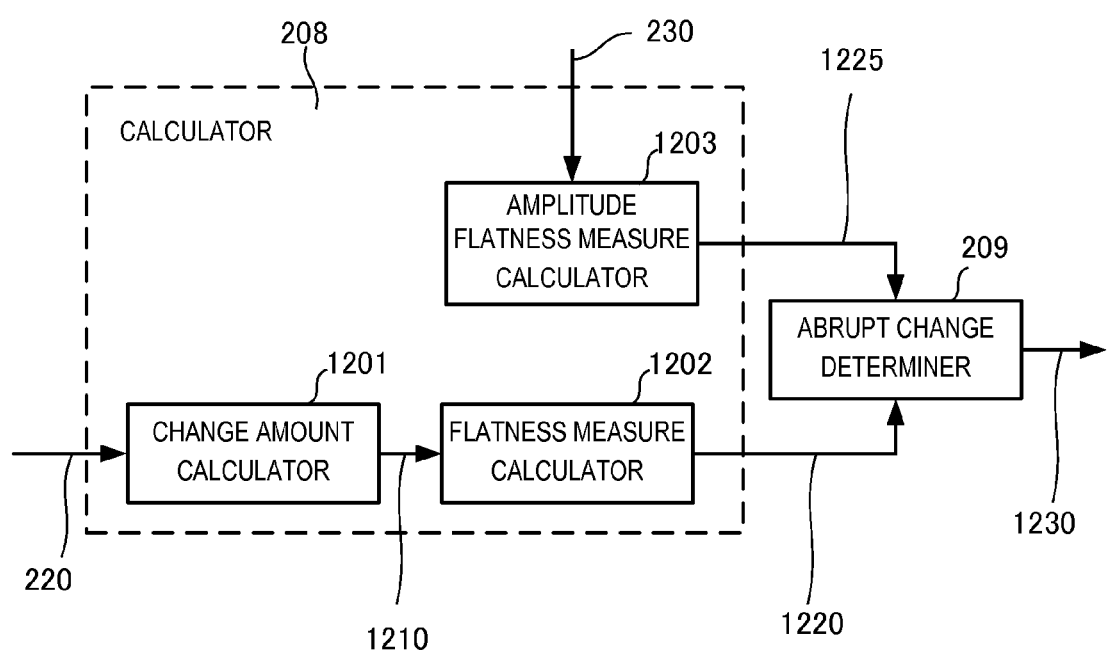
F I G. 12

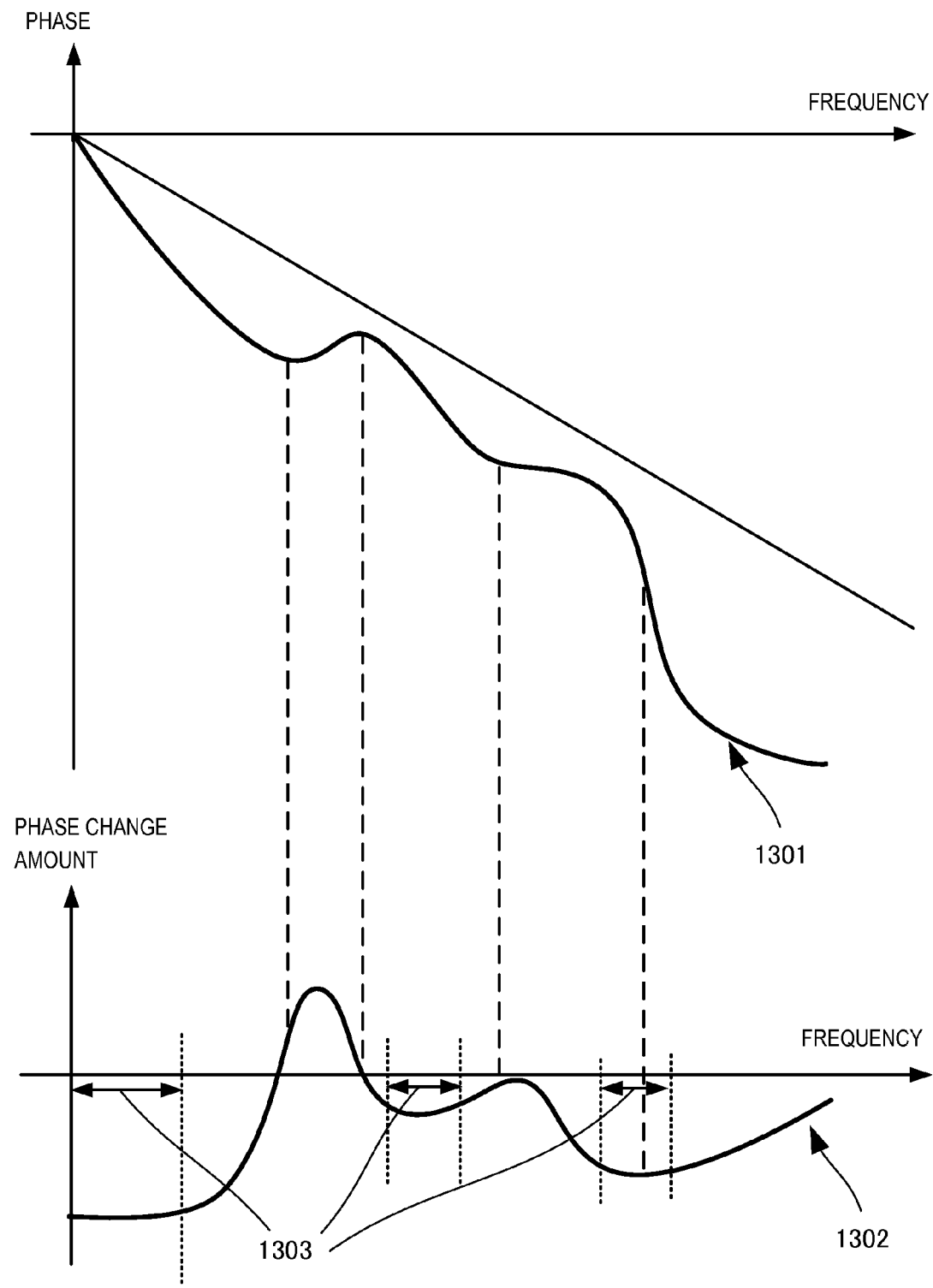
F I G. 13

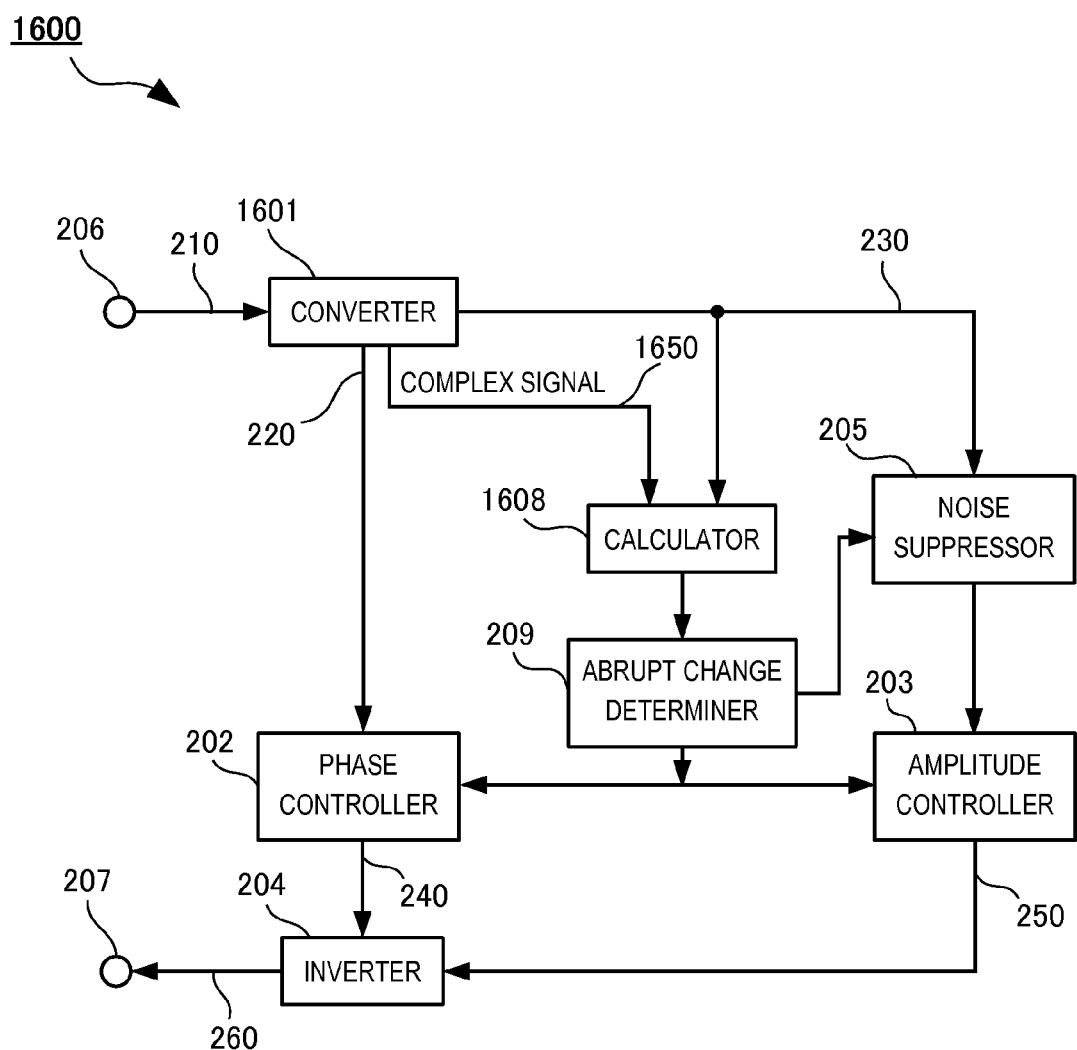
F I G. 16

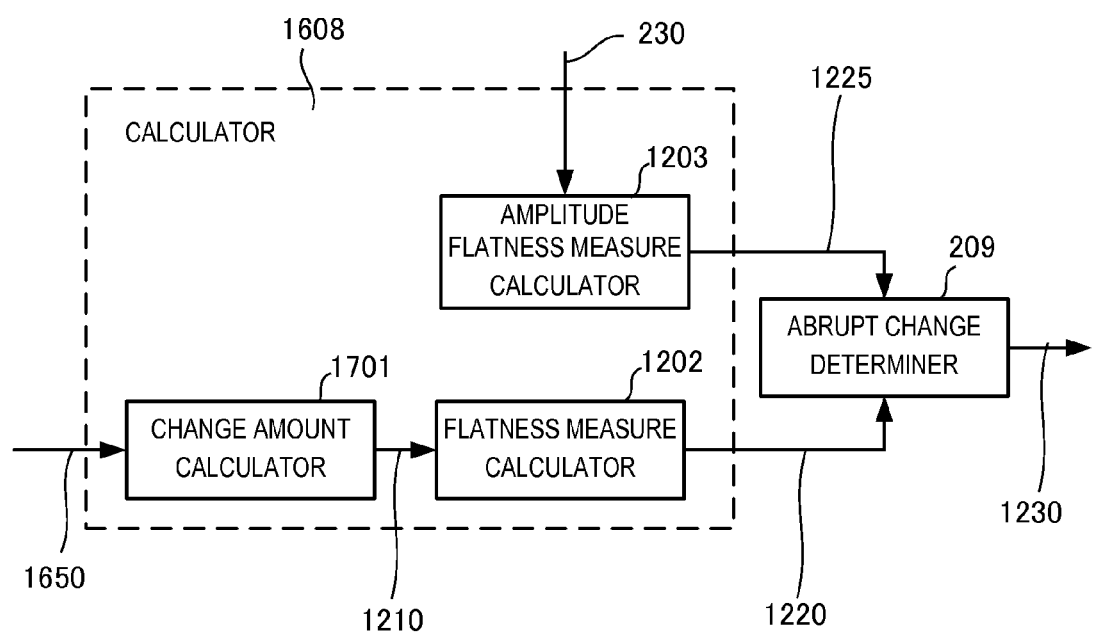
F I G. 17

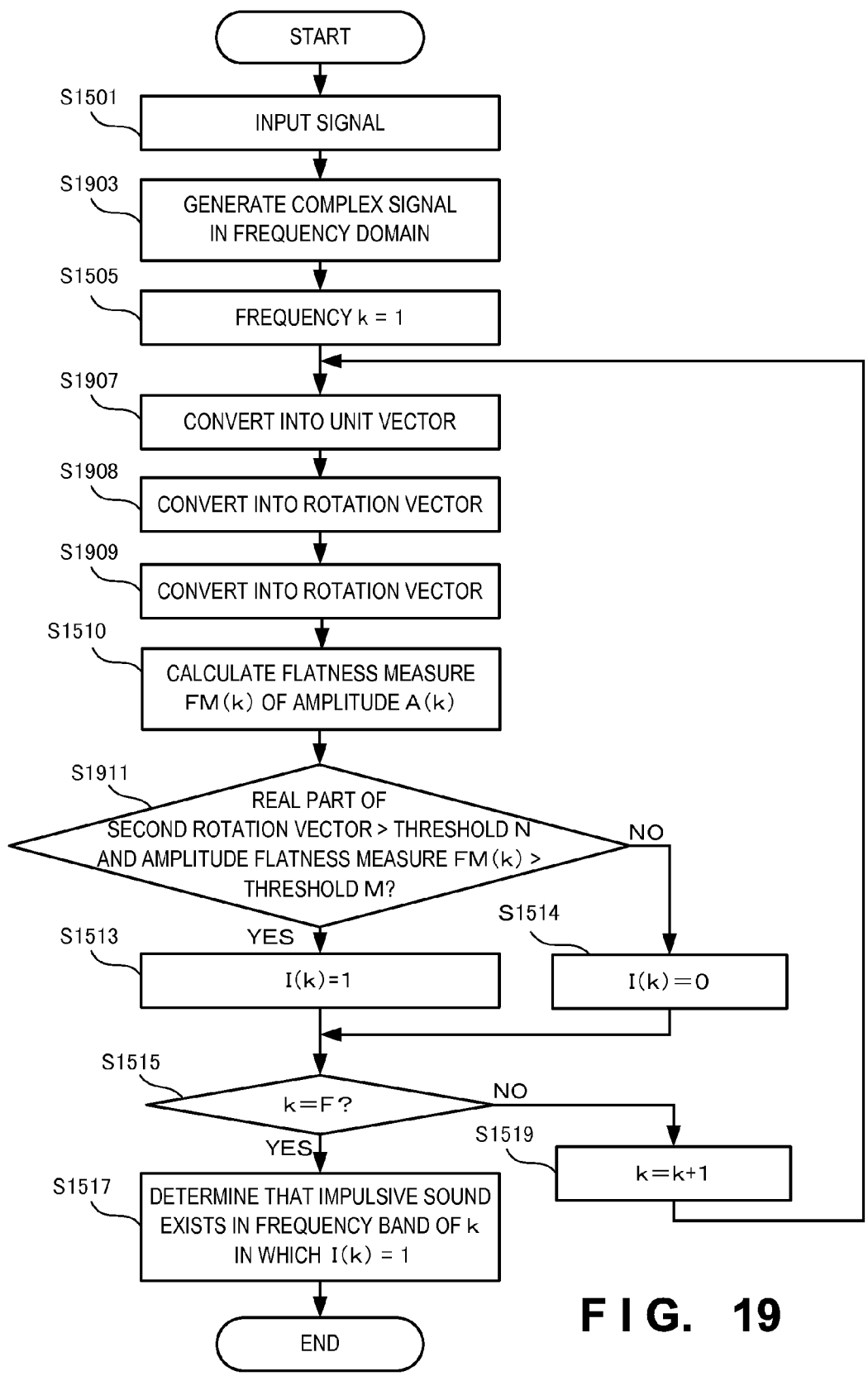
F I G. 19

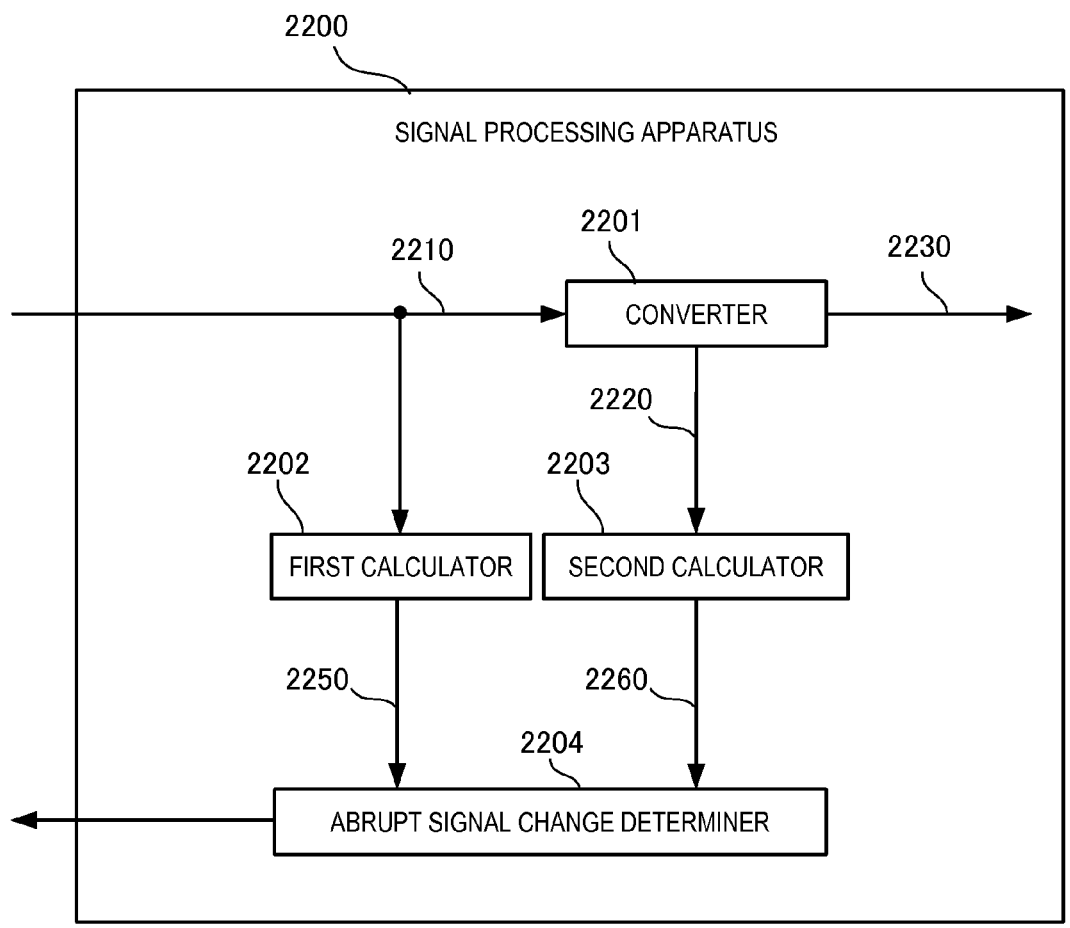
F I G. 22

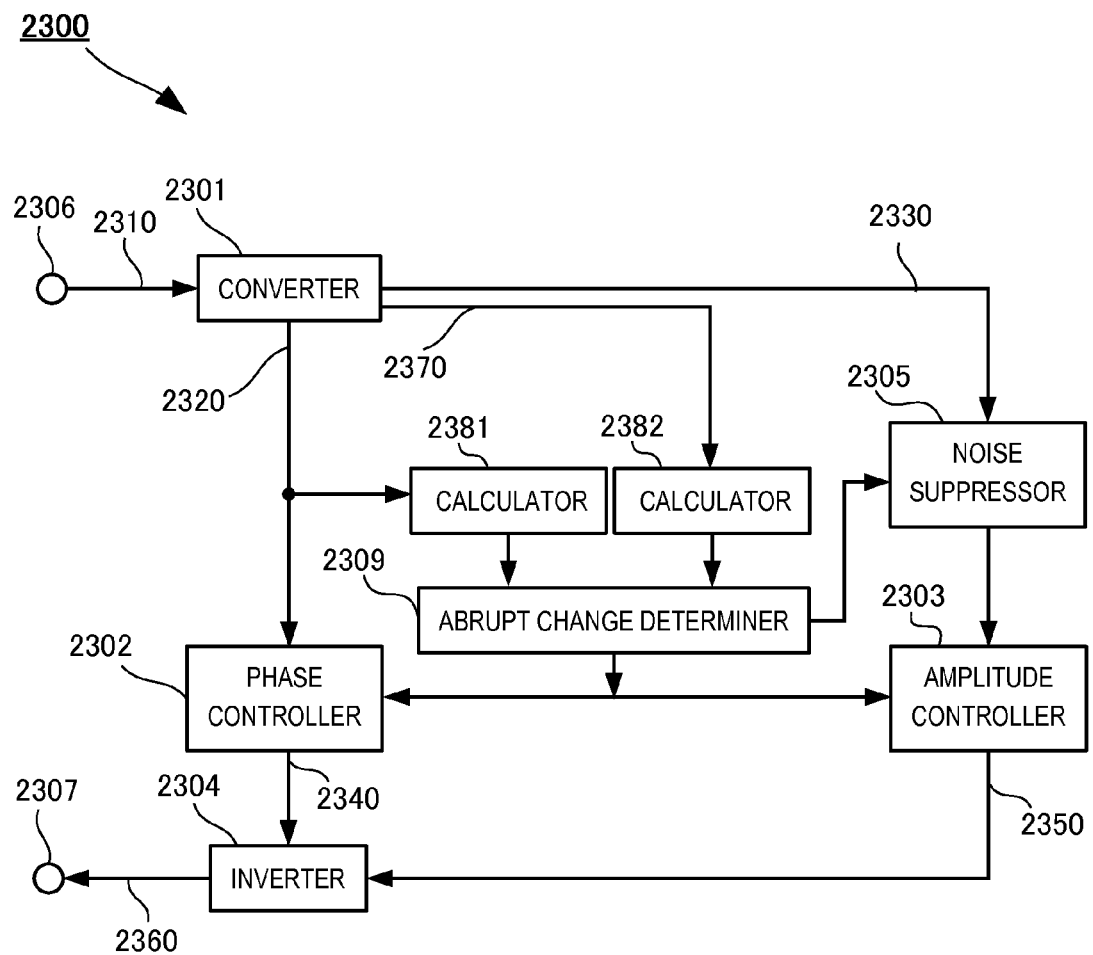
F I G. 23

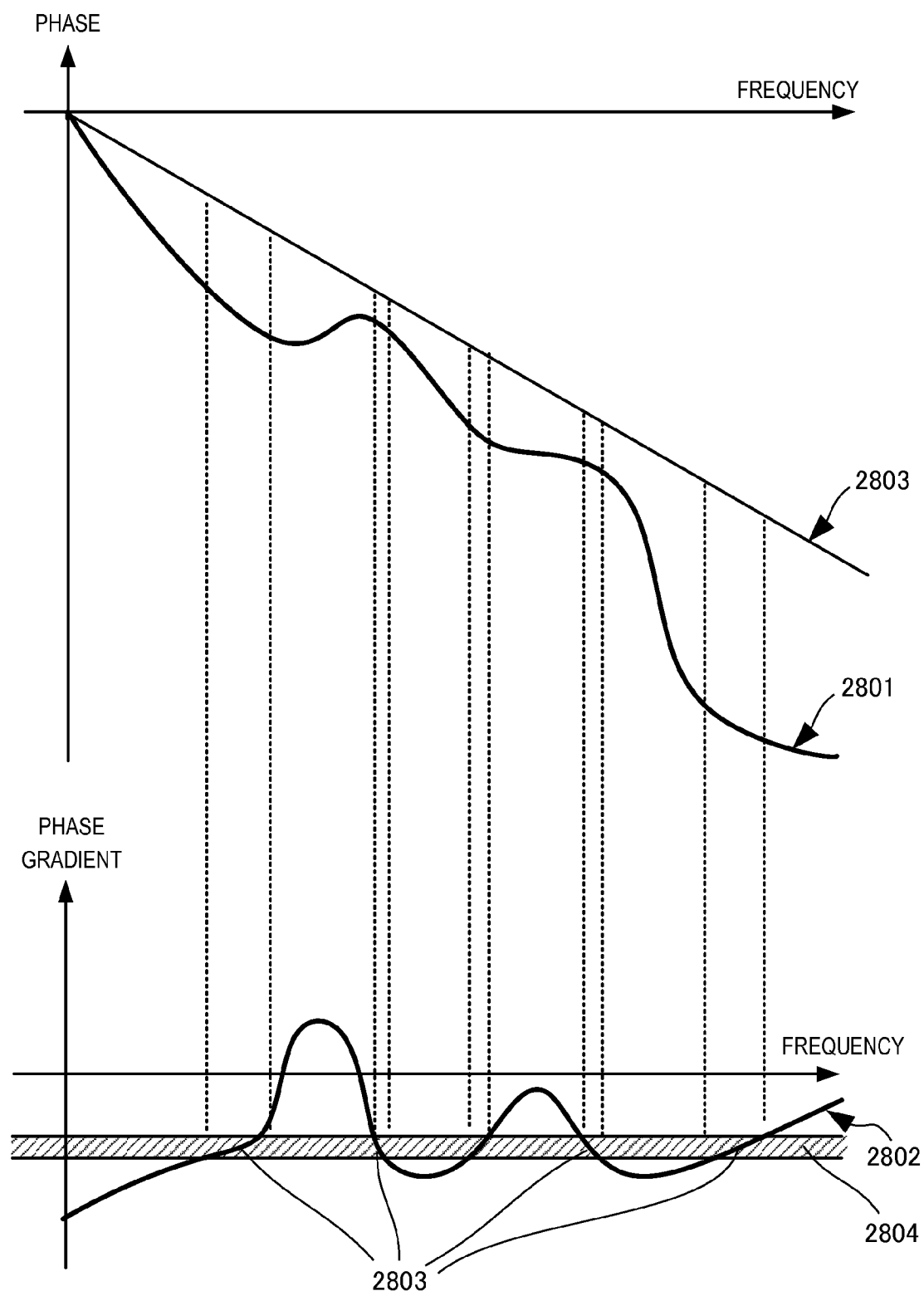
F I G. 28

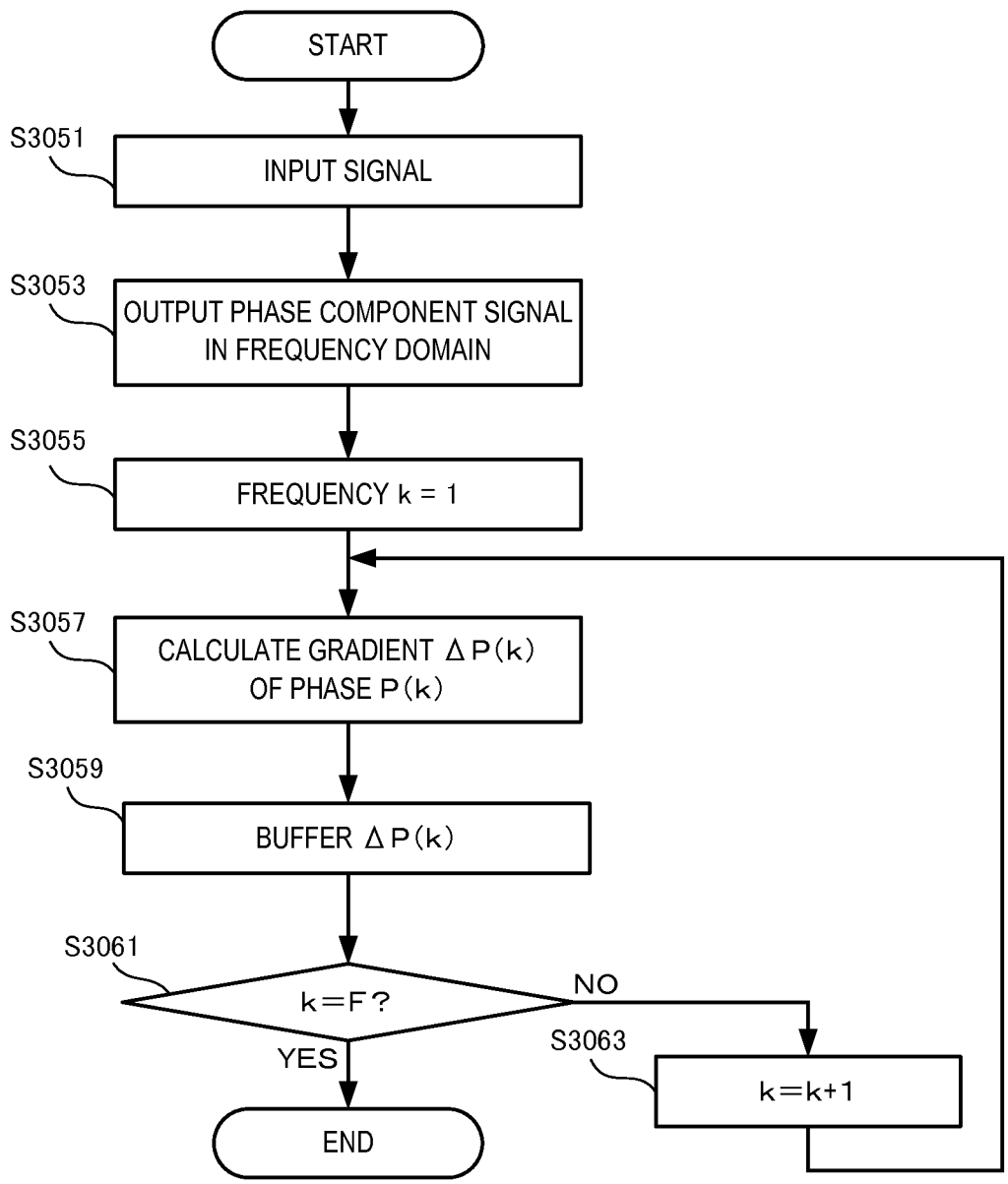
F I G. 30C

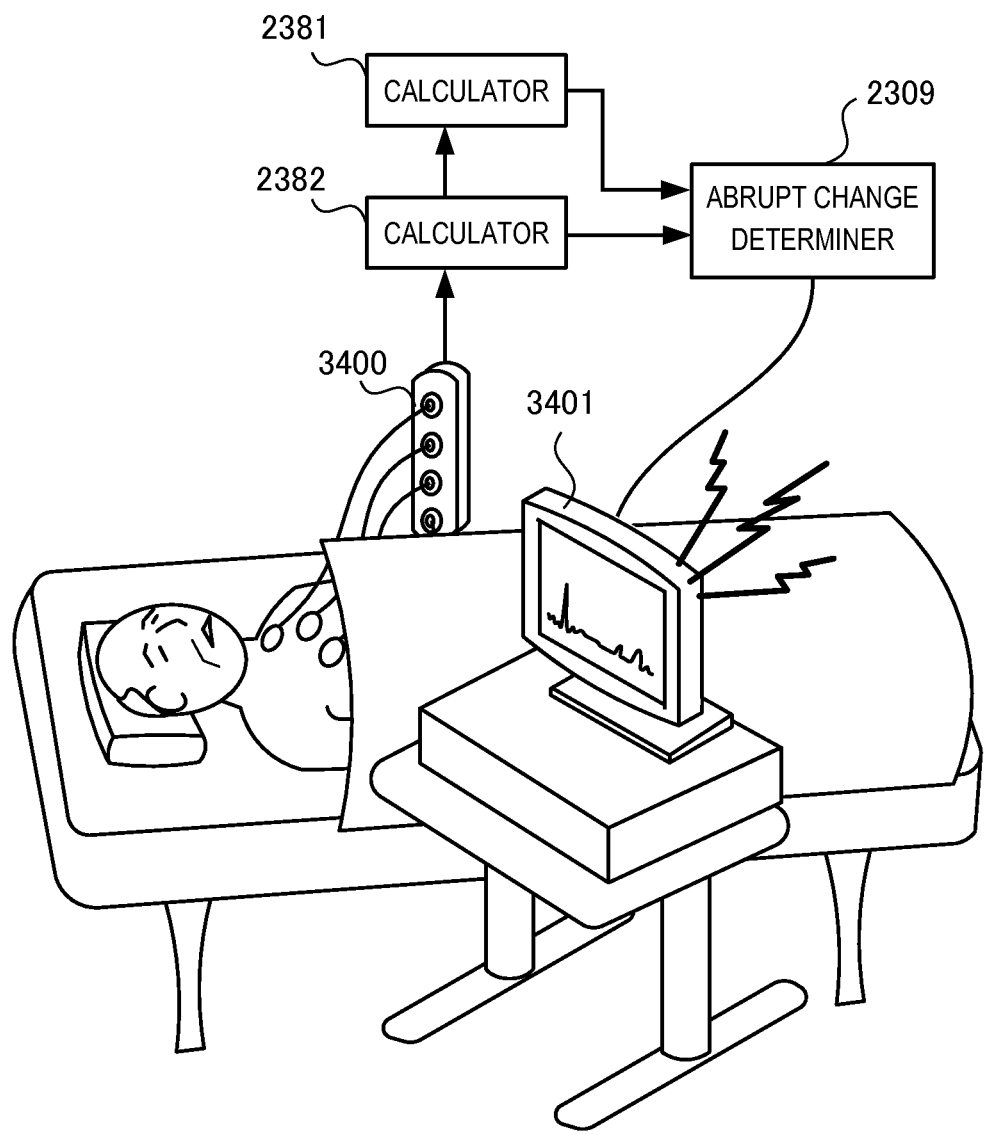
F I G. 34

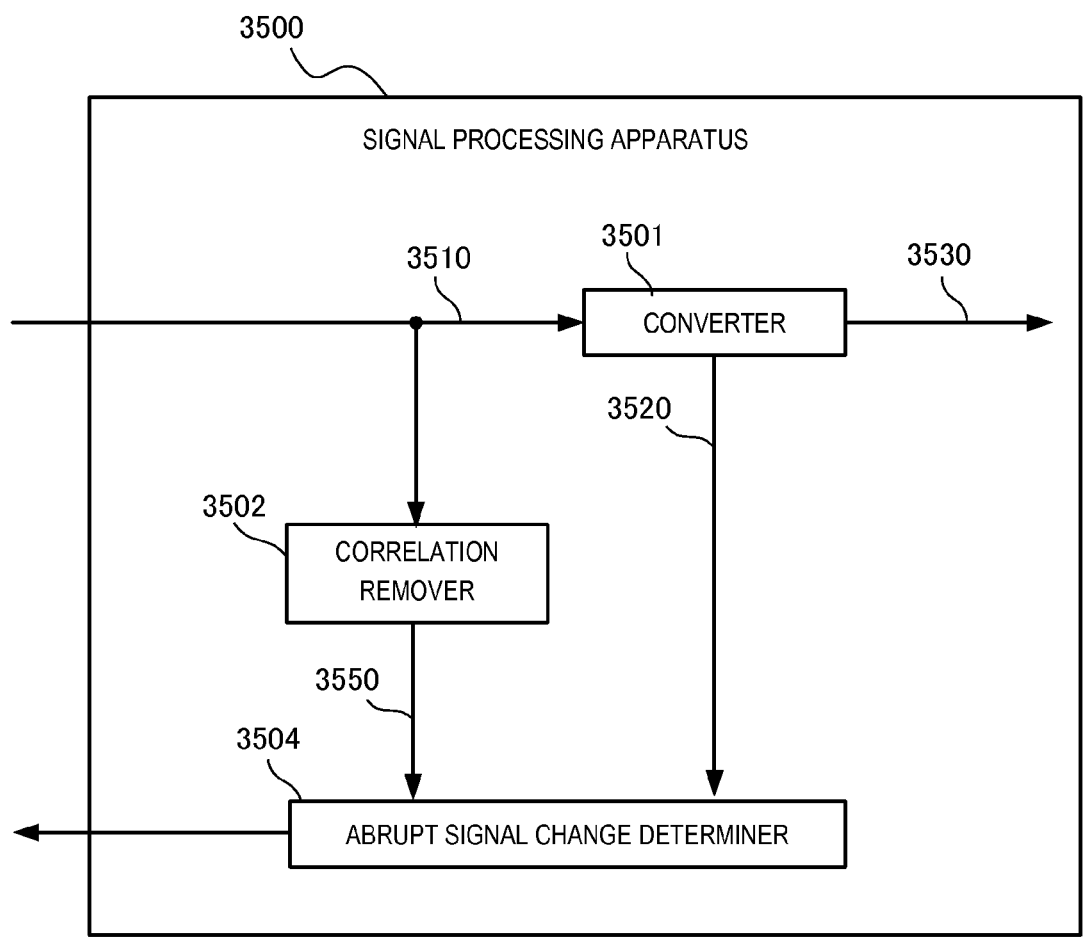
F I G. 35

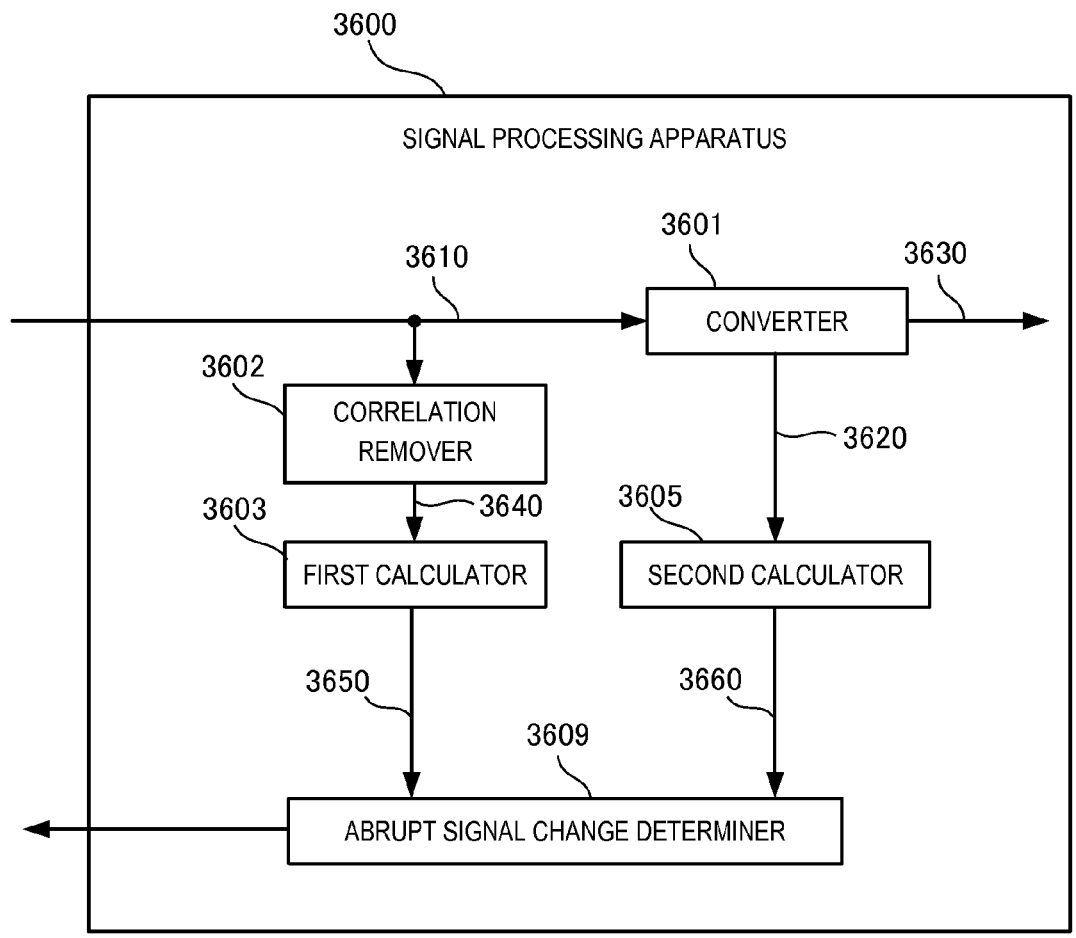
F I G. 36

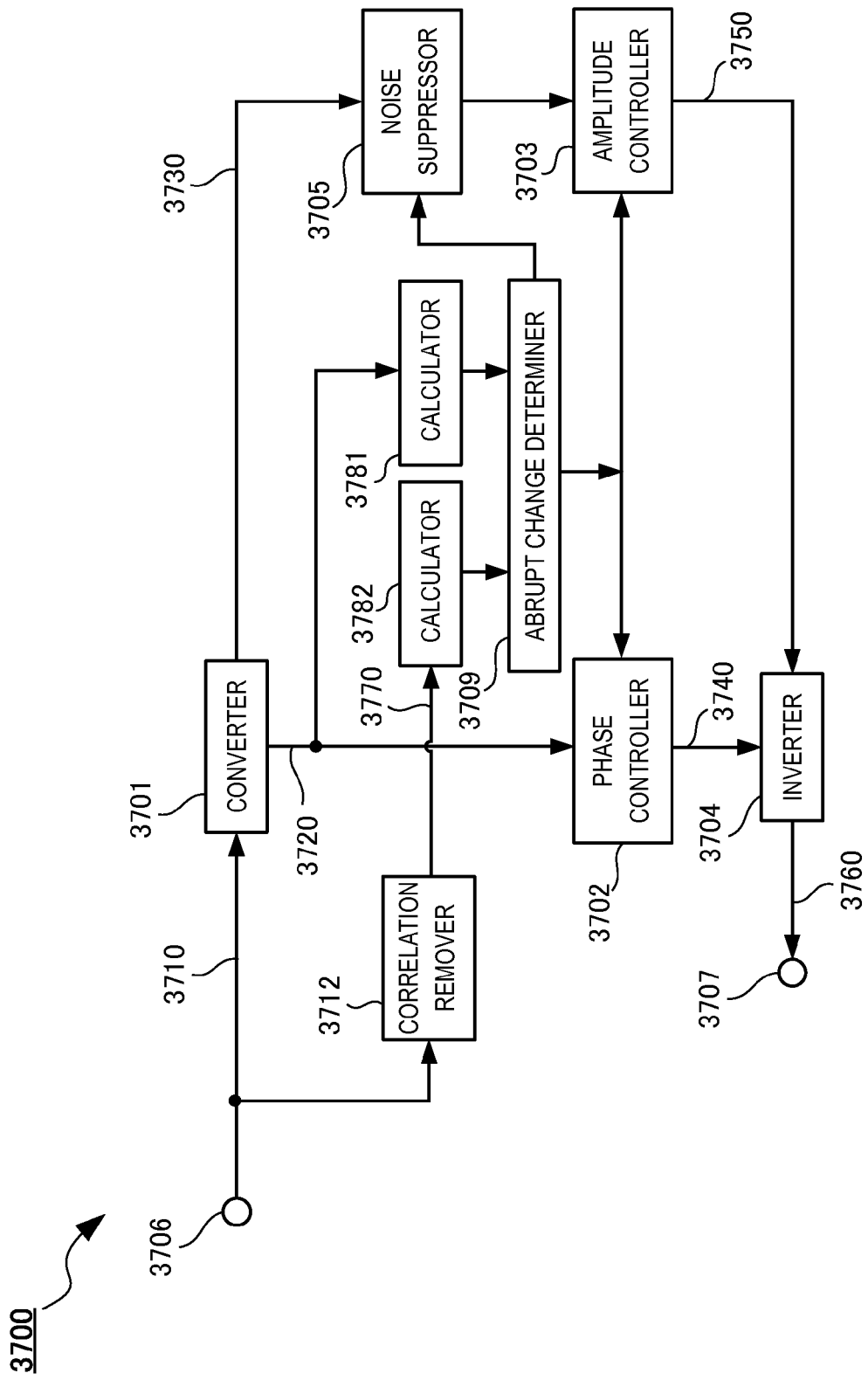
F I G. 37A

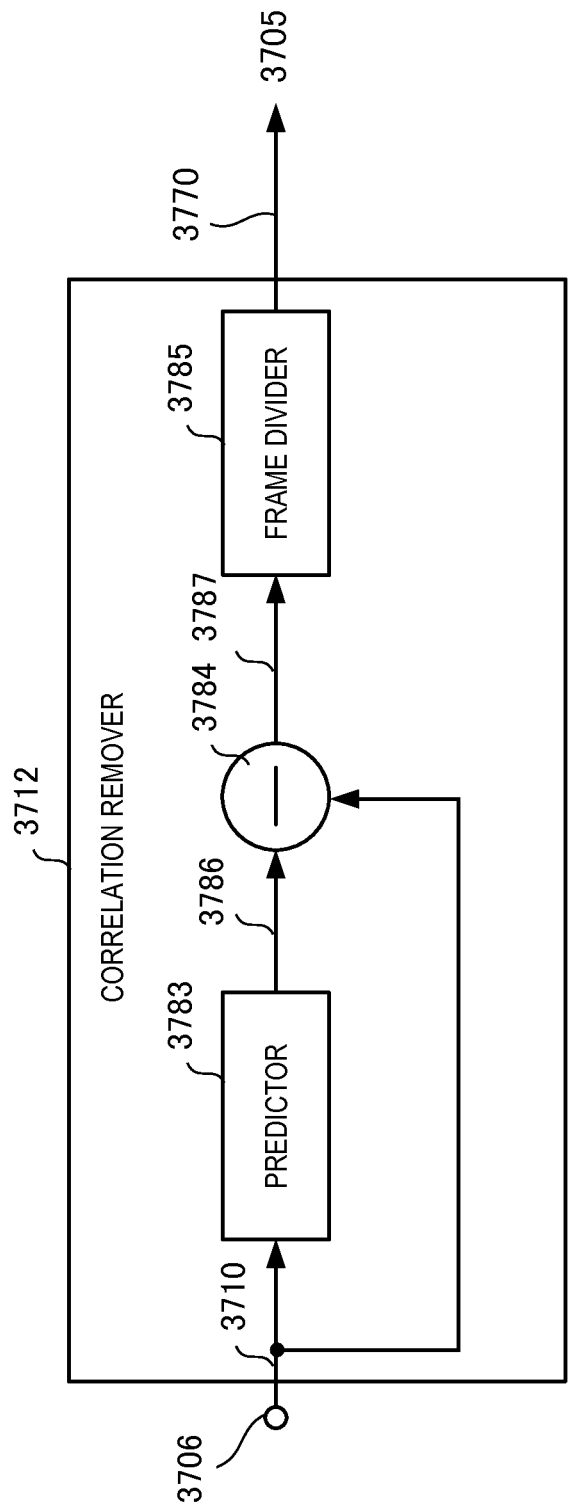
F I G. 37B

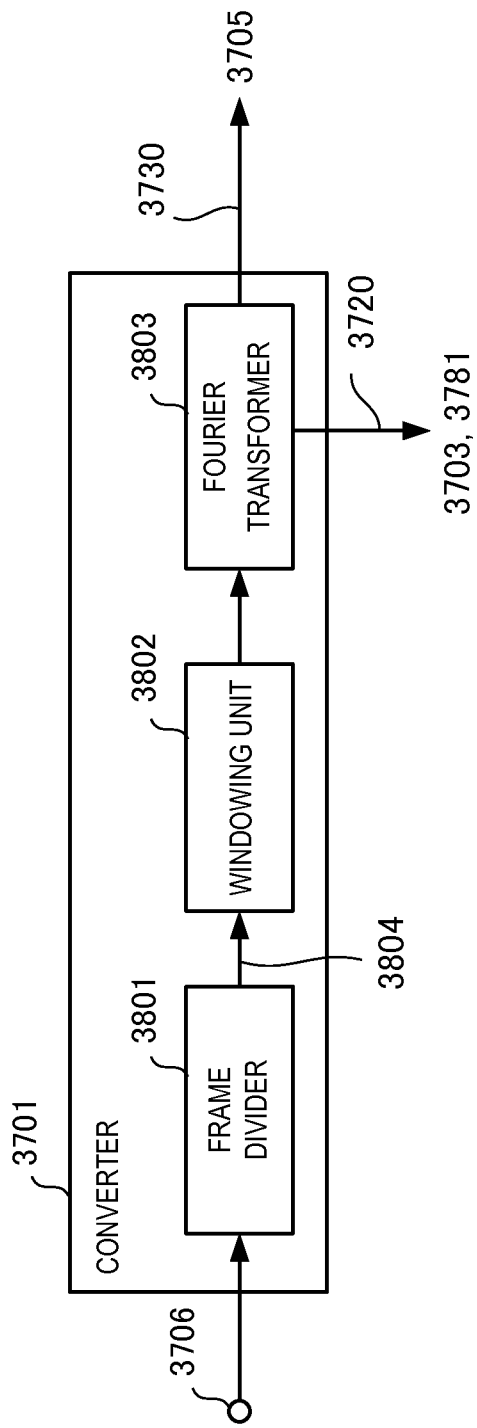
F I G. 38A

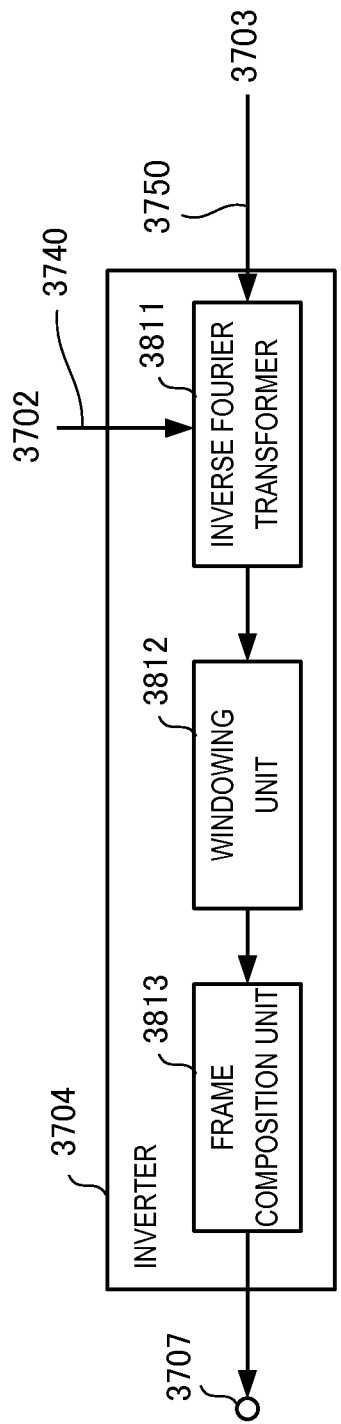
F I G. 38B

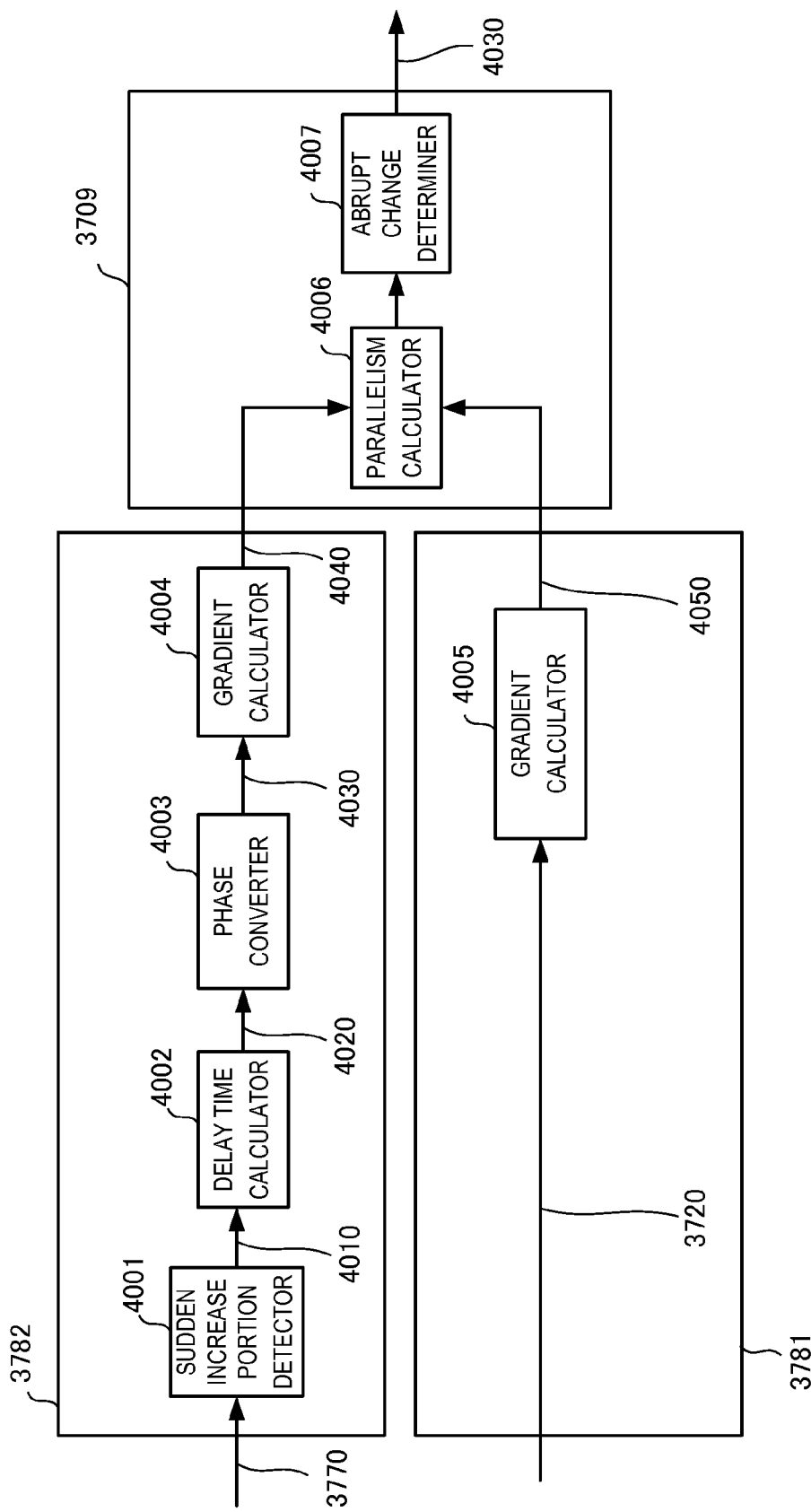
F I G. 40

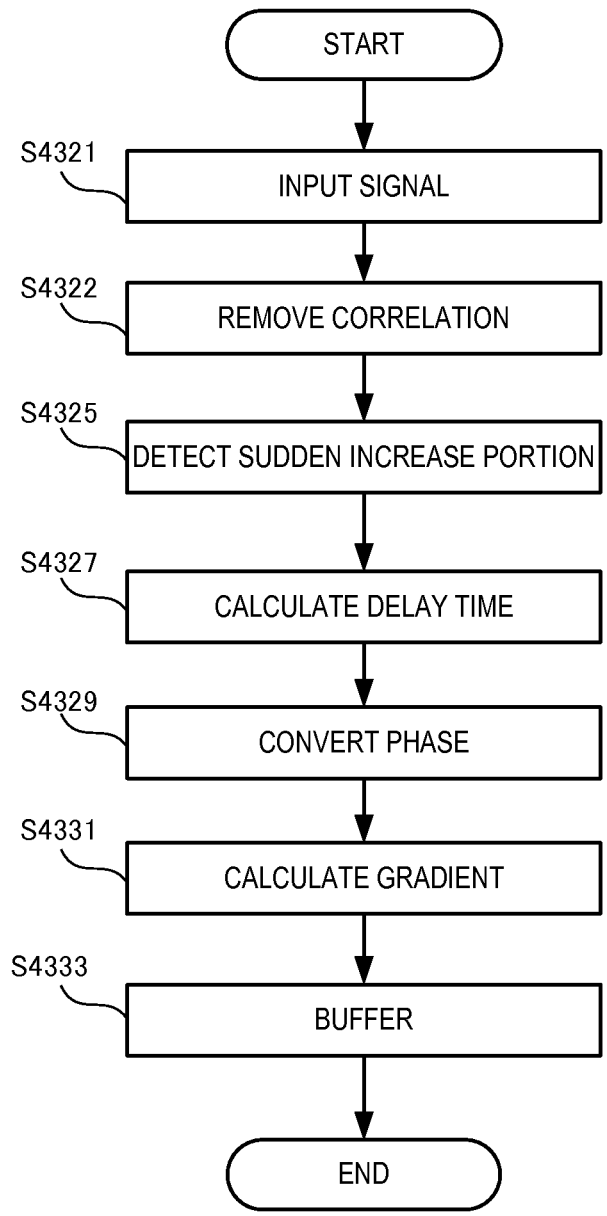
F I G. 43B

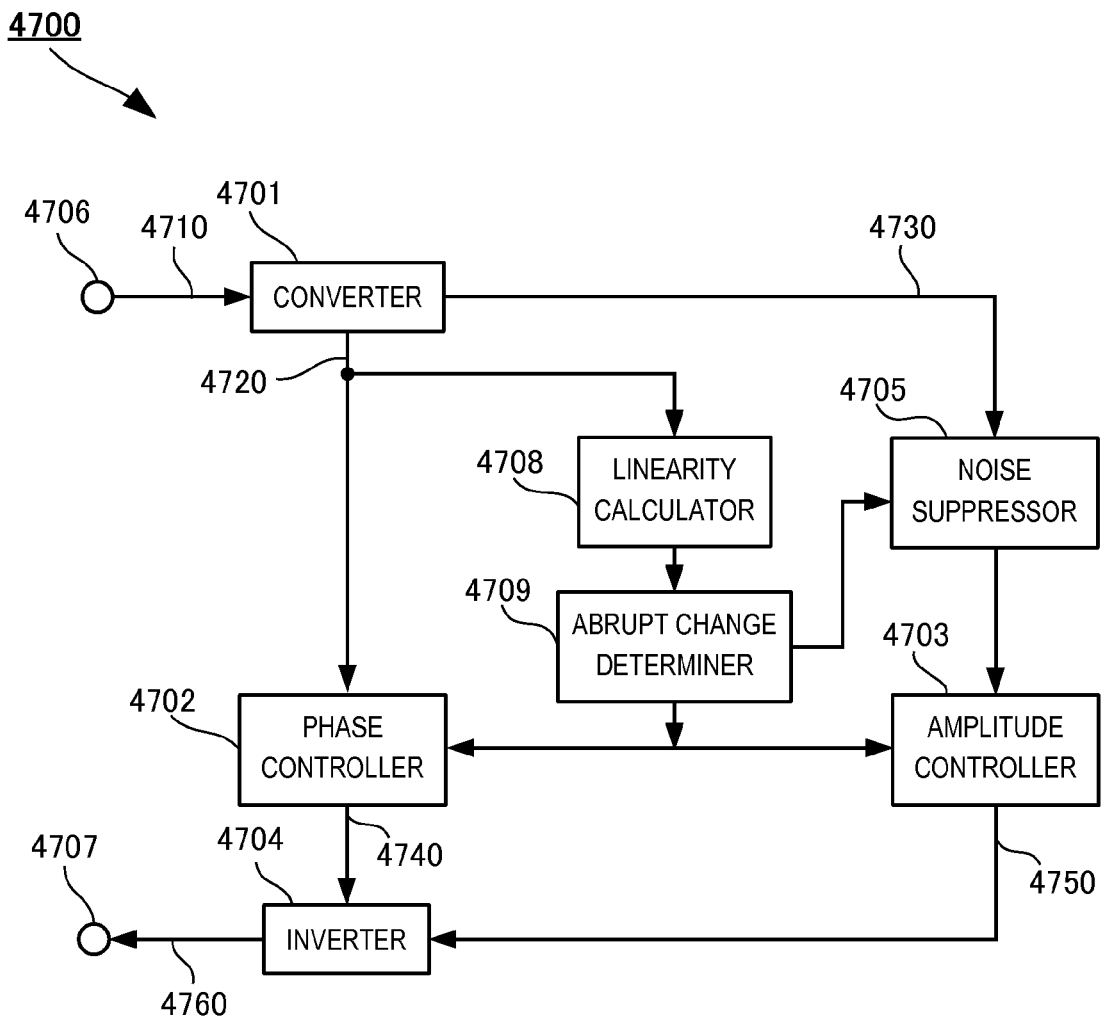
F I G. 47

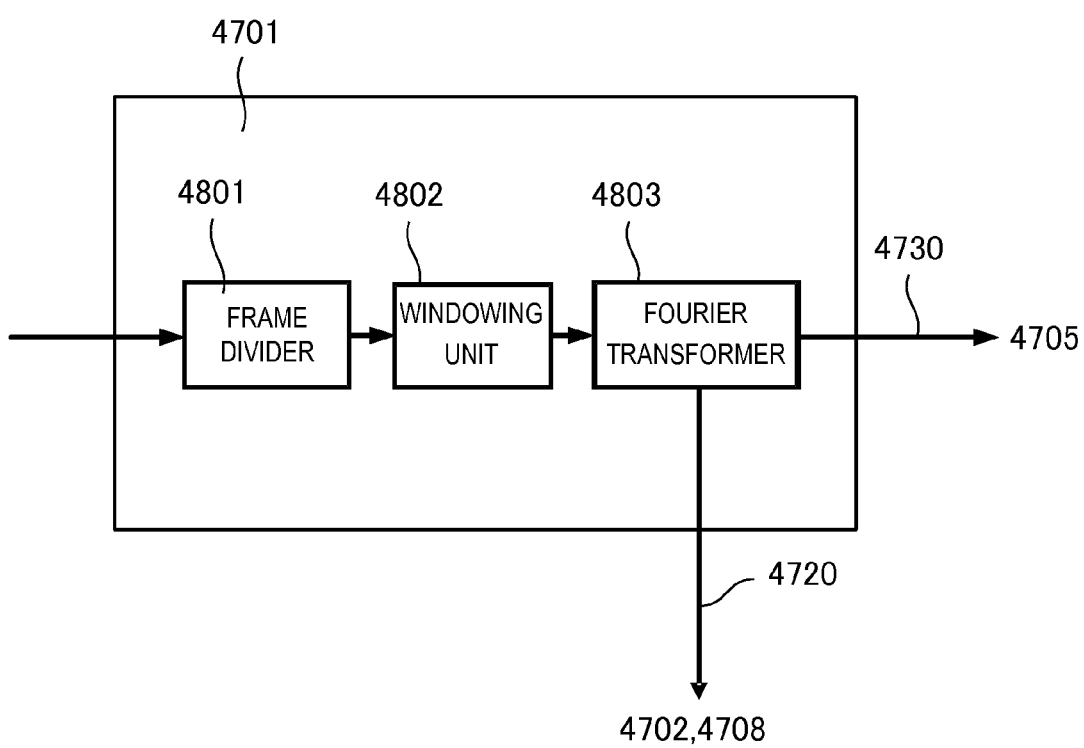
F I G. 48

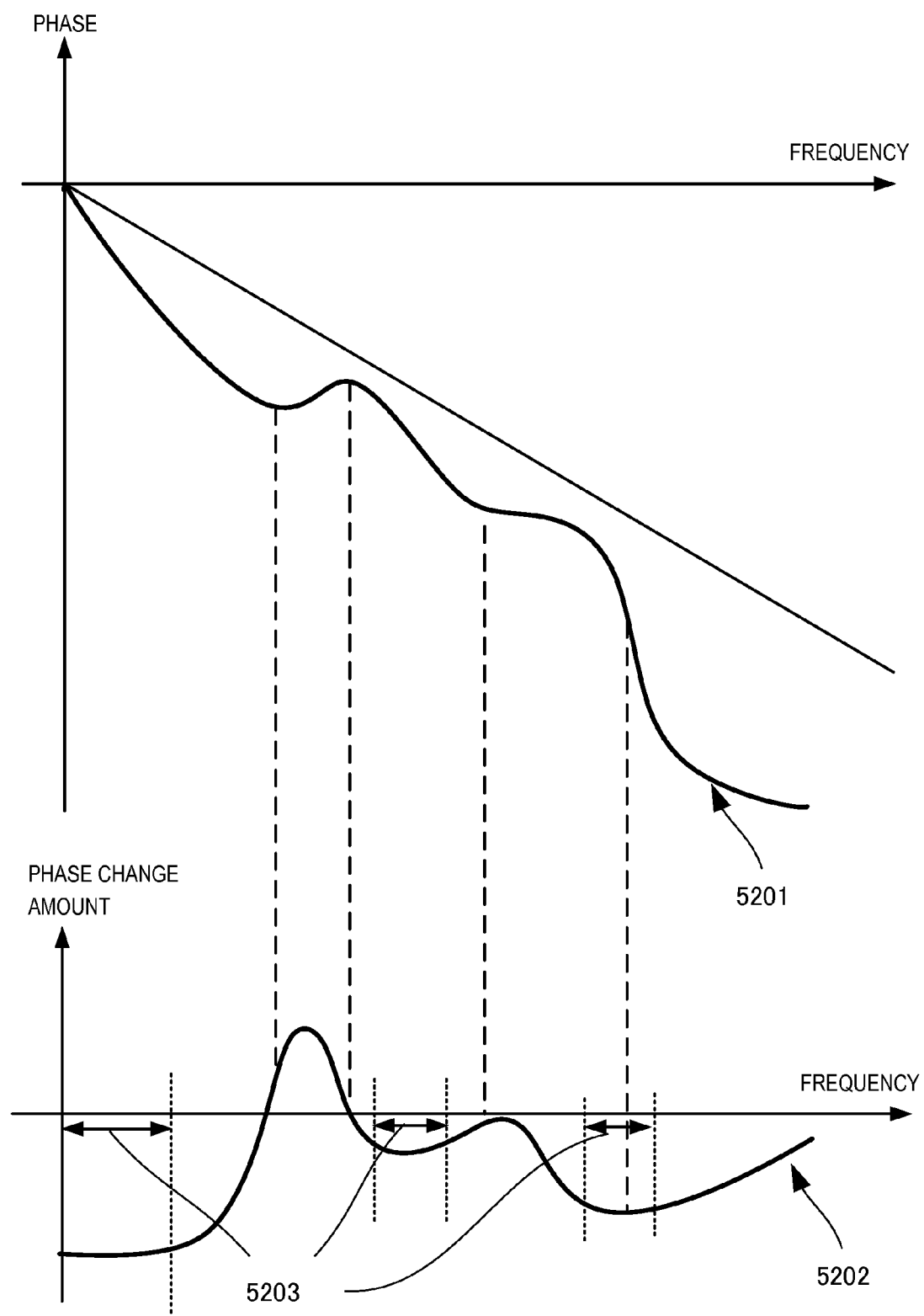
F I G. 52

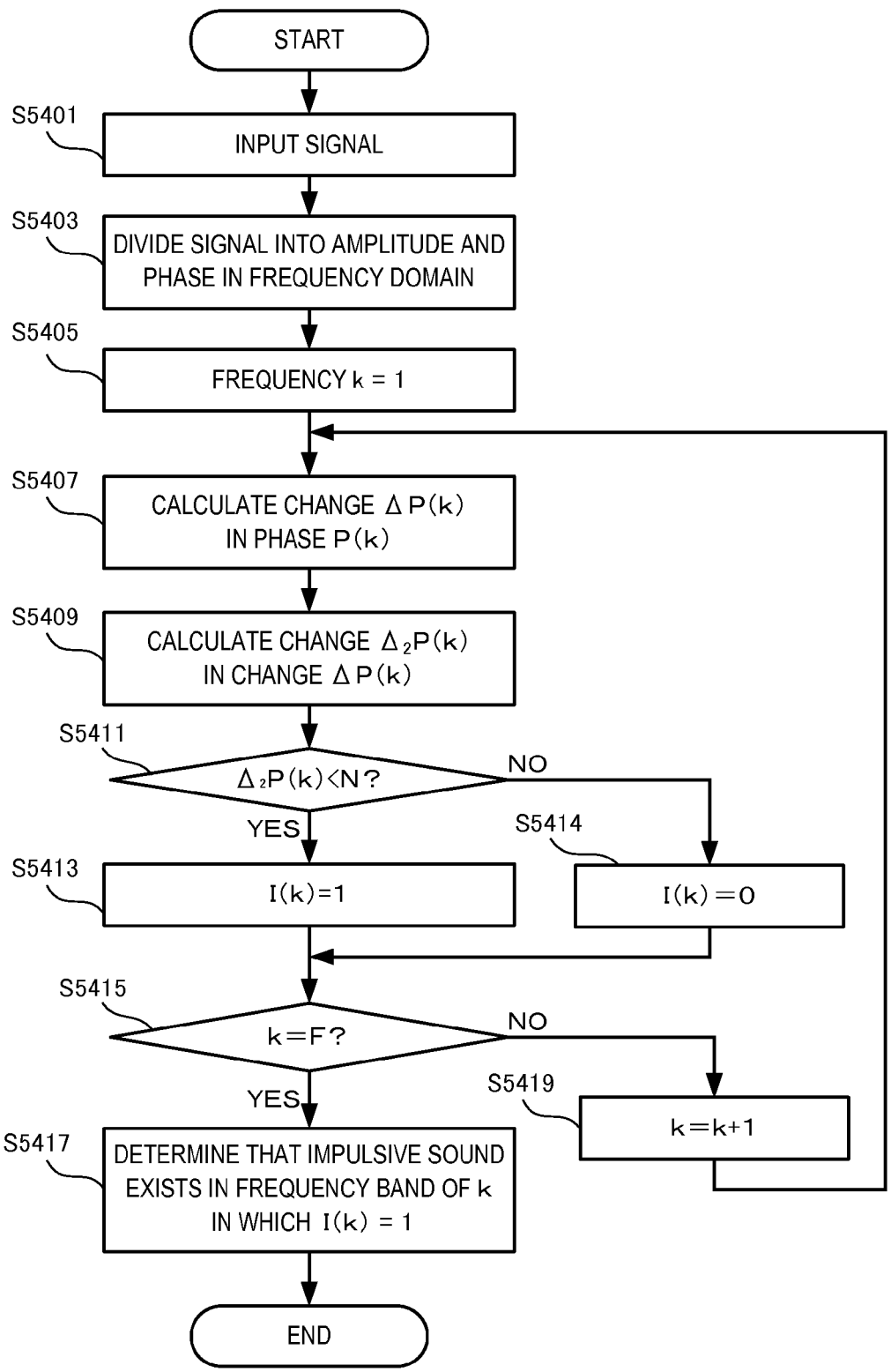
F I G. 54

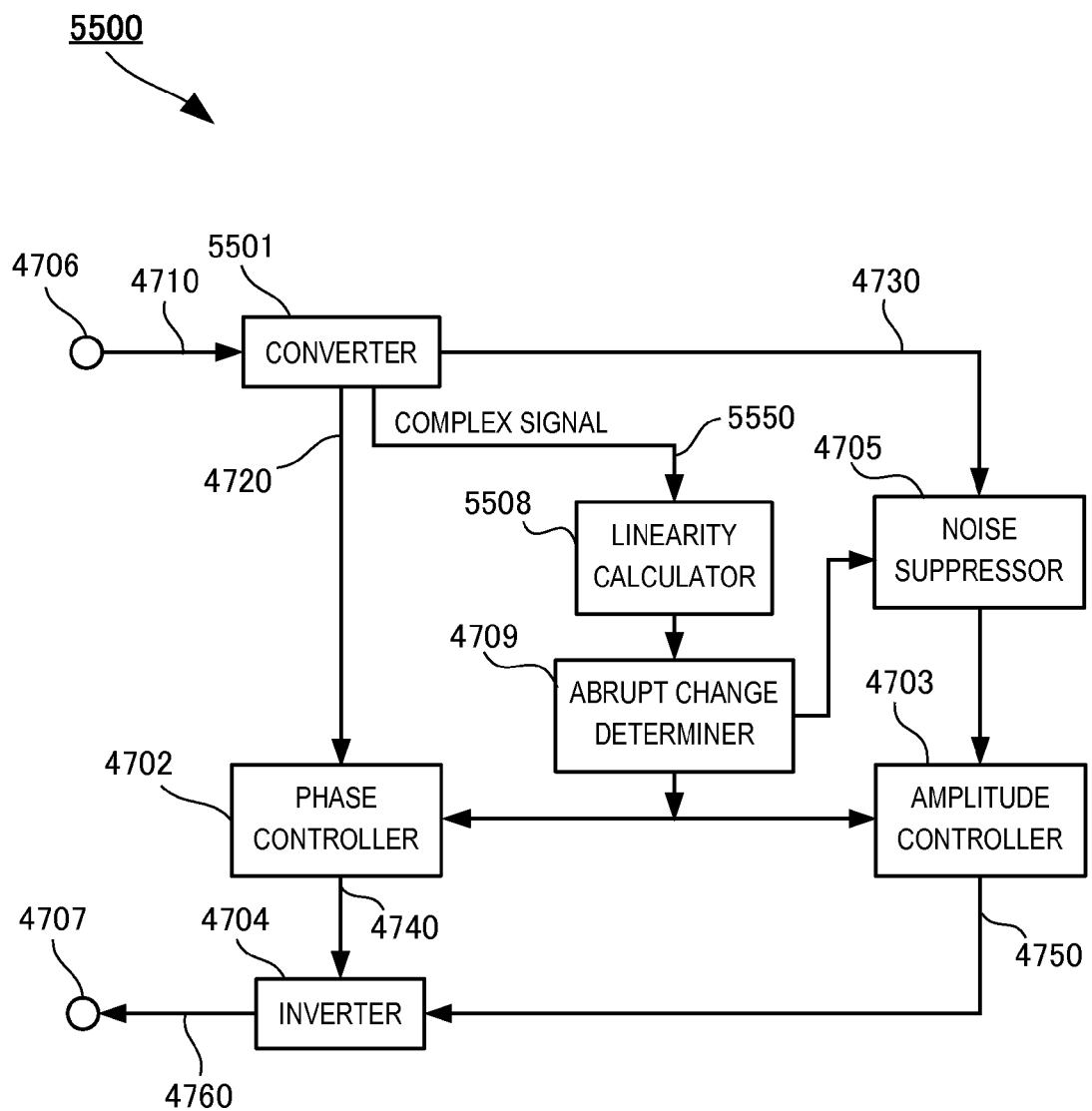
F I G. 55

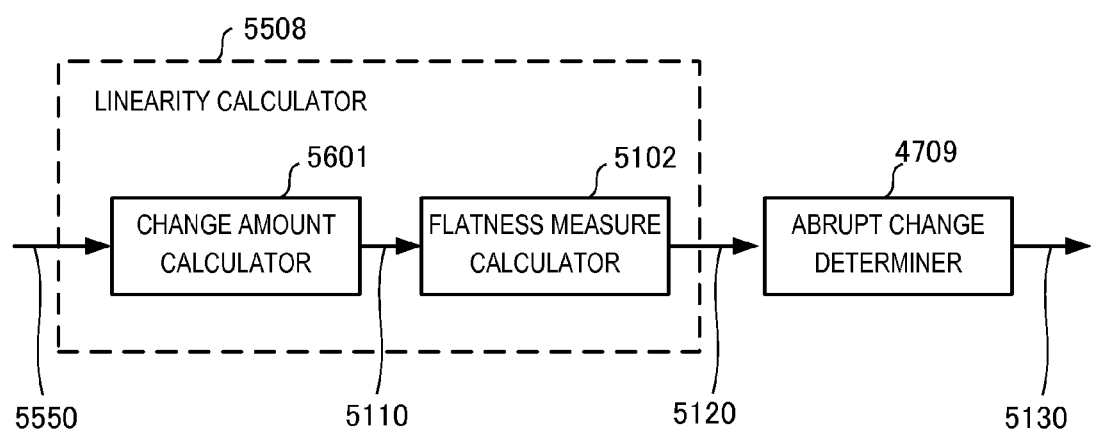
F I G. 56

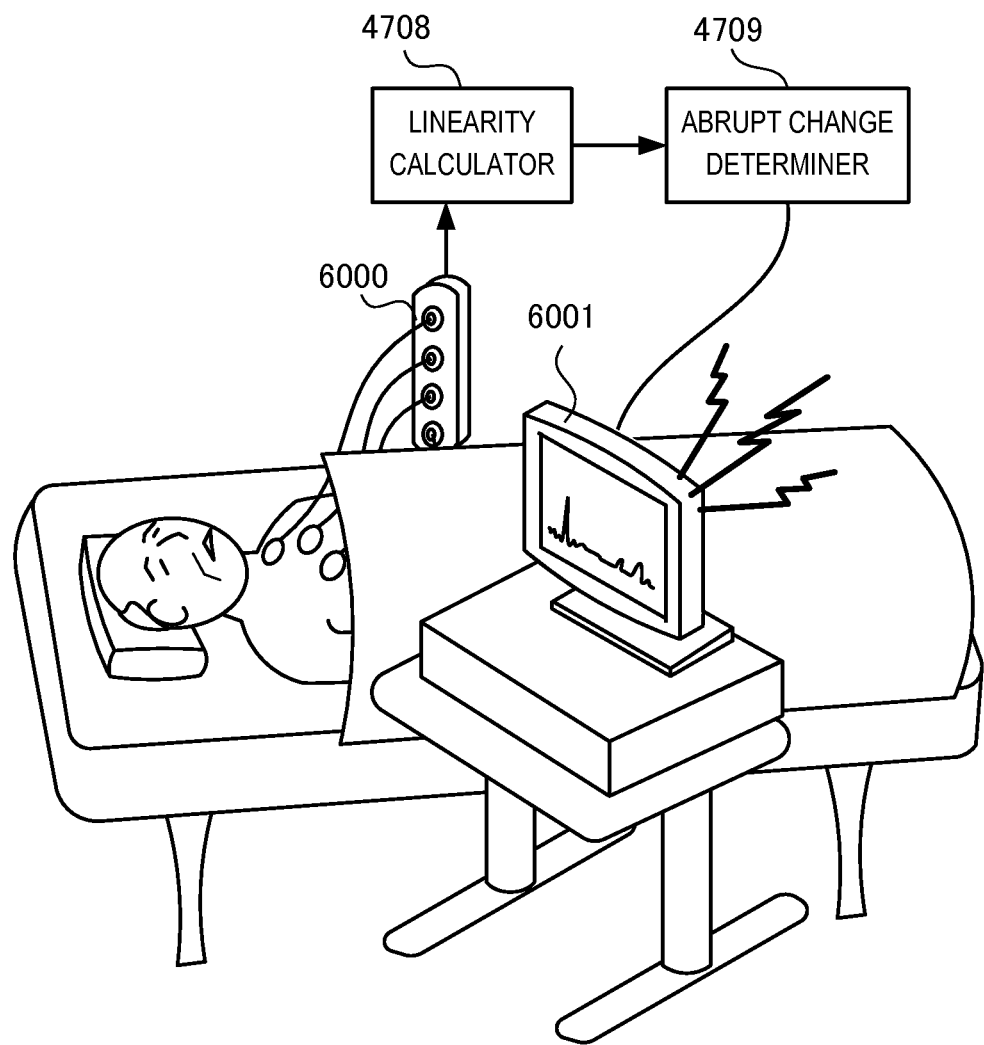
F I G. 60

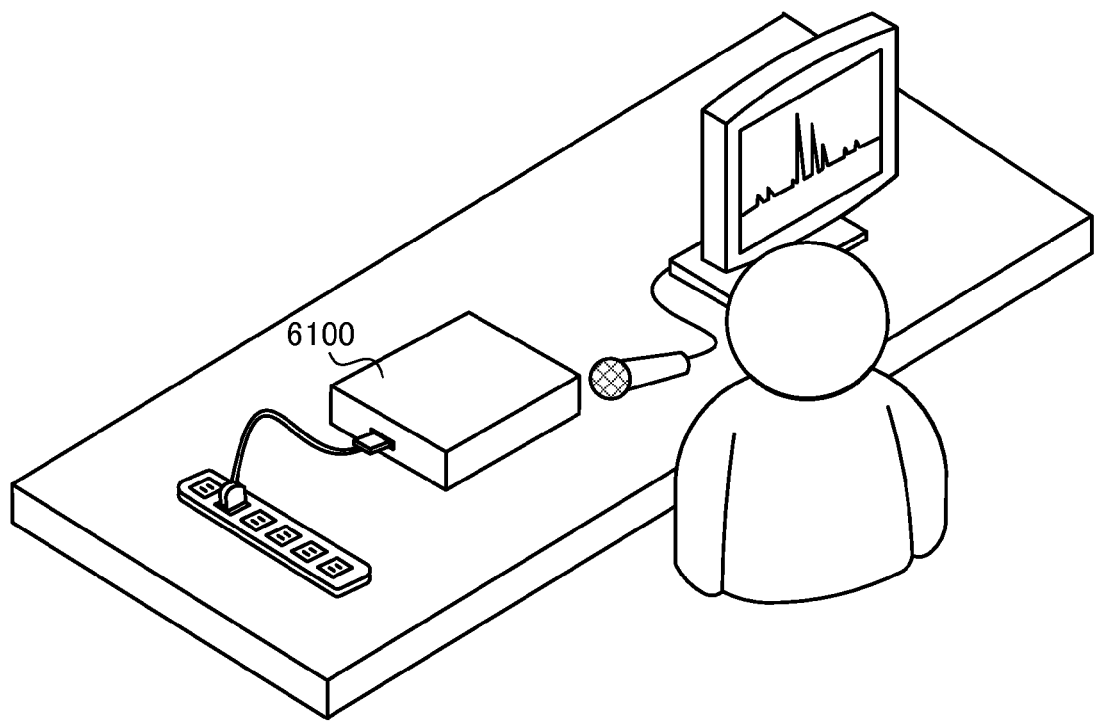
F I G. 61

SIGNAL PROCESSING APPARATUS, SIGNAL PROCESSING METHOD, AND SIGNAL PROCESSING PROGRAM

CROSS-REFERENCE TO RELATED PATENT APPLICATIONS

This application is a National Stage Entry of International Application No. PCT/JP2014/054634, filed Feb. 26, 2014, which claims priority from Japanese Patent Application No. 2013-042448, Japanese Patent Application No. 2013-042449, Japanese Patent Application No. 2013-042450, and Japanese Patent Application No. 2013-042451, each of which was filed Mar. 5, 2013. The entire contents of the above-referenced applications are expressly incorporated herein by reference.

TECHNICAL FIELD

The present invention relates to a technique of detecting a change in a signal.

BACKGROUND ART

In the above technical field, patent literature 1 discloses a technique of evaluating the continuity of a phase component in the time direction and smoothing an amplitude component for each frequency (paragraphs 0135 to 0138). Patent literature 2 describes detecting an abrupt frequency change by measuring a fluctuation in a phase in the time direction. Patent literature 3 describes, in paragraph 0024, that "a phase change in the complex vector of I and Q signals on a complex plane caused by superimposition of impulsive noise is always monitored, thereby reliably detecting the impulsive noise under a strong field environment". The phase change is a change along the time axis. Patent literature 4 describes, in paragraph 0031, that "a phase linearizer 25 corrects a hop in a phase signal θ input from a polar coordinate converter 24 by linearization and outputs a resultant phase signal θ' to a phase detector 26". In addition, patent literature 4 has a description of a phase gradient detector in paragraph 0051, and also describes, in paragraph 0040, that "FIG. 5 shows an example of the input and output signals (a phase θ' that is an input signal and a phase gradient dθ' that is an output signal) of the phase detector 26". Patent literature 5 discloses a technique of detecting an impulsive sound using an amplitude.

CITATION LIST

Patent Literature

Patent literature 1: Japanese Patent Laid-Open No. 2010-237703
Patent literature 2: Japanese Patent Laid-Open No. 2011-254122
Patent literature 3: Japanese Patent Laid-Open No. 2007-251908
Patent literature 4: Japanese Patent Laid-Open No. 2011-199808
Patent literature 5: WO 2008/111462

Non-Patent Literature

Non-patent literature 1: M. Kato, A. Sugiyama, and M. Serizawa, "Noise suppression with high speech quality based on weighted noise estimation and MMSE STSA", IEICE Trans. Fundamentals (Japanese Edition), vol. J87-A, no. 7, pp. 851-860, July 2004.
Non-patent literature 2: R. Martin, "Spectral subtraction based on minimum statistics", EUSPICO-94, pp. 1182-1185, September 1994.
Non-patent literature 3: "1.5-Mbit/s encoding of video signal and additional audio signal for digital storage media—section 3, audio", JIS X 4323, p. 99, November 1996.
Non-patent literature 4: A. D. Cheveigne and H. Kawahara, "YIN, a fundamental frequency estimator for speech and music", J. Acoustic Soc. Amer., vol. 111, no. 4, pp. 1917-1930 Non-patent literature 5: J. L. Flanagan et al., "Speech Coding", IEEE Transactions on Communications, Vol. 27, no. 4, April 1979.
Non-patent literature 6: A. Subramanya et al., "Automatic removal of typed keystrokes from speech signals", IEEE Signal Processing Letters, Vol. 14, No. 5, pp. 363-366, May 2007.
Non-patent literature 7: J. Murphy et al., "Joint Baysian removal of impulse and background noise", IEEE Proceedings of ICASSP, pp. 261-264, May 2011.
Non-patent literature 8: R. Talmon et al., "Transient noise reduction using nonlocal diffusion filters", IEEE Transactions on Audio, Speech, and Language Processing, Vol. 19, No. 6, pp. 1584-1599, June 2011.

SUMMARY OF THE INVENTION

Technical Problem

However, the techniques of patent literatures 1 and 4 out of the above-described related arts do not detect an abrupt change in an input signal. In addition, the technique of patent literature 2 detects an abrupt change in a "frequency", and the technique of patent literature 3 detects impulsive noise using a time-rate change in the phase of an AM signal. Patent literature 5 discloses a technique of detecting an impulsive sound using only an amplitude, which is poor in robustness. That is, the techniques described in these literatures cannot effectively detect an abrupt change in a signal.

The present invention enables to provide a technique of solving the above-described problems.

Solution to Problem

One aspect of the present invention provides a signal processing apparatus comprising:
a converter that converts an input signal into a phase component signal and an amplitude component signal in a frequency domain;
a calculator that calculates feature amounts of the phase component signal and the amplitude component signal; and
a determiner that determines presence probability of an abrupt change in the input signal based on the feature amounts calculated by the calculator.

Another aspect of the present invention provides a signal processing apparatus comprising:
a converter that converts an input signal into a phase component signal in a frequency domain;
a first calculator that calculates a first phase gradient based on a position of a sudden increase of the input signal;
a second calculator that calculates a second phase gradient of the phase component signal in the frequency domain; and
a determiner that determines presence probability of an abrupt change in the input signal based on the first phase gradient and the second phase gradient.

Still other aspect of the present invention provides a signal processing apparatus comprising:
a converter that converts an input signal into a phase component signal in a frequency domain;
a generator that generates a low correlation signal by removing, from the input signal, a component with time correlation included in the input signal; and
a determiner that determines presence probability of an abrupt change included in the input signal based on the low correlation signal and the phase component signal.

Still other aspect of the present invention provides a signal processing apparatus comprising:
a converter that converts an input signal into a phase component signal in a frequency domain;
a linearity calculator that calculates a linearity of the phase component signal in the frequency domain; and
a determiner that calculates presence probability of an abrupt change in the input signal based on the linearity calculated by the linearity calculator.

Still other aspect of the present invention provides a signal processing method comprising:
converting an input signal into a phase component signal and an amplitude component signal in a frequency domain;
calculating feature amounts of the phase component signal and the amplitude component signal; and
determining presence probability of an abrupt change in the input signal based on the calculated feature amounts.

Still other aspect of the present invention provides a signal processing method comprising:
converting an input signal into a phase component signal in a frequency domain;
calculating a first phase gradient based on a position of a sudden increase of the input signal;
calculating a second phase gradient of the phase component signal in the frequency domain; and
determining presence probability of an abrupt change in the input signal based on the first phase gradient and the second phase gradient.

Still other aspect of the present invention provides a signal processing method comprising:
converting an input signal into a phase component signal in a frequency domain;
generating a low correlation signal by removing, from the input signal, a component with time correlation included in the input signal; and
determining presence probability of an abrupt change included in the input signal based on the low correlation signal and the phase component signal.

Still other aspect of the present invention provides a signal processing method comprising:
converting an input signal into a phase component signal in a frequency domain;
calculating a linearity of the phase component signal in the frequency domain; and
calculating presence probability of an abrupt change in the input signal based on the calculated linearity.

Still other aspect of the present invention provides a signal processing program for causing a computer to execute a method comprising:
converting an input signal into a phase component signal and an amplitude component signal in a frequency domain;
calculating feature amounts of the phase component signal and the amplitude component signal; and
determining presence probability of an abrupt change in the input signal based on the calculated feature amounts.

Still other aspect of the present invention provides a signal processing program for causing a computer to execute a method comprising:
converting an input signal into a phase component signal in a frequency domain;
calculating a first phase gradient based on a position of a sudden increase of the input signal;
calculating a second phase gradient of the phase component signal in the frequency domain; and
determining presence probability of an abrupt change in the input signal based on the first phase gradient and the second phase gradient.

Still other aspect of the present invention provides a signal processing program for causing a computer to execute a method comprising:
converting an input signal into a phase component signal in a frequency domain;
generating a low correlation signal by removing, from the input signal, a component with time correlation included in the input signal; and
determining presence probability of an abrupt change included in the input signal based on the low correlation signal and the phase component signal.

Still other aspect of the present invention provides a signal processing program for causing a computer to execute a method comprising:
converting an input signal into a phase component signal in a frequency domain;
calculating a linearity of the phase component signal in the frequency domain; and
calculating presence probability of an abrupt change in the input signal based on the calculated linearity.

Advantageous Effects of Invention

According to the present invention, it is possible to effectively detect an abrupt change in a signal.

BRIEF DESCRIPTION OF THE DRAWINGS

FIG. 2 is a block diagram showing the arrangement of a noise suppression apparatus according to the second embodiment of the present invention;
FIG. 3 is a block diagram showing the arrangement of a converter according to the second embodiment of the present invention;
FIG. 7 is a view for explaining the operation of the phase controller according to the second embodiment of the present invention.

FIG. 10 is a view for explaining the operation of the phase controller according to the second embodiment of the present invention;

FIG. 11 is a view for explaining the operation of the phase controller according to the second embodiment of the present invention;

FIG. 12 is a block diagram for explaining the arrangement of a calculator and an abrupt change determiner according to the second embodiment of the present invention;

FIG. 13 is a graph for explaining processing of the calculator according to the second embodiment of the present invention;

FIG. 16 is a block diagram showing the arrangement of a noise suppression apparatus according to the third embodiment of the present invention;

FIG. 17 is a block diagram showing the arrangement of a phase controller and an amplitude controller according to the third embodiment of the present invention;

FIG. 19 is a flowchart for explaining the procedure of processing of a noise suppression apparatus according to the fourth embodiment of the present invention;

FIG. 22 is a block diagram showing the arrangement of a signal processing apparatus according to the sixth embodiment of the present invention;

FIG. 23 is a block diagram showing the arrangement of a noise suppression apparatus according to the seventh embodiment of the present invention;

FIG. 28 is a graph for explaining processing of the calculator according to the seventh embodiment of the present invention;

FIG. 30C is a flowchart for explaining the procedure of processing of the noise suppression apparatus according to the seventh embodiment of the present invention;

FIG. 34 is a view for explaining an application example according to the 10th embodiment of the present invention;

FIG. 35 is a block diagram showing the arrangement of a signal processing apparatus according to the 11th embodiment of the present invention;

FIG. 36 is a block diagram showing the arrangement of a noise suppression apparatus according to the 12th embodiment of the present invention;

FIG. 37A is a block diagram showing the arrangement of a noise suppression apparatus according to the 13th embodiment of the present invention;

FIG. 37B is a block diagram showing an example of the arrangement of a correlation remover according to the 13th embodiment of the present invention;

FIG. 38A is a block diagram showing the arrangement of a converter according to the 13th embodiment of the present invention;

FIG. 38B is a block diagram showing the arrangement of an inverter according to the 13th embodiment of the present invention;

FIG. 40 is a block diagram for explaining the arrangement of a calculator and an abrupt change determiner according to the 13th embodiment of the present invention;

FIG. 43B is a flowchart for explaining the procedure of processing of the noise suppression apparatus according to the 13th embodiment of the present invention;

FIG. 47 is a block diagram showing the arrangement of a noise suppression apparatus according to the 17th embodiment of the present invention;

FIG. 48 is a block diagram showing the arrangement of a converter according to the 17th embodiment of the present invention;

FIG. 52 is a graph for explaining processing of the linearity calculator according to the 17th embodiment of the present invention;

FIG. 54 is a flowchart for explaining the procedure of processing of the noise suppression apparatus according to the 17th embodiment of the present invention;

FIG. 55 is a block diagram showing the arrangement of a noise suppression apparatus according to the 18th embodiment of the present invention;

FIG. 56 is a block diagram showing the arrangement of a phase controller and an amplitude controller according to the 18th embodiment of the present invention;

FIG. 60 is a view for explaining an application example according to the 20th embodiment of the present invention;

FIG. 61 is a view for explaining an application example according to the 21st embodiment of the present invention.

DESCRIPTION OF THE EMBODIMENTS

Preferred embodiments of the present invention will now be described in detail with reference to the drawings. It should be noted that the relative arrangement of the components, the numerical expressions and numerical values set forth in these embodiments do not limit the scope of the present invention unless it is specifically stated otherwise. Note that "speech signal" in the following explanation indicates a direct electrical change that occurs in accordance with the influence of speech or another sound. The speech signal transmits speech or another sound and is not limited to speech.

First Embodiment

A signal processing apparatus 100 according to the first embodiment of the present invention will be described with reference to FIG. 1. The signal processing apparatus 100 is an apparatus for detecting an abrupt input signal change.

Figure 1:
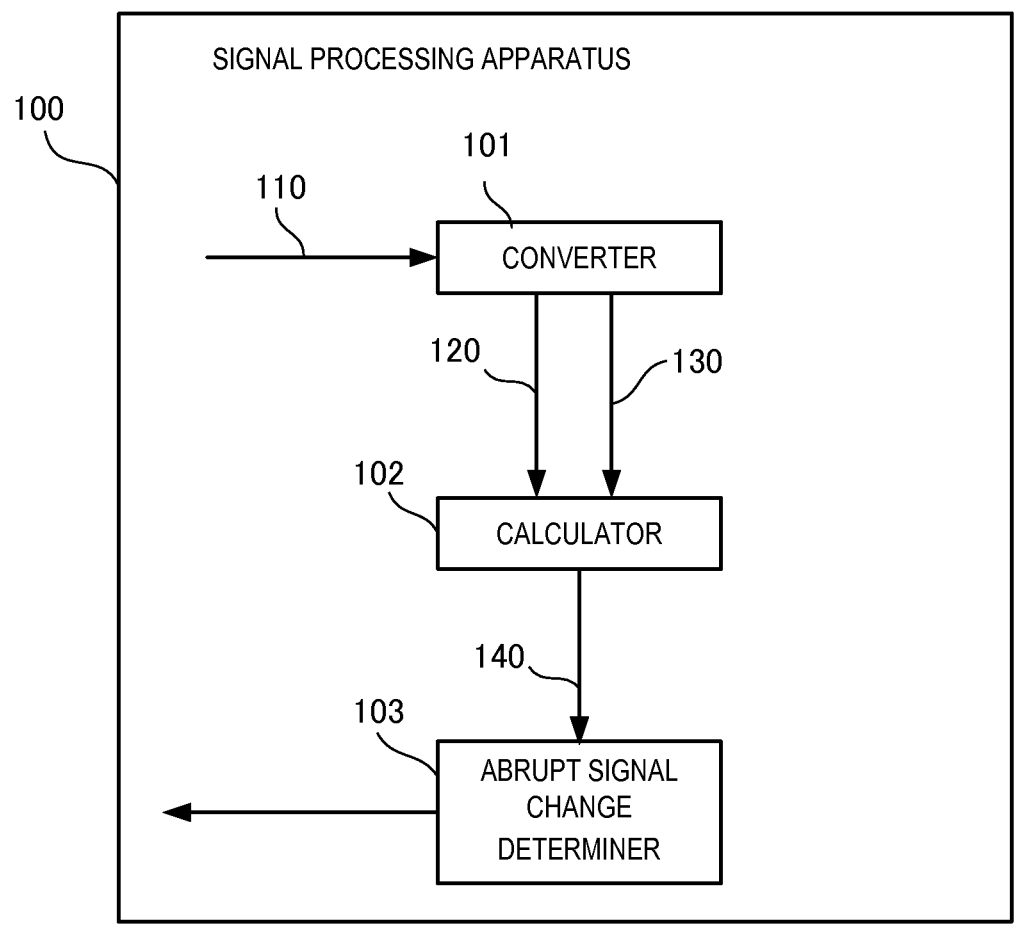
FIG. 1 is a block diagram showing the arrangement of a signal processing apparatus according to the first embodiment of the present invention.

As shown in FIG. 1, the signal processing apparatus 100 includes a converter 101, a calculator 102, and an abrupt signal change determiner 103. The converter 101 converts an input signal 110 into a phase component signal 120 and an amplitude component signal 130 in a frequency domain. The calculator 102 calculates changes in the phase component signal 120 and the amplitude component signal 130. The abrupt signal change determiner 103 determines an abrupt change in the input signal based on the calculated changes.

With the above-described arrangement, an abrupt change in the input signal can effectively be detected based on the changes in the phase component signal and the amplitude component signal in the frequency domain.

Second Embodiment

Overall Arrangement

A noise suppression apparatus according to the second embodiment of the present invention will be described with reference to FIGS. 2 to 11. The noise suppression apparatus according to this embodiment is applicable to suppress noise in, for example, a digital camera, a notebook personal computer, a mobile phone, a keyboard, a game machine controller, and the push buttons of a mobile phone. That is, the target signal of speech, music, environmental sound, or the like can be enhanced relative to a signal (noise or interfering signal) superimposed on it. However, the present invention is not limited to this, and the noise suppression apparatus is applicable to a signal processing apparatus of any type required to do abrupt signal change detection from an input signal. Note that in this embodiment, a noise suppression apparatus that detects and suppresses an impulsive sound as an example of an abrupt change in a signal will be described. The noise suppression apparatus according to this embodiment appropriately suppresses an impulsive sound generated by, for example, a button operation in a mode to perform an operation such as button pressing near a microphone. Simply speaking, a time domain signal including an impulsive sound is converted into a frequency domain signal, and changes in a phase component and an amplitude component in the frequency space are calculated. Then, the presence of an impulsive sound is determined in accordance with the combination of the changes.

FIG. 2 is a block diagram showing the overall arrangement of a noise suppression apparatus 200. A noisy signal (signal including both a desired signal and noise) is supplied to an input terminal 206 as a series of sample values. The noisy signal supplied to the input terminal 206 undergoes transform such as Fourier transform in a converter 201 and is divided into a plurality of frequency components. The plurality of frequency components are independently processed on a frequency basis. The description will be continued here concerning a specific frequency component of interest. Out of the frequency component, an amplitude spectrum (amplitude component) 230 is supplied to a noise suppressor 205 and a calculator 208, and a phase spectrum (phase component) 220 is supplied to a phase controller 202 and the calculator 208. Note that the converter 201 supplies the noisy signal amplitude spectrum 230 to the noise suppressor 205 here. However, the present invention is not limited to this, and a power spectrum corresponding to the square of the amplitude spectrum may be supplied to the noise suppressor 205.

The noise suppressor 205 estimates noise using the noisy signal amplitude spectrum 230 supplied from the converter 201, thereby generating an estimated noise spectrum. In addition, the noise suppressor 205 suppresses the noise using the generated estimated noise spectrum and the noisy signal amplitude spectrum 230 supplied from the converter 201, and transmits an enhanced signal amplitude spectrum as a noise suppression result to an amplitude controller 203. The noise suppressor 205 also receives a determination result from an abrupt change determiner 209, and changes the degree of noise suppression in accordance with the presence/absence or degree of an abrupt change in the signal. The noise suppressor 205 may protect a target sound using target sound detection, and may also replace the amplitude with an estimated background sound upon detecting an abrupt change in the signal.

The phase controller 202 rotates (shifts) the noisy signal phase spectrum 220 supplied from the converter 201, and supplies it to an inverter 204 as an enhanced signal phase spectrum 240. The phase controller 202 also transmits the phase rotation amount (shift amount) to the amplitude controller 203. The amplitude controller 203 receives the phase rotation amount (shift amount) from the phase controller 202, calculates an amplitude correction amount, corrects the enhanced signal amplitude spectrum in each frequency using the amplitude correction amount, and supplies a corrected amplitude spectrum 250 to the inverter 204. The inverter 204 performs inversion by compositing the enhanced signal phase spectrum 240 supplied from the phase controller 202 and the corrected amplitude spectrum 250 supplied from the amplitude controller 203, and supplies the resultant signal to an output terminal 207 as an enhanced signal.

Using the phase component signal 220 and the amplitude component signal 230 supplied from the converter 201, the calculator 208 calculates changes in these signals in the frequency domain. Based on the change calculated by the calculator 208, the abrupt change determiner 209 determines for each frequency point to what extent an abrupt change in the signal exists (presence probability).

<<Arrangement of Converter>>

FIG. 3 is a block diagram showing the arrangement of the converter 201. As shown in FIG. 3, the converter 201 includes a frame divider 301, a windowing unit 302, and a Fourier transformer 303. A noisy signal sample is supplied to the frame divider 301 and divided into frames on the basis of K/2 samples, where K is an even number. The noisy signal sample divided into frames is supplied to the windowing unit 302 and multiplied by a window function w(t). The signal obtained by windowing an nth frame input signal yn(t) (t=0, 1, . . . , K/2−1) by w(t) is given by $$\bar{y}_n(t) = w(t)y_n(t) \quad (1)$$

Two successive frames may partially be overlaid (overlapped) and windowed. Assume that the overlap length is 50% the frame length. For t=0, 1, . . . , K/2−1, the windowing unit 302 outputs the left-hand sides of $$\bar{y}_n(t) = w(t)y_{n-1}(t + K/2) \atop \bar{y}_n(t + K/2) = w(t + K/2)y_n(t) \quad (2)$$

A symmetric window function is used for a real signal. The window function is designed to make the input signal and the output signal match with each other except a calculation error when the output of the converter 201 is directly supplied to the inverter 204. This means $w^2(t) + w^2(t+K/2) = 1$.

The description will be continued below assuming an example in which windowing is performed for two successive frames that overlap 50%. As w(t), the windowing unit can use, for example, a Hanning window given by $$w(t) = \begin{cases} 0.5 + 0.5 \cos\left(\frac{\pi(t - K/2)}{K/2}\right), & 0 \leq t < K \\ 0, & \text{otherwise} \end{cases} \quad (3)$$

Various window functions such as a Hamming window and a triangle window are also known. The windowed output is supplied to the Fourier transformer 303 and transformed into a noisy signal spectrum Yn(k). The noisy signal spectrum Yn(k) is separated into the phase and the amplitude. A noisy signal phase spectrum argYn(k) is supplied to the phase controller 202 and the calculator 208, whereas a noisy signal amplitude spectrum |Yn(k)| is supplied to the noise suppressor 205 and the calculator 208. As already described, a power spectrum may be used in place of the amplitude spectrum.

<<Arrangement of Inverter>>

Figure 4:
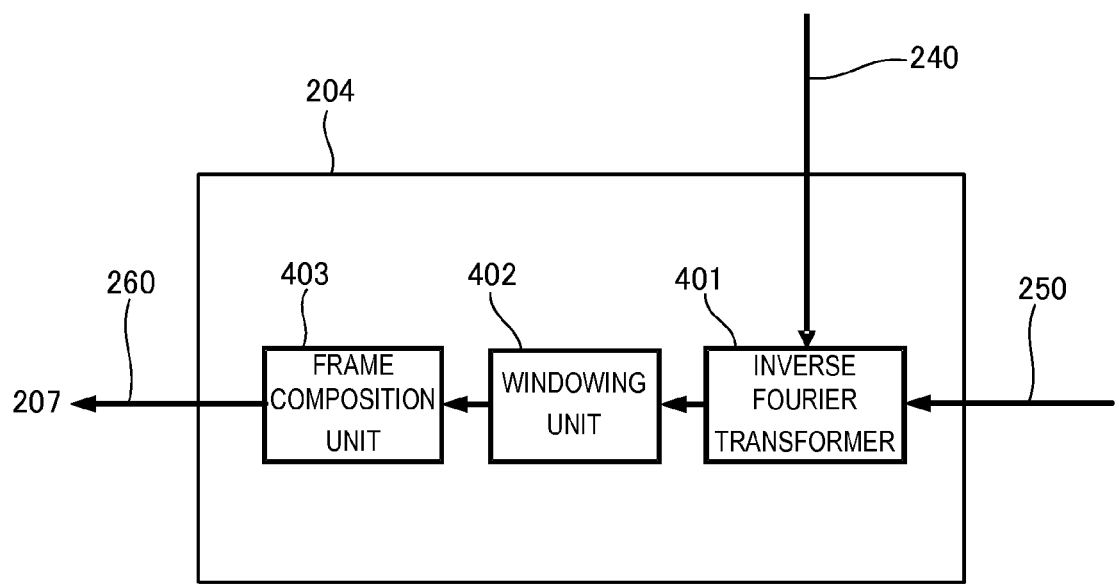
FIG. 4 is a block diagram showing the arrangement of an inverter according to the second embodiment of the present invention.

FIG. 4 is a block diagram showing the arrangement of the inverter 204. As shown in FIG. 4, the inverter 204 includes an inverse Fourier transformer 401, a windowing unit 402, and a frame composition unit 403. The inverse Fourier transformer 401 multiplies the enhanced signal amplitude spectrum 250 supplied from the amplitude controller 203 by the enhanced signal phase spectrum 240 (argXn(k)) supplied from the phase controller 202 to obtain an enhanced signal (the left-hand side of equation (4)).

$$\bar{X}_n(k) = |\bar{X}_n(k)| \cdot \arg X_n(k) \quad (4)$$

Inverse Fourier transform is performed for the obtained enhanced signal. The signal is supplied to the windowing unit 402 as a series of time domain sample values xn(t) (t=0, 1, . . . , K−1) in which one frame includes K samples, and multiplied by the window function w(t). A signal obtained by windowing an nth frame input signal xn(t) (t=0, 1, . . . , K/2−1) by w(t) is given by the left-hand side of $$\bar{x}_n(t) = w(t)x_n(t) \quad (5)$$

Two successive frames may partially be overlaid (overlapped) and windowed. Assume that the overlap length is 50% the frame length. For t=0, 1, . . . , K/2−1, the windowing unit 402 outputs the left-hand sides of $$\bar{x}_n(t) = w(t)x_{n-1}(t + K/2) \atop \bar{x}_n(t + K/2) = w(t + K/2)x_n(t) \quad (6)$$

and transmits them to the frame composition unit 403.

The frame composition unit 403 extracts the outputs of two adjacent frames from the windowing unit 402 on the basis of K/2 samples, overlays them, and obtains an output signal (left-hand sides of equation (7)) for t=0, 1, . . . , K−1 by $$\hat{x}_n(t) + \bar{x}_{n-1}(t + K/2) + \bar{x}_n(t) \quad (7)$$

An obtained enhanced speech signal 260 is transmitted from the frame composition unit 403 to the output terminal 207.

Note that the conversion in the converter and the inverter in FIGS. 3 and 4 has been described as Fourier transform. However, any other transform such as Hadamard transform, Haar transform, or Wavelet transform may be used in place of the Fourier transform. Haar transform does not need multiplication and can reduce the area of an LSI chip. Wavelet transform can change the time resolution depending on the frequency and is therefore expected to improve the noise suppression effect.

The noise suppressor 205 may perform actual suppression after a plurality of frequency components obtained by the converter 201 are integrated. At this time, high sound quality can be achieved by integrating more frequency components from the low frequency range where the discrimination capability of hearing characteristics is high to the high frequency range with a poorer capability. When noise suppression is executed after integrating a plurality of frequency components, the number of frequency components to which noise suppression is applied decreases, and the whole calculation amount can be decreased.

<<Arrangement of Noise Suppressor>>

The noise suppressor 205 estimates noise using the noisy signal amplitude spectrum supplied from the converter 201 and generates an estimated noise spectrum. The noise suppressor 205 then obtains a suppression coefficient using the noisy signal amplitude spectrum from the converter 201 and the generated estimated noise spectrum, multiplies the noisy signal amplitude spectrum by the suppression coefficient, and supplies the resultant spectrum to the amplitude controller 203 as an enhanced signal amplitude spectrum.

In addition, upon receiving information representing to what extent an abrupt change exists (likelihood that an abrupt signal change exists or presence probability) from the abrupt change determiner 209, the degree of noise suppression can be changed in accordance with the possibility that an abrupt signal change exists. It is also possible to determine the possibility that an abrupt signal change exists for each frequency component, frequency band (combination of an arbitrary number of continuous frequency components), or frame and perform different signal processing for each frequency component, frequency band, or frame to suppress the abrupt change.

To estimate noise, various estimation methods such as the methods described in non-patent literatures 1 and 2 are usable.

For example, non-patent literature 1 discloses a method of obtaining, as an estimated noise spectrum, the average value of noisy signal amplitude spectra of frames in which no target sound is generated. In this method, it is necessary to detect generation of the target sound. A section where the target sound is generated can be determined by the power of the enhanced signal.

As an ideal operation state, the enhanced signal is the target sound other than noise. In addition, the level of the target sound or noise does not largely change between adjacent frames. For these reasons, the enhanced signal level of an immediately preceding frame is used as an index to determine a noise section. If the enhanced signal level of the immediately preceding frame is equal to or smaller than a predetermined value, the current frame is determined as a noise section. A noise spectrum can be estimated by averaging the noisy signal amplitude spectra of frames determined as a noise section.

Non-patent literature 1 also discloses a method of obtaining, as an estimated noise spectrum, the average value of noisy signal amplitude spectra in the early stage in which supply of them has started. In this case, it is necessary to meet a condition that the target sound is not included immediately after the start of estimation. If the condition is met, the noisy signal amplitude spectrum in the early stage of estimation can be obtained as the estimated noise spectrum.

Non-patent literature 2 discloses a method of obtaining an estimated noise spectrum from the minimum value of the statistical noisy signal amplitude spectrum. In this method, the minimum value of the noisy signal amplitude spectrum within a predetermined time is statistically held, and a noise spectrum is estimated from the minimum value. The minimum value of the noisy signal amplitude spectrum is similar to the shape of a noise spectrum and can therefore be used as the estimated value of the noise spectrum shape. However, the minimum value is smaller than the original noise level. Hence, a spectrum obtained by appropriately amplifying the minimum value is used as an estimated noise spectrum.

The noise suppressor 205 can perform various kinds of suppression. Typical examples are the SS (Spectrum Subtraction) method and an MMSE STSA (Minimum Mean-Square Error Short-Time Spectral Amplitude Estimator) method. In the SS method, the estimated noise spectrum is subtracted from the noisy signal amplitude spectrum supplied from the converter 201. In the MMSE STSA method, a suppression coefficient is calculated using the noisy signal amplitude spectrum supplied from the converter 201 and the generated estimated noise spectrum, and the noisy signal amplitude spectrum is multiplied by the suppression coefficient. The suppression coefficient is decided so as to minimize the mean square power of the enhanced signal.

Additionally, the noise suppressor 205 receives the abrupt change determination result (information representing whether an abrupt signal change exists) from the abrupt change determiner 209, and changes the degree of noise suppression in accordance with the presence/absence or degree of an abrupt signal change. For example, signal processing can be performed for each frequency component, frequency band, or frame in which an abrupt signal change has occurred to suppress the abrupt change.

If the abrupt change determiner 209 determines that an abrupt change exists, a smaller one of the noisy signal amplitude spectrum and the estimated noise spectrum is supplied to the amplitude controller 203 as an enhanced signal amplitude spectrum. That is, if the noisy signal amplitude spectrum is smaller than the estimated noise spectrum, the noisy signal amplitude spectrum is directly output. Otherwise, the input signal can be replaced with the estimated noise spectrum and output.

It is also possible to, prior to the replacement, detect an important noisy signal amplitude spectrum component and exclude the detected important noisy signal amplitude spectrum component from the component to be replaced with the estimated noise spectrum. As the index of importance when detecting the important noisy signal amplitude spectrum component, the magnitude of the noisy signal amplitude spectrum can be used. A component having a large amplitude is a component of a target signal at a high probability. Holding this component contributes to prevention of a degradation in sound quality of the target signal.

The peak characteristic of the noisy signal amplitude spectrum can also be used as the index of importance. A noisy signal amplitude having a peak, that is, a value larger than peripheral values along the frequency axis is a component of a target signal at a high probability. Holding this component contributes to prevention of a degradation in sound quality of the target signal. In particular, a conspicuous peak, that is, an amplitude value much larger than peripheral amplitude values is important. When this component is reliably protected, sound quality of the target signal can further be increased.

To detect a peak, for example, a pure sound component detection method described in non-patent literature 3 or a method disclosed in non-patent literature 4 is usable. A detected peak may be evaluated in accordance with a predetermined condition, and a peak that does not meet the condition may be excluded. For example, there is little possibility that a peak having a value smaller than the estimated noise is the target signal. That is, it is possible to, using the estimated noise as a reference, leave only peaks much larger than the estimated noise and exclude others. Whether a peak is sufficiently large can be determined by comparing it with a constant multiple of the estimated noise. In this way, it is evaluated whether a detected peak meets a predetermined condition, and final peak components are then selected. This can reduce peak detection errors and enhance the effect of suppressing an abrupt signal change.

It is also possible to change the signal to be supplied to the amplitude controller 203 in accordance with the likelihood of presence of an abrupt change. The result of replacement and the noisy signal amplitude spectrum are mixed in correspondence with the likelihood of presence of an abrupt change, and the mixture is output as an enhanced signal amplitude spectrum. The mixing processing is executed by adding a large weight to the replacement result as the likelihood of presence of an abrupt change rises.

The noise suppressor 205 may perform suppression in multiple levels such as suppression level 0, suppression level 1, and suppression level 2 in accordance with the presence probability of an abrupt signal change. Alternatively, the degree of suppression may be continuously be changed in accordance with the determination result (for example, numerical values of 0 to 1) of the abrupt change determiner.

<<Arrangement of Phase Controller and Amplitude Controller>>

Figure 5:
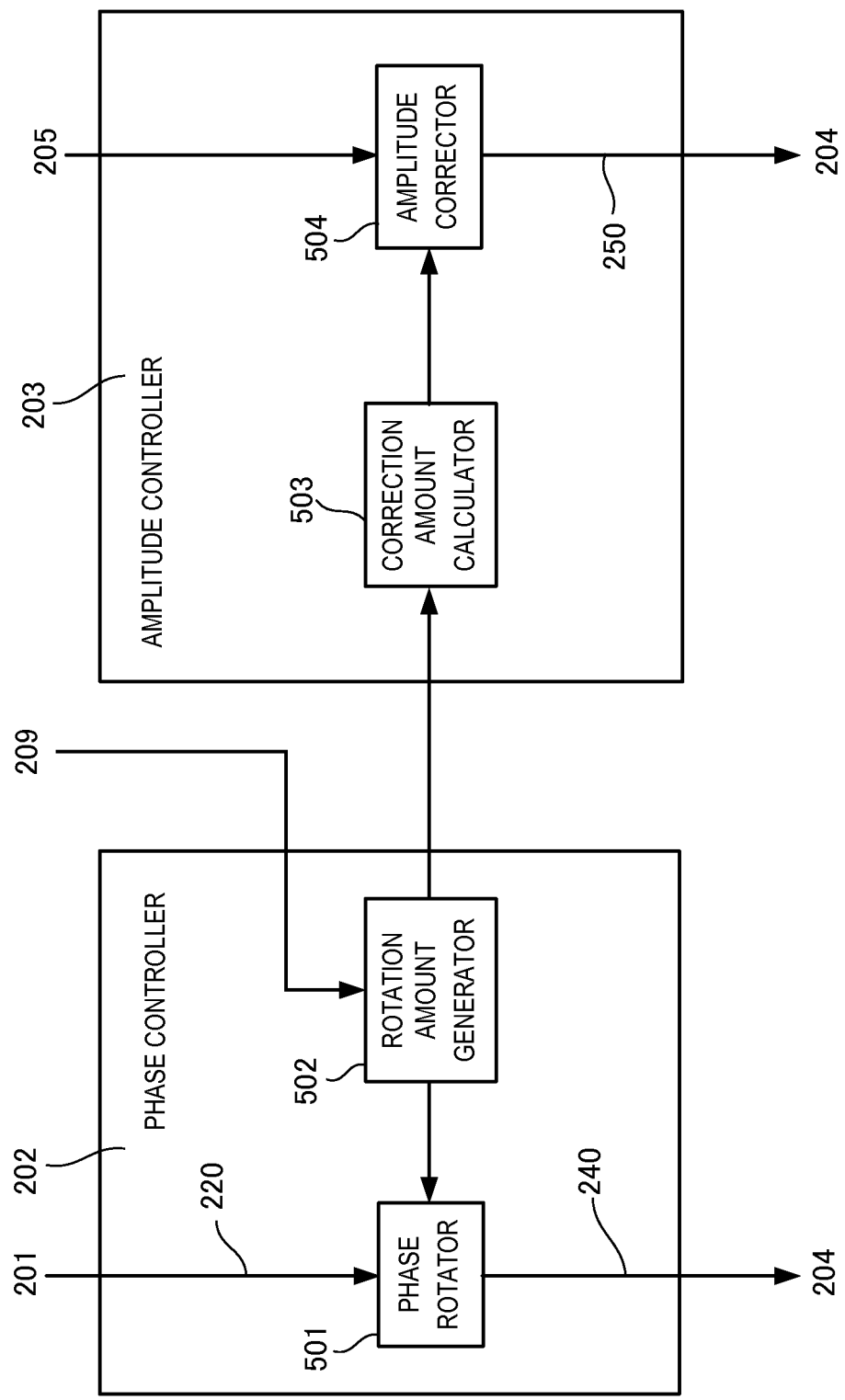
FIG. 5 is a block diagram showing the arrangement of a phase controller and an amplitude controller according to the second embodiment of the present invention.

FIG. 5 is a block diagram showing the arrangement of the phase controller 202 and the amplitude controller 203. As shown in FIG. 5, the phase controller 202 includes a phase rotator 501 and a rotation amount generator 502, and the amplitude controller 203 includes a correction amount calculator 503 and an amplitude corrector 504.

The rotation amount generator 502 generates the rotation amount of the noisy signal phase spectrum for a frequency component determined to "have an abrupt change in the signal" by the abrupt change determiner 209, and supplies the rotation amount to the phase rotator 501 and the correction amount calculator 503. Upon receiving the rotation amount supplied from the rotation amount generator 502, the phase rotator 501 rotates (shifts) the noisy signal phase spectrum 220 supplied from the converter 201 by the supplied rotation amount, and supplies the rotated spectrum to the inverter 204 as the enhanced signal phase spectrum 240.

The correction amount calculator 503 decides the correction coefficient of the amplitude based on the rotation amount supplied from the rotation amount generator 502, and supplies the correction coefficient to the amplitude corrector 504.

The rotation amount generator 502 generates the rotation amount by, for example, a random number. When the noisy signal phase spectrum is rotated for each frequency by a random number, the shape of the noisy signal phase spectrum 220 changes. With the change in the shape, the feature of an abrupt signal change such as an impulsive sound can be weakened.

Examples of the random number are a uniform random number whose occurrence probability is uniform and a normal random number whose occurrence probability exhibits a normal distribution. A rotation amount generation method using a uniform random number will be described first. A uniform random number can be generated by a linear congruential method or the like. For example, uniform random numbers generated by the linear congruential method are uniformly distributed within the range of 0 to $(2\hat{\ }M)-1$, where M is an arbitrary integer, and $\hat{\ }$ represents a power. Phase rotation amounts $\phi$ need to be distributed within the range of 0 to $2\pi$. To do this, the generated uniform random numbers are converted. The conversion is performed by $$\phi = 2\pi \frac{R}{R_{max}} \quad (8)$$

where R is the uniform random number, and Rmax is the maximum value capable of being generated by the uniform random number. When a uniform random number is generated by the above-described linear congruential method, $Rmax=(2\hat{\ }M)-1$.

To simplify the calculation, the value R may directly be decided as the rotation amount. As the rotation amount, $2\pi$ represents just one revolution. A case where the phase is rotated by $2\pi$ is equivalent to a case where the phase is not rotated. Hence, a rotation amount $2\pi+\alpha$ is equivalent to a rotation amount $\alpha$. A case where a uniform random number is generated by the linear congruential method has been explained here. Even in a case where a uniform random number is generated by another method, the rotation amount $\phi$ is obtained by equation (8). When and how many times random number generation is to be performed may be decided in accordance with the determination result of the abrupt change determiner 209.

The phase rotator 501 receives the rotation amount from the rotation amount generator 502 and rotates the noisy signal phase spectrum. If the noisy signal phase spectrum is expressed as an angle, it can be rotated by adding the value of the rotation amount $\phi$ to the angle. If the noisy signal phase spectrum is expressed as the normal vector of a complex number, it can be rotated by obtaining the normal vector of the rotation amount $\phi$ and multiplying the noisy signal phase spectrum by the normal vector.

The normal vector of the rotation amount $\phi$ can be obtained by $$\Phi = \cos(\phi) + j\sin(\phi) \quad (9)$$

In equation (9), $\Phi$ is the rotation vector, and j represents sqrt(-1). Note that sqrt is the square root.

Figure 6:
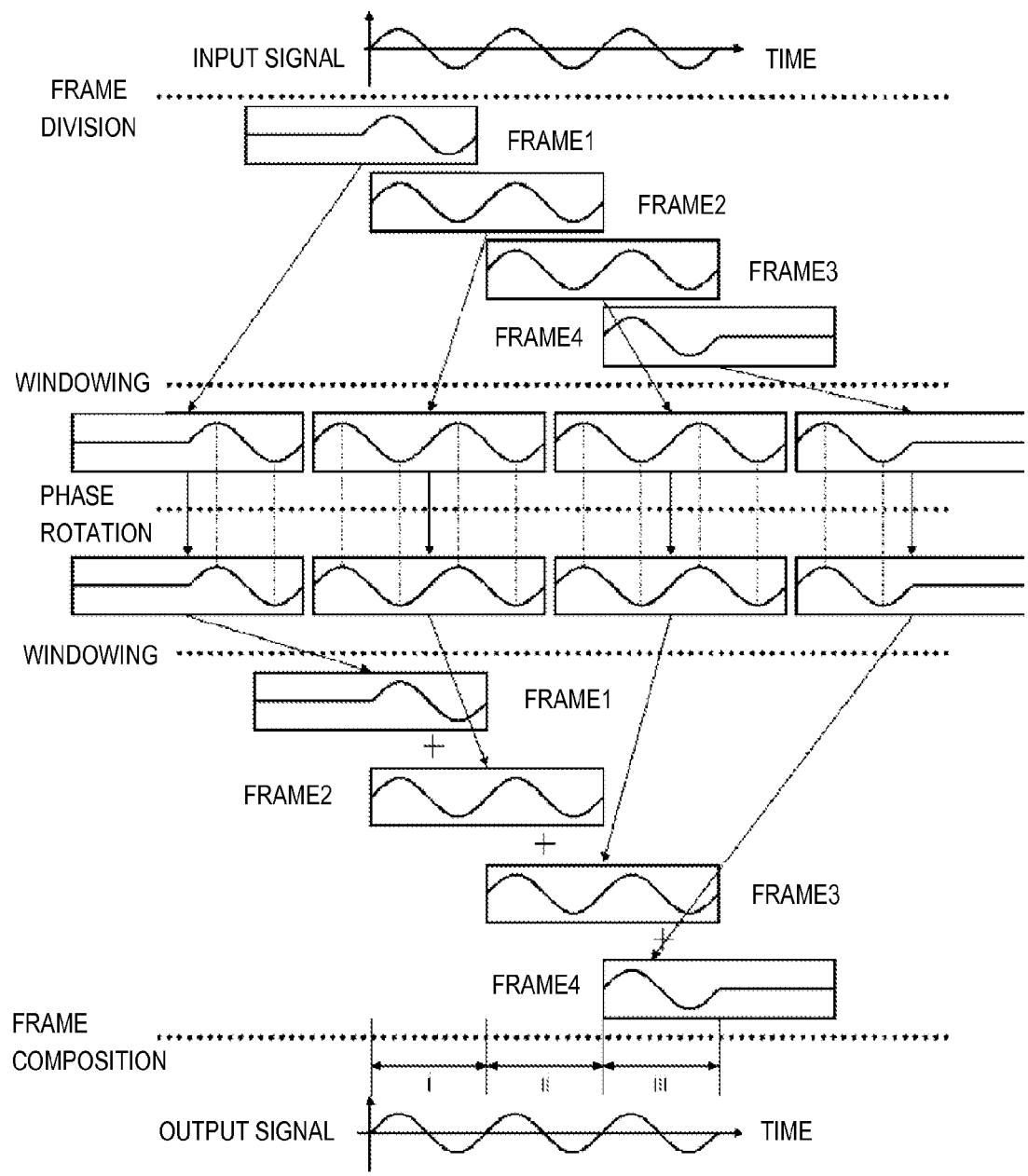
FIG. 6 is a view for explaining the operation of the phase controller according to the second embodiment of the present invention.

A correction coefficient calculation method by the correction amount calculator 503 will be described. First, a decrease in the output level caused by phase rotation will be described first with reference to FIGS. 6 and 7. FIGS. 6 and 7 show signals obtained by processing a noisy signal by the block diagram shown in FIG. 2. The difference between FIGS. 6 and 7 is the presence/absence of phase rotation. FIG. 6 shows a signal in a case where phase rotation is not performed, and FIG. 7 shows a signal in a case where phase rotation is performed from frame 3.

A signal in a case where phase rotation is not performed will be described with reference to FIG. 6. A noisy signal is illustrated at the top of FIG. 6. The noisy signal is divided into frames by the frame divider 301. The second signal from above is the signal after frame division. A signal corresponding to four successive frames is illustrated here. The frame overlap ratio is 50%.

The signal divided into frames is windowed by the windowing unit 302. The third signal from above, which is separated by a dotted line, is the signal after windowing. In FIG. 6, to clarify the influence of phase rotation, weighting using a rectangular window is performed.

Next, the Fourier transformer 303 transforms the signal into a signal in a frequency domain. The signal in the frequency domain is not illustrated in FIG. 6. A signal transformed into a time domain by the inverse Fourier transformer 401 of the inverter 204 is shown below the dotted line of phase rotation. The fourth signal from above, which is separated by a dotted line, is the signal after phase rotation. In FIG. 6, however, the signal does not change from that after windowing because phase rotation is not performed.

Windowing is performed again for an enhanced signal output from the inverse Fourier transformer 401 of the inverter 204. FIG. 6 shows a case where weighting using a rectangular window is performed. The windowed signals are composited by the frame composition unit 403. At this time, times between the frames need to match. Since the overlap ratio is 50%, the frames overlap just in half. If phase rotation is not executed, the input signal and the output signal match, as shown in FIG. 6.

A signal in a case where phase rotation is performed will be described with reference to FIG. 7. FIG. 7 shows a signal in a case where phase rotation is performed from frame 3. The same noisy signal as in FIG. 6 is illustrated at the top. The signal after frame division and the signal after windowing are also the same as in FIG. 6.

FIG. 7 illustrates a case where predetermined phase rotation is executed from frame 3. Place focus on the section of a right triangle shown below the dotted line of phase rotation processing. By phase rotation processing, the signals of frames 3 and 4 shift in the time direction. The signal that has undergone the phase rotation is windowed again, and the frames are composited. At this time, a difference is generated between the signal of frames 2 and that of frame 3 in a section ii where frames 2 and 3 overlap. This makes the output signal level after frame composition small in the section ii. That is, when phase rotation is executed, the output signal level lowers in the section ii in FIG. 7.

Lowering of the output signal level caused by phase rotation can also be explained in vector composition in a frequency domain by replacing addition in the time domain with addition in the frequency domain.

Figure 8:
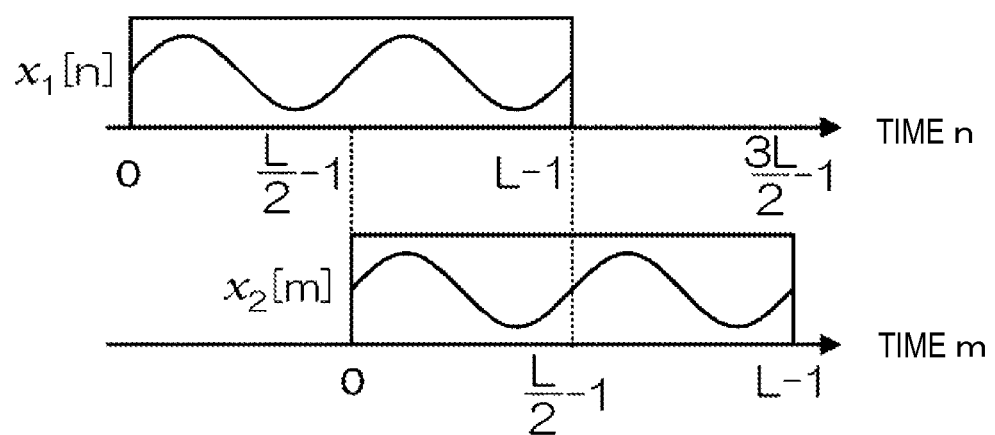
FIG. 8 is a view for explaining the operation of the phase controller according to the second embodiment of the present invention.

FIG. 8 shows the noisy signals of two successive frames after frame division and windowing as x1[n] and x2[m]. Note that the overlap ratio is 50%. Here, n indicates the discrete time of x1, and m indicates the discrete time of x2. When the overlap ratio is 50%, $$m = n + L/2 \quad (10)$$

holds.

In addition, the relationship between x1 and x2 is represented by $$x_2[m] = x_1[n+L/2] \quad (11)$$

The formula of transform from a time domain signal to a frequency domain signal and that of inverse transform will be described. By Fourier transform of a time domain signal x[n], a frequency domain signal X[k] is expressed as $$X[k] = \sum_{n=0}^{L-1} x[n] e^{-j2\pi \frac{n}{L} k} \quad (12)$$

where k is the discrete frequency, and L is the frame length.

When the frequency domain signal X[n] is returned to the time domain signal x[n] by inverse transform, the time domain signal x[n] is expressed as $$x[n] = \frac{1}{L} \sum_{k=0}^{L-1} X[k] e^{j2\pi \frac{n}{L} k} \quad (13)$$

When the time domain signals x1[n] and x2[m] are transformed into frequency domain signals X1[k] and X2[k] based on this equation, they are expressed as $$X_1[k] = \sum_{n=0}^{L-1} x_1[n] e^{-j2\pi \frac{n}{L} k} \quad (14)$$

$$X_2[k] = \sum_{m=0}^{L-1} x_2[m] e^{-j2\pi \frac{m}{L} k} \quad (15)$$

When the frequency domain signals X1[k] and X2[k] are returned to the time domain signals x1[n] and x2[m] by inverse transform, respectively, they are expressed, based on equation (13), as $$x_1[n] = \frac{1}{L} \sum_{k=0}^{L-1} X_1[k] e^{j2\pi \frac{n}{L} k} \quad (16)$$

$$x_2[m] = \frac{1}{L} \sum_{k=0}^{L-1} X_2[k] e^{j2\pi \frac{m}{L} k} \quad (17)$$

The inverter transforms each frequency domain signal into a time domain signal by Fourier transform. After that, the frame composition unit adds the enhanced signal of the preceding frame and that of the current frame which overlap. For example, when the overlap ratio is 50% as in the illustrated example, the adjacent frames are added in the section of the discrete time m=L/2 to L−1. Consider the addition section m=L/2 to L−1.

When equations (16) and (17) are substituted into time domain addition, the addition is expressed as $$x_1[n] + x_2[m] = \frac{1}{L} \sum_{k=0}^{L-1} X_1[k] e^{j2\pi \frac{n}{L} k} + \frac{1}{L} \sum_{k=0}^{L-1} X_2[k] e^{j2\pi \frac{m}{L} k} \quad (18)$$

When equations (14) and (15) are further substituted into the frequency domain signals X1[k] and X2[k] in equation (18), the addition is expressed as $$x_1[n] + x_2[m] = \frac{1}{L} \sum_{k=0}^{L-1} X_1[k] e^{j2\pi \frac{n}{L} k} + \frac{1}{L} \sum_{k=0}^{L-1} X_2[k] e^{j2\pi \frac{m}{L} k} \quad (19)$$

$$= \frac{1}{L} \sum_{k=0}^{L-1} \left( \sum_{n=0}^{L-1} x_1[n] e^{-j2\pi \frac{n}{L} k} \right) e^{j2\pi \frac{n}{L} k} +$$

$$\frac{1}{L} \sum_{k=0}^{L-1} \left( \sum_{m=0}^{L-1} x_2[m] e^{-j2\pi \frac{m}{L} k} \right) e^{j2\pi \frac{m}{L} k}$$

When equations (19) is expanded, the addition is expressed as $$x_1[n] + x_2[m] = \frac{1}{L}\sum_{k=0}^{L-1}\left(\sum_{n=0}^{L-1} x_1[n]e^{-j2\pi\frac{n}{L}k}\right)e^{j2\pi\frac{n}{L}k} + \quad (20)$$

$$\frac{1}{L}\sum_{k=0}^{L-1}\left(\sum_{m=0}^{L-1} x_2[m]e^{-j2\pi\frac{m}{L}k}\right)e^{j2\pi\frac{m}{L}k}$$

$$= \frac{1}{L}\sum_{k=0}^{L-1}\left(x_1[0]e^{-j2\pi\frac{0}{L}k} + x_1[1]e^{-j2\pi\frac{1}{L}k} + \ldots + \right.$$

$$\left. x_1[L-1]e^{-j2\pi\frac{L-1}{L}k}\right)e^{j2\pi\frac{n}{L}k} +$$

$$\frac{1}{L}\sum_{k=0}^{L-1}\left(x_2[0]e^{-j2\pi\frac{0}{L}k} + x_2[1]e^{-j2\pi\frac{1}{L}k} + \ldots + \right.$$

$$\left. x_2[L-1]e^{-j2\pi\frac{L-1}{L}k}\right)e^{j2\pi\frac{n}{L}k}$$

$$= \frac{1}{L}\left\{x_1[0]\sum_{k=0}^{L-1} e^{j\frac{2\pi}{L}(n-1)k} + x_1[1]\sum_{k=0}^{L-1} e^{j\frac{2\pi}{L}(n-1)k} + \ldots + \right.$$

$$\left. x_1[L-1]\sum_{k=0}^{L-1} e^{j\frac{2\pi}{L}(n-L-1)k}\right\} +$$

$$\frac{1}{L}\left\{x_2[0]\sum_{k=0}^{L-1} e^{j\frac{2\pi}{L}(m-0)k} + x_2[1]\sum_{k=0}^{L-1} e^{j\frac{2\pi}{L}(m-1)k} + \ldots + \right.$$

$$\left. x_2[L-1]\sum_{k=0}^{L-1} e^{j\frac{2\pi}{L}(m-L-1)k}\right\}$$

Consider the sum operation included in each term of equation (20). When an arbitrary integer g is introduced, $$\sum_{k=0}^{L-1} e^{j\frac{2\pi}{L}gk} \quad (21)$$

holds.

The inverse Fourier transformation of a delta function δ[g] is given by $$\delta[g] = \frac{1}{L}\sum_{k=0}^{L-1} e^{j\frac{2\pi}{L}gk} \quad (22)$$

The delta function δ[g] is represented by $$\delta[g] = \begin{cases} 1 & g = 0 \\ 0 & g \neq 0 \end{cases} \quad (23)$$

Based on equation (22), expression (21) can be rewritten as $$\sum_{k=0}^{L-1} e^{j\frac{2\pi}{L}gk} = L\cdot\delta[g] \quad (24)$$

From the relation of equation (24), equation (20) is represented by $$x_1[n] + x_2[m] = \quad (25)$$

$$\frac{1}{L}\{L\cdot x_1[0]\delta[0] + L\cdot x_1[1]\delta[n-1] + \ldots + L\cdot x_1[L-1]\delta[n-L+1]\} +$$

$$\frac{1}{L}\{L\cdot x_2[0]\delta[0] + L\cdot x_2[1]\delta[m-1] + \ldots + L\cdot x_2[L-1]\delta[m-L+1]\}$$

Hence, equation (20) changes to $$x_1[n] + x_2[m] = \frac{1}{L}\{L\cdot x_1[n]\} + \frac{1}{L}\{L\cdot x_2[m]\} \quad (26)$$

$$= x_1[n] + x_2[m]$$

Figure 9:
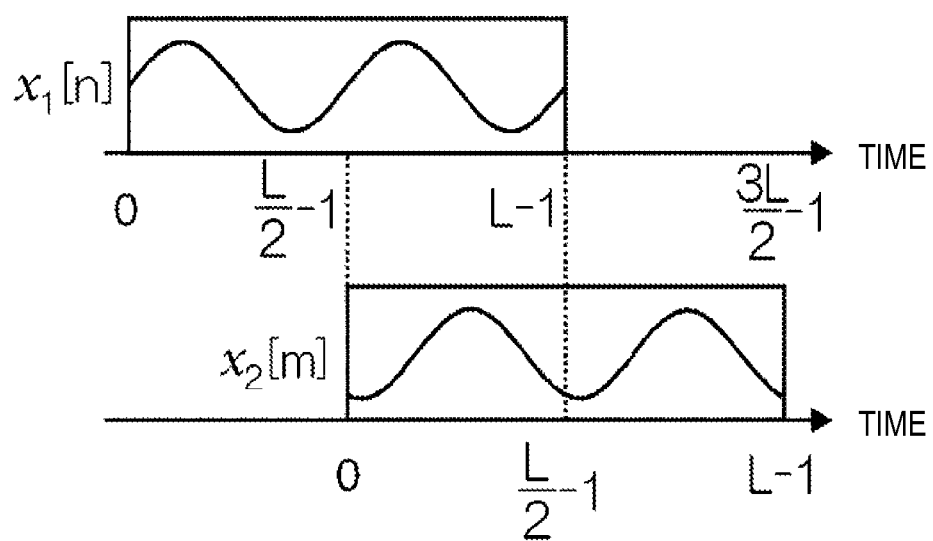
FIG. 9 is a view for explaining the operation of the phase controller according to the second embodiment of the present invention.

Consider a case where phase rotation is performed for the frequency domain signal X2[k]. At this time, a time domain signal as shown in FIG. 9 is obtained.

When the phase spectrum of X2[k] is rotated by φ[k], inverse transform is represented by $$x_2[m] = \frac{1}{L}\sum_{k=0}^{L-1} X_2[k]e^{j\phi[k]}e^{j2\pi\frac{m}{L}k} \quad (27)$$

When this is substituted into equation (18), $$x_1[n] + x_2[m] = \frac{1}{L}\sum_{k=0}^{L-1} X_1[k]e^{j2\pi\frac{n}{L}k} + \frac{1}{L}\sum_{k=0}^{L-1} X_2[k]e^{j\phi[k]}e^{j2\pi\frac{m}{L}k} \quad (28)$$

$$= \frac{1}{L}\sum_{k=0}^{L-1}\left(\sum_{n=0}^{L-1} x_1[n]e^{-j2\pi\frac{n}{L}k}\right)e^{j2\pi\frac{n}{L}k} +$$

$$\frac{1}{L}\sum_{k=0}^{L-1}\left(\sum_{m=0}^{L-1} x_2[m]e^{-(j2\pi\frac{m}{L}k+\phi[k])}\right)e^{j2\pi\frac{m}{L}k}$$

holds.

When this is expanded, $$x_1[n] + x_2[m] = \frac{1}{L}\left\{x_1[0]\sum_{k=0}^{L-1} e^{j\frac{2\pi}{L}(n-0)k} + \right. \quad (29)$$

$$\left. x_1[1]\sum_{k=0}^{L-1} e^{j\frac{2\pi}{L}(n-1)k} + \ldots + x_1[L-1]\sum_{k=0}^{L-1} e^{j\frac{2\pi}{L}(n-L+1)k}\right\} +$$

$$\frac{1}{L}\left\{x_2[0]\sum_{k=0}^{L-1} e^{j\frac{2\pi}{L}(m-0)k}e^{j\phi[k]} + x_2[1]\sum_{k=0}^{L-1} e^{j\frac{2\pi}{L}(m-1)k}e^{j\phi[k]} + \right.$$

$$\left. \ldots + x_2[L-1]\sum_{k=0}^{L-1} e^{j\frac{2\pi}{L}(m-L+1)k}e^{j\phi[k]}\right\}$$

holds.

Assume that the overlap ratio is 50%, and consider n=L/2 to L−1 of the overlap section. In the overlap section, equation (11) can be expanded to $$x_1\left[n+\frac{L}{2}\right]+x_2[m] = \frac{1}{L}\left\{x_1\left[\frac{L}{2}\right]\sum_{k=0}^{L-1} e^{j\frac{2\pi}{L}\left(n+\frac{L}{2}-\frac{L}{2}\right)k} + \right. \quad (30)$$

$$x_1\left[\frac{L}{2}+1\right]\sum_{k=0}^{L-1} e^{j\frac{2\pi}{L}\left(n+\frac{L}{2}-1-\frac{L}{2}-1\right)k} + \ldots +$$

$$\left. x_1[L-1]\sum_{k=0}^{L-1} e^{j\frac{2\pi}{L}\left(n-\frac{L}{2}-L+1-L+1\right)k}\right\} +$$

$$\frac{1}{L}\left\{x_2[0]\sum_{k=0}^{L-1} e^{j\frac{2\pi}{L}(n-0)k} e^{j\phi[k]} + \right.$$

$$x_2[1]\sum_{k=0}^{L-1} e^{j\frac{2\pi}{L}(n-1)k} e^{j\phi[k]} + \ldots +$$

$$\left. x_2\left[L-\frac{L}{2}-1\right]\sum_{k=0}^{L-1} e^{j\frac{2\pi}{L}\left(n-\frac{L}{2}-L+1\right)k} e^{j\phi[k]}\right\}$$

$$= \frac{1}{L}\left\{x_2[0]\sum_{k=0}^{L-1} e^{j\frac{2\pi}{L}nk} + x_2[1]\sum_{k=0}^{L-1} e^{j\frac{2\pi}{L}nk} + \ldots + \right.$$

$$\left. x_2\left[L-\frac{L}{2}-1\right]\sum_{k=0}^{L-1} e^{j\frac{2\pi}{L}nk}\right\} +$$

$$\frac{1}{L}\left\{x_2[0]\sum_{k=0}^{L-1} e^{j\frac{2\pi}{L}(n-0)k} e^{j\phi[k]} + \right.$$

$$x_2[1]\sum_{k=0}^{L-1} e^{j\frac{2\pi}{L}(n-1)k} e^{j\phi[k]} + \ldots +$$

$$\left. x_2\left[L-\frac{L}{2}-1\right]\sum_{k=0}^{L-1} e^{j\frac{2\pi}{L}\left(n-\frac{L}{2}-L+1\right)k} e^{j\phi[k]}\right\}$$

$$= \frac{1}{L}\left\{x_2[0]\sum_{k=0}^{L-1} e^{j\frac{2\pi}{L}nk}(1+e^{j\phi[k]}) + \right.$$

$$x_2[1]\sum_{k=0}^{L-1} e^{j\frac{2\pi}{L}(n-1)k}(1+e^{j\phi[k]}) + \ldots +$$

$$\left. x_2\left[\frac{L}{2}-1\right]\sum_{k=0}^{L-1} e^{j\frac{2\pi}{L}\left(n-\frac{L}{2}-1\right)k}(1+e^{j\phi[k]})\right\}$$

Here,
$$1+e^{j\phi[k]} \quad (31)$$

parenthesized in each term represents vector composition, and can be drawn as in FIG. 10 when placing focus on the specific frequency k. If phase rotation is not performed, that is, when φ[k]=0, it can be drawn as in FIG. 11.

The absolute value of equation (31) is obtained as $$|1+e^{j\phi[k]}| = |1+\cos\phi[k]+j\sin\phi[k]| \quad (32)$$

$$= \sqrt{(1+\cos\phi[k])^2+\sin^2\phi[k]}$$

$$= \sqrt{1+2\cos\phi[k]+\cos^2\phi[k]+\sin^2\phi[k]}$$

$$= \sqrt{2(1+\cos\phi[k])}$$

Hence, the condition to maximize the absolute value of equation (31) is φ[k]=0, and the value is 2. That is, when phase rotation is performed, the output signal becomes small, as is apparent. The correction amount calculator 503 decides the amplitude correction amount of the enhanced signal amplitude spectrum so as to correct the decrease amount of the output signal level.

A method of calculating a correction amount will be described here in detail assuming that the phase rotation amount is decided by a uniform random number. To simplify the problem, focus is placed on the variation in the magnitude caused by phase rotation, and each frequency component is assumed to have been normalized to a unit vector.

A case where phase rotation is not performed will be considered first. The composite vector in a case where the phase does not change between successive frames is represented by S shown in FIG. 11. The magnitude of the vector, |S| is given by $$|S| = \sqrt{\{1+1\}^2} \quad (33)$$

$$= \sqrt{2^2}$$

$$= 2$$

On the other hand, when phase rotation is performed by a uniform random number, the phase differences φ between successive frames are uniformly distributed within the range of −π to +π. The composite vector in a case where the phase changes between successive frames is represented by a vector S' shown in FIG. 10. The magnitude of the vector, |S'| is given by $$|S'| = \sqrt{\{1+\cos\phi\}^2+\{\sin\phi\}^2} \quad (34)$$

$$= \sqrt{2+2\{\cos\phi\}}$$

An expected value E(|S'|^2) is obtained as $$E(|S'|^2)=E(2+2\cos\phi)=E(2)+E(2\cos\phi) \quad (35)$$

Since the differences φ are uniformly distributed from −π to +π, we obtain $$E(2\cos(\phi))=0 \quad (36)$$

For this reason, the expected value E(|S'|^2) is given by $$E(|S'|^2)=0 \quad (37)$$

Based on equation (33), the expected value E(|S'|^2) in a case where phase rotation is not performed is given by $$E(|S|^2) = E(2^2) \quad (38)$$

$$= E(4)$$

$$= 4$$

When the ratio of equation (37) to equation (38) is calculated, $$E(|S'|^2)/E(|S|^2) = 2/4 \quad (39)$$

$$= 1/2$$

holds.

That is, when the phase is rotated by a uniform random number, the power average value of the output signal decreases to ½ as compared to the input. The amplitude corrector 504 performs correction of the amplitude value.

Hence, the correction amount calculator 503 obtains sqrt(2) as the correction coefficient and transmits it to the amplitude corrector 504.

Rotation amount generation by a uniform random number has been exampled above. The correction coefficient can also uniquely be determined using a normal random number if its variance and average value are determined. Correction coefficient derivation using a normal random number will be described below.

When a normal random number is used, the occurrence probability of $\phi$ is decided by a normal distribution. Hence, to obtain a power expected value in a case where phase rotation is executed using a normal random number, weighting needs to be performed based on the occurrence probability of $\phi$.

More specifically, a weight function $f(\phi)$ based on the occurrence probability of $\phi$ is introduced. By the weight function $f(\phi)$, $\cos(\phi)$ is weighted. The weighted value is further normalized by the integrated value of the weight function $f(\phi)$, thereby obtaining the power expected value.

By introducing the weight function $f(\phi)$ and its integrated vale into equation (35) representing the output power expected value for a uniform random number, an output power expected value $E(S''^2)$ in a case where phase rotation is performed using an normal random number can be expressed as $$E(|S''|^2) = E(2) + E\left(\frac{f(\phi)}{\int_{-\pi}^{\pi} f(\phi)\,d\phi}\cos(\phi)\right) \quad (40)$$

Since the weight function $f(\phi)$ can be expressed as a normal distribution, $$f(\phi) = \frac{1}{\sqrt{2\pi}\,\sigma}\exp\left(-\frac{(\phi-\mu)^2}{2\sigma^2}\right) \quad (41)$$

holds, where $\sigma$ is the variance, and $\mu$ is the average value.

For example, in a standard normal distribution in which the average value $\mu=0$, and the variance $\sigma=1$, $$f(\phi) = \frac{1}{\sqrt{2\pi}}\exp\left(-\frac{\phi^2}{2}\right) \quad (42)$$

holds. When this is substituted into equation (40), we obtain $$E(|S''|^2) = E(2) + E\left(\frac{\exp\left(-\frac{\phi^2}{2}\right)}{\int_{-\pi}^{\pi}\exp\left(-\frac{\phi^2}{2}\right)d\phi}\cos(\phi)\right) \quad (43)$$

By numerical calculation of the second term of the right-hand side of equation (43), $$E(|S''|^2) = 2\{1+0.609\} = 3.218 \quad (44)$$

holds. Hence, the ratio to $E(|S^2|)$ in a case where phase rotation is not performed is given by $$E(|S''|^2)/E(|S|^2) = 3.218/4 = 0.805 \quad (45)$$

In a case where the phase is rotated by a normal random number of a standard normal distribution, the correction amount calculator 503 obtains sqrt(1/0.805) as the correction coefficient and transmits it to the amplitude corrector 504. The phase rotation can be performed for all frequencies in the frame or for some frequencies where an abrupt change in the signal is detected. Amplitude correction is performed for a frequency that has undergone the phase rotation, that is, a frequency where an abrupt signal change is detected. Hence, the correction coefficient of a frequency that has not undergone the phase rotation is set to 1.0. Only the correction coefficient of the frequency that has undergone the phase rotation uses the value derived above.

As described above, in the amplitude controller 203, the amplitude correction coefficient is calculated using the phase rotation amount transmitted from the phase controller 202. The enhanced signal amplitude spectrum supplied from the noise suppressor 205 is multiplied by the correction coefficient and supplied to the inverter 204. This can eliminate lowering of the output level when the enhanced signal phase spectrum is obtained by rotating the noisy signal phase spectrum.

Note that the amplitude correction itself may be omitted if necessary, for example, if the calculated amplitude correction amount is negligible (the correction coefficient is close to 1.0), or the calculation amount in correction amount calculation and amplitude correction need to be decreased. At this time, only phase rotation by the phase rotator 501 is executed.

An example in which the phase is rotated using a random number has been described above. The same effect as described above can be obtained even by an arrangement that does not use a random number in a strict sense. The purpose of phase rotation is to eliminate or weaken a unique pattern that exists in the phase characteristic of an input noisy signal. Hence, any sequence capable of achieving the purpose can be used for phase rotation. For example, a sequence that has a period longer than the half of the frame length (the number of frequency components with independent amplitudes and power spectra) and a small correlation in one period can effectively be used.

<<Arrangement of Calculator and Abrupt Change Determiner>>

FIG. 12 is a block diagram for explaining the internal arrangement of the calculator 208 and the abrupt change determiner 209. As shown in FIG. 12, the calculator 208 includes a change amount calculator 1201 that calculates a phase change amount in the frequency direction, a flatness measure calculator 1202 that calculates the flatness measure of the phase change amount, and an amplitude flatness measure calculator 1203 that calculates the flatness measure of the amplitude in the frequency direction.

The change amount calculator 1201 receives the phase component signal 220 (p(k), k is a frequency), and obtains a phase difference $\Delta p(k)=p(k)-p(k-1)$ to an adjacent frequency as a phase change amount 1210 (phase gradient).

The flatness measure calculator 1202 checks the flatness measure (variation) of the phase change amount $\Delta p(k)=p(k)-p(k-1)$ obtained by the change amount calculator 1201 along the frequency axis. A difference $\Delta_2 p(k)=\Delta p(k)-\Delta p(k-1)$ of the phase change amount of the adjacent frequency is obtained as a flatness measure 1220. If the phase change amount is flat, the difference is 0. One flatness measure 1220 may be obtained in correspondence with each frequency component, each band, or all frequencies. Flatness measures in a single or a plurality of bands may be integrated and used in place of the flatness measure for all frequencies.

The reason why the phase change amount in the frequency direction becomes flat in a case where an abrupt change in the signal exists is as follows. Assume that an isolated pulse exists in a frame of the converter 201. The gradient of the phase in the frequency direction when the isolated pulse is Fourier-transformed is known to be obtained uniquely in correspondence with the position of the isolated pulse. For example, if the frame length in the converter corresponds to L samples, and the isolated pulse position is n0 (0≤n0≤L−1), the phase gradient is −2πn0/L. This is because the kth frequency component D(k) obtained by Fourier transform of an isolated pulse having an amplitude a is given by $D(k)=a\sim\exp(-j\theta(k))\theta(k)=-2\pi \cdot k \cdot n0/L$.

The phase θ(k) is obviously proportional to k, that is, the frequency. For this reason, the frequency-direction change amount corresponding to the differential of the phase is Δθ(k)=−2π·n0/L, which is a constant. That is, the phase change amount in the frequency direction has a predetermined value (flat).

If the determination is done not for each frequency but for each frequency band (sub-band) or frame, determination errors by phase components other than abrupt signal change components can be reduced by determination in boarder aspects. In addition, the determination result for each frequency may be corrected using the determination result for each frequency band or frame. For example, if the determination result for a certain frequency band indicates that "an abrupt signal change exists", the determination result for all frequencies within the frequency band is forcibly set to "an abrupt signal change exists", thereby reducing determination errors caused by disturbance of other signal components. To the contrary, if the determination result for a certain frequency band indicates that "no abrupt signal change exists", the determination result for all frequencies within the frequency band is forcibly set to "no abrupt signal change exists", thereby reducing determination errors caused by disturbance of other signal components. Alternatively, the ease (threshold) of determination for each frequency within the band may be corrected in a direction to easily determine "presence", and the configuration for independently performing determination for each frequency may be maintained in itself. When the determination result is obtained for each frequency or frequency band, an abrupt change can be suppressed for each frequency or frequency band. Hence, more accurate suppression can be performed.

In addition, the differential value of the phase may be obtained as the phase change amount, and the differential value of the differential value of the phase change amount may be obtained as the flatness measure 1220. In this case, if the quadratic differential value of the phase is close to 0 (equal to or smaller than a predetermined value), the phase change amount can be determined as flat. When the determination is performed for each band or frequency component, abrupt signal change determination processing can be performed in a more sophisticated manner. That is, it is possible to suppress an abrupt signal change independently for each band or frequency component and more accurately suppress the abrupt signal change.

The change amount calculator 1201 calculates the change amount using the phase difference between adjacent frequencies. However, the present invention is not limited to this. The linearity (flatness measure of a phase change) may be determined by differentiation of the frequency of the phase. The smaller the variation between a plurality of differential results of a plurality of frequencies is, the higher the linearity is. A local linearity can be evaluated using a local differential result. In particular, the differential between two adjacent frequency components can be approximated by a difference. In this case, the smaller the variation between a plurality of differences is, the higher the linearity is determined to be. The flatness measure can be used as the index of the variation.

The amplitude flatness measure calculator 1203 calculates an amplitude change 1225 along the frequency axis and supplies it to the abrupt change determiner 209. A frequency whose amplitude change with respect to an adjacent frequency is small represents an abrupt signal change. As the amplitude change, one flatness measure 1225 may be obtained for each band or all frequencies. More specifically, FM (Flatness Measure) representing a flatness measure is obtained by $$FM = \frac{\sqrt[N]{\prod_{n=0}^{N-1} x(n)}}{\frac{\sum_{n=0}^{N-1} x(n)}{N}} = \frac{\exp\left(\frac{1}{N}\sum_{n=0}^{N-1} \ln x(n)\right)}{\frac{1}{N}\sum_{n=0}^{N-1} x(n)} \qquad (46)$$

where x(n) is the amplitude or power spectrum at a frequency n, and N is the number of frequency components included in the flatness measure calculation section.

FM takes a value of 0.0 to 1.0. If the amplitude is completely flat, FM is 1.0. The flatness measure is disclosed in non-patent literature 3.

The flatness measure can also be expressed using another index. For example, it is possible to obtain the average of x(n) for each band or all frequencies and calculate the sum of squared differences of x(n) of each frequency component n and the average value as the flatness measure for each band or all frequencies. One sum of squared differences may be obtained not for all frequencies but in a single or a plurality of frequency bands and used as the flatness measure. The thus obtained flatness measure has a value of 0.0 if the amplitude is completely flat, and takes a larger vale as the flatness measure lowers.

A smoothness may be used as another index of the flatness measure. The smoothness can be expressed as the sum of absolute differences between adjacent samples along the frequency axis. The smoothness takes a large value for a waveform having large unevenness (not smooth), and a small value for a waveform having small unevenness (smooth). This index is known as TV (Total Variation).

As the flatness measure, a flatness measure along the frequency axis is used above. However, a flatness measure along the time axis is also usable. At an abrupt signal change, the amplitude and power abruptly increase. Using this characteristic, an abrupt signal change can be determined to exist when the flatness measure along the time axis is low. More specifically, if the amplitude or power difference between the current frame and the immediately preceding frame is a predetermined value or more, it is determined that the flatness measure is low, that is, an abrupt signal change exists. Alternatively, the amplitude or power difference between adjacent frames may be obtained for a plurality of frames including several past frames and the current frame, and the result of linearly or nonlinearly combining the differences may be defined as the flatness measure. When the information of the past frames is used, a dulled abrupt signal change including low frequency components can easily be detected, and the suppression performance can be improved. Note that when calculating the amplitude or power difference between adjacent frames, the calculation may be done for each frequency component, band, or all frequencies. The amplitude or power difference can also be calculated for a single or a plurality of bands. For example, when the amplitude or power difference can also be calculated in a single band, particularly, in a high frequency band, the influence of speech and other signals can be reduced, and the abrupt signal change can more correctly be detected.

The above-described two flatness measures, that is, the flatness measure along the frequency axis and the flatness measure along the time axis can be used singly or in combination. As examples of combination, an abrupt signal change is detected based on linear or nonlinear combination of the two flatness measures, or detection results based on the flatness measures are combined. It is determined that an abrupt signal change is detected when the flatness measure in the frequency direction is large or the flatness measure in the time direction is small. Hence, when combining, a contrivance such as changing one of the flatness measures to a reciprocal is needed.

The abrupt change determiner 209 determines an abrupt change in the signal using two indices, that is, the flatness measure of the phase change amount and the amplitude flatness measure. This is because when the amplitude is flat (variation is small) along the frequency axis, an abrupt signal change is assumed to exist at a high possibility. This is self-evident from the fact that the abrupt signal change is impulsive (the amplitude increases and decreases in a short time), and the Fourier transform of the impulse yields a white signal (the amplitude and power are equal throughout the frequencies). As the determination method, for example, one of the following methods can be selected.

(1) If both the flatness measure of the phase change amount and the amplitude flatness measure meet corresponding conditions (for example, the quadratic differential value of the phase is N=0.1 or less, and the amplitude flatness measure FM is M=0.8 or more), it is determined that an abrupt change in the signal exists.

(2) The OR of determination results obtained by solely using the parallelism and the amplitude flatness measure is used. To calculate presence probability of an abrupt signal change, determination is performed based on a larger one (or smaller one) of presence probability by the parallelism and presence probability by the amplitude flatness measure.

(3) If the average of the flatness measure of the phase change amount and the amplitude flatness measure meets a condition (for example, an average AV1 of a quadratic differential value PX of the phase and a difference value QX between 1.0 and the amplitude flatness measure FM, that is, QX=(1.0−FM) is AV1=(PX+QX)/2=0.1 or less), it is determined that an abrupt change in the signal exists.

(4) If a value obtained by combining the flatness measure of the phase change amount and the amplitude flatness measure while adding weights to them meets a compound condition (for example, a weighted average AV2 of the quadratic differential value PX of the phase and the difference value between 1.0 and the amplitude flatness measure FM, that is, QX=(1.0−FM) is AV2=(0.8×PX+0.2×QX)=0.1 or less), it is determined that an abrupt change in the signal exists.

(5) The flatness measure of the phase change amount and the amplitude flatness measure are combined using a linear or nonlinear function, and the result of combination is larger than a predetermined value, it is determined that an abrupt change in the signal exists. If an amplitude flatness measure in the time direction is included, its reciprocal is used in place of the amplitude flatness measure.

(6) Only a larger one (flatness measure closer to an ideal value) of the flatness measure of the phase change amount and the amplitude flatness measure is used, and if the larger flatness measure meets a condition (for example, a larger one of the quadratic differential value PX of the phase and the difference value QX between 1.0 and the amplitude flatness measure FM is compared with a threshold), it is determined that an abrupt change in the signal exists. If an amplitude flatness measure in the time direction is included, its reciprocal is used in place of the amplitude flatness measure.

(7) If information about the amplitude or power spectrum of an abrupt change signal to be detected is obtained in advance, and the amplitude or power spectrum is flat, the weight of the phase flatness measure is made small.

(8) If information about the amplitude or power spectrum of an abrupt change signal to be detected is obtained in advance, and the amplitude or power spectrum of the input noisy signal is smaller than the minimum value of the amplitude or power spectrum, the threshold used to detect an abrupt signal change is temporarily largely changed to make detection hard.

When processing a specific signal, for example, when detecting/suppressing an impulsive sound of small noise close to an impulse, information about the amplitude or power is sometimes more reliable than phase information. For example, when detecting a gunshot of a pistol in a quiet environment, the detection may be performed using only the amplitude. On the other hand, when the amplitude or power spectrum of noise largely changes, for example, when detecting a gunshot in airport security, it is effective to change the weights of the amplitude and phase between a quiet situation (with small noise) and a situation with large noise. In this case, the weights of the amplitude and phase may be changed in accordance with the presence/absence of noise or time zone. For example, if the latest information of flight schedule can be acquired from the control tower, the takeoff and landing times of airplanes are known. Hence, at a timing of airplane arrival (timing with much noise), the phase to which a large weight is added can be used to detect a gunshot. This is because in a case where signals other than a gunshot (impulsive sound to be detected) coexist, impulsive sound detection using phase information is more effective than detection using an amplitude. On the other hand, in a situation with small noise, the impulsive sound can effectively be detected by performing determination while attaching importance to the absolute value of the frequency domain vector, that is, the amplitude value of an input noisy signal. In this case as well, the power spectrum value may be used in place of the amplitude spectrum, as a matter of course. The amplitude of the impulsive sound is not flat in some cases depending on the type of the signal. In this case, when detection is performed while making the weight of the phase flatness measure large, an abrupt change in the signal can accurately be detected. If information about the amplitude or power spectrum of an impulsive sound is obtained in advance, the amplitude flatness measure calculation result can be corrected using the obtained information so as to obtain the same result as in a case where the amplitude is flat. More specifically, the amplitude flatness measure is calculated after the amplitude spectrum 230 is multiplied for each frequency component by the reciprocal of the amplitude or power spectrum shape of an impulsive sound.

The abrupt change determiner 209 outputs abrupt signal change present (1) or abrupt signal change absent (0) as a determination result 1230. However, a value between 0 and 1 associated with the absolute value of the flatness measure may be output as the determination result 1230. In this case, likelihood or probability of presence of an abrupt signal change can be obtained. The presence probability can be obtained, for example, in the following way. First, a positive value is determined as a threshold. A positive value is used as a threshold because both the phase flatness measure and the amplitude flatness measure represent higher presence probability of an abrupt signal change by a larger positive value. The minimum value of them is 0. When a value (combined index) obtained by combining the indices exceeds a threshold, the presence probability of an abrupt signal change is 1. When the combined index is 0, the presence probability is 0. A general value of presence probability is defined as a function of the combined index. The simplest function is a line. A value proportional to the combined index is determined as presence probability. The slope and y-intercept (function value when the combined index is 0) of the line are determined so as to meet a boundary condition when the above-described combined index equals 0 or 1. As the function, an arbitrary linear or nonlinear function or polynomial may be used.

FIG. 13 is a graph showing a phase and its change amount. When the phase changes along the frequency axis in the frequency domain, like a graph 1301, the phase change amount changes as indicated by a graph 1302 along the frequency axis in the frequency domain. The linearity of the phase is discriminated by deriving a frequency 1303 at which the change is flat.

The phase is known to linearly change at a location where the signal abruptly changes. It is therefore possible to determine the presence or degree of an abrupt change in the signal by obtaining the linearity of the phase and determining the flatness measure in the above-described way. The abrupt change can be suppressed, or its influence can be weakened by rotating the phase spectrum or suppressing the amplitude spectrum in a frequency component, frequency band, or all frequencies in which the abrupt signal change such as an impulsive sound exists. Hence, a high-quality enhanced signal can be obtained.

Figure 14:
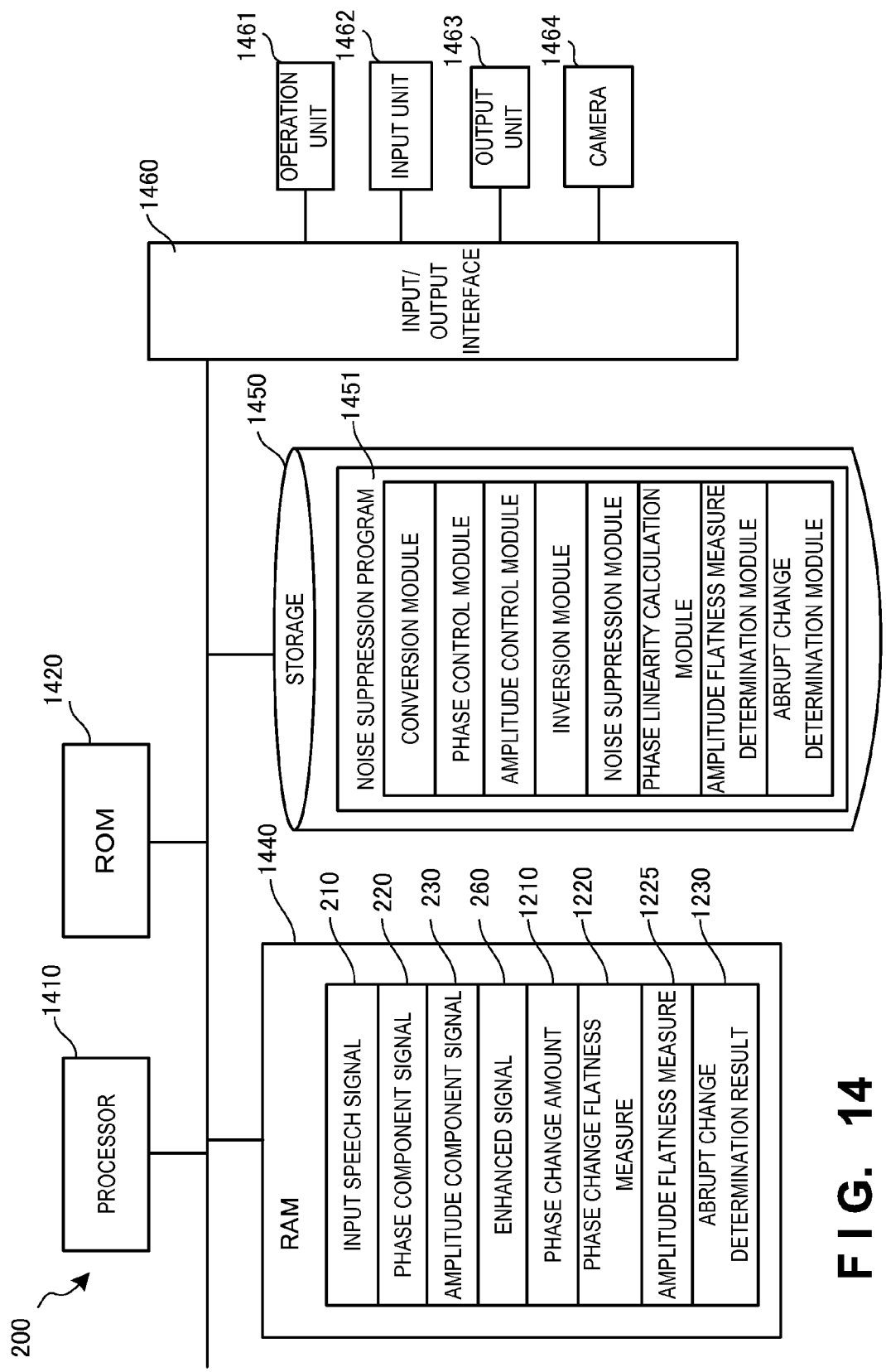
FIG. 14 is a block diagram showing the hardware arrangement of the noise suppression apparatus according to the second embodiment of the present invention.

FIG. 14 is a block diagram for explaining a hardware arrangement when the noise suppression apparatus 200 according to this embodiment is implemented using software.

The noise suppression apparatus 200 includes a processor 1410, a ROM (Read Only Memory) 1420, a RAM (Random Access Memory) 1440, a storage 1450, an input/output interface 1460, an operation unit 1461, an input unit 1462, and an output unit 1463. The noise suppression apparatus 200 may include a camera 1464. The processor 1410 is a central processing unit and executes various programs, thereby controlling the overall noise suppression apparatus 200.

The ROM 1420 stores various parameters as well as a boot program to be executed first by the processor 1410. The RAM 1440 includes an area to store an input signal 210, the phase component signal 220, the amplitude component signal 230, the enhanced signal 260, the phase change amount 1210, the phase change flatness measure 1220, the amplitude flatness measure 1225, the abrupt change determination result 1230, and the like as well as a program load area (not shown).

The storage 1450 stores a noise suppression program 1451. The noise suppression program 1451 includes a conversion module, a phase control module, an amplitude control module, an inversion module, a noise suppression module, a phase linearity calculation module, an amplitude flatness measure determination module, and an abrupt change determination module. When the processor 1410 executes the modules included in the noise suppression program 1451, the functions of the converter 201, the phase controller 202, the amplitude controller 203, the inverter 204, the noise suppressor 205, the calculator 208, and the abrupt change determiner 209 shown in FIG. 2 can be implemented. Note that the storage 1450 may store a noise database.

An enhanced signal that is the output of the noise suppression program 1451 executed by the processor 1410 is output from the output unit 1463 via the input/output interface 1460. This can suppress, for example, the operation sound of the operation unit 1461 input from the input unit 1462. Also possible is an application method of, for example, detecting abrupt signal change inclusion in the input signal input from the input unit 1462 and starting shooting by the camera 1464.

Figure 15:
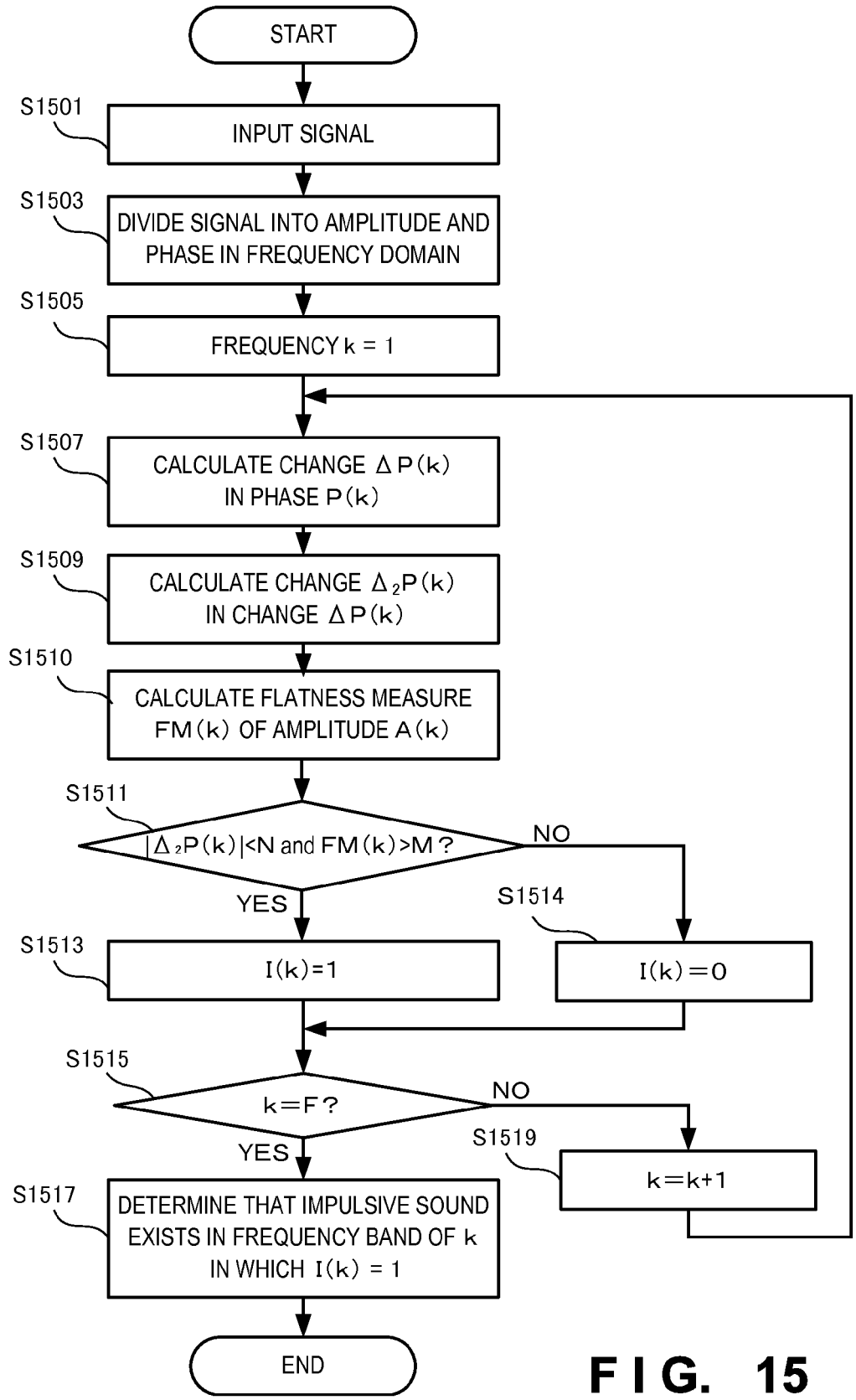
FIG. 15 is a flowchart for explaining the procedure of processing of the noise suppression apparatus according to the second embodiment of the present invention.

FIG. 15 is a flowchart for explaining the procedure of abrupt signal change determination processing of the noise suppression program 1451. When a signal is input from the input unit 1462 in step S1501, the process advances to step S1503. In step S1503, the converter 210 converts the input signal into a frequency domain and divides it into an amplitude and a phase. In step S1505, the calculator 208 sets the discrete frequency k to 1 and the count value I(k) to 0, and sequentially starts processing in the frequency space. When the process advances to step S1507, the calculator 208 calculates a change (differential value or difference value) in the phase at the set frequency. In step S1509, the calculator 208 calculates a change in the phase change (differential value or difference value). In step S1510, the calculator 208 calculates the flatness measure FM(k) of the amplitude A(k) using equation (46) described above. In step S1511, the abrupt change determiner 209 compares the absolute value of the flatness measure of the phase change and the amplitude flatness measure with thresholds N and M, respectively. More specifically, if the absolute value of the change in the phase change does not exceed the predetermined threshold N, and the amplitude flatness measure FM is equal to or larger than the threshold M, the process advances to step S1513 to determine that an abrupt change in the signal exists at the frequency k and set a flag (set I(k)=1). On the other hand, if the phase change and the amplitude change do not meet the conditions, I(k)=0 is set in step S1514. Steps S1507 to S1514 are repeated until k=F (F is the number of frequency components in the entire frame). Finally in step S1517, it is determined that an abrupt signal change exists at the frequency k when I(k)=1, and the determination result is supplied to the noise suppressor 205 and the phase controller 202. The processes of steps S1501 to S1514 are repetitively performed for all frames. Note that in place of step S1517, I(k) may be integrated in the frame, and the integral value of I(k) exceeds a predetermined threshold, the abrupt change determiner 209 may determine that the frame includes an abrupt signal change. At this time, the abrupt change determination result may be integrated in the next frequency band.

As a hangover function, the threshold N in the next frame may be set large, and the threshold M may be set small. When the thresholds in the next frame are thus set, it is possible to easily detect an abrupt signal change (impulsive sound) and reduce detection omissions. As for setting of the thresholds N and M in the next frame, one of the thresholds may be set, or both thresholds may be set simultaneously.

With the above-described processing, an abrupt signal change (impulsive sound) can more correctly be detected, and the abrupt signal change (impulsive sound) can appropriately be suppressed as needed.

Third Embodiment

A noise suppression apparatus according to the third embodiment of the present invention will be described next with reference to FIG. 16. FIG. 16 is a block diagram for explaining the functional arrangement of a noise suppression apparatus 1600 according to this embodiment. The noise suppression apparatus 1600 according to this embodiment is different from the second embodiment in that a converter 1601 generates a complex signal 1650, and a calculator 1608 and an abrupt change determiner 1609 perform phase linearity calculation and abrupt signal change determination, respectively, based on the complex signal 1650. The rest of the components and operations is the same as in the second embodiment. Hence, the same reference numerals denote the same components and operations, and a detailed description thereof will be omitted.

FIG. 17 is a block diagram for explaining the internal arrangement of the calculator 1608 and the abrupt change determiner 209. As shown in FIG. 17, the calculator 1608 includes a change amount calculator 1701 that calculates a phase change amount in the frequency direction, and a flatness measure calculator 1202 that calculates the flatness measure of the phase change amount. The change amount calculator 1701 receives the complex signal 1650 (q(k), k is a frequency), and obtains a phase difference $\Delta p(k)=p(k)-p(k-1)$ to an adjacent frequency as a phase change amount 1210 (phase gradient).

The flatness measure calculator 1202 checks the flatness measure (variation) of the phase change amount $\Delta p(k)=p(k)-p(k-1)$ obtained by the change amount calculator 1701 along the frequency axis. A difference $\Delta_2 p(k)=\Delta p(k)-\Delta p(k-1)$ of the phase change amount of the adjacent frequency is obtained as a flatness measure 1220. If the phase change amount is flat, the difference is 0. One flatness measure 1220 may be obtained in correspondence with each frequency component, each band, or all frequencies. Flatness measures in a single or a plurality of bands may be integrated and used in place of the flatness measure for all frequencies.

In addition, the differential value of the phase may be obtained as the phase change amount, and the differential value of the differential value of the phase change amount may be obtained as the flatness measure 1220. In this case, if the quadratic differential value of the phase is close to 0 (equal to or smaller than a predetermined value), the phase change amount can be determined as flat. When the determination is performed for each band or frequency component, abrupt signal change detection processing can be performed in a more sophisticated manner. That is, it is possible to suppress an abrupt signal change independently for each band or frequency component and more accurately suppress the abrupt signal change.

If the absolute value of the calculated flatness measure is a predetermined value or less, the abrupt change determiner 209 determines that the frequency (one frequency component, frequency band, or all frequencies (that is, one frame)) corresponding to the flatness measure includes an abrupt signal change. The abrupt change determiner 209 outputs abrupt signal change present (1) or abrupt signal change absent (0) as a determination result 1230. However, a value between 0 and 1 associated with the absolute value of the flatness measure may be output as the determination result 1230. In this case, likelihood (possibility) of presence of an abrupt signal change can be obtained.

As described above, according to this embodiment, the linearity of the phase can be detected using a complex signal in place of a phase component signal.

Fourth Embodiment

Figure 18:
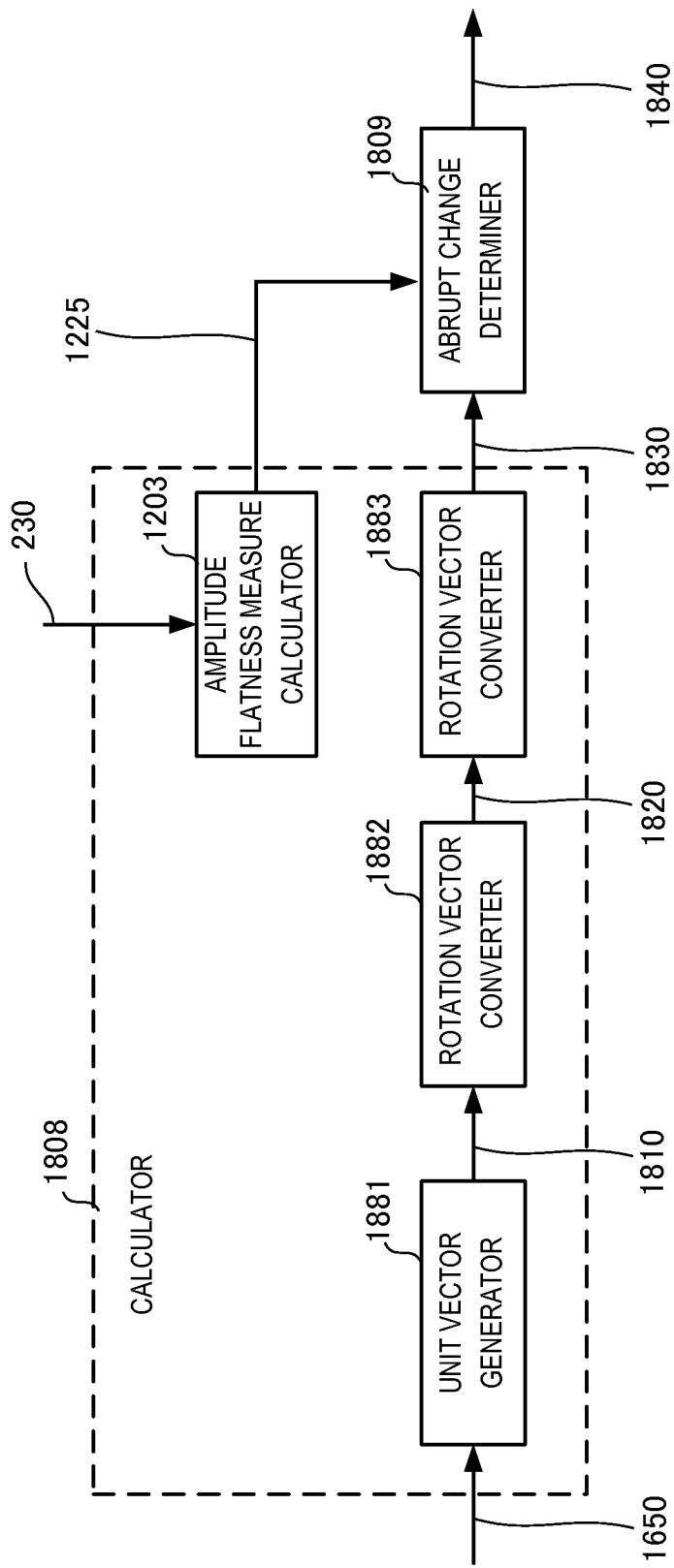
FIG. 18 is a block diagram showing the arrangement of a phase controller and an amplitude controller according to the fourth embodiment of the present invention.

A noise suppression apparatus according to the fourth embodiment of the present invention will be described next with reference to FIG. 18. A noise suppression apparatus 1800 according to this embodiment is different from the third embodiment in that a calculator 1808 is provided in place of the calculator 1608. FIG. 18 is a block diagram for explaining the functional arrangement of the calculator 1808 included in the noise suppression apparatus according to this embodiment. The calculator 1808 according to this embodiment is different from the third embodiment in that a unit vector generator 1881 and rotation vector converter 1882 and 1883 are provided. The calculator 1808 is also different in that an abrupt change determiner 1809 determines the presence/absence or degree of an abrupt change in a signal based on a rotation vector. The rest of the components and operations is the same as in the third embodiment. Hence, the same reference numerals denote the same components and operations, and a detailed description thereof will be omitted.

The unit vector generator 1881 converts an input spectrum (complex vector) into unit vectors on a frequency component basis using a complex signal 1650. More specifically, each of the real part and the imaginary part of the complex signal 1650 is divided by an amplitude value.

The rotation vector converter 1882 converts a unit vector 1810 into a rotation vector (first rotation vector 1820) between adjacent frequencies. The rotation amount (phase) of the rotation vector here is equivalent to the phase change amount between unit vectors of adjacent frequencies. Multiplication to obtain the inner product of a conjugate A* of a reference vector and a vector B after rotation is performed, thereby obtaining a rotation vector RotVec given by RotVec=A*·B.

More specifically, the sum of the product of real parts of the reference vector and the product of imaginary parts is obtained as the real part of the rotation vector, and the difference between the two products of the real parts and imaginary parts of the reference vector is obtained as the imaginary part of the rotation vector, thereby calculating the rotation vector 1820.

The rotation vector converter 1883 checks the flatness measure (variation) of the first rotation vector 1820 obtained by the rotation vector converter 1882 along the frequency axis. If the phase change amount along the frequency axis is constant, the variation in the rotation vector becomes small. Hence, the change amount of the first rotation vector 1820 is obtained along the frequency axis. More specifically, a rotation vector (second rotation vector 1830) between adjacent frequencies is obtained for the first rotation vector 1820. This is equivalent to differentiating the first rotation vector. The abrupt change determiner 1809 recognizes the real part of the second rotation vector 1830 as a flatness measure. The reason for this is as follows.

Since the second rotation vector 1830 is a unit vector as well, the real part takes a value of −1 to 1. The more linearly the phase changes, the smaller the angle change amount of the first rotation vector is (the smaller the variation in the rotation vector is). The smaller the change amount of the first rotation vector is (the smaller the variation in the rotation vector is), the smaller the angle of the second rotation vector is. The smaller the angle of the second rotation vector is, the larger its real part is. In this case as well, one flatness measure may be obtained in correspondence with each frequency point, each band, or all frequencies.

Note that the method of obtaining the flatness measure is not limited to the above-described method. For example, the magnitude of a difference vector obtained by calculating the difference vector between the first rotation vectors for each adjacent frequency component, squaring each of the real part and the imaginary part of the difference vector, and adding the results may be used as the flatness measure. The angle of the second rotation vector may also be used as the flatness measure. The angle of the second rotation vector corresponds to the angle difference between the first rotation vectors of adjacent frequency components.

The abrupt change determiner 1809 determines an abrupt change in a signal using two indices, that is, the real part of the second rotation vector 1830 and an amplitude flatness measure FM. Use of the amplitude flatness measure in the determination is the same as already described concerning the operation of the abrupt change determiner 209. As for the real part of the second rotation vector 1830, the presence or degree of an abrupt change is determined depending on whether the real part exceeds a predetermined threshold N (for example, 0.7 or 0.8) close to +1 or where the real part is located between N and +1. The abrupt change determiner 1809 outputs abrupt signal change present (1) or abrupt signal change absent (0) as a determination result 1840. However, a value between 0 and 1 associated with the absolute value of the flatness measure may be output as the determination result 1840. In this case, likelihood (possibility) of presence of an abrupt signal change can be obtained. For example, the flatness measure is compared with a first threshold on a frequency component basis, and the number of frequency bins whose flatness measures have been determined to be equal to or less than the first threshold is counted. If the count value is equal to or more than a second threshold, it may be determined that the frame includes an abrupt change, thereby detecting an abrupt change in each frame.

Note that in this case as well, an abrupt signal change can be detected using the flatness measure of the phase change and the flatness measure of the amplitude in balance, as described in the second embodiment. When the determination is performed for each band or frequency component, abrupt signal change detection processing can be performed in a more sophisticated manner. That is, it is possible to suppress an abrupt signal change independently for each band or frequency component and more accurately suppress the abrupt signal change.

FIG. 19 is a flowchart for explaining the procedure of abrupt signal change detection processing when a noise suppression program according to this embodiment is executed. When a speech signal is input from an input unit 1462 in step S1501, the process advances to step S1903. In step S1903, a converter 201 converts the input signal into a frequency domain and generates a complex signal for each frequency component. In step S1505, a discrete frequency k is set to 1, a count value I(k) is set to 0, and processing in the frequency space is sequentially started. When the process advances to step S1907, the complex signal is converted into a unit vector for the set frequency. In step S1908, the unit vector of an adjacent frequency component is converted into the first rotation vector. In step S1909, the first rotation vector of the adjacent frequency component is converted into the second rotation vector. In step S1510, a calculator 1203 calculates a flatness measure FM(k) of an amplitude A(k) using equation (46) described above. In step S1911, the real part of the second rotation vector is compared with a threshold N, and the amplitude flatness measure is compared with a threshold M. As a result, if the real part exceeds the threshold N, and the amplitude flatness measure exceeds the threshold M, the process advances to step S1513 to set I(k)=1. On the other hand, if the real part is equal to or less than the threshold N, or the amplitude flatness measure is equal to or less than the threshold M, I(k)=0 is set in step S1514. Steps S1907 to S1514 are repeated until k=F (F is the number of frequency components in the entire frame). Finally in step S1517, it is determined that an abrupt signal change exists at the frequency k when I(k)=1, and the determination result is supplied to a noise suppressor 205 and a phase controller 202.

As described above, according to this embodiment, it is possible to detect the linearity from the rotation vector of the rotation vector of the phase using a complex signal and detect an impulsive sound based on the linearity and the flatness measure. Note that although a unit vector is generated to use the real part of a rotation vector in flatness measure determination, the present invention is not limited to this. In addition, not the real part of the second rotation vector but the magnitude of the angle of the second rotation vector may be compared with the threshold, and if the angle is larger than the threshold, it may be determined that an abrupt signal change exists.

Fifth Embodiment

Note that in the first to fourth embodiments, a case where an abrupt signal change detection method is applied to a noise suppression apparatus aiming at suppressing an abrupt signal change has been described. However, the present invention is not limited to this. The abrupt signal change detection method is useful in various apparatuses, systems, and situations aiming at detecting an impulsive sound. In addition, the detection target is not limited to an impulsive sound (a speech signal that abruptly rises and immediately falls). A signal that abruptly rises (or falls) and remains intact can also be detected as an abrupt change.

For example, a present audio encoding method (for example, an encoder of MPEG AAC) employs a different information compression method at an abrupt signal change called an attack. At the abrupt signal change, the analysis window length is changed, and preceding noise called a pre-echo is suppressed. Hence, the abrupt signal change needs to be detected. As compared to a method of detection using a change in the amplitude or entropy, it is possible to accurately detect an abrupt change and effectively compress information.

Figure 20:
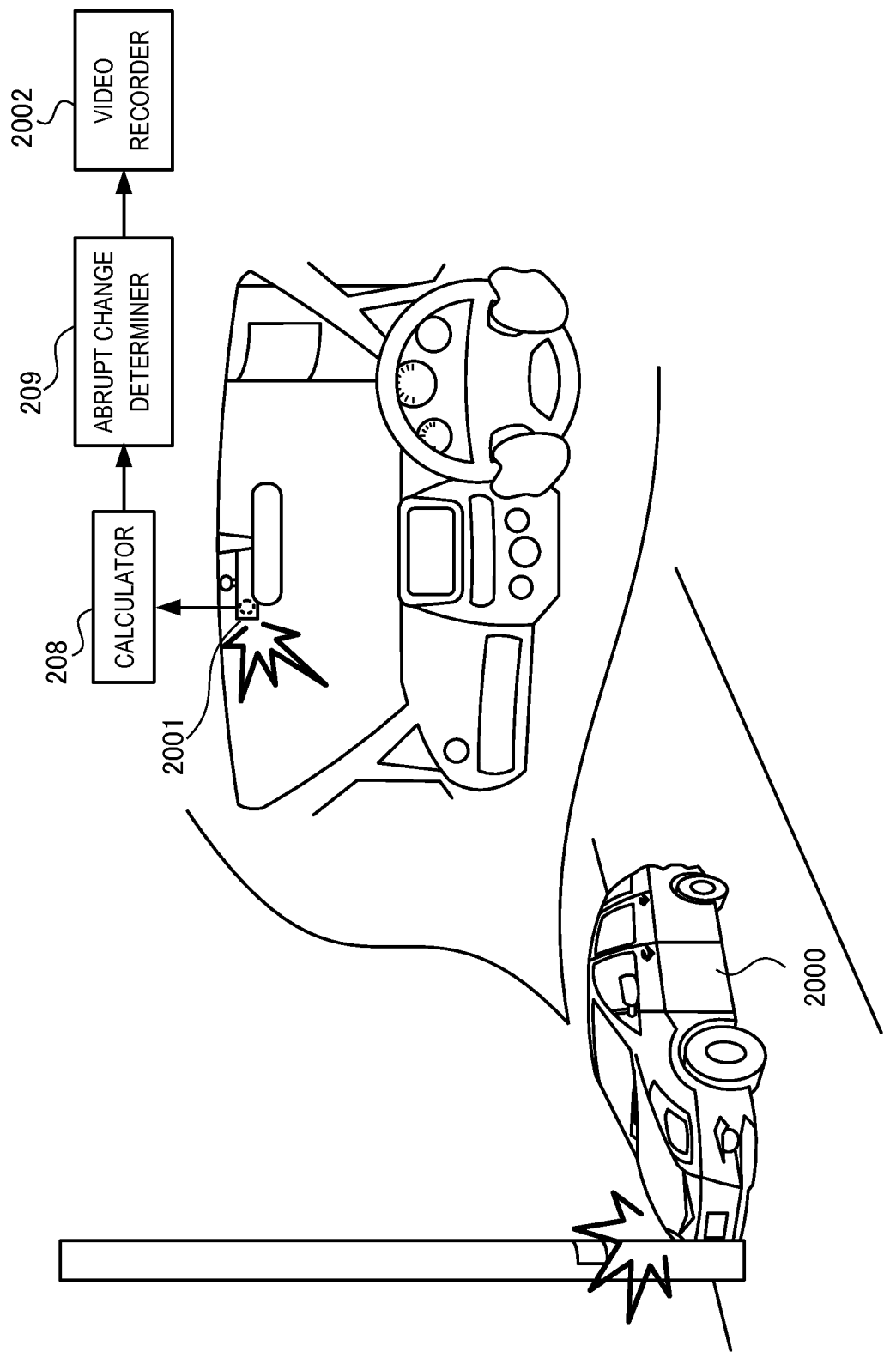
FIG. 20 is a view for explaining an application example according to the fifth embodiment of the present invention.

It is also possible to assume an application example in which a microphone 2001, a calculator 208, an abrupt change determiner 209, and a video recorder 2002 are provided aboard a vehicle 2000, as shown in FIG. 20. Triggered by impulsive sound detection, the video recorder 2002 prohibits an image shot by a camera from being overwritten and saved, thereby leaving the record of an accident situation. At this time, overwrite saving may be prohibited after a delay of a predetermined time from impulsive sound detection. Unlike a case where an impulsive sound itself is used as a trigger, an accident situation can automatically be recorded even when the impact is small, or another vehicle is involved in an accident.

Figure 21:
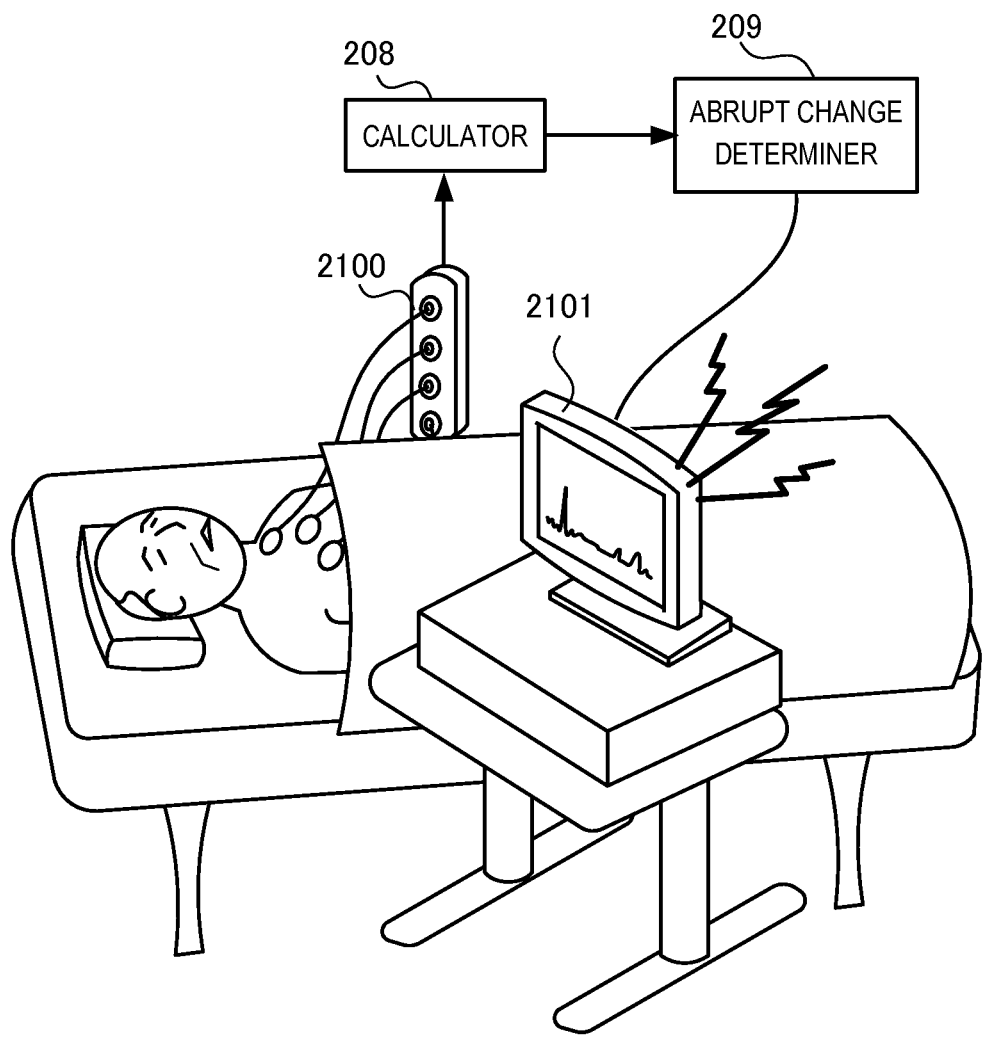
FIG. 21 is a view for explaining an application example according to the fifth embodiment of the present invention.

Also assume an application example in which the calculator 208, the abrupt change determiner 209, and an alarm unit 2101 are connected to an electrocardiograph 2100, as shown in FIG. 21. It is possible to more correctly and effectively detect an abnormal heartbeat in an electrocardiogram. In particular, this configuration is effective in a case where much noise is included. This method is also applicable to monitor the echo of an embryo. In some cases, a heart sound cannot correctly be monitored due to disturbance of noise. This technique is effective in such a case. That is, the technique is widely applicable to detect an abrupt change in a biomedical signal.

Sixth Embodiment

A signal processing apparatus 2200 according to the sixth embodiment of the present invention will be described with reference to FIG. 22. The signal processing apparatus 2200 is an apparatus for detecting an abrupt input signal change. As shown in FIG. 22, the signal processing apparatus 2200 includes a converter 2201, a first calculator 2202, a second calculator 2203, and an abrupt signal change determiner 2204.

The converter 2201 converts an input signal 2210 into a phase component signal 2220 and an amplitude component signal 2230 in a frequency domain. The first calculator 2202 calculates a gradient 2250 of a phase based on the position of a sudden increase of the input signal 2210 in the time domain. The gradient of the phase in the frequency direction when an isolated pulse is Fourier-transformed is known to be obtained uniquely in correspondence with the position of the isolated pulse. For example, if the frame length in the converter corresponds to L samples, and the isolated pulse position is n0, the phase gradient is $-2\pi n0/L$. As an index to identify a sudden increase, for example, the maximum value of the absolute amplitude can be used. This index gives a correct position if an actual signal is close to an isolated pulse (having an almost unimodal shape). On the other hand, if a pulse has a bimodal shape, the maximum amplitude value does not give a correct position. In this case, an index using the maximum value of the absolute amplitude and the second largest value of the absolute amplitude is effective. For example, the intermediate value between the two values or the weighted average of the positions of the two values is usable. If the pulse more spreads along the time axis, the correct position can be obtained using an approximate center of the pulse. Such an index has a center of gravity. The second calculator 2202 calculates a gradient 2260 of the phase of the phase component signal 2220 in the frequency domain. The abrupt signal change determiner 2204 determines an abrupt change in the input signal based on the gradient calculated by the first calculator 2202 and that calculated by the second calculator 2203.

With the above-described arrangement, it is possible to effectively detect an abrupt change in the input signal using the level of matching between the gradient of the phase component signal in the frequency domain and the phase gradient obtained from the position of the sudden increase of the time domain signal.

Seventh Embodiment

Overall Arrangement

A noise suppression apparatus according to the seventh embodiment of the present invention will be described with reference to FIGS. 23 to 30C. The noise suppression apparatus according to this embodiment is applicable to suppress noise in, for example, a digital camera, a notebook personal computer, a mobile phone, a keyboard, a game machine controller, and the push buttons of a mobile phone. That is, the target signal of speech, music, environmental sound, or the like can be enhanced relative to a signal (noise or interfering signal) superimposed on it. However, the present invention is not limited to this, and the noise suppression apparatus is applicable to a signal processing apparatus of any type required to do abrupt signal change detection from an input signal. Note that in this embodiment, a noise suppression apparatus that detects and suppresses an impulsive sound as an example of an abrupt change in a signal will be described. The noise suppression apparatus according to this embodiment appropriately suppresses an impulsive sound generated by, for example, a button operation in a mode to perform an operation such as button pressing near a microphone. Simply speaking, a time domain signal including an impulsive sound is converted into a frequency domain signal, and the gradient of a phase component in the frequency space is calculated. In addition, the gradient of the phase in the frequency domain when a sudden increase of the time domain signal is regarded as an isolated pulse, that is, $-2\pi n0/N$ is obtained. Then, the presence of an impulsive sound is determined in accordance with the level of matching between the two types of phases.

FIG. 23 is a block diagram showing the overall arrangement of a noise suppression apparatus 2300. A noisy signal (signal including both a desired signal and noise) is supplied to an input terminal 2306 as a series of sample values. The noisy signal supplied to the input terminal 2306 undergoes transform such as Fourier transform in a converter 2301 and is divided into a plurality of frequency components. The plurality of frequency components are independently processed on a frequency basis. The description will be continued here concerning a specific frequency component of interest. Out of the frequency component, an amplitude spectrum (amplitude component) 2330 is supplied to a noise suppressor 2305, and a phase spectrum (phase component) 2320 is supplied to a phase controller 2302 and a calculator 2381. In addition, the converter 2301 supplies a time domain signal 2370 after frame division before conversion such as fast Fourier transform to a calculator 2382. Note that the converter 2301 supplies the noisy signal amplitude spectrum 2330 to the noise suppressor 2305 here. However, the present invention is not limited to this, and a power spectrum corresponding to the square of the amplitude spectrum may be supplied to the noise suppressor 2305.

The noise suppressor 2305 estimates noise using the noisy signal amplitude spectrum 2330 supplied from the converter 2301, thereby generating an estimated noise spectrum. In addition, the noise suppressor 2305 suppresses the noise using the generated estimated noise spectrum and the noisy signal amplitude spectrum 2330 supplied from the converter 2301, and transmits an enhanced signal amplitude spectrum as a noise suppression result to an amplitude controller 2303. The noise suppressor 2305 also receives a determination result from an abrupt change determiner 2309, and changes the degree of noise suppression in accordance with the presence/absence or degree of an abrupt change in the signal. The noise suppressor 2305 may detect a desired signal and protect the desired signal component for each frequency, and may also replace the amplitude with an estimated background sound if an abrupt signal change exists, and the desired signal component is not detected.

The phase controller 2302 rotates (shifts) the noisy signal phase spectrum 2320 supplied from the converter 2301, and supplies it to an inverter 2304 as an enhanced signal phase spectrum 2340. The phase controller 2302 also transmits the phase rotation amount (shift amount) to the amplitude controller 2303. The amplitude controller 2303 receives the phase rotation amount (shift amount) from the phase controller 2302, calculates an amplitude correction amount, corrects the enhanced signal amplitude spectrum in each frequency using the amplitude correction amount, and supplies a corrected amplitude spectrum 2350 to the inverter 2304. The inverter 2304 performs inversion by compositing the enhanced signal phase spectrum 2340 supplied from the phase controller 2302 and the corrected amplitude spectrum 2350 supplied from the amplitude controller 2303, and supplies the resultant signal to an output terminal 2307 as an enhanced signal.

The calculator 2381 calculates the gradient (change) of the phase at each frequency by differentiating the phase component signal 2320 supplied from the converter 2301 by the frequency. On the other hand, the calculator 2382 receives the noisy signal sample 2370 divided into frames from the converter 2301, calculates the absolute signal value of each frame, and calculates the gradient of the phase in the frequency domain from a time representing a sudden increase. The abrupt change determiner 2309 compares the phase gradients provided by the calculators 2381 and 2382, and based on the similarity of the gradients, determines for each frequency point how likely an abrupt change in the signal exists (presence probability).

As the similarity of the gradients, the absolute difference between the gradient obtained from the time domain signal and the gradient obtained from the frequency domain signal can be used. However, the present invention is not limited to this. The distance between 1 and the value of the ratio of the two gradients or the distance between 1 and a value obtained by normalizing the sum of the gradients by twice of one of them may be used. The presence probability can be obtained, for example, in the following way. First, a positive value is determined as a threshold. When the absolute difference is larger than the threshold, the presence probability is 0. When the absolute difference is equal to 0, the presence probability is 1. A general value of presence probability is defined as a function of the absolute difference. The simplest function is a line. A value proportional to the absolute difference is determined as presence probability. The slope and y-intercept (function value when the absolute difference is 0) of the line are determined so as to meet a boundary condition when the above-described absolute difference equals 0 or 1. As the function, an arbitrary linear or nonlinear function or polynomial may be used.

<<Arrangement of Converter>>

Figure 24:
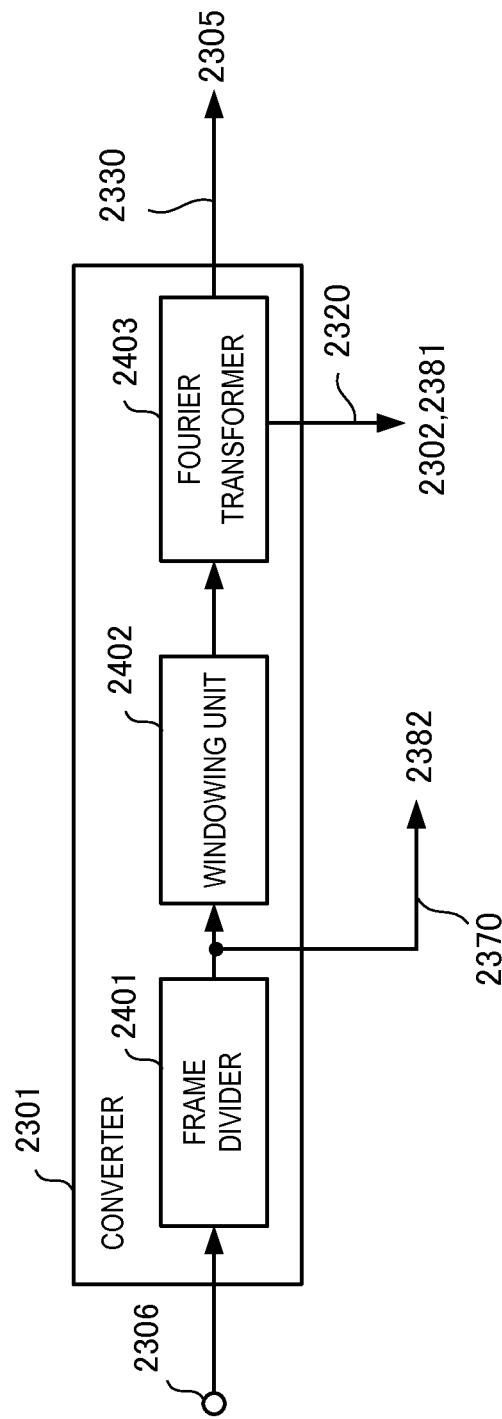
FIG. 24 is a block diagram showing the arrangement of a converter according to the seventh embodiment of the present invention.

FIG. 24 is a block diagram showing the arrangement of the converter 2301. As shown in FIG. 24, the converter 2301 includes a frame divider 2401, a windowing unit 2402, and a Fourier transformer 2403. A noisy signal sample is supplied to the frame divider 2401 and divided into frames on the basis of K/2 samples, where K is an even number. The noisy signal sample 2370 divided into frames is supplied to the windowing unit 2402 and the calculator 2382, and the windowing unit 2402 multiplies the noisy signal sample 2370 by a window function w(t). The signal obtained by windowing an nth frame input signal yn(t) (t=0, 1, ..., K/2-1) by w(t) is given by $$\bar{y}_n(t) = w(t)y_n(t) \quad (1)$$

Two successive frames may partially be overlaid (overlapped) and windowed. Assume that the overlap length is 50% the frame length. For t=0, 1, ..., K/2-1, the windowing unit 2402 outputs the left-hand sides of $$\left.\begin{array}{l}\bar{y}_n(t) = w(t)y_{n-1}(t+K/2)\\ \bar{y}_n(t+K/2) = w(t+K/2)y_n(t)\end{array}\right\} \quad (2)$$

A symmetric window function is used for a real signal. The window function is designed to make the input signal and the output signal match with each other except a calculation error when the output of the converter 2301 is directly supplied to the inverter 2304. This means $w^2(t)+w^2(t+K/2)=1$.

The description will be continued below assuming an example in which windowing is performed for two successive frames that overlap 50%. As w(t), the windowing unit can use, for example, a Hanning window given by $$w(t) = \begin{cases} 0.5 + 0.5\cos\left(\dfrac{\pi(t-K/2)}{K/2}\right), & 0 \le t < K \\ 0, & \text{otherwise} \end{cases} \quad (3)$$

Various window functions such as a Hamming window and a triangle window are also known. The windowed output is supplied to the Fourier transformer 2403 and transformed into a noisy signal spectrum Yn(k). The noisy signal spectrum Yn(k) is separated into the phase and the amplitude. A noisy signal phase spectrum argYn(k) is supplied to the phase controller 2302 and the calculator 2381, whereas a noisy signal amplitude spectrum |Yn(k)| is supplied to the noise suppressor 2305 and the calculator 2382. As already described, a power spectrum may be used in place of the amplitude spectrum.

<<Arrangement of Inverter>>

Figure 25:
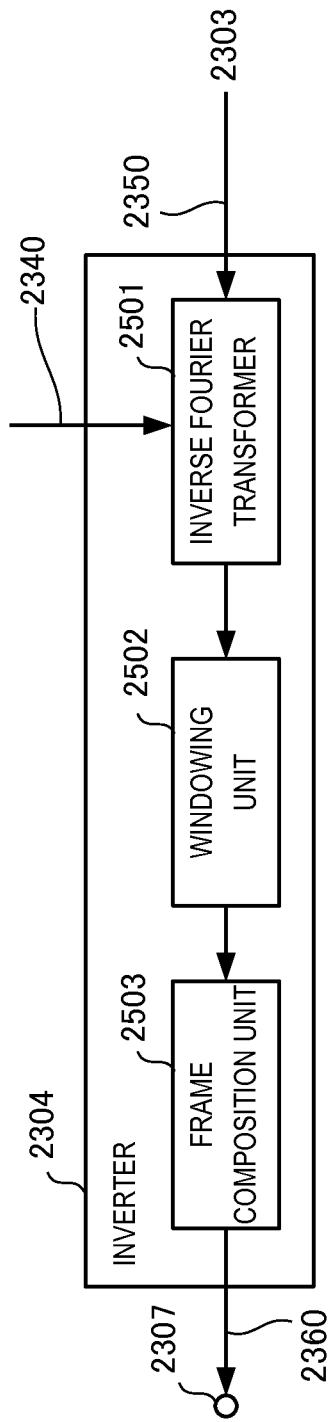
FIG. 25 is a block diagram showing the arrangement of an inverter according to the seventh embodiment of the present invention.

FIG. 25 is a block diagram showing the arrangement of the inverter 2304. As shown in FIG. 25, the inverter 2304 includes an inverse Fourier transformer 2501, a windowing unit 2502, and a frame composition unit 2503. The inverse Fourier transformer 2501 multiplies the enhanced signal amplitude spectrum 2350 supplied from the amplitude controller 2303 by the enhanced signal phase spectrum 2340 (argXn(k)) supplied from the phase controller 2302 to obtain an enhanced signal (the left-hand side of equation below).

$$\overline{X}_n(k) = |\overline{X}_n(k)| \cdot argX_n(k) \quad (4)$$

Inverse Fourier transform is performed for the obtained enhanced signal. The signal is supplied to the windowing unit 2502 as a series of time domain sample values xn(t) (t=0, 1, ..., K-1) in which one frame includes K samples, and multiplied by the window function w(t). A signal obtained by windowing an nth frame input signal xn(t) (t=0, 1, ..., K/2-1) by w(t) is given by the left-hand side of $$\bar{x}_n(t) = w(t)x_n(t) \quad (5)$$

Two successive frames may partially be overlaid (overlapped) and windowed. Assume that the overlap length is 50% the frame length. For t=0, 1, ..., K/2-1, the windowing unit 2502 outputs the left-hand sides of $$\left.\begin{array}{l}\bar{x}_n(t) = w(t)x_{n-1}(t+K/2)\\ \bar{x}_n(t+K/2) = w(t+K/2)x_n(t)\end{array}\right\} \quad (6)$$

and transmits them to the frame composition unit 2503.

The frame composition unit 2503 extracts the outputs of two adjacent frames from the windowing unit 2502 on the basis of K/2 samples, overlays them, and obtains an output signal (left-hand sides) for t=0, 1, ..., K−1 by $$\hat{x}_n(t) + \bar{x}_{n-1}(t+K/2) + \bar{x}_n(t) \qquad (7)$$

An obtained enhanced speech signal 2360 is transmitted from the frame composition unit 2503 to the output terminal 2307.

Note that the conversion in the converter and the inverter in FIGS. 24 and 25 has been described as Fourier transform. However, any other transform such as Hadamard transform, Haar transform, or Wavelet transform may be used in place of the Fourier transform. Haar transform does not need multiplication and can reduce the area of an LSI chip. Wavelet transform can change the time resolution depending on the frequency and is therefore expected to improve the noise suppression effect.

The noise suppressor 2305 may perform actual suppression after a plurality of frequency components obtained by the converter 2301 are integrated. The number of frequency components after integration is smaller than the number of frequency components before integration. More specifically, a common suppression level is obtained for integrated frequency components obtained by integrating the frequency components. The suppression level is commonly used for individual frequency components belonging to the integrated frequency components. At this time, high sound quality can be achieved by integrating more frequency components from the low frequency range where the discrimination capability of hearing characteristics is high to the high frequency range with a poorer capability. When noise suppression is executed after integrating a plurality of frequency components, the number of frequency components to which noise suppression is applied decreases, and the whole calculation amount can be decreased.

<<Arrangement of Noise Suppressor>>

Referring back to FIG. 23, the noise suppressor 2305 estimates noise using the noisy signal amplitude spectrum supplied from the converter 2301 and generates an estimated noise spectrum. The noise suppressor 2305 then obtains a suppression coefficient using the noisy signal amplitude spectrum from the converter 2301 and the generated estimated noise spectrum, multiplies the noisy signal amplitude spectrum by the suppression coefficient, and supplies the resultant spectrum to the amplitude controller 2303 as an enhanced signal amplitude spectrum. In addition, the noise suppressor 2305 receives an abrupt change determination result (information representing whether an abrupt signal change exists) from the abrupt change determiner 2309. If it is determined that an abrupt change exists, a smaller one of the noisy signal amplitude spectrum and the estimated noise spectrum is supplied to the amplitude controller 2303 as an enhanced signal amplitude spectrum. At this time, the noise suppressor 2305 may detect a desired signal and protect the desired signal component for each frequency.

In addition, upon receiving information representing to what extent an abrupt change exists (likelihood that an abrupt signal change exists or presence probability) from the abrupt change determiner 2309, the degree of noise suppression can be changed in accordance with the possibility that an abrupt signal change exists. It is also possible to determine the possibility that an abrupt signal change exists for each frequency component, frequency band (combination of an arbitrary number of continuous frequency components), or frame and perform different signal processing for each frequency component, frequency band, or frame to suppress the abrupt change.

To estimate noise, various estimation methods such as the methods described in non-patent literatures 1 and 2 are usable.

For example, non-patent literature 1 discloses a method of obtaining, as an estimated noise spectrum, the average value of noisy signal amplitude spectra of frames in which no desired signal is generated. In this method, it is necessary to detect the presence of the desired signal. A section where the desired signal exists can be determined by the power of the enhanced signal.

As an ideal operation state, the enhanced signal is the desired signal other than noise. In addition, the level of the desired signal or noise does not largely change between adjacent frames. For these reasons, the enhanced signal level of an immediately preceding frame is used as an index to determine a noise section. If the enhanced signal level of the immediately preceding frame is equal to or smaller than a predetermined value, the current frame is determined as a noise section. A noise spectrum can be estimated by averaging the noisy signal amplitude spectra of frames determined as a noise section.

Non-patent literature 1 also discloses a method of obtaining, as an estimated noise spectrum, the average value of noisy signal amplitude spectra in the early stage in which supply of them has started. In this case, it is necessary to meet a condition that the desired signal is not included immediately after the start of estimation. If the condition is met, the noisy signal amplitude spectrum in the early stage of estimation can be obtained as the estimated noise spectrum.

Non-patent literature 2 discloses a method of obtaining an estimated noise spectrum from the minimum value of the statistical noisy signal amplitude spectrum. In this method, the minimum value of the noisy signal amplitude spectrum within a predetermined time is statistically held, and a noise spectrum is estimated from the minimum value. The minimum value of the noisy signal amplitude spectrum is similar to the shape of a noise spectrum and can therefore be used as the estimated value of the noise spectrum shape. However, the minimum value is smaller than the original noise level. Hence, a spectrum obtained by appropriately amplifying the minimum value is used as an estimated noise spectrum.

The noise suppressor 2305 can perform various kinds of suppression. Typical examples are the SS (Spectrum Subtraction) method and an MMSE STSA (Minimum Mean-Square Error Short-Time Spectral Amplitude Estimator) method. In the SS method, the estimated noise spectrum is subtracted from the noisy signal amplitude spectrum supplied from the converter 2301. In the MMSE STSA method, a suppression coefficient is calculated using the noisy signal amplitude spectrum supplied from the converter 2301 and the generated estimated noise spectrum, and the noisy signal amplitude spectrum is multiplied by the suppression coefficient. The suppression coefficient is decided so as to minimize the mean square power of the enhanced signal.

Additionally, the noise suppressor 2305 receives the abrupt change determination result (information representing whether an abrupt signal change exists) from the abrupt change determiner 2309, and changes the degree of noise suppression in accordance with the presence/absence or degree of an abrupt signal change. For example, signal processing can be performed for each frequency component, frequency band, or frame in which an abrupt signal change has occurred to suppress the abrupt change.

If the abrupt change determiner 2309 determines that an abrupt change exists, a smaller one of the noisy signal amplitude spectrum and the estimated noise spectrum is supplied to the amplitude controller 2303 as an enhanced signal amplitude spectrum. That is, if the noisy signal amplitude spectrum is smaller than the estimated noise spectrum, the noisy signal amplitude spectrum is directly output. Otherwise, the input signal can be replaced with the estimated noise spectrum and output.

It is also possible to, prior to the replacement, detect an important noisy signal amplitude spectrum component and exclude the detected important noisy signal amplitude spectrum component from the component to be replaced with the estimated noise spectrum. As the index of importance when detecting the important noisy signal amplitude spectrum component, the magnitude of the noisy signal amplitude spectrum can be used. A component having a large amplitude is a component of a target signal at a high probability. Holding this component contributes to prevention of a degradation in sound quality of the target signal.

The peak characteristic of the noisy signal amplitude spectrum can also be used as the index of importance. A noisy signal amplitude having a peak, that is, a value larger than peripheral values along the frequency axis is a component of a target signal at a high probability. Holding this component contributes to prevention of a degradation in sound quality of the target signal. In particular, a conspicuous peak, that is, an amplitude value much larger than peripheral amplitude values is important. When this component is reliably protected, sound quality of the target signal can further be increased.

To detect a peak, for example, a pure sound component detection method described in non-patent literature 3 or a method disclosed in non-patent literature 4 is usable. A detected peak may be evaluated in accordance with a predetermined condition, and a peak that does not meet the condition may be excluded. For example, there is little possibility that a peak having a value smaller than the estimated noise is the target signal. That is, it is possible to, using the estimated noise as a reference, leave only peaks much larger than the estimated noise and exclude others. Whether a peak is sufficiently large can be determined by comparing it with a constant multiple of the estimated noise. In this way, it is evaluated whether a detected peak meets a predetermined condition, and final peak components are then selected. This can reduce peak detection errors and enhance the effect of suppressing an abrupt signal change.

It is also possible to change the signal to be supplied to the amplitude controller 2303 in accordance with the likelihood of presence of an abrupt change. The result of replacement and the noisy signal amplitude spectrum are mixed in correspondence with the likelihood of presence of an abrupt change, and the mixture is output as an enhanced signal amplitude spectrum. The mixing processing is executed by adding a large weight to the replacement result as the likelihood of presence of an abrupt change rises.

The noise suppressor 2305 may perform suppression in multiple levels such as suppression level 0, suppression level 1, and suppression level 2 in accordance with the presence probability of an abrupt signal change. Alternatively, the degree of suppression may continuously be changed in accordance with the determination result (for example, numerical values of 0 to 1) of the abrupt change determiner.

<<Arrangement of Phase Controller and Amplitude Controller>>

Figure 26:
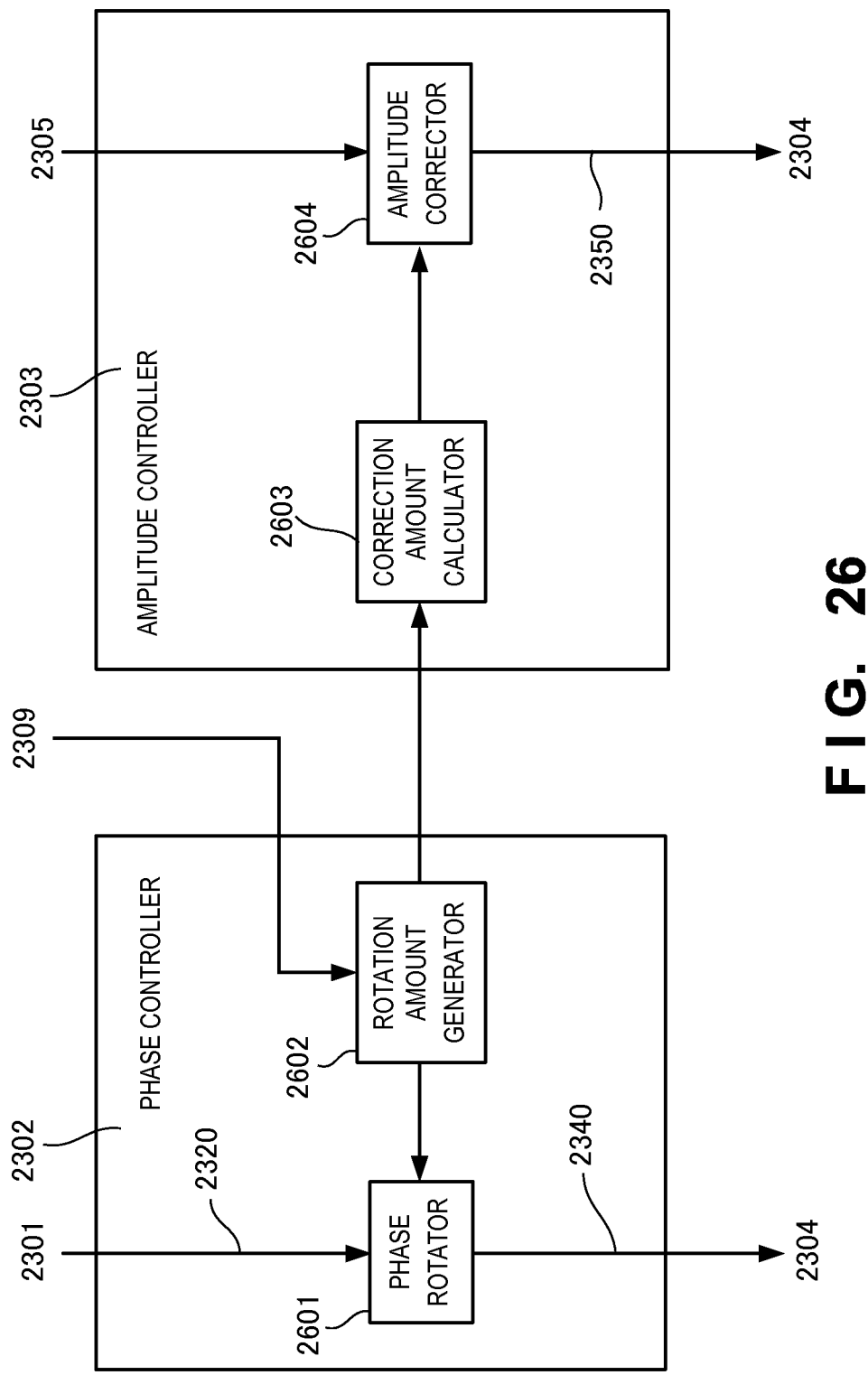
FIG. 26 is a block diagram showing the arrangement of a phase controller and an amplitude controller according to the seventh embodiment of the present invention.

FIG. 26 is a block diagram showing the arrangement of the phase controller 2302 and the amplitude controller 2303. As shown in FIG. 26, the phase controller 2302 includes a phase rotator 2601 and a rotation amount generator 2602, and the amplitude controller 2303 includes a correction amount calculator 2603 and an amplitude corrector 2604.

The rotation amount generator 2602 generates the rotation amount of the noisy signal phase spectrum for a frequency component determined to "have an abrupt change in the signal" by the abrupt change determiner 2309, and supplies the rotation amount to the phase rotator 2601 and the correction amount calculator 2603. Upon receiving the rotation amount supplied from the rotation amount generator 2602, the phase rotator 2601 rotates (shifts) the noisy signal phase spectrum 2320 supplied from the converter 2301 by the supplied rotation amount, and supplies the rotated spectrum to the inverter 2304 as the enhanced signal phase spectrum 2340.

The correction amount calculator 2603 decides the correction coefficient of the amplitude based on the rotation amount supplied from the rotation amount generator 2602, and supplies the correction coefficient to the amplitude corrector 2604.

The rotation amount generator 2602 generates the rotation amount by, for example, a random number. When the noisy signal phase spectrum is rotated for each frequency by a random number, the shape of the noisy signal phase spectrum 2320 changes. With the change in the shape, the feature of an abrupt signal change such as an impulsive sound can be weakened.

Examples of the random number are a uniform random number whose occurrence probability is uniform and a normal random number whose occurrence probability exhibits a normal distribution. A rotation amount generation method using a uniform random number will be described first. A uniform random number can be generated by a linear congruential method or the like. For example, uniform random numbers generated by the linear congruential method are uniformly distributed within the range of 0 to (2^M)−1, where M is an arbitrary integer, and ^ represents a power. Phase rotation amounts $\phi$ need to be distributed within the range of 0 to $2\pi$. To do this, the generated uniform random numbers are converted. The conversion is performed by $$\phi = 2\pi \frac{R}{R_{max}} \quad (8)$$

where R is the uniform random number, and Rmax is the maximum value capable of being generated by the uniform random number. When a uniform random number is generated by the above-described linear congruential method, Rmax=(2^M)−1.

To simplify the calculation, the value R may directly be decided as the rotation amount. As the rotation amount, $2\pi$ represents just one revolution. A case where the phase is rotated by $2\pi$ is equivalent to a case where the phase is not rotated. Hence, a rotation amount $2\pi+\alpha$ is equivalent to a rotation amount $\alpha$. A case where a uniform random number is generated by the linear congruential method has been explained here. Even in a case where a uniform random number is generated by another method, the rotation amount $\phi$ is obtained by the above equation. When and how many times random number generation is to be performed may be decided in accordance with the determination result of the abrupt change determiner 2309.

The phase rotator 2601 receives the rotation amount from the rotation amount generator 2602 and rotates the noisy signal phase spectrum. If the noisy signal phase spectrum is expressed as an angle, it can be rotated by adding the value of the rotation amount φ to the angle. If the noisy signal phase spectrum is expressed as the normal vector of a complex number, it can be rotated by obtaining the normal vector of the rotation amount φ and multiplying the noisy signal phase spectrum by the normal vector.

The normal vector of the rotation amount φ can be obtained by $$\Phi = \cos(\phi) + j \sin(\phi) \quad (9)$$

In equation (9), Φ is the rotation vector, and j represents sqrt(−1). Note that sqrt is the square root.

A correction coefficient calculation method by the correction amount calculator 2603 is the same as the method described concerning the correction amount calculator 503 shown in FIG. 5, and a description thereof will be omitted.

<<Arrangement of Calculators and Abrupt Change Determiner>>

Figure 27:
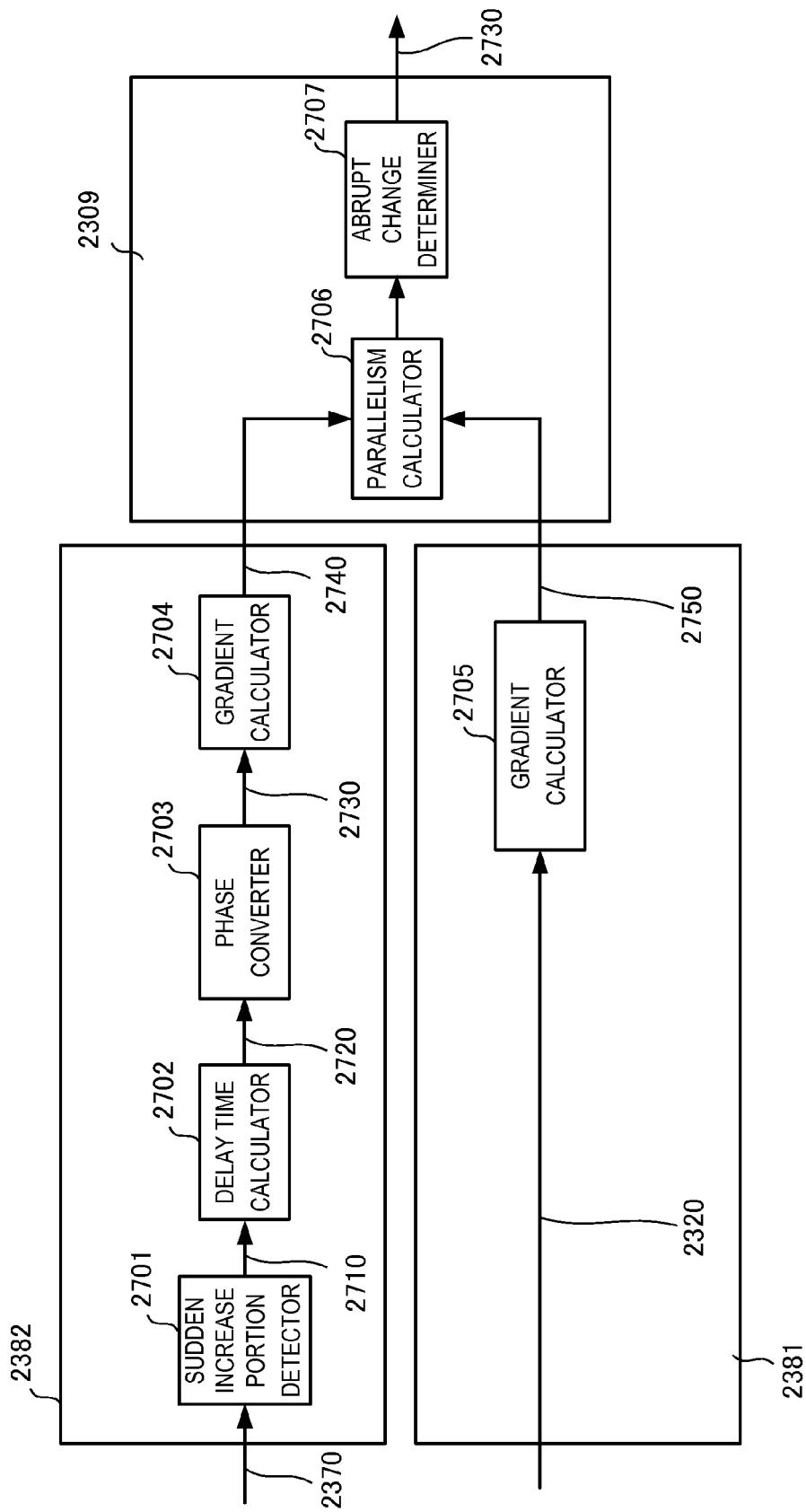
FIG. 27 is a block diagram for explaining the arrangement of a calculator and an abrupt change determiner according to the seventh embodiment of the present invention.

FIG. 27 is a block diagram for explaining the internal arrangement of the calculators 2381 and 2382 and the abrupt change determiner 2309. As shown in FIG. 27, the calculator 2382 includes a sudden increase detector 2701, a delay time calculator 2702, a phase converter 2703, and a gradient calculator 2704. On the other hand, the calculator 2381 includes a gradient calculator 2705.

The sudden increase detector 2701 calculates the absolute value of the signal in a frame, and detects a maximum value 2710 of the absolute value. The delay time calculator 2702 outputs a relative position representing the maximum value in the frame (time from the start of the frame to the timing at which the maximum value exists) as n0.

Next, the phase converter 2703 converts a delay time n0 2720 into a phase in the frequency domain. More specifically, conversion is performed based on the following equation. Here, L is the frame length of the converter 2301, and $0 \le n0 \le L-1$. Assume that the input is an isolated pulse having an amplitude a. Then, a kth frequency component D(k) obtained by Fourier transform is given by $D(k) = a \cdot \exp(-j\theta(k))\theta(k) = -2\pi \cdot k \cdot n0/L$.

The gradient calculator 2704 differentiates a thus derived phase 2730 to derive a gradient 2740 of the phase in the frequency domain as gradient $2740 = -2\pi \cdot n0/L$.

On the other hand, the gradient calculator 2705 differentiates the phase component signal input from the converter 2301 to derive a gradient 2750 of the phase in the frequency domain. Each of the gradient calculators 2704 and 2705 may calculate the gradient by differentiation using the frequency of the phase or by another method.

A parallelism calculator 2706 compares the gradient 2740 provided by the gradient calculator 2704 with the gradient 2750 provided by the gradient calculator 2705 on a frequency basis, and calculates the similarity of the gradients. That is, the parallelism of the line calculated by the calculator 2381 for the phase component signal in the frequency domain with respect to the line calculated by the calculator 2382 is calculated on a frequency basis. If the parallelism exceeds a predetermined value, an abrupt change determiner 2707 determines that an abrupt signal change exists at the frequency.

If the determination is done not for each frequency but for each frequency band (sub-band) or frame, determination errors by phase components other than abrupt signal change components can be reduced by determination in boarder aspects. In addition, the determination result for each frequency may be corrected using the determination result for each frequency band or frame. For example, if the determination result for a certain frequency band indicates that "an abrupt signal change exists", the determination result for all frequencies within the frequency band is forcibly set to "an abrupt signal change exists", thereby reducing determination errors caused by disturbance of other signal components. To the contrary, if the determination result for a certain frequency band indicates that "no abrupt signal change exists", the determination result for all frequencies within the frequency band is forcibly set to "no abrupt signal change exists", thereby reducing determination errors caused by disturbance of other signal components. Alternatively, the ease (threshold) of determination for each frequency within the band may be corrected in a direction to easily determine "presence", and the configuration for independently performing determination for each frequency may be maintained in itself. When the determination result is obtained for each frequency or frequency band, an abrupt change can be suppressed for each frequency or frequency band. Hence, more accurate abrupt signal change suppression can be performed.

The abrupt change determiner 2309 outputs abrupt signal change present (1) or abrupt signal change absent (0) as the determination result 2730. However, if the abrupt change determiner 2707 outputs a value between 0 and 1 associated with the parallelism as the abrupt change presence probability, the determination result 2730 is the value between 0 and 1, which represents the abrupt change presence probability. In this case, likelihood (abrupt change presence probability) of inclusion of an abrupt signal change can be obtained. The presence probability can be obtained, for example, in the following way. First, each of the gradients 2740 and 2750 is converted into an angle corresponding to the gradient using an arctangent. The angle is assumed to range from −90° to 90°. The closer to 0 the absolute difference between the two angles is, the higher the abrupt signal change presence probability is. The maximum value of the absolute difference between the two angles is 180°. Hence, a positive value is determined as a threshold. When the difference between the two angles exceeds the threshold, the abrupt signal change presence probability is 0. When the difference between the angles is 0, the presence probability is 1. A general value of presence probability is defined as a function of the angle difference. The simplest function is a line. A value proportional to the difference between the two angles is determined as presence probability. The slope and y-intercept (function value when the difference between the two angles is 0) of the line are determined so as to meet a boundary condition when the angle difference equals 0 or 1. As the function, an arbitrary linear or nonlinear function or polynomial may be used.

FIG. 28 is a graph showing a phase and its change amount. When the phase changes along the frequency axis in the frequency domain, like a graph 2801, the phase change amount changes as indicated by a graph 2802 along the frequency axis in the frequency domain.

On the other hand, a phase represented by a line 2803 in the frequency domain can be calculated from the intra-frame relative position of the sudden increase.

In this embodiment, the presence of an abrupt signal change is determined based on to what extent a portion where the phase component signal 2801 and the line 2803 are parallel exists.

When the phase gradient is plotted along the ordinate, and the frequency is plotted along the abscissa, a range approximate to the slope of the line 2803 is represented by a range 2804. Hence, if the overlap between the range 2804 and the graph 2802 is larger than a predetermined threshold, the abrupt change determiner 2309 determines that an abrupt change in the signal exists.

Figure 29:
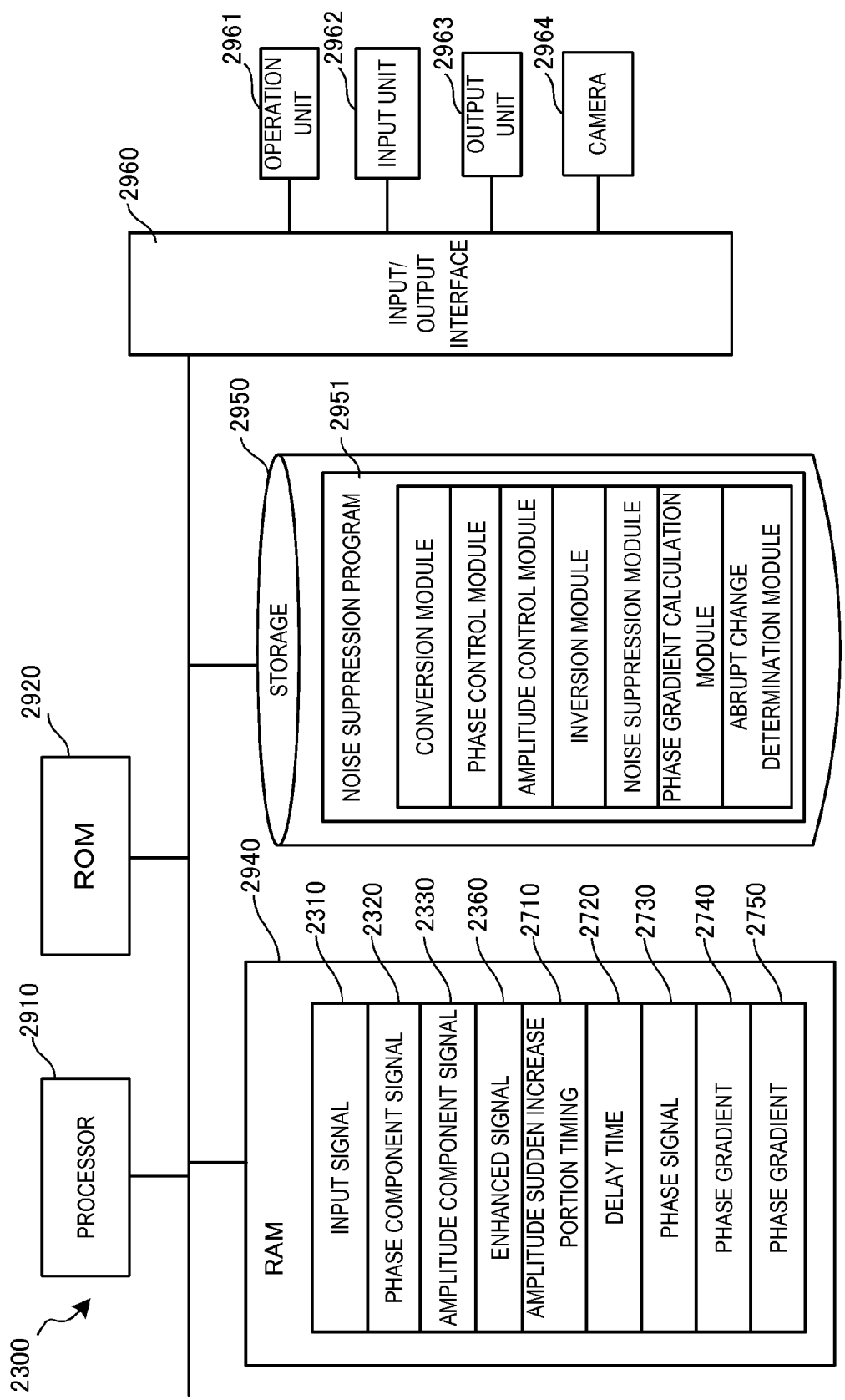
FIG. 29 is a block diagram showing the hardware arrangement of the noise suppression apparatus according to the seventh embodiment of the present invention.

FIG. 29 is a block diagram for explaining a hardware arrangement when the noise suppression apparatus 2300 according to this embodiment is implemented using software.

The noise suppression apparatus 2300 includes a processor 2910, a ROM (Read Only Memory) 2920, a RAM (Random Access Memory) 2940, a storage 2950, an input/output interface 2960, an operation unit 2961, an input unit 2962, and an output unit 2963. The noise suppression apparatus 2300 may include a camera 2964. The processor 2910 is a central processing unit and executes various programs, thereby controlling the overall noise suppression apparatus 2300.

The ROM 2920 stores various parameters as well as a boot program to be executed first by the processor 2910. The RAM 2940 includes an area to store an input signal 2310, the phase component signal 2320, the amplitude component signal 2330, and the enhanced signal 2360 as well as a program load area (not shown). In addition, the RAM 2940 includes an area to store the maximum amplitude value timing 2710, the delay time 2720, the phase signal 2730, the phase gradients 2740 and 2750, and the like.

The storage 2950 stores a noise suppression program 2951. The noise suppression program 2951 includes a conversion module, a phase control module, an amplitude control module, an inversion module, a noise suppression module, a phase gradient calculation module, and an abrupt change determination module. When the processor 2910 executes the modules included in the noise suppression program 2951, the functions of the converter 2301, the phase controller 2302, the amplitude controller 2303, the inverter 2304, the noise suppressor 2305, the calculators 2381 and 2382, and the abrupt change determiner 2309 shown in FIG. 23 can be implemented. Note that the storage 2950 may store a noise database.

An enhanced signal that is the output concerning the noise suppression program 2951 executed by the processor 2910 is output from the output unit 2963 via the input/output interface 2960. This can suppress, for example, the operation sound of the operation unit 2961 input from the input unit 2962. Also possible is an application method of, for example, detecting abrupt signal change inclusion in the input signal input from the input unit 2962 and starting shooting by the camera 2964.

Figure 30A:
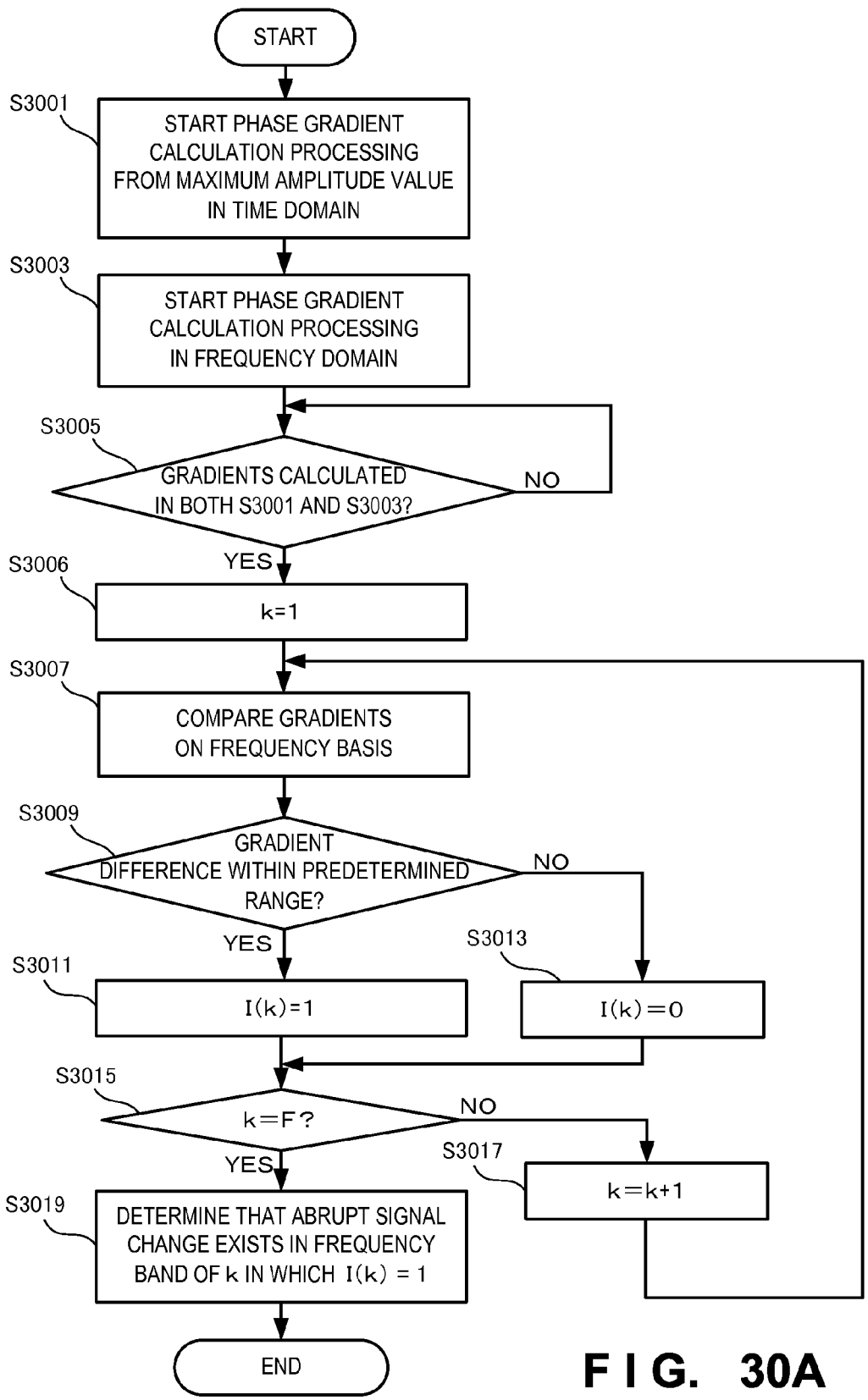
FIG. 30A is a flowchart for explaining the procedure of processing of the noise suppression apparatus according to the seventh embodiment of the present invention.

FIG. 30A is a flowchart for explaining the procedure of abrupt signal change determination processing of the noise suppression program 2951. In step S3001, the calculator 2382 starts phase gradient calculation processing from the maximum amplitude value in the time domain. In step S3003, the calculator 2381 starts phase gradient calculation processing in the frequency domain.

In step S3005, the process waits until gradients are calculated in both of steps S3001 and S3003. When the gradients can be calculated by both methods, the process advances to step S3007 to compare the calculated gradients on a frequency basis. In step S3009, it is determined whether the absolute difference between the gradients is equal to or smaller than the predetermined threshold N. If the absolute difference is N or less, the process advances to step S3011 to set a flag (set I(k)=1) for the frequency k. On the other hand, if the absolute difference is not N or less, I(k)=0 is set in step S3013. In step S3015, it is determined whether k=F (F is the number of frequency components in the entire frame). If k≠F, the process advances to step S3017 to set k=k+1. The process then returns to step S3007 to compare the gradients on a frequency basis throughout the frame. Finally in step S3019, it is determined that an abrupt signal change exists at the frequency k when I(k)=1, and the determination result is supplied to the noise suppressor 2305 and the phase controller 2302. Note that in place of step S3019, I(k) may be integrated in the frame, and the integral value of I(k) exceeds a predetermined threshold, the abrupt change determiner 2309 may determine that the frame includes an abrupt signal change. At this time, the abrupt change determination result may be hanged over and integrated in the next frequency band.

As a hangover function, the threshold N in the next frame may be set large. When the thresholds in the next frame are thus set, it is possible to easily detect an abrupt signal change (for example, impulsive sound) and reduce detection omissions.

Figure 30B:
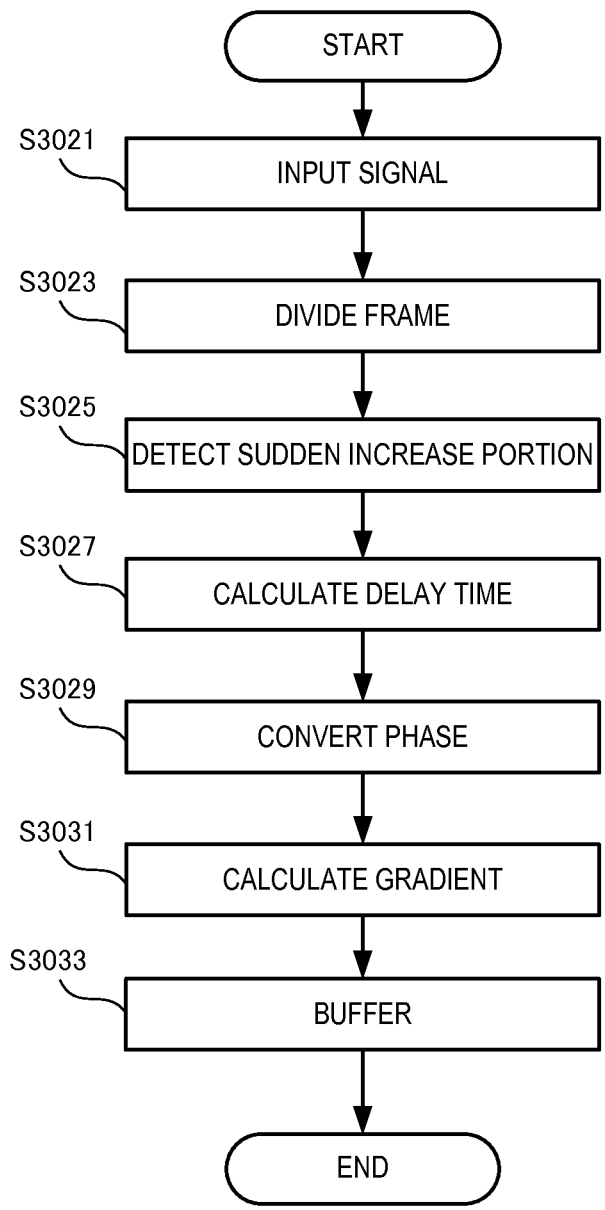
FIG. 30B is a flowchart for explaining the procedure of processing of the noise suppression apparatus according to the seventh embodiment of the present invention.

FIG. 30B is a flowchart for explaining the procedure of gradient calculation processing performed by the calculator 2382. When a signal is input in step S3021, the process advances to step S3023, and the frame divider 2401 divides a frame. In step S3025, the sudden increase detector 2701 detects a sudden increase of a low correlation signal. In step S3027, the delay time calculator 2702 outputs the intra-frame relative position of the sudden increase (time from the start of the frame to the timing at which the sudden increase exists) as n0.

In step S3029, the phase converter 2703 converts the delay time n0 2720 into a phase in the frequency domain. The gradient calculator 2704 differentiates the derived phase to derive the gradient of the phase in the frequency domain in step S3031, and buffers it in step S3033.

FIG. 30C is a flowchart for explaining the procedure of gradient calculation processing performed by the calculator 2381. When a signal is input in step S3051, the process advances to step S3053. After frame division and windowing, Fourier transform is performed to extract the phase component signal in the frequency domain. In step S3055, the step k of the frequency is set to 1. In step S3057, the phase p(k) is differentiated to calculate the gradient ΔP(k). In step S3059, the gradient is buffered. In step S3061, it is determined whether k=F (F is the number of frequency components in the entire frame). If k≠F, the process advances to step S3063 to set k=k+1. The process then returns to step S3057 to calculate the gradient on a frequency basis throughout the frame.

With the above-described processing, an abrupt signal change can more correctly be detected, and the abrupt change can appropriately be suppressed as needed. Note that in this embodiment, the phase gradient is obtained as a differential value. However, another index such as the rotation amount of a unit vector may be obtained and used for determination.

Eighth Embodiment

Figure 31:
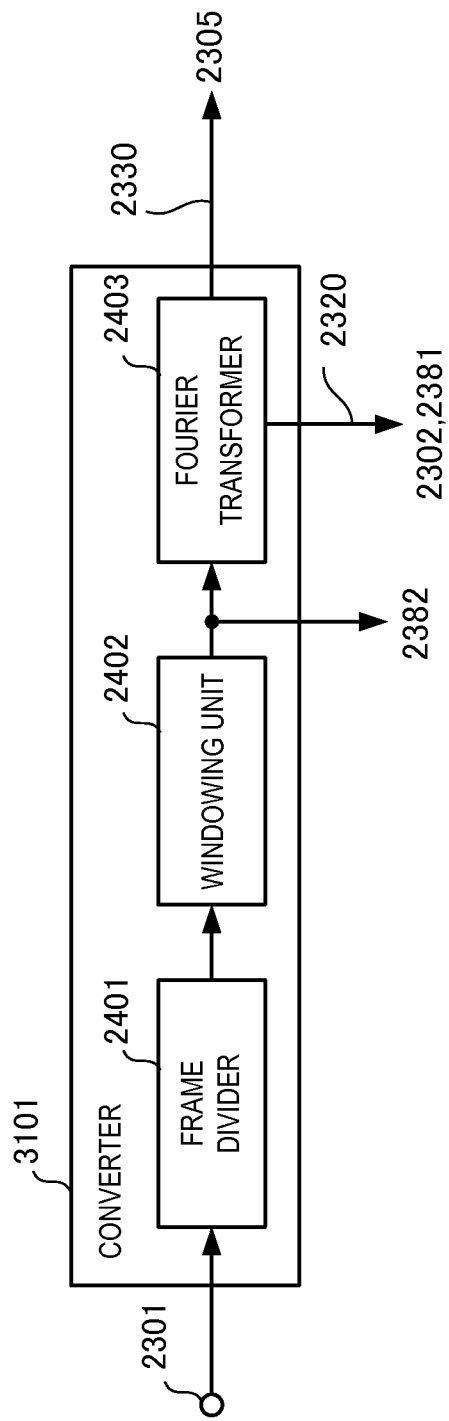
FIG. 31 is a block diagram showing the arrangement of a converter according to the eighth embodiment of the present invention.

A noise suppression apparatus according to the eighth embodiment of the present invention will be described with reference to FIG. 31. FIG. 31 is a block diagram for explaining the functional arrangement of the noise suppression apparatus according to this embodiment. The noise suppression apparatus according to this embodiment is different from the seventh embodiment in that in a converter 3101, a signal after windowing by a windowing unit 2402 is output to a calculator 2382. The rest of the components and operations is the same as in the seventh embodiment. Hence, the same reference numerals denote the same components and operations, and a detailed description thereof will be omitted.

According to this embodiment, a parallelism can be obtained using a gradient obtained from a time domain signal after windowing, that is, the same signal as that used for Fourier transform. The degree of matching with a phase obtained using a frequency domain signal is thus raised, and an abrupt signal change can more correctly be determined.

Ninth Embodiment

Figure 32:
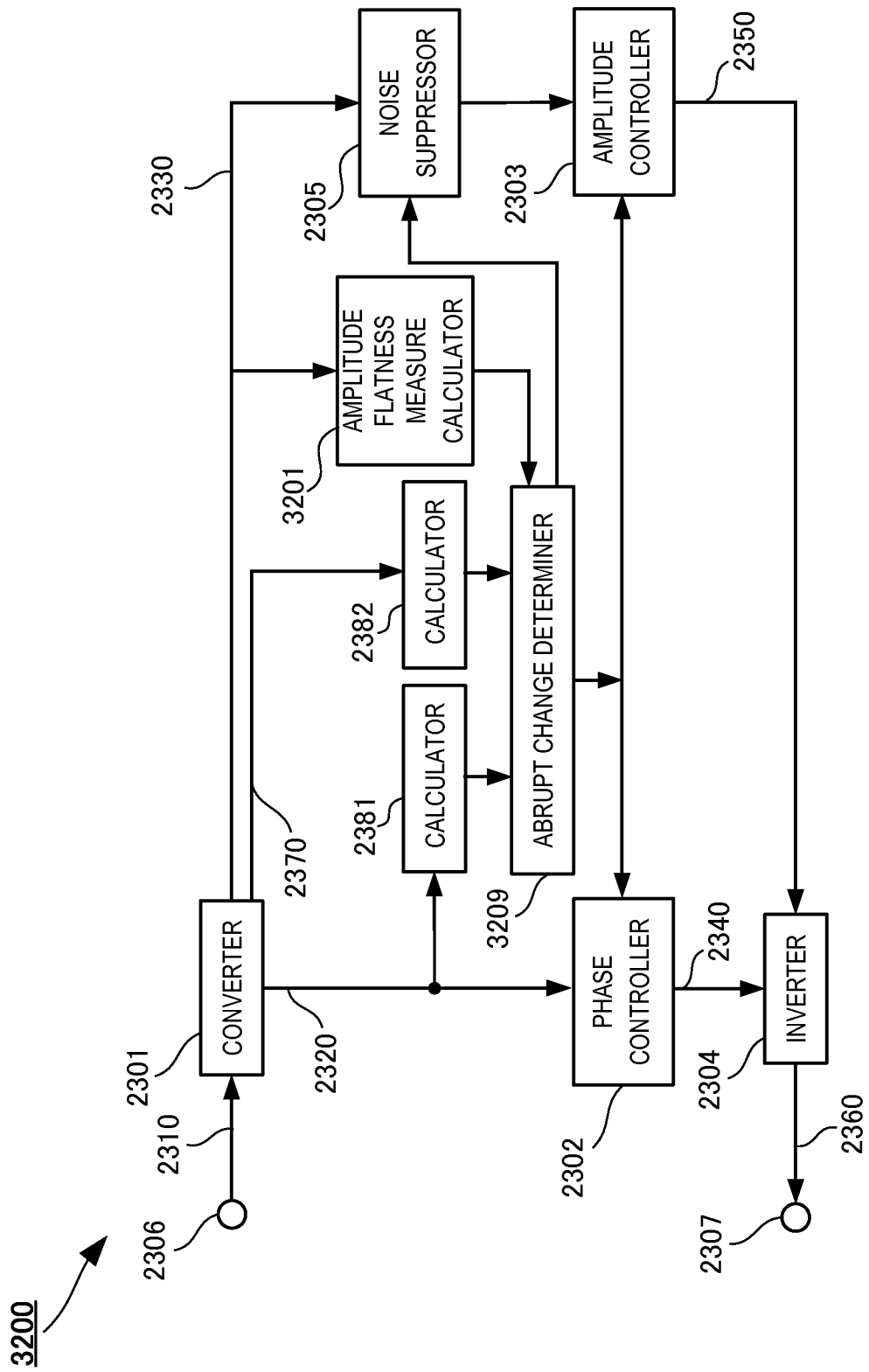
FIG. 32 is a block diagram showing the arrangement of a noise suppression apparatus according to the ninth embodiment of the present invention.

A noise suppression apparatus 3200 according to the ninth embodiment of the present invention will be described next with reference to FIG. 32. FIG. 32 is a block diagram for explaining the functional arrangement of the noise suppression apparatus 3200 according to this embodiment. The noise suppression apparatus 3200 according to this embodiment is different from the seventh embodiment in that an amplitude flatness measure calculator 3201 is additionally provided. The rest of the components and operations is the same as in the second embodiment. Hence, the same reference numerals denote the same components and operations, and a detailed description thereof will be omitted.

The amplitude flatness measure calculator 3201 calculates an amplitude change along the frequency axis and supplies it to an abrupt change determiner 3209. A frequency whose amplitude change with respect to an adjacent frequency is small represents an abrupt signal change. As the amplitude change, one flatness measure may be obtained for each band or all frequencies. More specifically, FM (Flatness Measure) representing a flatness measure is obtained by $$FM = \frac{\sqrt[N]{\prod_{n=0}^{N-1} x(n)}}{\frac{\sum_{n=0}^{N-1} x(n)}{N}} = \frac{\exp\left(\frac{1}{N}\sum_{n=0}^{N-1} \ln x(n)\right)}{\frac{1}{N}\sum_{n=0}^{N-1} x(n)} \quad (46)$$

where x(n) is the amplitude or power spectrum at a frequency n, and N is the number of frequency components included in the flatness measure calculation section.

FM takes a value of 0.0 to 1.0. If the amplitude is completely flat, FM is 1.0. The flatness measure is disclosed in non-patent literature 3.

The flatness measure can also be expressed using another index.

For example, it is possible to obtain the average of x(n) for each band or all frequencies and calculate the sum of squared differences of x(n) of each frequency component n and the average value as the flatness measure for each band or all frequencies. One sum of squared differences may be obtained not for all frequencies but in a single or a plurality of frequency bands and used as the flatness measure. The thus obtained flatness measure has a value of 0.0 if the amplitude is completely flat, and takes a larger vale as the flatness measure lowers.

A smoothness may be used as another index of the flatness measure. The smoothness can be expressed as the sum of absolute differences between adjacent samples along the frequency axis. The smoothness takes a large value for a waveform having large unevenness (not smooth), and a small value for a waveform having small unevenness (smooth). This index is known as TV (Total Variation).

As the flatness measure, a flatness measure along the frequency axis is used above. However, a flatness measure along the time axis is also usable. At an abrupt signal change, the amplitude and power abruptly increase. Using this characteristic, an abrupt signal change can be determined to exist when the flatness measure along the time axis is low. More specifically, if the amplitude or power difference between the current frame and the immediately preceding frame is a predetermined value or more, it is determined that the flatness measure is low, that is, an abrupt signal change exists. Alternatively, the amplitude or power difference between adjacent frames may be obtained for a plurality of frames including several past frames and the current frame, and the result of linearly or nonlinearly combining the differences may be defined as the flatness measure. When the information of the past frames is used, a dulled abrupt signal change including low frequency components can easily be detected, and the suppression performance can be improved. Note that when calculating the amplitude or power difference between adjacent frames, the calculation may be done for each frequency component, band, or all frequencies. The amplitude or power difference can also be calculated for a single or a plurality of bands. For example, when the amplitude or power difference can also be calculated in a single band, particularly, in a high frequency band, the influence of speech and other signals can be reduced, and the abrupt signal change can more correctly be detected.

The above-described two flatness measures, that is, the flatness measure along the frequency axis and the flatness measure along the time axis can be used solely or in combination. As examples of combination, an abrupt signal change is detected based on linear or nonlinear combination of the two flatness measures, or detection results based on the flatness measures are combined. It is determined that an abrupt signal change is detected when the flatness measure in the frequency direction is large or the flatness measure in the time direction is small. Hence, when combining, a contrivance such as changing one of the flatness measures to a reciprocal is needed.

The essential function of the amplitude flatness measure calculator 3201 is to obtain the presence probability of an abrupt signal change using amplitude information, and another method may be used as a substitute.

A technique of detecting an abrupt signal change using amplitude information is disclosed in non-patent literature 6, non-patent literature 7, non-patent literature 8, and the like.

The abrupt change determiner 3209 determines an abrupt change in the signal using two indices, that is, a gradient similarity (parallelism) and an amplitude flatness measure. This is because when the amplitude is flat (variation is small) along the frequency axis, an abrupt signal change is assumed to exist at a high possibility. This is self-evident from the fact that the abrupt signal change is impulsive (the amplitude increases and decreases in a short time), and the Fourier transform of the impulse yields a white signal (the amplitude and power are equal throughout the frequencies). As the determination method, for example, one of the following methods can be selected.

(1) If both the parallelism and the amplitude flatness measure meet corresponding conditions (for example, the gradient difference value is N=0.1 or less, and the amplitude flatness measure FM is M=0.8 or more), it is determined that an abrupt change in the signal exists.

(1.5) The OR of determination results obtained by solely using the parallelism and the amplitude flatness measure is used. To calculate presence probability of an abrupt signal change, determination is performed based on a larger one (or smaller one) of presence probability by the parallelism and presence probability by the amplitude flatness measure.

(2) If the average of the parallelism and the amplitude flatness measure meets a condition (for example, an average AV1 of a gradient difference value PX of the phase and a difference value QX between 1.0 and the amplitude flatness measure FM, that is, QX=(1.0−FM) is AV1=(PX+QX)/2=0.1 or less), it is determined that an abrupt change in the signal exists.

(3) If a value obtained by combining the gradient difference value and the amplitude flatness measure while adding weights to them meets a compound condition (for example, a weighted average AV2 of the gradient difference value PX and the difference value between 1.0 and the amplitude flatness measure FM, that is, QX=(1.0−FM) is AV2=(0.8×PX+0.2×QX)=0.1 or less), it is determined that an abrupt change in the signal exists.

(4) The gradient difference value and the amplitude flatness measure are combined using a linear or nonlinear function, and the result of combination is larger than a predetermined value, it is determined that an abrupt change in the signal exists. If an amplitude flatness measure in the time direction is included, its reciprocal is used in place of the amplitude flatness measure.

(5) Only one of the gradient difference value and the amplitude flatness measure closer to an ideal value (the difference value as a smaller value, and the flatness measure as a larger value) is used, and if the value closer to the ideal value meets a condition, it is determined that an abrupt change in the signal exists. If an amplitude flatness measure in the time direction is included, its reciprocal is used in place of the amplitude flatness measure.

(6) If information about the amplitude or power spectrum of an abrupt change signal to be detected is obtained in advance, and the amplitude or power spectrum is flat, the weight of the gradient difference value is made small.

(7) If information about the amplitude or power spectrum of an abrupt change signal to be detected is obtained in advance, and the amplitude or power spectrum of the input noisy signal is smaller than the minimum value of the amplitude or power spectrum, the threshold used to detect an abrupt signal change is temporarily largely changed to make detection hard.

When processing a specific signal, for example, when detecting/suppressing an impulsive sound of small noise close to an impulse, information about the amplitude or power is sometimes more reliable than phase information. For example, when detecting a gunshot of a pistol in a quiet environment, the detection may be performed using only the amplitude. On the other hand, when the amplitude or power spectrum of noise largely changes, for example, when detecting a gunshot in airport security, it is effective to change the weights of the amplitude and phase between a quiet situation (with small noise) and a situation with large noise. In this case, the weights of the amplitude and phase may be changed in accordance with the presence/absence of noise or time zone. For example, if the latest information of flight schedule can be acquired from the control tower, the takeoff and landing times of airplanes are known. Hence, at a timing of airplane arrival (timing with much noise), the phase to which a large weight is added can be used to detect a gunshot. This is because in a case where signals other than a gunshot (impulsive sound to be detected) coexist, impulsive sound detection using phase information is more effective than detection using an amplitude.

On the other hand, in a situation with small noise, the impulsive sound can effectively be detected by performing determination while attaching importance to the absolute value of the frequency domain vector, that is, the amplitude value of an input noisy signal. In this case as well, the power spectrum value may be used in place of the amplitude spectrum, as a matter of course. The amplitude of the impulsive sound is not flat in some cases depending on the type of the signal. In this case, when detection is performed while making the weight of the phase flatness measure large, an abrupt change in the signal can accurately be detected. If information about the amplitude or power spectrum of an impulsive sound is obtained in advance, the amplitude flatness measure calculation result can be corrected using the obtained information so as to obtain the same result as in a case where the amplitude is flat. More specifically, the amplitude flatness measure is calculated after an amplitude spectrum 2330 is multiplied for each frequency component by the reciprocal of the amplitude or power spectrum shape of an impulsive sound.

As described above, according to this embodiment, an abrupt signal change can be detected using the amplitude flatness measure together. With this processing, an abrupt signal change (impulsive sound) can more correctly be detected, and the abrupt signal change (impulsive sound) can appropriately be suppressed as needed.

10th Embodiment

Note that in the sixth to ninth embodiments, a case where an abrupt signal change detection method is applied to a noise suppression apparatus aiming at suppressing an abrupt signal change has been described. However, the present invention is not limited to this. The abrupt signal change detection method is usable in various apparatuses, systems, and situations aiming at detecting an impulsive sound (a signal that abruptly rises and immediately falls). A signal that abruptly rises (or falls) and remains intact can also be detected as an abrupt change.

For example, a present audio encoding method (for example, encoder of MPEG AAC) employs a different information compression method at an abrupt signal change called an attack. At the abrupt signal change, the analysis window length is changed, and preceding noise called a pre-echo is suppressed. Hence, the abrupt signal change needs to be detected. As compared to a method of doing detection using a change in the amplitude or entropy, it is possible to accurately detect an abrupt change and effectively compress information.

Figure 33:
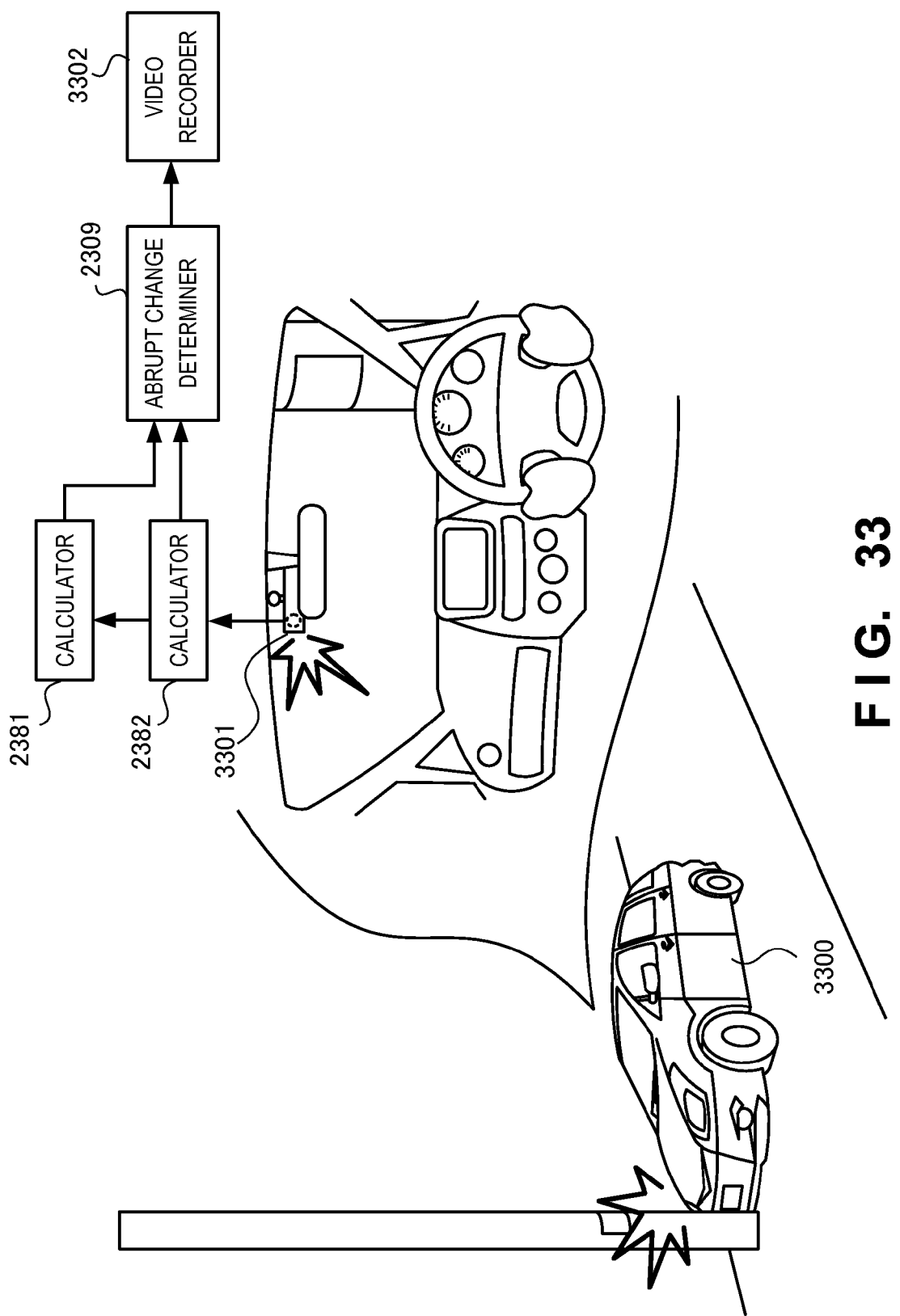
FIG. 33 is a view for explaining an application example according to the 10th embodiment of the present invention.

It is also possible to assume an application example in which a microphone 3301, calculators 2381 and 2382, an abrupt change determiner 2309, and a video recorder 3302 are provided aboard a vehicle 3300, as shown in FIG. 33. Triggered by impulsive sound detection, the video recorder 3302 prohibits an image shot by a camera from being overwritten and saved, thereby leaving the record of an accident situation. At this time, overwrite saving may be prohibited after a delay of a predetermined time from impulsive sound detection. Unlike a case where an impulsive sound itself is used as a trigger, an accident situation can automatically be recorded even when the impact is small, or another vehicle is involved in an accident.

Also assume an application example in which the calculators 2381 and 2382, the abrupt change determiner 2309, and an alarm unit 3401 are connected to an electrocardiograph 3400, as shown in FIG. 34. It is possible to more correctly and effectively detect an abnormal heartbeat in an electrocardiogram. In particular, this configuration is effective in a case where much noise is included. This method is also applicable to monitor the echo of an embryo. In some cases, a heart sound cannot correctly be monitored due to disturbance of noise. This technique is effective in such a case. That is, the technique is widely applicable to detect an abrupt change in a biomedical signal.

11th Embodiment

A signal processing apparatus 3500 according to the 11th embodiment of the present invention will be described with reference to FIG. 35. The signal processing apparatus 3500 is an apparatus for detecting an abrupt input signal change. As shown in FIG. 35, the signal processing apparatus 3500 includes a converter 3501, a correlation remover 3502, and an abrupt signal change determiner 3504.

The converter 3501 converts an input signal 3510 into a phase component signal 3520 and an amplitude component signal 3530 in a frequency domain.

The correlation remover 3502 removes a component with time correlation included in the input signal 3510, thereby generating a low correlation signal 3550 whose time correlation is smaller than that of the input signal 3510.

A component that forms an abrupt signal change cannot be predicted based on a past signal, and has a small time correlation. On the other hand, the correlation remover 3502 removes a component having a large time correlation other than the abrupt signal change component, and enhances the abrupt signal change component.

Correlation removal normally includes two processes, that is, correlation component prediction and output calculation by subtracting a predicted signal from an input signal. Prediction can be representing by linear combination of past signal samples. As the weight coefficient of linear combination, that is, the coefficient of a prediction filter, a Levinson-Durbin method, a covariance method, a least square method, and the like are known. A thus obtained prediction filter coefficient minimizes a prediction error.

The abrupt change determiner 3504 determines an abrupt change included in the input signal 3510 based on the low correlation signal 3550 and the phase component signal 3520.

With the above-described arrangement, since the low correlation signal corresponding to an abrupt signal change and the phase component signal are used, an abrupt change in the input signal can effectively be detected.

12th Embodiment

A signal processing apparatus 3600 according to the 12th embodiment of the present invention will be described with reference to FIG. 36. The signal processing apparatus 3600 is an apparatus for detecting an abrupt input signal change. As shown in FIG. 36, the signal processing apparatus 3600 includes a converter 3601, a correlation remover 3602, a first calculator 3603, a second calculator 3605, and an abrupt signal change determiner 3609.

The converter 3601 converts an input signal 3610 into a phase component signal 3620 and an amplitude component signal 3630 in a frequency domain. The correlation remover 3602 removes a component with time correlation included in the input signal 3610 to generate a low correlation signal 3640 whose time correlation is smaller than that of the input signal 3610, and supplies it to the first calculator 3603. The first calculator 3603 calculates a gradient 3650 of a phase based on the position of a sudden increase of the low correlation signal 3640 in the time domain. The gradient of the phase in the frequency direction when an isolated pulse is Fourier-transformed is known to be obtained uniquely in correspondence with the position of the isolated pulse. For example, if the frame length in the converter corresponds to N samples, and the isolated pulse position is n0, the phase gradient is $-2\pi n0/N$. As an index to identify a sudden increase, for example, the maximum value of the absolute amplitude can be used. This index gives a correct position if an actual signal is close to an isolated pulse (having an almost unimodal shape). On the other hand, if a pulse has a bimodal shape, the maximum amplitude value does not give a correct position. In this case, an index using the maximum value of the absolute amplitude and the second largest value of the absolute amplitude is effective. For example, the intermediate value between the two values or the weighted average of the positions of the two values is usable. If the pulse more spreads along the time axis, the correct position can be obtained using an approximate center of the pulse. Such an index has a center of gravity. The second calculator 3605 calculates a gradient 3660 of the phase of the phase component signal 3620 in the frequency domain. The abrupt signal change determiner 3609 determines an abrupt change in the input signal based on the gradient calculated by the first calculator 3603 and that calculated by the second calculator 3605.

With the above-described arrangement, it is possible to effectively detect an abrupt change in the input signal using the level of matching between the gradient of the phase component signal in the frequency domain and the phase gradient obtained from the sudden increase of the low correlation signal corresponding to the abrupt change component of the signal.

13th Embodiment

Overall Arrangement

A noise suppression apparatus according to the 13th embodiment of the present invention will be described with reference to FIGS. 37A to 45. The noise suppression apparatus according to this embodiment is applicable to suppress noise in, for example, a digital camera, a notebook personal computer, a mobile phone, a keyboard, a game machine controller, and the push buttons of a mobile phone. That is, the target signal of speech, music, environmental sound, or the like can be enhanced relative to a signal (noise or interfering signal) superimposed on it. However, the present invention is not limited to this, and the noise suppression apparatus is applicable to a signal processing apparatus of any type required to do abrupt signal change detection from an input signal. Note that in this embodiment, a noise suppression apparatus that detects and suppresses an impulsive sound as an example of an abrupt change in a signal will be described. The noise suppression apparatus according to this embodiment appropriately suppresses an impulsive sound generated by, for example, a button operation in a mode to perform an operation such as button pressing near a microphone. Simply speaking, a time domain signal including an impulsive sound is converted into a frequency domain signal, and the gradient of a phase component in the frequency space is calculated. In addition, the gradient of the phase in the frequency domain when a sudden increase of a low correlation signal obtained by removing correlation of the time domain signal is regarded as an isolated pulse, that is, $-2\pi n0/N$ is obtained. n0 is the position of the sudden increase. Then, the presence of an impulsive sound is determined in accordance with the level of matching between the two types of phases.

FIG. 37A is a block diagram showing the overall arrangement of a noise suppression apparatus 3700. A noisy signal (signal including both a desired signal and noise) is supplied to an input terminal 3706 as a series of sample values. The noisy signal supplied to the input terminal 3706 undergoes transform such as Fourier transform in a converter 3701 and is divided into a plurality of frequency components. The plurality of frequency components are independently processed on a frequency basis. The description will be continued here concerning a specific frequency component of interest. Out of the frequency component, an amplitude spectrum (amplitude component) 3730 is supplied to a noise suppressor 3705, and a phase spectrum (phase component) 3720 is supplied to a phase controller 3702 and a calculator 3781. In addition, a correlation remover 3712 removes a correlation component from the noisy signal supplied to the input terminal 3706, and supplies a low correlation signal 3770 to a calculator 3782. Note that the converter 3701 supplies the noisy signal amplitude spectrum 3730 to the noise suppressor 3705 here. However, the present invention is not limited to this, and a power spectrum corresponding to the square of the amplitude spectrum may be supplied to the noise suppressor 3705.

The noise suppressor 3705 estimates noise using the noisy signal amplitude spectrum 3730 supplied from the converter 3701, thereby generating an estimated noise spectrum. In addition, the noise suppressor 3705 suppresses the noise using the generated estimated noise spectrum and the noisy signal amplitude spectrum 3730 supplied from the converter 3701, and transmits an enhanced signal amplitude spectrum as a noise suppression result to an amplitude controller 3703. The noise suppressor 3705 also receives a determination result from an abrupt change determiner 3709, and changes the degree of noise suppression in accordance with the presence/absence or degree of an abrupt change in the signal. The noise suppressor 3705 performs protection using target sound detection, and also replaces the amplitude with an estimated background sound upon detecting an impulsive sound.

The phase controller 3702 rotates (shifts) the noisy signal phase spectrum 3720 supplied from the converter 3701, and supplies it to an inverter 3704 as an enhanced signal phase spectrum 3740. The phase controller 3702 also transmits the phase rotation amount (shift amount) to the amplitude controller 3703. The amplitude controller 3703 receives the phase rotation amount (shift amount) from the phase controller 3702, calculates an amplitude correction amount, corrects the enhanced signal amplitude spectrum in each frequency using the amplitude correction amount, and supplies a corrected amplitude spectrum 3750 to the inverter 3704. The inverter 3704 performs inversion by compositing the enhanced signal phase spectrum 3740 supplied from the phase controller 3702 and the corrected amplitude spectrum 3750 supplied from the amplitude controller 3703, and supplies the resultant signal to an output terminal 3707 as an enhanced signal.

The calculator 3781 calculates the gradient (change) of the phase at each frequency by differentiating the phase component signal 3720 supplied from the converter 3701 by the frequency. On the other hand, the calculator 3782 receives the low correlation signal 3770 divided into frames, calculates the absolute signal value, and calculates the gradient of the phase in the frequency domain based on a position representing the sudden increase of the absolute signal value.

The abrupt change determiner 3709 compares the phase gradients provided by the calculators 3781 and 3782, and based on the similarity of the gradients, determines for each frequency point to what extent an abrupt change in the signal exists (presence probability). More specifically, the abrupt change determiner 3709 receives a rotation vector corresponding to the phase component signal from each of the calculators 3781 and 3782, calculates a rotation vector between the two rotation vectors, and if the absolute value is close to 0 (if the absolute value is equal to or smaller than a predetermined threshold of 0.1), determines that an abrupt change in the signal exists.

As the similarity of the gradients, the absolute difference between the gradient obtained from the time domain signal and the gradient obtained from the frequency domain signal can be used. However, the present invention is not limited to this. The distance between 1 and the value of the ratio of the two gradients or the distance between 1 and a value obtained by normalizing the sum of the gradients by twice of one of them may be used. The presence probability can be obtained, for example, in the following way. First, a positive value is determined as a threshold. When the absolute difference is larger than the threshold, the presence probability is 0. When the absolute difference is equal to 0, the presence probability is 1. A general value of presence probability is defined as a function of the absolute difference. The simplest function is a line. A value proportional to the absolute difference is determined as presence probability. The slope and y-intercept (function value when the absolute difference is 0) of the line are determined so as to meet a boundary condition when the above-described absolute difference equals 0 or 1. As the function, an arbitrary linear or nonlinear function or polynomial may be used.

<<Arrangement of Correlation Remover>>

Figure 37C:
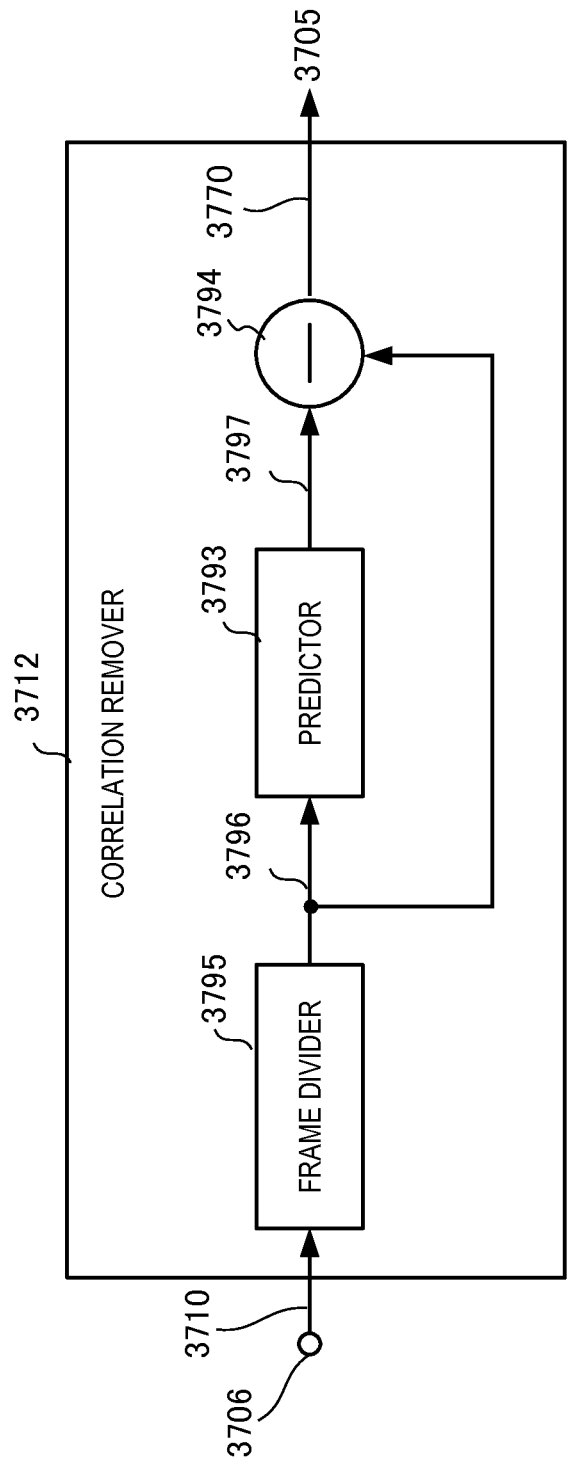
FIG. 37C is a block diagram showing another example of the arrangement of the correlation remover according to the 13th embodiment of the present invention.

FIGS. 37B and 37C are block diagrams showing the arrangement of the correlation remover 3712. As shown in FIG. 37B, the correlation remover 3712 includes a predictor 3783, a subtractor 3784, and a frame divider 3785. A noisy signal sample 3710 is supplied to the predictor 3783. The predictor 3783 predicts a signal 3786 having correlation and supplies it to the subtractor 3784. As a prediction method, linear prediction using an adaptive filter, a Levinson-Durbin method, and the like are known. The subtractor 3784 subtracts the predicted signal 3786 supplied from the predictor 3783 from the noisy signal 3710, and supplies the difference to the frame divider 3785 as a low correlation signal 3787. The frame divider 3785 performs frame division for the low correlation signal 3787 and outputs it as the low correlation signal 3770 divided into frames.

In FIG. 37C, it is possible to first perform frame division and then perform prediction, unlike FIG. 37B. FIG. 37C shows an arrangement that performs prediction after frame division. Referring to FIG. 37C, the correlation remover 3712 includes a frame divider 3795, a predictor 3793, and a subtractor 3794. The frame divider 3795 performs frame division for the noisy signal 3710, and supplies a divided signal sample 3796 to the predictor 3793 and the subtractor 3794. The predictor 3793 predicts a signal having correlation included in the signal sample 3796 divided into frames, and supplies it to the subtractor 3794. The subtractor 3794 subtracts a predicted signal 3797 supplied from the predictor 3793 from the noisy signal 3796 divided into frames, and outputs the difference as the low correlation signal 3770 divided into frames.

<<Arrangement of Converter>>

FIG. 38A is a block diagram showing the arrangement of the converter 3701. As shown in FIG. 38A, the converter 3701 includes a frame divider 3801, a windowing unit 3802, and a Fourier transformer 3803. A noisy signal sample is supplied to the frame divider 3801 and divided into frames on the basis of K/2 samples, where K is an even number. A noisy signal sample 3804 divided into frames is supplied to the windowing unit 3802 and multiplied by a window function w(t). The signal obtained by windowing an nth frame input signal yn(t) (t=0, 1, . . . , K/2−1) by w(t) is given by $$\bar{y}_n(t) = w(t)y_n(t) \qquad (1)$$

Two successive frames may partially be overlaid (overlapped) and windowed. Assume that the overlap length is 50% the frame length. For t=0, 1, . . . , K/2−1, the windowing unit 3802 outputs the left-hand sides of $$\left. \begin{array}{l} \bar{y}_n(t) = w(t)y_{n-1}(t+K/2) \\ \bar{y}_n(t+K/2) = w(t+K/2)y_n(t) \end{array} \right\} \qquad (2)$$

A symmetric window function is used for a real signal. The window function is designed to make the input signal and the output signal match with each other except a calculation error when the output of the converter 3701 is directly supplied to the inverter 3704. This means $w^2(t)+w^2(t+K/2)=1$.

The description will be continued below assuming an example in which windowing is performed for two successive frames that overlap 50%. As w(t), the windowing unit can use, for example, a Hanning window given by $$w(t) = \begin{cases} 0.5 + 0.5\cos\left(\dfrac{\pi(t-K/2)}{K/2}\right), & 0 \le t < K \\ 0, & \text{otherwise} \end{cases} \qquad (3)$$

Various window functions such as a Hamming window and a triangle window are also known. The windowed output is supplied to the Fourier transformer 3803 and transformed into a noisy signal spectrum Yn(k). The noisy signal spectrum Yn(k) is separated into the phase and the amplitude. A noisy signal phase spectrum argYn(k) is supplied to the phase controller 3702 and the calculator 3781, whereas a noisy signal amplitude spectrum |Yn(k)| is supplied to the noise suppressor 3705. As already described, a power spectrum may be used in place of the amplitude spectrum.

<<Arrangement of Inverter>>

FIG. 38B is a block diagram showing the arrangement of the inverter 3704. As shown in FIG. 38B, the inverter 3704 includes an inverse Fourier transformer 3811, a windowing unit 3812, and a frame composition unit 3813. The inverse Fourier transformer 3811 multiplies the enhanced signal amplitude spectrum 3750 supplied from the amplitude controller 3703 by the enhanced signal phase spectrum 3740 argXn(k) supplied from the phase controller 3702 to obtain an enhanced signal (the left-hand side of equation below).

$$\bar{X}_n(k) = |\bar{X}_n(k)| \cdot \arg X_n(k) \qquad (4)$$

Inverse Fourier transform is performed for the obtained enhanced signal. The signal is supplied to the windowing unit 3812 as a series of time domain sample values xn(t) (t=0, 1, . . . , K−1) in which one frame includes K samples, and multiplied by the window function w(t). A signal obtained by windowing an nth frame input signal xn(t) (t=0, 1, . . . , K/2−1) by w(t) is given by the left-hand side of $$\bar{x}_n(t) = w(t)x_n(t) \qquad (5)$$

Two successive frames may partially be overlaid (overlapped) and windowed. Assume that the overlap length is 50% the frame length. For t=0, 1, . . . , K/2−1, the windowing unit 3812 outputs the left-hand sides of $$\left. \begin{array}{l} \bar{x}_n(t) = w(t)x_{n-1}(t+K/2) \\ \bar{x}_n(t+K/2) = w(t+K/2)x_n(t) \end{array} \right\} \qquad (6)$$

and transmits them to the frame composition unit 3813.

The frame composition unit 3813 extracts the outputs of two adjacent frames from the windowing unit 3812 on the basis of K/2 samples, overlays them, and obtains an output signal (left-hand sides) for t=0, 1, . . . , K−1 by $$\hat{x}_n(t) + \bar{x}_{n-1}(t+K/2) + \bar{x}_n(t) \qquad (7)$$

An obtained enhanced speech signal 3760 is transmitted from the frame composition unit 3813 to the output terminal 3707.

Note that the conversion in the converter and the inverter in FIGS. 38A and 38B has been described as Fourier transform. However, any other transform such as Hadamard transform, Haar transform, or Wavelet transform may be used in place of the Fourier transform. Haar transform does not need multiplication and can reduce the area of an LSI chip. Wavelet transform can change the time resolution depending on the frequency and is therefore expected to improve the noise suppression effect.

The noise suppressor 3705 may perform actual suppression after a plurality of frequency components obtained by the converter 3701 are integrated. At this time, high sound quality can be achieved by integrating more frequency components from the low frequency range where the discrimination capability of hearing characteristics is high to the high frequency range with a poorer capability. When noise suppression is executed after integrating a plurality of frequency components, the number of frequency components to which noise suppression is applied decreases, and the whole calculation amount can be decreased.

<<Arrangement of Noise Suppressor>>

The noise suppressor 3705 estimates noise using the noisy signal amplitude spectrum supplied from the converter 3701 and generates an estimated noise spectrum. The noise suppressor 3705 then obtains a suppression coefficient using the noisy signal amplitude spectrum from the converter 3701 and the generated estimated noise spectrum, multiplies the noisy signal amplitude spectrum by the suppression coefficient, and supplies the resultant spectrum to the amplitude controller 3703 as an enhanced signal amplitude spectrum.

In addition, upon receiving information representing to what extent an abrupt change exists (likelihood that an abrupt signal change exists or presence probability) from the abrupt change determiner 3709, the degree of noise suppression can be changed in accordance with the possibility that an abrupt signal change exists. It is also possible to determine the possibility that an abrupt signal change exists for each frequency component, frequency band (combination of an arbitrary number of continuous frequency components), or frame and perform different signal processing for each frequency component, frequency band, or frame to suppress the abrupt change.

To estimate noise, various estimation methods such as the methods described in non-patent literatures 1 and 2 are usable.

For example, non-patent literature 1 discloses a method of obtaining, as an estimated noise spectrum, the average value of noisy signal amplitude spectra of frames in which no target sound is generated. In this method, it is necessary to detect generation of the target sound. A section where the target sound is generated can be determined by the power of the enhanced signal.

As an ideal operation state, the enhanced signal is the target sound other than noise. In addition, the level of the target sound or noise does not largely change between adjacent frames. For these reasons, the enhanced signal level of an immediately preceding frame is used as an index to determine a noise section. If the enhanced signal level of the immediately preceding frame is equal to or smaller than a predetermined value, the current frame is determined as a noise section. A noise spectrum can be estimated by averaging the noisy signal amplitude spectra of frames determined as a noise section.

Non-patent literature 1 also discloses a method of obtaining, as an estimated noise spectrum, the average value of noisy signal amplitude spectra in the early stage in which supply of them has started. In this case, it is necessary to meet a condition that the target sound is not included immediately after the start of estimation. If the condition is met, the noisy signal amplitude spectrum in the early stage of estimation can be obtained as the estimated noise spectrum.

Non-patent literature 2 discloses a method of obtaining an estimated noise spectrum from the minimum value of the statistical noisy signal amplitude spectrum. In this method, the minimum value of the noisy signal amplitude spectrum within a predetermined time is statistically held, and a noise spectrum is estimated from the minimum value. The minimum value of the noisy signal amplitude spectrum is similar to the shape of a noise spectrum and can therefore be used as the estimated value of the noise spectrum shape. However, the minimum value is smaller than the original noise level. Hence, a spectrum obtained by appropriately amplifying the minimum value is used as an estimated noise spectrum.

The noise suppressor 3705 can perform various kinds of suppression. Typical examples are the SS (Spectrum Subtraction) method and an MMSE STSA (Minimum Mean-Square Error Short-Time Spectral Amplitude Estimator) method. In the SS method, the estimated noise spectrum is subtracted from the noisy signal amplitude spectrum supplied from the converter 3701. In the MMSE STSA method, a suppression coefficient is calculated using the noisy signal amplitude spectrum supplied from the converter 3701 and the generated estimated noise spectrum, and the noisy signal amplitude spectrum is multiplied by the suppression coefficient. The suppression coefficient is decided so as to minimize the mean square power of the enhanced signal.

Additionally, the noise suppressor 3705 receives the abrupt change determination result (information representing whether an abrupt signal change exists) from the abrupt change determiner 3709, and changes the degree of noise suppression in accordance with the presence/absence or degree of an abrupt signal change. For example, signal processing can be performed for each frequency component, frequency band, or frame in which an abrupt signal change has occurred to suppress the abrupt change.

If the abrupt change determiner 3709 determines that an abrupt change exists, a smaller one of the noisy signal amplitude spectrum and the estimated noise spectrum is supplied to the amplitude controller 3703 as an enhanced signal amplitude spectrum. That is, if the noisy signal amplitude spectrum is smaller than the estimated noise spectrum, the noisy signal amplitude spectrum is directly output. Otherwise, the input signal can be replaced with the estimated noise spectrum and output.

It is also possible to, prior to the replacement, detect an important noisy signal amplitude spectrum component and exclude the detected important noisy signal amplitude spectrum component from the component to be replaced with the estimated noise spectrum. As the index of importance when detecting the important noisy signal amplitude spectrum component, the magnitude of the noisy signal amplitude spectrum can be used. A component having a large amplitude is a component of a target signal at a high probability. Holding this component contributes to prevention of a degradation in sound quality of the target signal.

The peak characteristic of the noisy signal amplitude spectrum can also be used as the index of importance. A noisy signal amplitude having a peak, that is, a value larger than peripheral values along the frequency axis is a component of a target signal at a high probability. Holding this component contributes to prevention of a degradation in sound quality of the target signal. In particular, a conspicuous peak, that is, an amplitude value much larger than peripheral amplitude values is important. When this component is reliably protected, sound quality of the target signal can further be increased.

To detect a peak, for example, a pure sound component detection method described in non-patent literature 3 or a method disclosed in non-patent literature 4 is usable. A detected peak may be evaluated in accordance with a predetermined condition, and a peak that does not meet the condition may be excluded. For example, there is little possibility that a peak having a value smaller than the estimated noise is the target signal. That is, it is possible to, using the estimated noise as a reference, leave only peaks much larger than the estimated noise and exclude others. Whether a peak is sufficiently large can be determined by comparing it with a constant multiple of the estimated noise. In this way, it is evaluated whether a detected peak meets a predetermined condition, and final peak components are then selected. This can reduce peak detection errors and enhance the effect of suppressing an abrupt si z gnal change.

It is also possible to change the signal to be supplied to the amplitude controller 3703 in accordance with the likelihood of presence of an abrupt change. The result of replacement and the noisy signal amplitude spectrum are mixed in correspondence with the likelihood of presence of an abrupt change, and the mixture is output as an enhanced signal amplitude spectrum. The mixing processing is executed by adding a large weight to the replacement result as the likelihood of presence of an abrupt change rises.

That is, the noise suppressor 3705 may perform suppression in multiple levels such as suppression level 0, suppression level 1, and suppression level 2 in accordance with the presence probability of an abrupt signal change. Alternatively, the degree of suppression may continuously be changed in accordance with the determination result (for example, numerical values of 0 to 1) of the abrupt change determiner.

<<Arrangement of Phase Controller and Amplitude Controller>>

Figure 39:
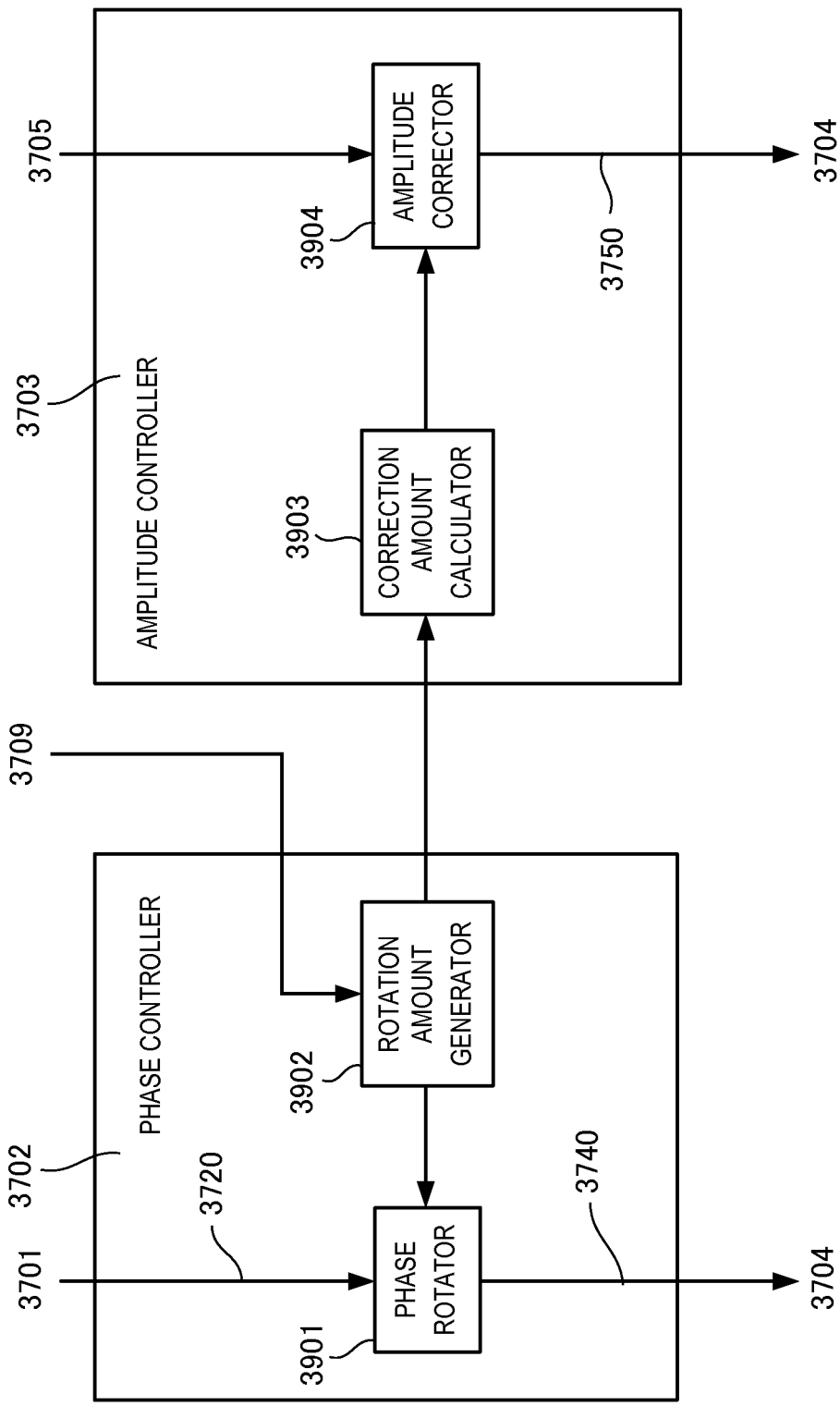
FIG. 39 is a block diagram showing the arrangement of a phase controller and an amplitude controller according to the 13th embodiment of the present invention.

FIG. 39 is a block diagram showing the arrangement of the phase controller 3702 and the amplitude controller 3703. As shown in FIG. 39, the phase controller 3702 includes a phase rotator 3901 and a rotation amount generator 3902, and the amplitude controller 3703 includes a correction amount calculator 3903 and an amplitude corrector 3904.

The rotation amount generator 3902 generates the rotation amount of the noisy signal phase spectrum for a frequency component determined to "have an abrupt change in the signal" by the abrupt change determiner 3709, and supplies the rotation amount to the phase rotator 3901 and the correction amount calculator 3903. Upon receiving the rotation amount supplied from the rotation amount generator 3902, the phase rotator 3901 rotates (shifts) the noisy signal phase spectrum 3720 supplied from the converter 3701 by the supplied rotation amount, and supplies the rotated spectrum to the inverter 3704 as the enhanced signal phase spectrum 3740.

The correction amount calculator 3903 decides the correction coefficient of the amplitude based on the rotation amount supplied from the rotation amount generator 3902, and supplies the correction coefficient to the amplitude corrector 3904.

The rotation amount generator 3902 generates the rotation amount by, for example, a random number. When the noisy signal phase spectrum is rotated for each frequency by a random number, the shape of the noisy signal phase spectrum 3720 changes. With the change in the shape, the feature of an abrupt signal change such as an impulsive sound can be weakened.

Examples of the random number are a uniform random number whose occurrence probability is uniform and a normal random number whose occurrence probability exhibits a normal distribution. A rotation amount generation method using a uniform random number will be described first. A uniform random number can be generated by a linear congruential method or the like. For example, uniform random numbers generated by the linear congruential method are uniformly distributed within the range of 0 to (2^M)−1, where M is an arbitrary integer, and ^ represents a power. Phase rotation amounts φ need to be distributed within the range of 0 to 2π. To do this, the generated uniform random numbers are converted. The conversion is performed by $$\phi = 2\pi \frac{R}{R_{max}} \quad (8)$$

where R is the uniform random number, and Rmax is the maximum value capable of being generated by the uniform random number. When a uniform random number is generated by the above-described linear congruential method, Rmax=(2^M)−1.

To simplify the calculation, the value R may directly be decided as the rotation amount. As the rotation amount, 2π represents just one revolution. A case where the phase is rotated by 2π is equivalent to a case where the phase is not rotated. Hence, a rotation amount 2π+α is equivalent to a rotation amount α. A case where a uniform random number is generated by the linear congruential method has been explained here. Even in a case where a uniform random number is generated by another method, the rotation amount φ is obtained by the above equation. When and how many times random number generation is to be performed may be decided in accordance with the determination result of the abrupt change determiner 3709.

The phase rotator 3901 receives the rotation amount from the rotation amount generator 3902 and rotates the noisy signal phase spectrum. If the noisy signal phase spectrum is expressed as an angle, it can be rotated by adding the value of the rotation amount φ to the angle. If the noisy signal phase spectrum is expressed as the normal vector of a complex number, it can be rotated by obtaining the normal vector of the rotation amount φ and multiplying the noisy signal phase spectrum by the normal vector.

The normal vector of the rotation amount φ can be obtained by $$\Phi = \cos(\phi) + j\,\sin(\phi) \quad (9)$$

In equation (9), Φ is the rotation vector, and j represents sqrt(−1). Note that sqrt is the square root.

A correction coefficient calculation method by the correction amount calculator 3903 is the same as the method described concerning the correction amount calculator 503 shown in FIG. 5, and a description thereof will be omitted.

<<Arrangement of Calculator and Abrupt Change Determiner>>

FIG. 40 is a block diagram for explaining the internal arrangement of the calculators 3781 and 3782 and the abrupt change determiner 3709. As shown in FIG. 40, the calculator 3782 includes a sudden increase detector 4001, a delay time calculator 4002, a phase converter 4003, and a gradient calculator 4004. On the other hand, the calculator 3781 includes a gradient calculator 4005.

The sudden increase detector 4001 calculates the absolute value of the signal in a frame, and detects a maximum value 4010 of the absolute value. The delay time calculator 4002 outputs a relative position representing the maximum value in the frame (time from the start of the frame to the timing at which the maximum value exists) as n0.

Next, the phase converter 4003 converts a delay time τ 4020 into a phase in the frequency domain. More specifically, conversion is performed based on the following equation. Here, L is the frame length of the converter 3701, and 0≤n0≤L−1. Assume that the input is an isolated pulse having an amplitude a. Then, a kth frequency component D(k) obtained by Fourier transform is given by $$D(k) = a \cdot \exp(-j\theta(k))\,\theta(k) = -2\pi \cdot k \cdot n0/L$$

The gradient calculator 4004 differentiates a thus derived phase 4030 to derive a gradient 4040 of the phase in the frequency domain as gradient 4040=−2·n0/L.

On the other hand, the gradient calculator 4005 differentiates the phase component signal input from the converter 3701 to derive a gradient 4050 of the phase in the frequency domain. Each of the gradient calculators 4004 and 4005 may calculate the gradient by differentiation using the frequency of the phase or by another method.

A parallelism calculator 4006 compares the gradient 4040 provided by the gradient calculator 4004 with the gradient 4050 provided by the gradient calculator 4005 on a frequency basis, and calculates the similarity of the gradients. That is, the parallelism of the line calculated by the calculator 3781 for the phase component signal in the frequency domain with respect to the line calculated by the calculator 3782 is calculated on a frequency basis. If the parallelism exceeds a predetermined value, an abrupt change determiner 4007 determines that an abrupt signal change exists at the frequency.

If the determination is done not for each frequency but for each frequency band (sub-band) or frame, determination errors by phase components other than abrupt signal change components can be reduced by determination in boarder aspects. In addition, the determination result for each frequency may be corrected using the determination result for each frequency band or frame. For example, if the determination result for a certain frequency band indicates that "an abrupt signal change exists", the determination result for all frequencies within the frequency band is forcibly set to "an abrupt signal change exists", thereby reducing determination errors caused by disturbance of other signal components. To the contrary, if the determination result for a certain frequency band indicates that "no abrupt signal change exists", the determination result for all frequencies within the frequency band is forcibly set to "no abrupt signal change exists", thereby reducing determination errors caused by disturbance of other signal components. Alternatively, the ease (threshold) of determination for each frequency within the band may be corrected in a direction to easily determine "presence", and the configuration for independently performing determination for each frequency may be maintained in itself. When the determination result is obtained for each frequency or frequency band, an abrupt change can be suppressed for each frequency or frequency band. Hence, more accurate abrupt signal change suppression can be performed.

The abrupt change determiner 3709 outputs abrupt signal change present (1) or abrupt signal change absent (0) as the determination result 4030. However, if the abrupt change determiner 4007 outputs a value between 0 and 1 associated with the parallelism as the abrupt change presence probability, the determination result 4030 is the value between 0 and 1, which represents the abrupt change presence probability. In this case, likelihood of inclusion of an abrupt signal change can be obtained.

Figure 41:
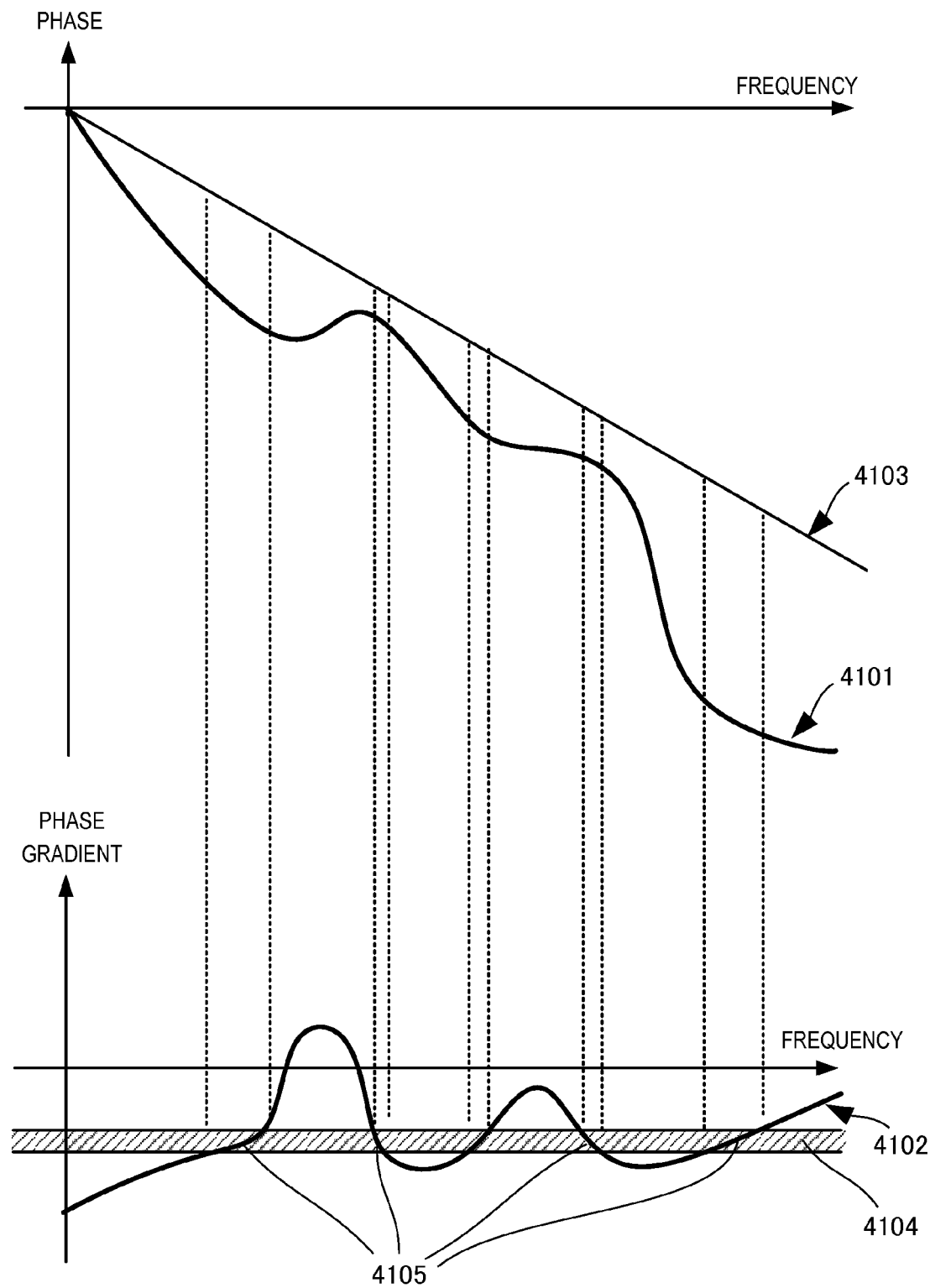
FIG. 41 is a graph for explaining processing of the calculator according to the 13th embodiment of the present invention.

FIG. 41 is a graph showing a phase and its change amount. When the phase changes along the frequency axis in the frequency domain, like a graph 4101, the phase change amount changes as indicated by a graph 4102 along the frequency axis in the frequency domain.

On the other hand, a phase represented by a line 4103 in the frequency domain can be calculated from the intra-frame relative position of the sudden increase.

In this embodiment, the presence of an abrupt signal change is determined based on how large a portion where the phase component signal 4101 and the line 4103 are parallel.

When the phase gradient is plotted along the ordinate, and the frequency is plotted along the abscissa, a range approximate to the slope of the line 4103 is represented by a range 4104. Hence, if an overlap 4105 between the range 4104 and the graph 4102 is larger than a predetermined threshold, the abrupt change determiner 4007 determines that an abrupt change in the signal exists.

Figure 42:
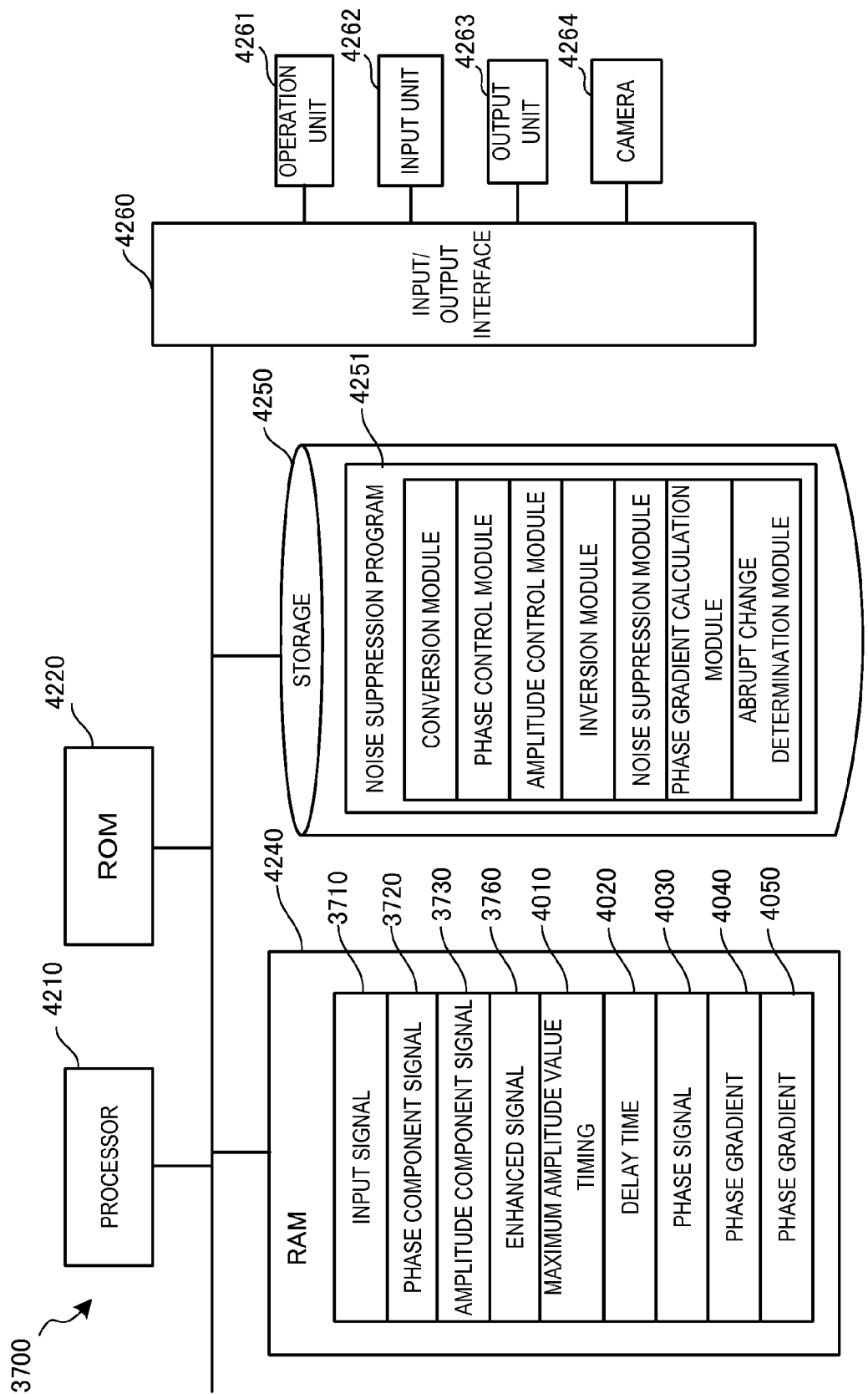
FIG. 42 is a block diagram showing the hardware arrangement of the noise suppression apparatus according to the 13th embodiment of the present invention.

FIG. 42 is a block diagram for explaining a hardware arrangement when the noise suppression apparatus 3700 according to this embodiment is implemented using software.

The noise suppression apparatus 3700 includes a processor 4210, a ROM (Read Only Memory) 4220, a RAM (Random Access Memory) 4240, a storage 4250, an input/output interface 4260, an operation unit 4261, an input unit 4262, and an output unit 4263. The noise suppression apparatus 3700 may include a camera 4264. The processor 4210 is a central processing unit and executes various programs, thereby controlling the overall noise suppression apparatus 3700.

The ROM 4220 stores various parameters as well as a boot program to be executed first by the processor 4210. The RAM 4240 includes an area to store the input signal 3710, the phase component signal 3720, the amplitude component signal 3730, and the enhanced signal 3760 as well as a program load area (not shown). In addition, the RAM 4240 includes an area to store the maximum amplitude value timing 4010, the delay time 4020, the phase signal 4030, the phase gradients 4040 and 4050, and the like.

The storage 4250 stores a noise suppression program 4251. The noise suppression program 4251 includes a conversion module, a phase control module, an amplitude control module, an inversion module, a noise suppression module, a phase gradient calculation module, and an abrupt change determination module. When the processor 4210 executes the modules included in the noise suppression program 4251, the functions of the converter 3701, the phase controller 3702, the amplitude controller 3703, the inverter 3704, the noise suppressor 3705, the calculators 3781 and 3782, and the abrupt change determiner 3709 shown in FIG. 37A can be implemented. Note that the storage 4250 may store a noise database.

An enhanced signal that is the output concerning the noise suppression program 4251 executed by the processor 4210 is output from the output unit 4263 via the input/output interface 4260. This can suppress, for example, the operation sound of the operation unit 4261 input from the input unit 4262. Also possible is an application method of, for example, detecting abrupt signal change inclusion in the input signal input from the input unit 4262 and starting shooting by the camera 4264.

Figure 43A:
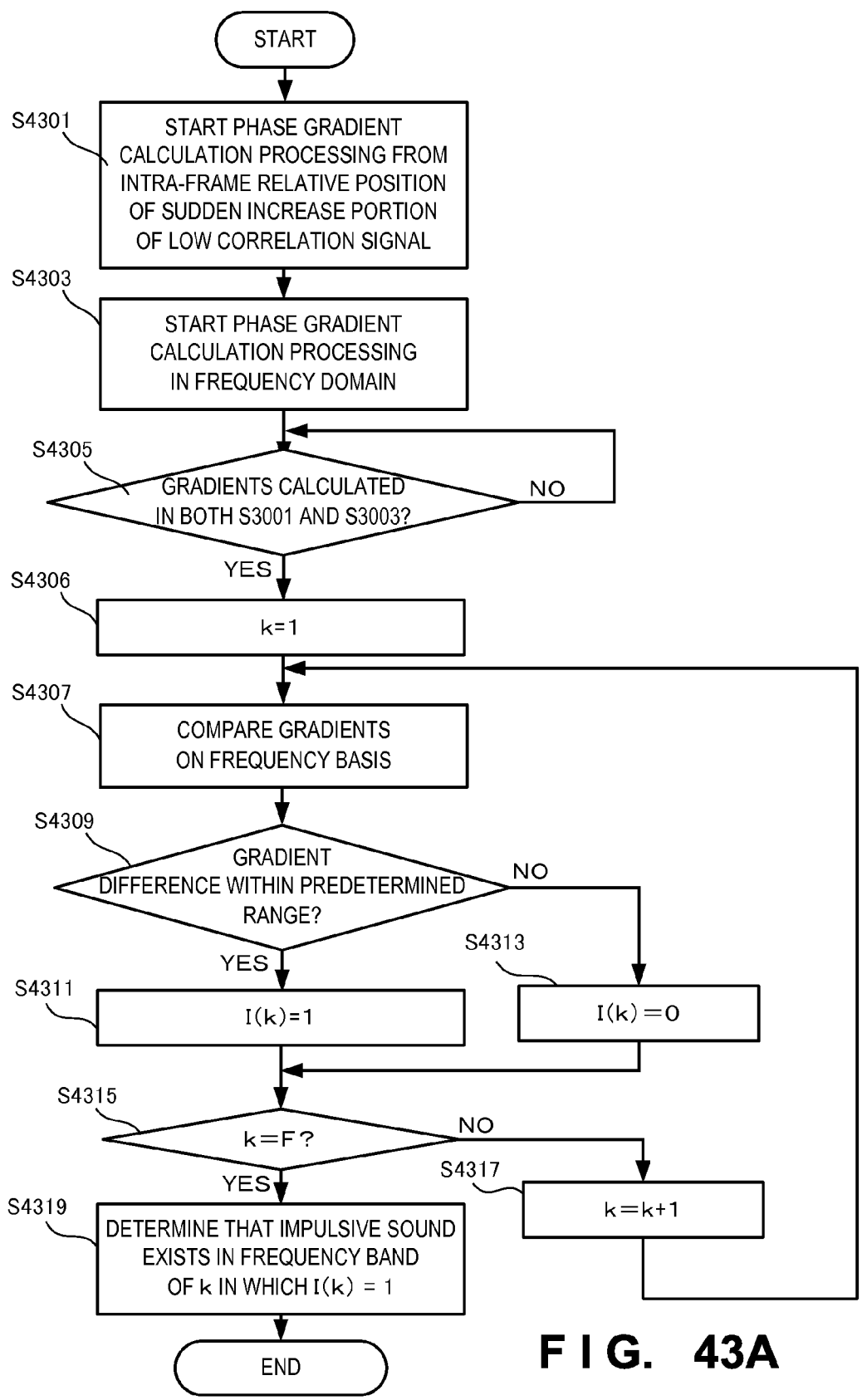
FIG. 43A is a flowchart for explaining the procedure of processing of the noise suppression apparatus according to the 13th embodiment of the present invention.

FIG. 43A is a flowchart for explaining the procedure of abrupt signal change determination processing of the noise suppression program 4251. In step S4301, the correlation remover 3712 and the calculator 3782 start phase gradient calculation processing corresponding to the sudden increase of a low correlation signal. In step S4303, the calculator 3781 starts phase gradient calculation processing in the frequency domain.

In step S4305, the process waits until gradients are calculated in both of steps S4301 and S4303. When the gradients can be calculated by both methods, the process advances to step S4307 to compare the calculated gradients on a frequency basis. In step S4309, it is determined whether the absolute difference between the gradients is equal to or smaller than the predetermined threshold N. If the absolute difference is N or less, the process advances to step S4311 to set a flag (set I(k)=1) for the frequency k. On the other hand, if the absolute difference is not N or less, I(k)=0 is set in step S4313. In step S4315, it is determined whether k=F (F is the number of frequency components in the entire frame). If k≠F, the process advances to step S4317 to set k=k+1. The process then returns to step S4307 to compare the gradients on a frequency basis throughout the frame. Finally in step S4319, it is determined that an abrupt signal change exists at the frequency k when I(k)=1, and the determination result is supplied to the noise suppressor 3705 and the phase controller 3702. Note that in place of step S4319, I(k) may be integrated in the frame, and the integral value of I(k) exceeds a predetermined threshold, the abrupt change determiner 3709 may determine that the frame includes an abrupt signal change. At this time, the abrupt change determination result may be hanged over and integrated in the next frequency band.

As a hangover function, the threshold N in the next frame may be set large. When the thresholds in the next frame are thus set, it is possible to easily detect an abrupt signal change (impulsive sound) and reduce detection omissions.

FIG. 43B is a flowchart for explaining the procedure of gradient calculation processing performed by the correlation remover 3712 and the calculator 3782. When a signal is input in step S4321, the process advances to step S4322. After the correlation remover 3712 predicts and removes a component with time correlation included in the input signal 3710 to generate a low correlation signal, frame division is performed. In step S4325, the sudden increase detector 4001 detects a sudden increase of a low correlation signal. In step S4327, the delay time calculator 4002 outputs the intraframe relative position of the sudden increase (time from the start of the frame to the timing at which the sudden increase exists) as n0.

In step S4329, the phase converter 4003 converts the delay time n0 4020 into a phase in the frequency domain. The gradient calculator 4004 differentiates the derived phase to derive the gradient of the phase in the frequency domain in step S4331, and buffers it in step S4333.

Figure 43C:
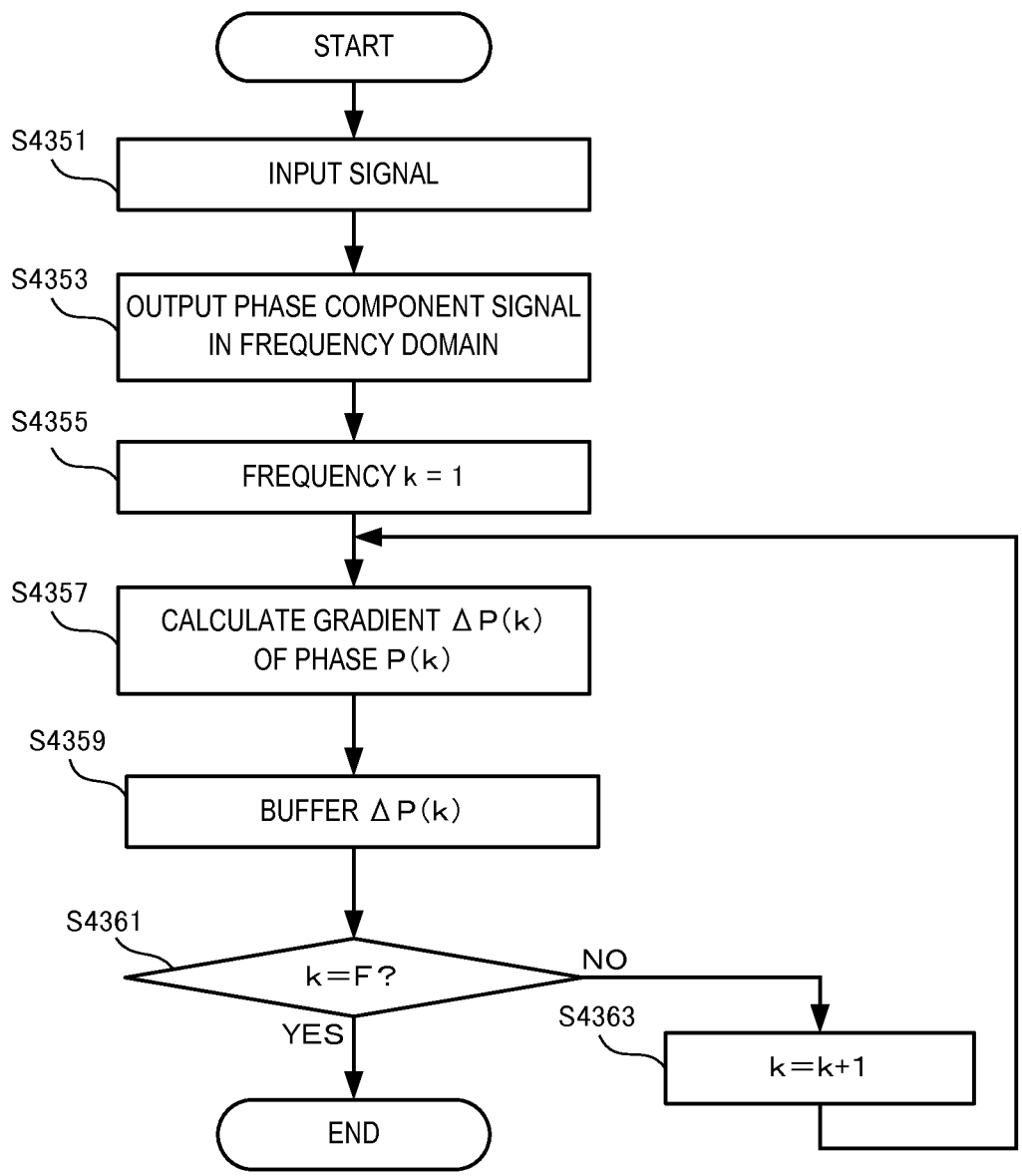
FIG. 43C is a flowchart for explaining the procedure of processing of the noise suppression apparatus according to the 13th embodiment of the present invention.

FIG. 43C is a flowchart for explaining the procedure of gradient calculation processing performed by the calculator 3781. When a signal is input in step S4351, the process advances to step S4353. After frame division and windowing, Fourier transform is performed to extract the phase component signal in the frequency domain. In step S4355, the step k of the frequency is set to 1. In step S4357, the phase p(k) is differentiated to calculate the gradient ΔP(k). In step S4359, the gradient is buffered. In step S4361, it is determined whether k=F (F is the number of frequency components in the entire frame). If k≠F, the process advances to step S4363 to set k=k+1. The process then returns to step S4357 to calculate the gradient on a frequency basis throughout the frame.

With the above-described processing, the phase gradient at the abrupt signal change is estimated and compared using the low correlation signal obtained by removing correlation. It is therefore possible to largely improve the abrupt signal change detection accuracy in a situation in which a component with time correlation is included in the input signal. For example, when an abrupt signal change occurs in a situation where music is playing loudly, the detection accuracy can greatly be improved according to the method of this embodiment. As a result, an abrupt signal change can more correctly be detected, and the abrupt change can appropriately be suppressed as needed. Note that in this embodiment, the phase gradient is obtained as a differential value. However, another index such as the rotation amount of a unit vector may be obtained and used for determination.

14th Embodiment

Figure 44:
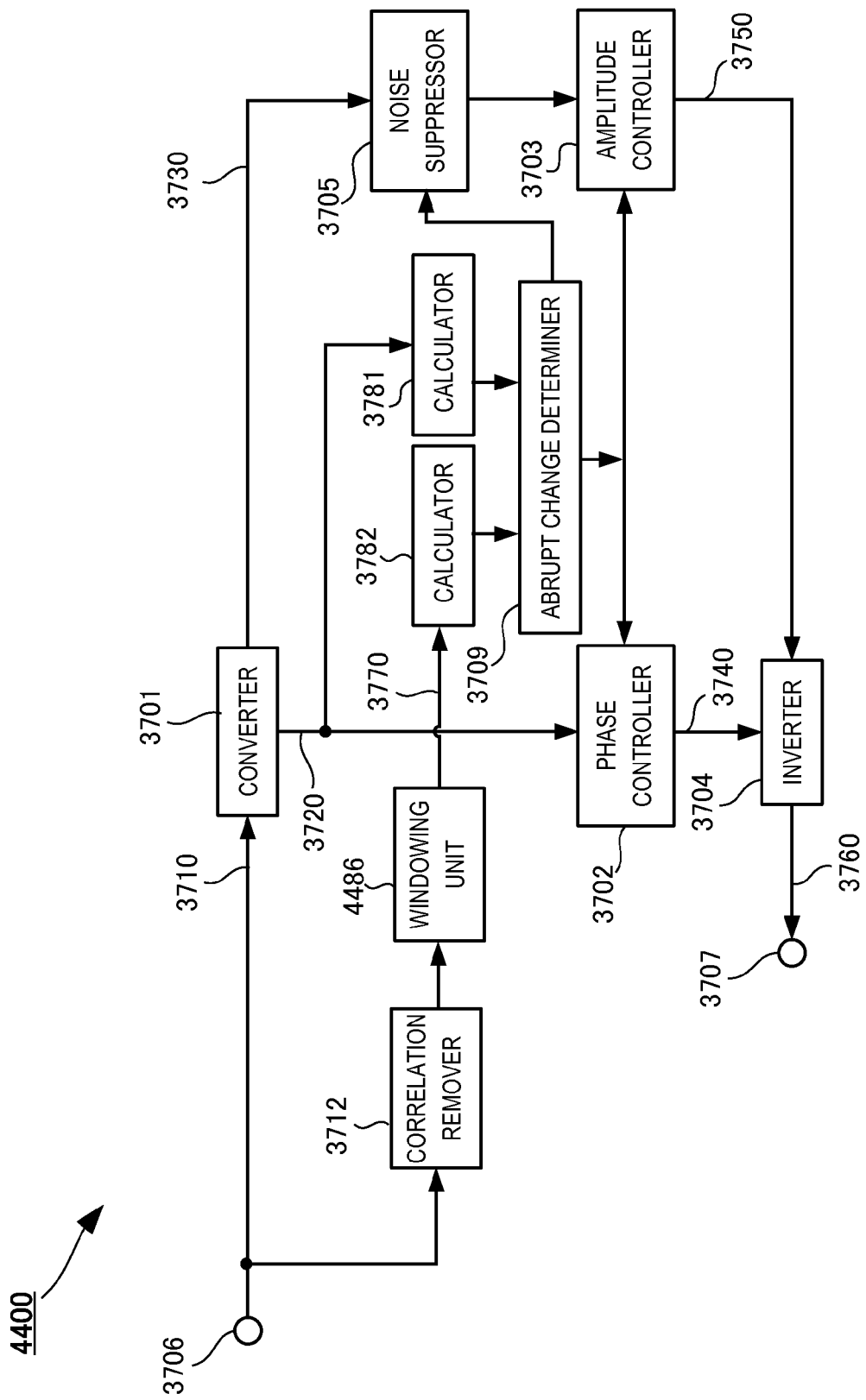
FIG. 44 is a block diagram showing the arrangement of a noise suppression apparatus according to the 14th embodiment of the present invention.

A noise suppression apparatus according to the 14th embodiment of the present invention will be described next with reference to FIG. 44. FIG. 44 is a block diagram for explaining the functional arrangement of a noise suppression apparatus 4400 according to this embodiment. The noise suppression apparatus 4400 according to this embodiment is different from the 13th embodiment in that a windowing unit 4486 is provided between a correlation remover 3712 and a calculator 3782. The rest of the components and operations is the same as in the 13th embodiment. Hence, the same reference numerals denote the same components and operations, and a detailed description thereof will be omitted.

As described above, according to this embodiment, a parallelism can be obtained using a gradient obtained from a time domain signal after windowing, that is, the same signal as that used for Fourier transform. The degree of matching with a phase obtained using a frequency domain signal is thus raised, and an abrupt signal change can more correctly be determined.

15th Embodiment

Figure 45:
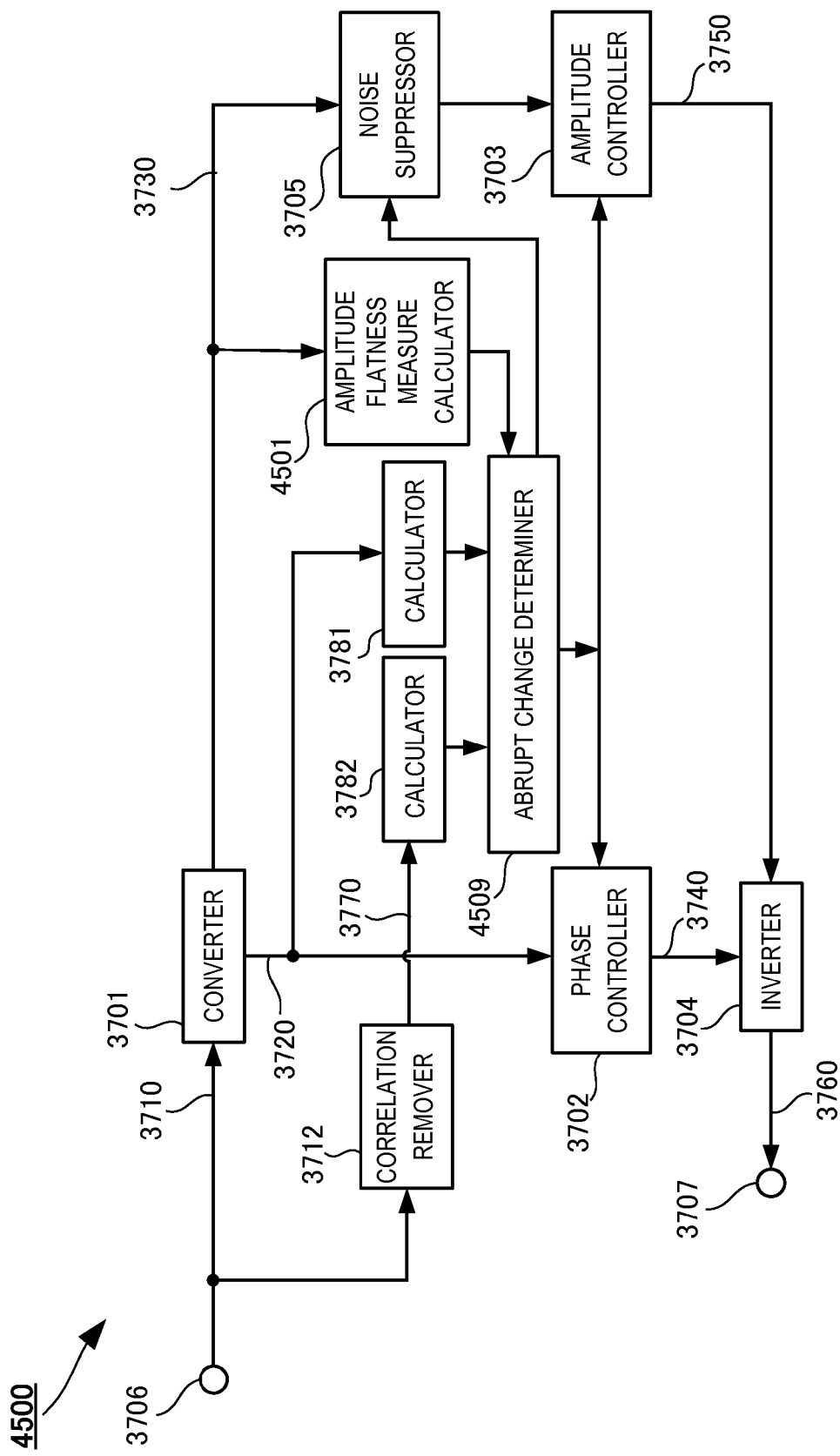
FIG. 45 is a block diagram showing the arrangement of a noise suppression apparatus according to the 15th embodiment of the present invention.

A noise suppression apparatus 4500 according to the 15th embodiment of the present invention will be described next with reference to FIG. 45. FIG. 45 is a block diagram for explaining the functional arrangement of the noise suppression apparatus 4500 according to this embodiment. The noise suppression apparatus 4500 according to this embodiment is different from the 13th embodiment in that an amplitude flatness measure calculator 4501 is additionally provided. The rest of the components and operations is the same as in the 13th embodiment. Hence, the same reference numerals denote the same components and operations, and a detailed description thereof will be omitted.

The amplitude flatness measure calculator 4501 calculates an amplitude change along the frequency axis and supplies it to an abrupt change determiner 4509. A frequency whose amplitude change with respect to an adjacent frequency is small represents an abrupt signal change. As the amplitude change, one flatness measure may be obtained for each band or all frequencies. More specifically, FM (Flatness Measure) representing a flatness measure is obtained by $$FM = \frac{\sqrt[N]{\prod_{n=0}^{N-1} x(n)}}{\frac{\sum_{n=0}^{N-1} x(n)}{N}} = \frac{\exp\left(\frac{1}{N}\sum_{n=0}^{N-1} \ln x(n)\right)}{\frac{1}{N}\sum_{n=0}^{N-1} x(n)} \tag{46}$$

where x(n) is the amplitude or power spectrum at a frequency n, and N is the number of frequency components included in the flatness measure calculation section.

FM takes a value of 0.0 to 1.0. If the amplitude is completely flat, FM is 1.0. The flatness measure is disclosed in non-patent literature 3. The flatness measure can also be expressed using another index. For example, it is possible to obtain the average of x(n) for each band or all frequencies and calculate the sum of squared differences of x(n) of each frequency component n and the average value as the flatness measure for each band or all frequencies. One sum of squared differences may be obtained not for all frequencies but in a single or a plurality of frequency bands and used as the flatness measure. The thus obtained flatness measure has a value of 0.0 if the amplitude is completely flat, and takes a larger vale as the flatness measure lowers.

A smoothness may be used as another index of the flatness measure. The smoothness can be expressed as the sum of absolute differences between adjacent samples along the frequency axis. The smoothness takes a large value for a waveform having large unevenness (not smooth), and a small value for a waveform having small unevenness (smooth). This index is known as TV (Total Variation).

As the flatness measure, a flatness measure along the frequency axis is used above. However, a flatness measure along the time axis is also usable. In an abrupt signal change, the amplitude and power abruptly increase. Using this characteristic, an abrupt signal change can be determined to exist when the flatness measure along the time axis is low. More specifically, if the amplitude or power difference between the current frame and the immediately preceding frame is a predetermined value or more, it is determined that the flatness measure is low, that is, an abrupt signal change exists. Alternatively, the amplitude or power difference between adjacent frames may be obtained for a plurality of frames including several past frames and the current frame, and the result of linearly or nonlinearly combining the differences may be defined as the flatness measure. When the information of the past frames is used, a dulled abrupt signal change including low frequency components can easily be detected, and the suppression performance can be improved. Note that when calculating the amplitude or power difference between adjacent frames, the calculation may be done for each frequency component, band, or all frequencies. The amplitude or power difference can also be calculated for a single or a plurality of bands. For example, when the amplitude or power difference can also be calculated in a single band, particularly, in a high frequency band, the influence of speech and other signals can be reduced, and the abrupt signal change can more correctly be detected.

The above-described two flatness measures, that is, the flatness measure along the frequency axis and the flatness measure along the time axis can be used solely or in combination. As examples of combination, an abrupt signal change is detected based on linear or nonlinear combination of the two flatness measures, or detection results based on the flatness measures are combined. It is determined that an abrupt signal change is detected when the flatness measure in the frequency direction is large or the flatness measure in the time direction is small. Hence, when combining, a contrivance such as changing one of the flatness measures to a reciprocal is needed.

The abrupt change determiner 4509 determines an abrupt change in the signal using two indices, that is, a gradient similarity (parallelism) and an amplitude flatness measure. This is because when the amplitude is flat (variation is small) along the frequency axis, an abrupt signal change is assumed to exist at a high possibility. This is self-evident from the fact that the abrupt signal change is impulsive (the amplitude increases and decreases in a short time), and the Fourier transform of the impulse yields a white signal (the amplitude and power are equal throughout the frequencies). As the determination method, for example, one of the following methods can be selected.

(1) If both the parallelism and the amplitude flatness measure meet corresponding conditions (for example, the gradient difference value is N=0.1 or less, and the amplitude flatness measure FM is M=0.8 or more), it is determined that an abrupt change in the signal exists.

(2) The OR of determination results obtained by solely using the parallelism and the amplitude flatness measure is used. To calculate presence probability of an abrupt signal change, determination is performed based on a larger one (or smaller one) of presence probability by the parallelism and presence probability by the amplitude flatness measure.

(3) If the average of the parallelism and the amplitude flatness measure meets a condition (for example, an average AV1 of a gradient difference value PX of the phase and a difference value QX between 1.0 and the amplitude flatness measure FM, that is, QX=(1.0−FM) is AV1=(PX+QX)/2=0.1 or less), it is determined that an abrupt change in the signal exists.

(4) If a value obtained by combining the gradient difference value and the amplitude flatness measure while adding weights to them meets a compound condition (for example, a weighted average AV2 of the gradient difference value PX and the difference value between 1.0 and the amplitude flatness measure FM, that is, QX=(1.0−FM) is AV2=(0.8×PX+0.2×QX)=0.1 or less), it is determined that an abrupt change in the signal exists.

(5) The gradient difference value and the amplitude flatness measure are combined using a linear or nonlinear function, and the result of combination is larger than a predetermined value, it is determined that an abrupt change in the signal exists. If an amplitude flatness measure in the time direction is included, its reciprocal is used in place of the amplitude flatness measure.

(6) Only one of the gradient difference value and the amplitude flatness measure closer to an ideal value (the difference value as a smaller value, and the flatness measure as a larger value) is used, and if the value closer to the ideal value meets a condition, it is determined that an abrupt change in the signal exists. If an amplitude flatness measure in the time direction is included, its reciprocal is used in place of the amplitude flatness measure.

(7) If information about the amplitude or power spectrum of an abrupt change signal to be detected is obtained in advance, and the amplitude or power spectrum is flat, the weight of the gradient difference value is made small.

(8) If information about the amplitude or power spectrum of an abrupt change signal to be detected is obtained in advance, and the amplitude or power spectrum of the input noisy signal is smaller than the minimum value of the amplitude or power spectrum, the threshold used to detect an abrupt signal change is temporarily largely changed to make detection hard.

When processing a specific signal, for example, when detecting/suppressing an impulsive sound of small noise close to an impulse, information about the amplitude or power is sometimes more reliable than phase information. For example, when detecting a gunshot of a pistol in a quiet environment, the detection may be performed using only the amplitude. On the other hand, when the amplitude or power spectrum of noise largely changes, for example, when detecting a gunshot in airport security, it is effective to change the weights of the amplitude and phase between a quiet situation (with small noise) and a situation with large noise. In this case, the weights of the amplitude and phase may be changed in accordance with the presence/absence of noise or time zone. For example, if the latest information of flight schedule can be acquired from the control tower, the takeoff and landing times of airplanes are known. Hence, at a timing of airplane arrival (timing with much noise), the phase to which a large weight is added can be used to detect a gunshot. This is because in a case where signals other than a gunshot (impulsive sound to be detected) coexist, impulsive sound detection using phase information is more effective than detection using an amplitude. On the other hand, in a situation with small noise, the impulsive sound can effectively be detected by performing determination while attaching importance to the absolute value of the frequency domain vector, that is, the amplitude value of an input noisy signal. In this case as well, the power spectrum value may be used in place of the amplitude spectrum, as a matter of course. The amplitude of the impulsive sound is not flat in some cases depending on the type of the signal. In this case, when detection is performed while making the weight of the phase flatness measure large, an abrupt change in the signal can accurately be detected.

If information about the amplitude or power spectrum of an impulsive sound is obtained in advance, the amplitude flatness measure calculation result can be corrected using the obtained information so as to obtain the same result as in a case where the amplitude is flat. More specifically, the amplitude flatness measure is calculated after an amplitude spectrum 3730 is multiplied for each frequency component by the reciprocal of the amplitude or power spectrum shape of an impulsive sound.

As described above, according to this embodiment, an abrupt signal change can be detected using the amplitude flatness measure together. With this processing, an abrupt signal change (impulsive sound) can more correctly be detected, and the abrupt signal change (impulsive sound) can appropriately be suppressed as needed.

16th Embodiment

A signal processing apparatus 4600 according to the 16th embodiment of the present invention will be described with reference to FIG. 46. The signal processing apparatus 4600 is an apparatus for detecting an abrupt input signal change.

Figure 46:
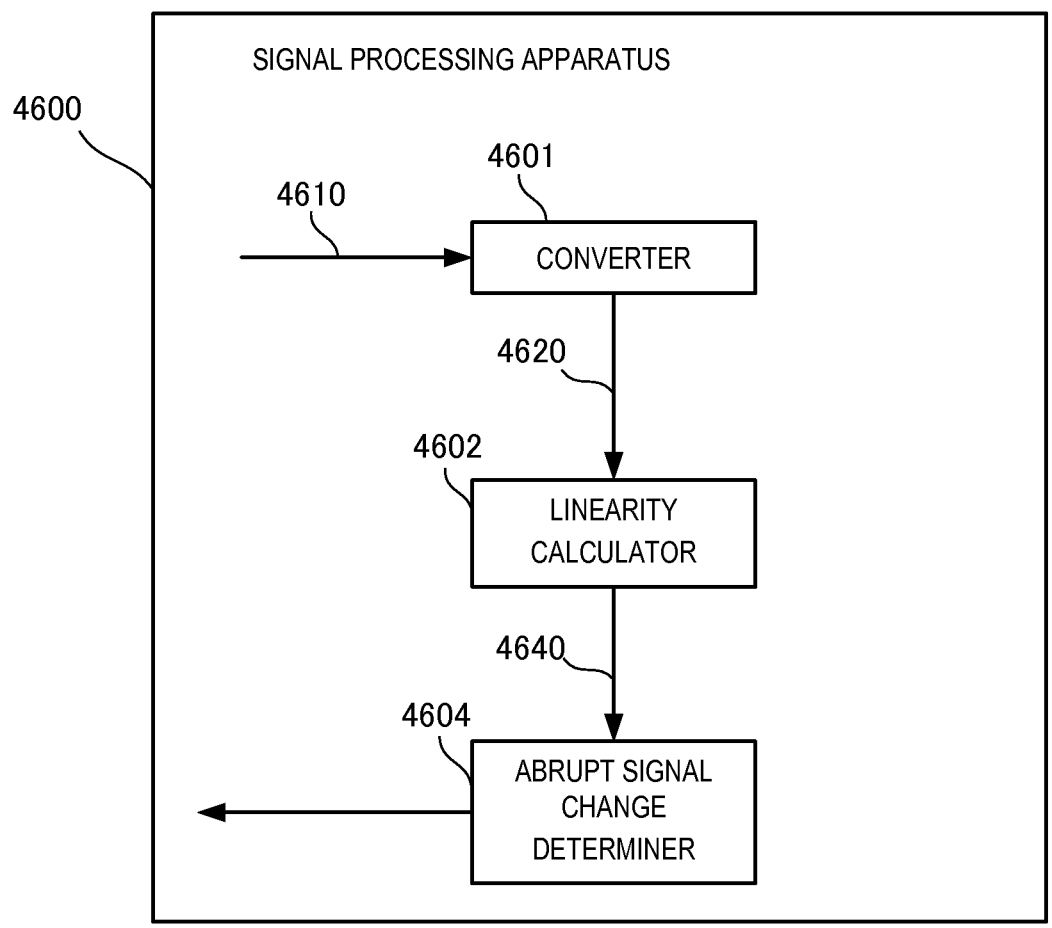
FIG. 46 is a block diagram showing the arrangement of a signal processing apparatus according to the 16th embodiment of the present invention.

As shown in FIG. 46, the signal processing apparatus 4600 includes a converter 4601, a linearity calculator 4602, and an abrupt signal change determiner 4604. The converter 4601 converts an input signal 4610 into a phase component signal 4620 and an amplitude component signal 4630 in a frequency domain. The linearity calculator 4602 calculates a linearity 4640 of the phase component signal 4620. The abrupt signal change determiner 4604 calculates the presence probability (estimated existence probability) of an abrupt input signal change based on the linearity 4640 calculated by the linearity calculator 4602.

With the above-described arrangement, it is possible to accurately detect an abrupt change in the input signal based on to what extent the phase component signal in the frequency domain is linear.

17th Embodiment

Overall Arrangement

A noise suppression apparatus according to the 17th embodiment of the present invention will be described with reference to FIGS. 47 to 54. The noise suppression apparatus according to this embodiment is applicable to suppress noise in, for example, a digital camera, a notebook personal computer, a mobile phone, a keyboard, a game machine controller, and the push buttons of a mobile phone. That is, the target signal (desired signal) of speech, music, environmental sound, or the like can be enhanced relative to a signal (noise or interfering signal) superimposed on it. However, the present invention is not limited to this, and the noise suppression apparatus is applicable to a signal processing apparatus of any type required to do abrupt signal change detection from an input signal. Note that in this embodiment, a noise suppression apparatus that detects and suppresses an impulsive sound as an example of an abrupt change in a signal will be described. The noise suppression apparatus according to this embodiment appropriately suppresses an impulsive sound generated by, for example, a button operation in a mode to perform an operation such as button pressing near a microphone. Simply speaking, a time domain signal including an impulsive sound is converted into a frequency domain signal, and the linearity of a phase component in the frequency space is calculated. Then, the presence probability (estimated existence probability) of an impulsive sound is calculated in accordance with the level of linearity (variation in the gradient).

FIG. 47 is a block diagram showing the overall arrangement of a noise suppression apparatus 4700. A noisy signal (signal including both a desired signal and noise) is supplied to an input terminal 4706 as a series of sample values. The noisy signal supplied to the input terminal 4706 undergoes transform such as Fourier transform in a converter 4701 and is divided into a plurality of frequency components. The plurality of frequency components are independently processed on a frequency basis. The description will be continued here concerning a specific frequency component of interest. Out of the frequency component, an amplitude spectrum (amplitude component) 4730 is supplied to a noise suppressor 4705, and a phase spectrum (phase component) 4720 is supplied to a phase controller 4702 and a linearity calculator 4708. Note that the converter 4701 supplies the noisy signal amplitude spectrum 4730 to the noise suppressor 4705 here. However, the present invention is not limited to this, and a power spectrum corresponding to the square of the amplitude spectrum may be supplied to the noise suppressor 4705.

The noise suppressor 4705 estimates noise using the noisy signal amplitude spectrum 4730 supplied from the converter 4701, thereby generating an estimated noise spectrum. In addition, the noise suppressor 4705 suppresses the noise using the generated estimated noise spectrum and the noisy signal amplitude spectrum 4730 supplied from the converter 4701, and transmits an enhanced signal amplitude spectrum as a noise suppression result to an amplitude controller 4703. The noise suppressor 4705 also receives a determination result from an abrupt change determiner 4709, and suppresses noise with different strengths in accordance with the presence/absence or degree of an abrupt signal change. The noise suppressor 4705 may detect a desired signal and protect the desired signal component for each frequency, and may also replace the amplitude with an estimated background sound if an abrupt signal change exists, and the desired signal component is not detected.

The phase controller 4702 rotates (shifts) the noisy signal phase spectrum 4720 supplied from the converter 4701, and supplies it to an inverter 4704 as an enhanced signal phase spectrum 4740. The phase controller 4702 also transmits the phase rotation amount (shift amount) to the amplitude controller 4703. The amplitude controller 4703 receives the phase rotation amount (shift amount) from the phase controller 4702, calculates an amplitude correction amount, corrects the enhanced signal amplitude spectrum in each frequency using the amplitude correction amount, and supplies a corrected amplitude spectrum 4750 to the inverter 4704. The inverter 4704 performs inversion by compositing the enhanced signal phase spectrum 4740 supplied from the phase controller 4702 and the corrected amplitude spectrum 4750 supplied from the amplitude controller 4703, and supplies the resultant signal to an output terminal 4707 as an enhanced signal.

The linearity calculator 4708 calculates the linearity in the frequency domain using the phase spectrum 4720 supplied from the converter 4701. The abrupt change determiner 4709 calculates the presence probability (estimated existence probability) of an abrupt signal change based on the linearity calculated by the linearity calculator 4708.

When an impulsive sound (abrupt signal change) exists, the presence probability can be estimated using the linearity of the phase due to the following reason. Assume that an isolated pulse exists in a frame of the converter 4701. The gradient of the phase in the frequency direction when the isolated pulse is Fourier-transformed is known to be obtained uniquely in correspondence with the position of the isolated pulse. For example, if the frame length in the converter corresponds to L samples, and the isolated pulse position is n0 ($0 \leq n0 \leq L-1$), the phase gradient is $-2\pi n0/L$. This is because the kth frequency component D(k) obtained by Fourier transform of an isolated pulse having an amplitude a is given by $$D(k) = a \cdot \exp(-j\theta(k)) \theta(k) = -2\pi \cdot k \cdot n0/L$$

The phase θ(k) is obviously proportional to k, that is, the frequency, and exhibits a line that slopes downward.

<<Arrangement of Converter>>

FIG. 48 is a block diagram showing the arrangement of the converter 4701. As shown in FIG. 48, the converter 4701 includes a frame divider 4801, a windowing unit 4802, and a Fourier transformer 4803. A noisy signal sample is supplied to the frame divider 4801 and divided into frames on the basis of K/2 samples, where K is an even number. The noisy signal sample divided into frames is supplied to the windowing unit 4802 and multiplied by a window function w(t). The signal obtained by windowing an nth frame input signal yn(t) (t=0, 1, ..., K/2−1) by w(t) is given by $$\bar{y}_n(t) = w(t)y_n(t) \quad (1)$$

Two successive frames may partially be overlaid (overlapped) and windowed. Assume that the overlap length is 50% the frame length. For t=0, 1, ..., K/2−1, the windowing unit 4802 outputs the left-hand sides of $$\left.\begin{array}{l}\bar{y}_n(t) = w(t)y_{n-1}(t+K/2)\\ \bar{y}_n(t+K/2) = w(t+K/2)y_n(t)\end{array}\right\} \quad (2)$$

A symmetric window function is used for a real signal. The window function is designed to make the input signal and the output signal match with each other except a calculation error when the output of the converter 4701 is directly supplied to the inverter 4704. This means $w^2(t)+w^2(t+K/2)=1$.

The description will be continued below assuming an example in which windowing is performed for two successive frames that overlap 50%. As w(t), the windowing unit can use, for example, a Hanning window given by $$w(t) = \begin{cases} 0.5 + 0.5\cos\left(\dfrac{\pi(t-K/2)}{K/2}\right), & 0 \le t < K \\ 0, & \text{otherwise} \end{cases} \quad (3)$$

Various window functions such as a Hamming window and a triangle window are also known. The windowed output is supplied to the Fourier transformer 4803 and transformed into a noisy signal spectrum Yn(k). The noisy signal spectrum Yn(k) is separated into the phase and the amplitude. A noisy signal phase spectrum argYn(k) is supplied to the phase controller 4702 and the linearity calculator 4708, whereas a noisy signal amplitude spectrum |Yn(k)| is supplied to the noise suppressor 4705. As already described, a power spectrum may be used in place of the amplitude spectrum.

<<Arrangement of Inverter>>

Figure 49:
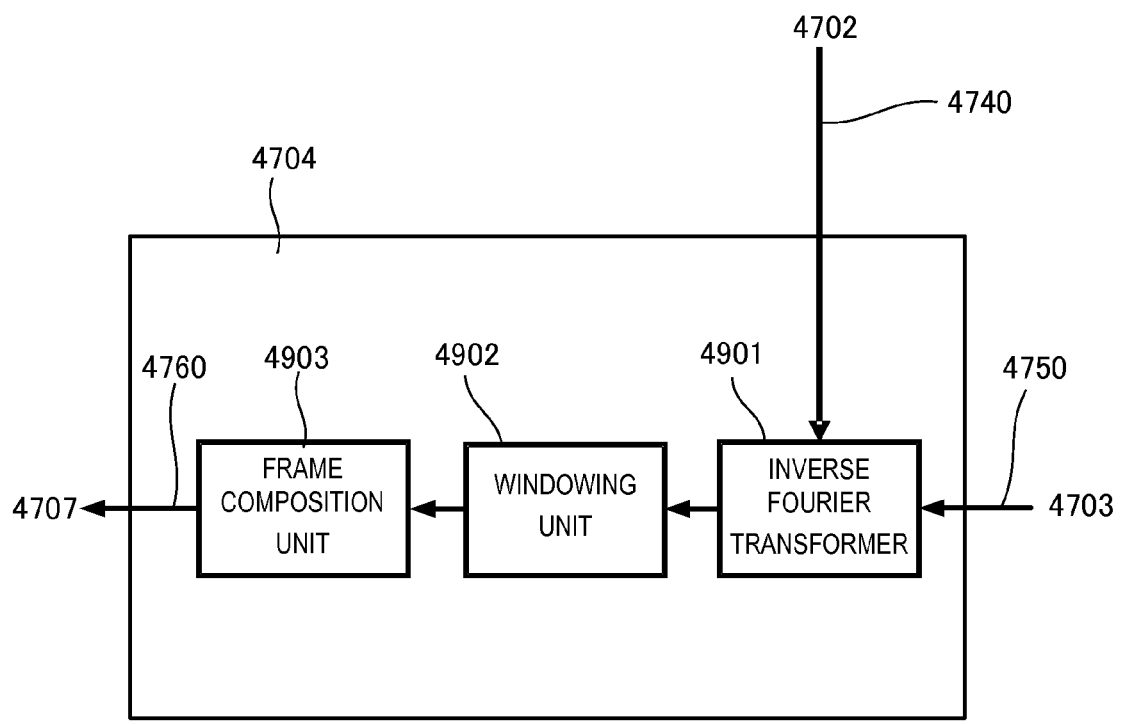
FIG. 49 is a block diagram showing the arrangement of an inverter according to the 17th embodiment of the present invention.

FIG. 49 is a block diagram showing the arrangement of the inverter 4704. As shown in FIG. 49, the inverter 4704 includes an inverse Fourier transformer 4901, a windowing unit 4902, and a frame composition unit 4903. The inverse Fourier transformer 4901 multiplies the enhanced signal amplitude spectrum 4750 supplied from the amplitude controller 4703 by the enhanced signal phase spectrum 4740 argXn(k) supplied from the phase controller 4702 to obtain an enhanced signal (the left-hand side of equation below).

$$X_n(k) = |X_n(k)| \cdot \arg X_n(k) \quad (4)$$

Inverse Fourier transform is performed for the obtained enhanced signal. The signal is supplied to the windowing unit 4902 as a series of time domain sample values xn(t) (t=0, 1, ..., K−1) in which one frame includes K samples, and multiplied by the window function w(t). A signal obtained by windowing an nth frame input signal xn(t) (t=0, 1, ..., K/2−1) by w(t) is given by the left-hand side of $$\bar{x}_n(t) = w(t)x_n(t) \quad (5)$$

Two successive frames may partially be overlaid (overlapped) and windowed. Assume that the overlap length is 50% the frame length. For t=0, 1, ..., K/2−1, the windowing unit 4902 outputs the left-hand sides of $$\left.\begin{array}{l}\bar{x}_n(t) = w(t)x_{n-1}(t+K/2)\\ \bar{x}_n(t+K/2) = w(t+K/2)x_n(t)\end{array}\right\} \quad (6)$$

and transmits them to the frame composition unit 4903.

The frame composition unit 4903 extracts the outputs of two adjacent frames from the windowing unit 4902 on the basis of K/2 samples, overlays them, and obtains an output signal (left-hand sides) for t=0, 1, ..., K−1 by $$\hat{x}_n(t) + \bar{x}_{n-1}(t+K/2) + \bar{x}_n(t) \quad (7)$$

An obtained enhanced speech signal 4760 is transmitted from the frame composition unit 4903 to the output terminal 4707.

Note that the conversion in the converter and the inverter in FIGS. 48 and 49 has been described as Fourier transform. However, any other transform such as Hadamard transform, Haar transform, or Wavelet transform may be used in place of the Fourier transform. Haar transform does not need multiplication and can reduce the area of an LSI chip. Wavelet transform can change the time resolution depending on the frequency and is therefore expected to improve the noise suppression effect.

The noise suppressor 4705 may perform actual suppression after a plurality of frequency components obtained by the converter 4701 are integrated. The number of frequency components after integration is smaller than the number of frequency components before integration. More specifically, a common suppression level is obtained for integrated frequency components obtained by integrating the frequency components. The suppression level is commonly used for individual frequency components belonging to the integrated frequency components. At this time, high sound quality can be achieved by integrating more frequency components from the low frequency range where the discrimination capability of hearing characteristics is high to the high frequency range with a poorer capability. When noise suppression is executed after integrating a plurality of frequency components, the number of frequency components to which noise suppression is applied decreases, and the whole calculation amount can be decreased.

<<Arrangement of Noise Suppressor>>

The noise suppressor 4705 estimates noise using the noisy signal amplitude spectrum supplied from the converter 4701 and generates an estimated noise spectrum. The noise suppressor 4705 then obtains a suppression coefficient using the noisy signal amplitude spectrum from the converter 4701 and the generated estimated noise spectrum, multiplies the noisy signal amplitude spectrum by the suppression coefficient, and supplies the resultant spectrum to the amplitude controller 4703 as an enhanced signal amplitude spectrum. In addition, upon receiving abrupt signal change presence probability (information representing to what extent an abrupt signal change exists) from the abrupt change determiner 4709, the noise suppressor 4705 supplies a mixture of the noisy signal amplitude spectrum and the estimated noise spectrum based on the presence probability to the amplitude controller 4703 as an enhanced signal amplitude spectrum. At this time, the noise suppressor 4705 may detect a desired signal and protect the desired signal component for each frequency.

To estimate noise, various estimation methods such as the methods described in non-patent literatures 1 and 2 are usable.

For example, non-patent literature 1 discloses a method of obtaining, as an estimated noise spectrum, the average value of noisy signal amplitude spectra of frames in which no desired signal is generated. In this method, it is necessary to detect the presence of the desired signal. A section where the desired signal exists can be determined by the power of the enhanced signal.

As an ideal operation state, the enhanced signal is the desired signal other than noise. In addition, the level of the desired signal or noise does not largely change between adjacent frames. For these reasons, the enhanced signal level of an immediately preceding frame is used as an index to determine a noise section. If the enhanced signal level of the immediately preceding frame is equal to or smaller than a predetermined value, the current frame is determined as a noise section. A noise spectrum can be estimated by averaging the noisy signal amplitude spectra of frames determined as a noise section.

Non-patent literature 1 also discloses a method of obtaining, as an estimated noise spectrum, the average value of noisy signal amplitude spectra in the early stage in which supply of them has started. In this case, it is necessary to meet a condition that the desired signal is not included immediately after the start of estimation. If the condition is met, the noisy signal amplitude spectrum in the early stage of estimation can be obtained as the estimated noise spectrum.

Non-patent literature 2 discloses a method of obtaining an estimated noise spectrum from the minimum value of the statistical noisy signal amplitude spectrum. In this method, the minimum value of the noisy signal amplitude spectrum within a predetermined time is statistically held, and a noise spectrum is estimated from the minimum value. The minimum value of the noisy signal amplitude spectrum is similar to the shape of a noise spectrum and can therefore be used as the estimated value of the noise spectrum shape. However, the minimum value is smaller than the original noise level. Hence, a spectrum obtained by appropriately amplifying the minimum value is used as an estimated noise spectrum.

The noise suppressor 4705 can perform various kinds of suppression. Typical examples are the SS (Spectrum Subtraction) method and an MMSE STSA (Minimum Mean-Square Error Short-Time Spectral Amplitude Estimator) method. In the SS method, the estimated noise spectrum is subtracted from the noisy signal amplitude spectrum supplied from the converter 4701. In the MMSE STSA method, a suppression coefficient is calculated using the noisy signal amplitude spectrum supplied from the converter 4701 and the generated estimated noise spectrum, and the noisy signal amplitude spectrum is multiplied by the suppression coefficient. The suppression coefficient is decided so as to minimize the mean square power of the enhanced signal.

Additionally, the noise suppressor 4705 changes the degree of noise suppression in accordance with the abrupt change presence probability (information representing to what extent an abrupt signal change exists) received from the abrupt change determiner 4709. For example, a mixture of the noisy signal amplitude spectrum and the estimated noise spectrum based on the presence probability may be supplied to the amplitude controller 4703 as the an enhanced signal amplitude spectrum. More specifically, on the basis of a frequency component, frequency band, or frame with high abrupt signal change presence probability, the mixing ratio of the estimated noise spectrum is increased (strong suppression is applied) to suppress the abrupt change. The degree of suppression may continuously be controlled in accordance with the presence probability. Alternatively, suppression may be performed in multiple levels (discrete levels) such as suppression level 0, suppression level 1, and suppression level 2.

It is also possible to, prior to the replacement, detect an important noisy signal amplitude spectrum component and exclude the detected important noisy signal amplitude spectrum component from the component to be replaced with the estimated noise spectrum, or increase the mixing ratio of the noisy signal amplitude spectrum. As the index of importance when detecting the important noisy signal amplitude spectrum component, the magnitude of the noisy signal amplitude spectrum can be used. A component having a large amplitude is a component of a target signal at a high probability. Holding this component contributes to prevention of a degradation in sound quality of the target signal.

The peak characteristic of the noisy signal amplitude spectrum can also be used as the index of importance. A noisy signal amplitude having a peak, that is, a value larger than peripheral values along the frequency axis is a component of a target signal at a high probability. Holding this component contributes to prevention of a degradation in sound quality of the target signal. In particular, a conspicuous peak, that is, an amplitude value much larger than peripheral amplitude values is important. When this component is reliably protected, sound quality of the target signal can further be increased.

To detect a peak, for example, a pure sound component detection method described in non-patent literature 3 or a method disclosed in non-patent literature 5 is usable. A detected peak may be evaluated in accordance with a predetermined condition, and a peak that does not meet the condition may be excluded. For example, there is little possibility that a peak having a value smaller than the estimated noise is the target signal. That is, it is possible to, using the estimated noise as a reference, leave only peaks much larger than the estimated noise and exclude others. Whether a peak is sufficiently large can be determined by comparing it with a constant multiple of the estimated noise. In this way, it is evaluated whether a detected peak meets a predetermined condition, and final peak components are then selected. This can reduce peak detection errors and enhance the effect of suppressing an abrupt signal change.

<<Arrangement of Phase Controller and Amplitude Controller>>

Figure 50:
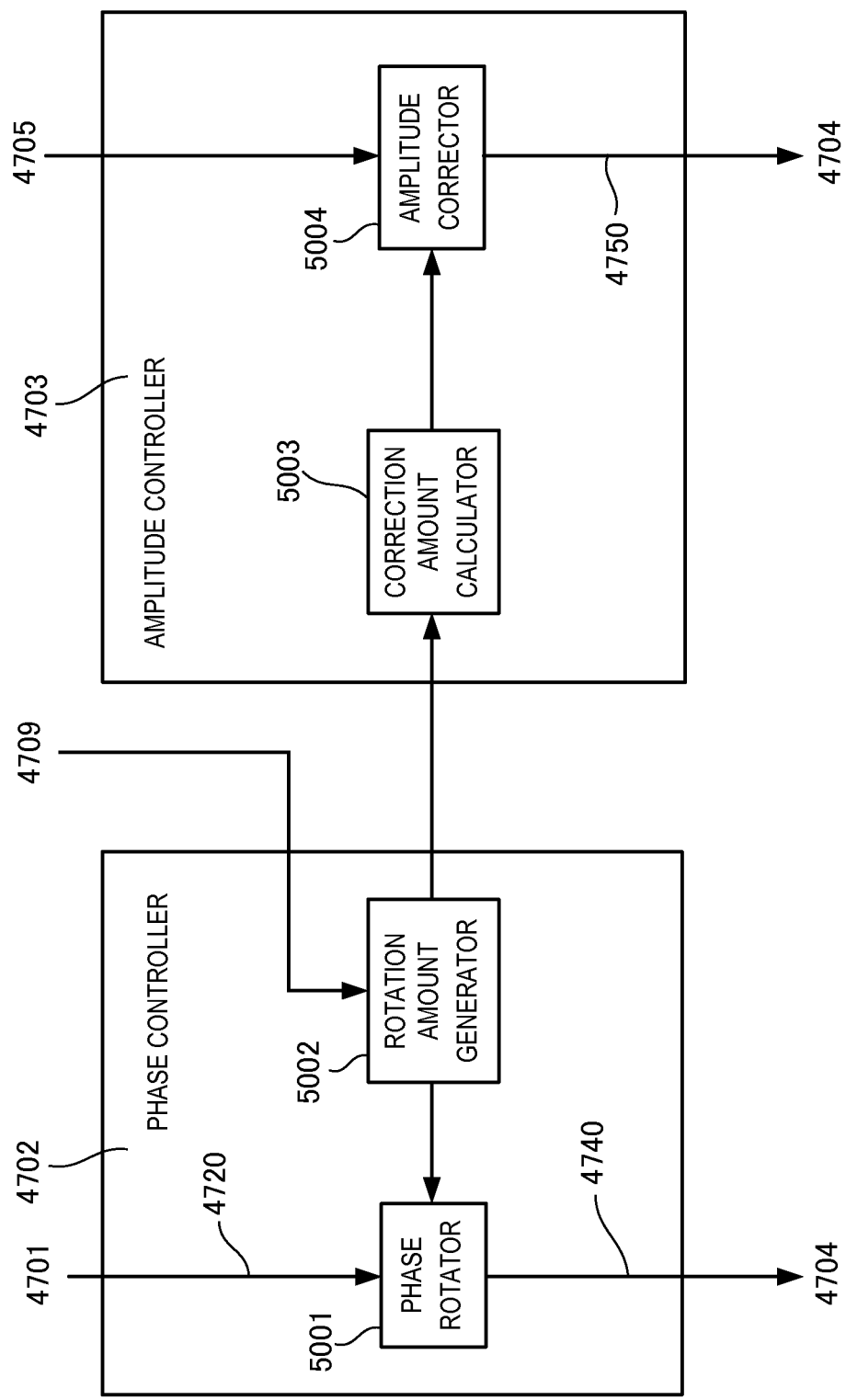
FIG. 50 is a block diagram showing the arrangement of a phase controller and an amplitude controller according to the 17th embodiment of the present invention.

FIG. 50 is a block diagram showing the arrangement of the phase controller 4702 and the amplitude controller 4703. As shown in FIG. 50, the phase controller 4702 includes a phase rotator 5001 and a rotation amount generator 5002, and the amplitude controller 4703 includes a correction amount calculator 5003 and an amplitude corrector 5004.

The rotation amount generator 5002 generates the rotation amount of the noisy signal phase spectrum for a frequency component determined to "have an abrupt change in the signal" by the abrupt change determiner 4709, and supplies the rotation amount to the phase rotator 5001 and the correction amount calculator 5003. Upon receiving the rotation amount supplied from the rotation amount generator 5002, the phase rotator 5001 rotates (shifts) the noisy signal phase spectrum 4720 supplied from the converter 4701 by the supplied rotation amount, and supplies the rotated spectrum to the inverter 4704 as the enhanced signal phase spectrum 4740.

The correction amount calculator 5003 decides the correction coefficient of the amplitude based on the rotation amount supplied from the rotation amount generator 5002, and supplies the correction coefficient to the amplitude corrector 5004.

The rotation amount generator 5002 generates the rotation amount by, for example, a random number. When the noisy signal phase spectrum is rotated for each frequency by a random number, the shape of the noisy signal phase spectrum 4720 changes. With the change in the shape, the feature of an abrupt signal change such as an impulsive sound can be weakened.

Examples of the random number are a uniform random number whose occurrence probability is uniform and a normal random number whose occurrence probability exhibits a normal distribution. A rotation amount generation method using a uniform random number will be described first. A uniform random number can be generated by a linear congruential method or the like. For example, uniform random numbers generated by the linear congruential method are uniformly distributed within the range of 0 to (2^M)−1, where M is an arbitrary integer, and ^ represents a power. Phase rotation amounts φ need to be distributed within the range of 0 to 2π. To do this, the generated uniform random numbers are converted. The conversion is performed by $$\phi = 2\pi \frac{R}{R_{max}} \quad (8)$$

where R is the uniform random number, and Rmax is the maximum value capable of being generated by the uniform random number. When a uniform random number is generated by the above-described linear congruential method, Rmax=(2^M)−1.

To simplify the calculation, the value R may directly be decided as the rotation amount. As the rotation amount, 2π represents just one revolution. A case where the phase is rotated by 2π is equivalent to a case where the phase is not rotated. Hence, a rotation amount 2π+α is equivalent to a rotation amount α. A case where a uniform random number is generated by the linear congruential method has been explained here. Even in a case where a uniform random number is generated by another method, the rotation amount φ is obtained by the above equation. When and how many times random number generation is to be performed may be decided in accordance with the determination result of the abrupt change determiner 4709.

The phase rotator 5001 receives the rotation amount from the rotation amount generator 5002 and rotates the noisy signal phase spectrum. If the noisy signal phase spectrum is expressed as an angle, it can be rotated by adding the value of the rotation amount φ to the angle. If the noisy signal phase spectrum is expressed as the normal vector of a complex number, it can be rotated by obtaining the normal vector of the rotation amount φ and multiplying the noisy signal phase spectrum by the normal vector.

The normal vector of the rotation amount φ can be obtained by $$\Phi = \cos(\phi) + j\sin(\phi) \quad (9)$$

In equation (9), Φ is the rotation vector, and j represents sqrt(−1). Note that sqrt is the square root.

A correction coefficient calculation method by the correction amount calculator 5003 is the same as the method described concerning the correction amount calculator 503 shown in FIG. 5, and a description thereof will be omitted.

<<Arrangement of Linearity Calculator and Abrupt Change Determiner>>

Figure 51:
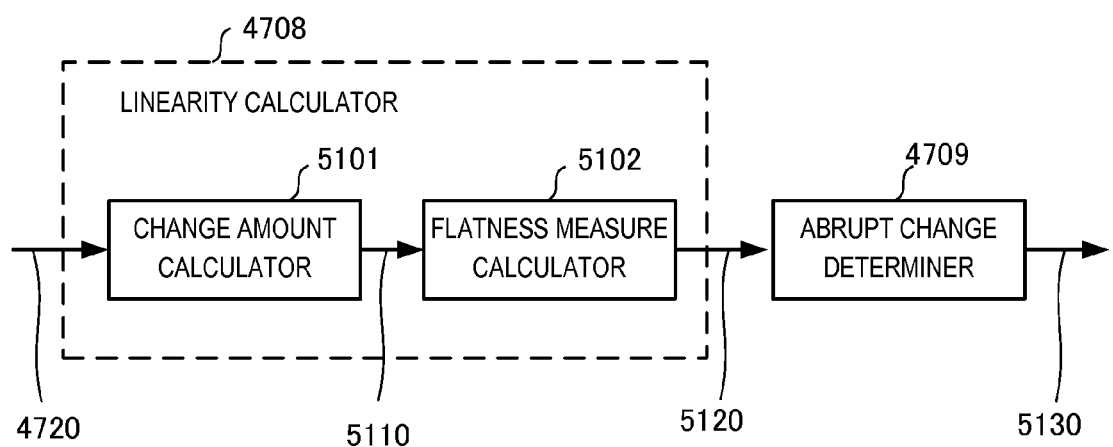
FIG. 51 is a block diagram for explaining the arrangement of a linearity calculator and an abrupt change determiner according to the 17th embodiment of the present invention.

FIG. 51 is a block diagram for explaining the internal arrangement of the linearity calculator 4708 and the abrupt change determiner 4709. As shown in FIG. 51, the linearity calculator 4708 includes a change amount calculator 5101 that calculates a phase change amount in the frequency direction, and a flatness measure calculator 5102 that calculates the flatness measure of the phase change amount. The change amount calculator 5101 receives the phase component signal 4720 (p(k), k is a frequency), and obtains a phase difference Δp(k)=p(k)−p(k−1) to an adjacent frequency as a phase change amount 5110 (phase gradient).

The flatness measure calculator 5102 checks the flatness measure (variation) of the phase change amount Δp(k)=p(k)−p(k−1) obtained by the change amount calculator 5101 along the frequency axis. A difference $\Delta_2 p(k) = \Delta p(k) - \Delta p(k-1)$ of the phase change amount of the adjacent frequency is obtained as a flatness measure 5120. If the phase change amount is flat, the difference is 0. One flatness measure 5120 may be obtained in correspondence with each frequency component, each band, or all frequencies. Flatness measures in a single or a plurality of bands may be integrated and used in place of the flatness measure for all frequencies.

If the flatness measure is obtained not for each frequency but for each frequency band (sub-band) or frame, flatness measure errors by phase components other than abrupt signal change components can be reduced by determination in boarder aspects. For example, the sum of flatness measures for the respective frequencies in the frequency direction may be obtained as the flatness measure for each frame. By this correction, the reliability of the flatness measure for each frequency can be increased. In addition, the flatness measure for each frequency may be corrected using the flatness measure for each frequency band or frame. For example, if the flatness measure for a certain frequency band represents that "an abrupt signal change exists", the flatness measure for all frequencies within the frequency band is forcibly corrected so as to represent "an abrupt signal change exists", thereby reducing flatness measure errors caused by disturbance of other signal components. To the contrary, if the flatness measure for a certain frequency band represents that "no abrupt signal change exists", the flatness measure for all frequencies within the frequency band is forcibly corrected so as to represent "no abrupt signal change exists", thereby reducing flatness measure errors caused by disturbance of other signal components. Alternatively, the flatness measure for each frequency within the band may evenly be corrected in a direction to easily determine "presence", and the configuration for independently obtaining the flatness measure for each frequency may be maintained in itself. When the flatness measure is obtained for each frequency or frequency band, the degree of abrupt change suppression can be changed for each frequency or frequency band, and more accurate suppression can be performed.

In addition, the differential value of the phase may be obtained as the phase change amount, and the differential value of the differential value of the phase change amount may be obtained as the flatness measure 5120. In this case, if the quadratic differential value of the phase is close to 0 (equal to or smaller than a predetermined value), the flatness measure is high.

The change amount calculator 5101 calculates the change amount using the phase difference between adjacent frequencies. However, the present invention is not limited to this. The linearity (flatness measure of a phase change) may be determined by differentiation of the frequency of the phase. The smaller the variation between a plurality of differential results of a plurality of frequencies is, the higher the linearity is. A local linearity can be evaluated using a local differential result. In particular, the differential between two adjacent frequency components can be approximated by a difference. In this case, the smaller the variation between a plurality of differences is, the higher the linearity is determined to be. The flatness measure can be used as the index of the variation.

The abrupt change determiner 4709 determines the calculated flatness measure as presence probability of an abrupt signal change. In addition, a result of converting the flatness measure using a predetermined linear function, nonlinear function, polynomial, or the like may be output as presence probability 5130 of an abrupt signal change. When an abrupt signal change is detected as the "presence probability" of the abrupt signal change, suppression of higher quality can be achieved a compared to "existence itself". This is because if a determination error occurs in determination of "existence itself", that is, binary determination, the influence on suppression is fatal. There are only two choices, "suppress" and "not suppress". Hence, if suppression is applied due to a determination error in a case where suppression should not be performed, fatal distortion is given to the target signal and perceived. To the contrary, if suppression is not applied in a case where suppression should be performed, the abrupt signal change remains intact and is perceived. On the other hand, if determination is done using "presence probability", that is, a continuous value, and suppression of level according to the determination result is performed, the influence of both determination errors can be reduced.

FIG. 52 is a graph showing a phase and its change amount. When the phase changes along the frequency axis in the frequency domain, like a graph 5201, the phase change amount changes as indicated by a graph 5202 along the frequency axis in the frequency domain. The linearity of the phase is discriminated by deriving a flatness measure 5203 of the change.

The phase is known to linearly change at a timing when the signal abruptly changes. It is therefore possible to evaluate the presence probability of an abrupt signal change by calculating the linearity of the phase, that is, the flatness measure of the phase change in the above-described way. The abrupt change can be suppressed, or its influence can be reduced by rotating the phase spectrum in a frame in which the abrupt signal change such as an impulsive sound exists. Hence, a high-quality enhanced signal can be obtained.

Figure 53:
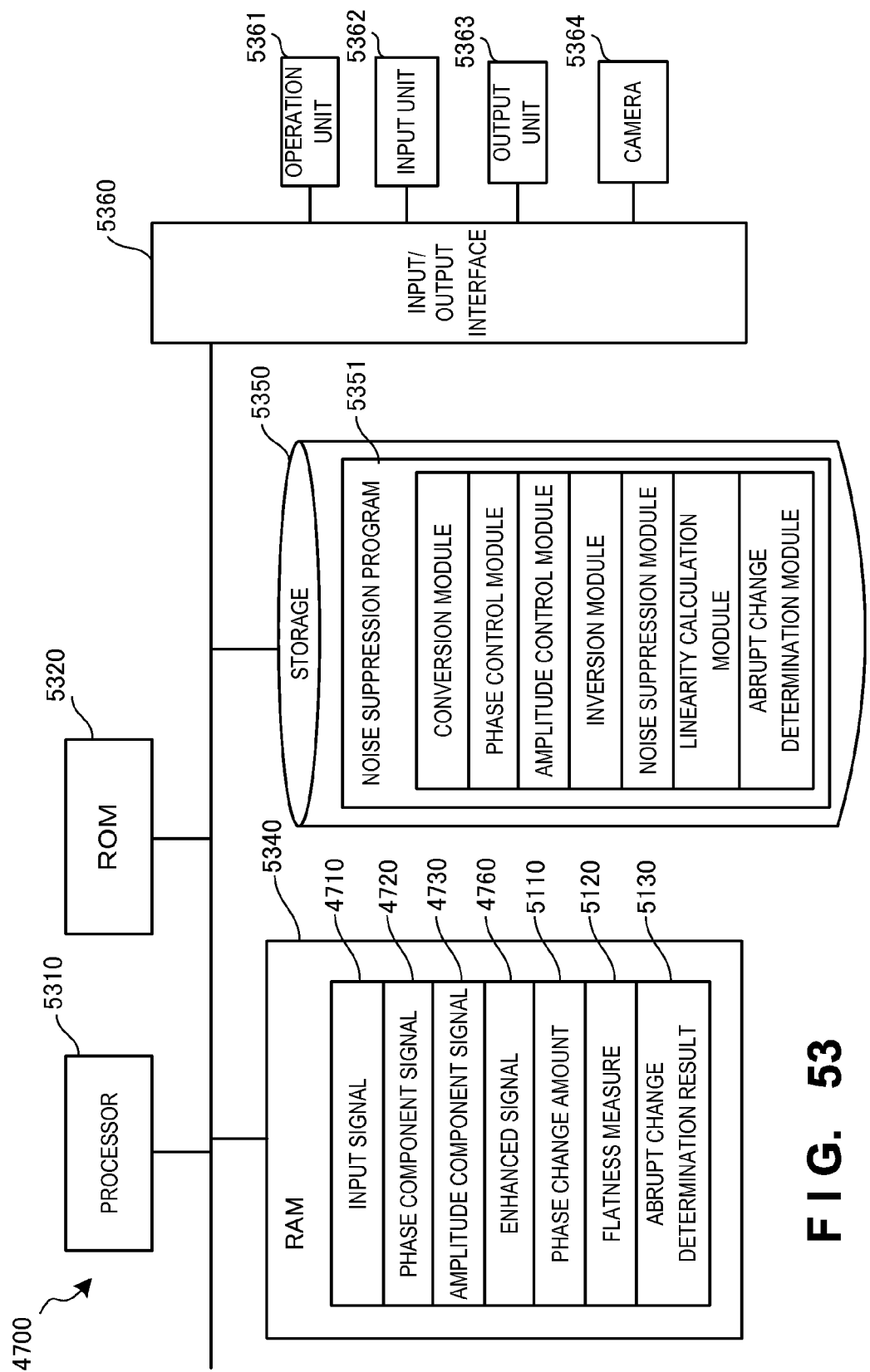
FIG. 53 is a block diagram showing the hardware arrangement of the noise suppression apparatus according to the 17th embodiment of the present invention.

FIG. 53 is a block diagram for explaining a hardware arrangement when the noise suppression apparatus 4700 according to this embodiment is implemented using software.

The noise suppression apparatus 4700 includes a processor 5310, a ROM (Read Only Memory) 5320, a RAM (Random Access Memory) 5340, a storage 5350, an input/output interface 5360, an operation unit 5361, an input unit 5362, and an output unit 5363. The noise suppression apparatus 4700 may include a camera 5364. The processor 5310 is a central processing unit and executes various programs, thereby controlling the overall noise suppression apparatus 4700.

The ROM 5320 stores various parameters as well as a boot program to be executed first by the processor 5310. The RAM 5340 includes an area to store the input signal 4710, the phase component signal 4720, the amplitude component signal 4730, the enhanced signal 4760, the phase change amount 5110, the flatness measure 5120, the abrupt change determination result 5130, and the like as well as a program load area (not shown).

The storage 5350 stores a noise suppression program 5351. The noise suppression program 5351 includes a conversion module, a phase control module, an amplitude control module, an inversion module, a noise suppression module, a linearity calculation module, and an abrupt change determination module. When the processor 5310 executes the modules included in the noise suppression program 5351, the functions of the converter 4701, the phase controller 4702, the amplitude controller 4703, the inverter 4704, the noise suppressor 4705, the linearity calculator 4708, and the abrupt change determiner 4709 shown in FIG. 47 can be implemented. Note that the storage 5350 may store a noise database.

An enhanced signal that is the output of the noise suppression program 5351 executed by the processor 5310 is output from the output unit 5363 via the input/output interface 5360. This can suppress, for example, the operation sound of the operation unit 5361 input from the input unit 5362. Also possible is an application method of, for example, detecting impulsive sound inclusion in the input signal input from the input unit 5362 and starting shooting by the camera 5364.

FIG. 54 is a flowchart for explaining the procedure of abrupt signal change determination processing of the noise suppression program 5351. When a signal is input from the input unit 5362 in step S5401, the process advances to step S5403. In step S5403, the converter 4701 converts the input signal into a frequency domain and divides it into an amplitude and a phase. In step S5405, the discrete frequency k is set to 1, the count value I is set to 0, and processing in the frequency space is sequentially started. When the process advances to step S5407, a change in the phase at the set frequency is calculated. In step S5409, a change in the phase change is calculated. The linearity of the phase is determined in accordance with the change in the phase change. More specifically, the level of linearity at the frequency k is obtained based on to what extent the change in the phase change is close to 0. In addition, to calculate the presence probability of an abrupt signal change for each frame, if the change in the phase change is less than a predetermined threshold N, I is incremented in step S5413.

On the other hand, if the change in the phase change is equal to or more than the predetermined threshold N, it is determined that the phase change is not flat, that is, the linearity of the phase is low, and the process advances to step S5415 without incrementing I. Steps S5407 to S5413 described above are repeated until k=F (F is the number of frequency components in the entire frame). Finally in step S5417, I (frequency of high linearity) is compared with a predetermined threshold M. If I is equal to or more than M, the frame is determined to include an impulsive sound (abrupt signal change) (step S5421). Otherwise, it is determined that no impulsive sound (abrupt signal change) exists (step S5423). The abrupt signal change presence probability for each frequency is supplied to the noise suppressor 4705 and the phase controller 4702 (step S5425). A determination result representing the presence/absence of an abrupt signal change in each frame may also be supplied to the noise suppressor 4705 and the phase controller 4702.

With the above-described processing, an abrupt signal change represented by an impulsive sound can more correctly be detected, and the impulsive sound (abrupt signal change) can appropriately be suppressed as needed.

18th Embodiment

A noise suppression apparatus according to the 18th embodiment of the present invention will be described next with reference to FIG. 55. FIG. 55 is a block diagram for explaining the functional arrangement of a noise suppression apparatus 5500 according to this embodiment. The noise suppression apparatus 5500 according to this embodiment is different from the 17th embodiment in that a converter 5501 generates a complex signal 5550, and a linearity detector 5508 and an abrupt change determiner 4709 perform detection and determination, respectively, based on the complex signal 5550. The rest of the components and operations is the same as in the 17th embodiment. Hence, the same reference numerals denote the same components and operations, and a detailed description thereof will be omitted.

FIG. 56 is a block diagram for explaining the internal arrangement of the linearity detector 5508 and the abrupt change determiner 4709. As shown in FIG. 56, the linearity detector 5508 includes a change amount calculator 5601 that calculates a phase change amount in the frequency direction, and a flatness measure calculator 5102 that calculates the flatness measure of the phase change amount. The change amount calculator 5601 receives the complex signal 5550 (q(k), k is a frequency), and obtains a phase difference $\Delta p(k)=p(k)-p(k-1)$ to an adjacent frequency as a phase change amount 5110 (phase gradient).

The flatness measure calculator 5102 checks the flatness measure (variation) of the phase change amount $\Delta p(k)=p(k)-p(k-1)$ obtained by the change amount calculator 5601 along the frequency axis. A difference $\Delta_2 p(k)=\Delta p(k)-\Delta p(k-1)$ of the phase change amount of the adjacent frequency is obtained as a flatness measure 5120. If the phase change amount is flat, the difference is 0. One flatness measure 5120 may be obtained in correspondence with each frequency component, each band (band formed by dividing the frequency into arbitrary widths), or all frequencies. In addition, the differential value of the phase may be obtained as the phase change amount, and the differential value of the differential value of the phase change amount may be obtained as the flatness measure 5120. In this case, if the quadratic differential value of the phase is close to 0 (equal to or smaller than a predetermined value), the phase change amount can be determined as flat. When the determination is performed for each band, processing can be performed in a more sophisticated manner. That is, it is possible to erase an impulsive sound for each band and more accurately suppress the impulsive sound.

If the absolute value of the calculated flatness measure is a predetermined value or less, the abrupt change determiner 4709 determines that the frequency (one frequency component, frequency band, or all frequencies (that is, one frame)) corresponding to the flatness measure includes an impulsive sound. As a determination result 5130, a value between 0 and 1 associated with the absolute value of the flatness measure is output as the determination result 5130. Likelihood of presence of an impulsive sound can thus be obtained.

As described above, according to this embodiment, the linearity of the phase can be detected using a complex signal in place of a phase component signal.

19th Embodiment

Figure 57:
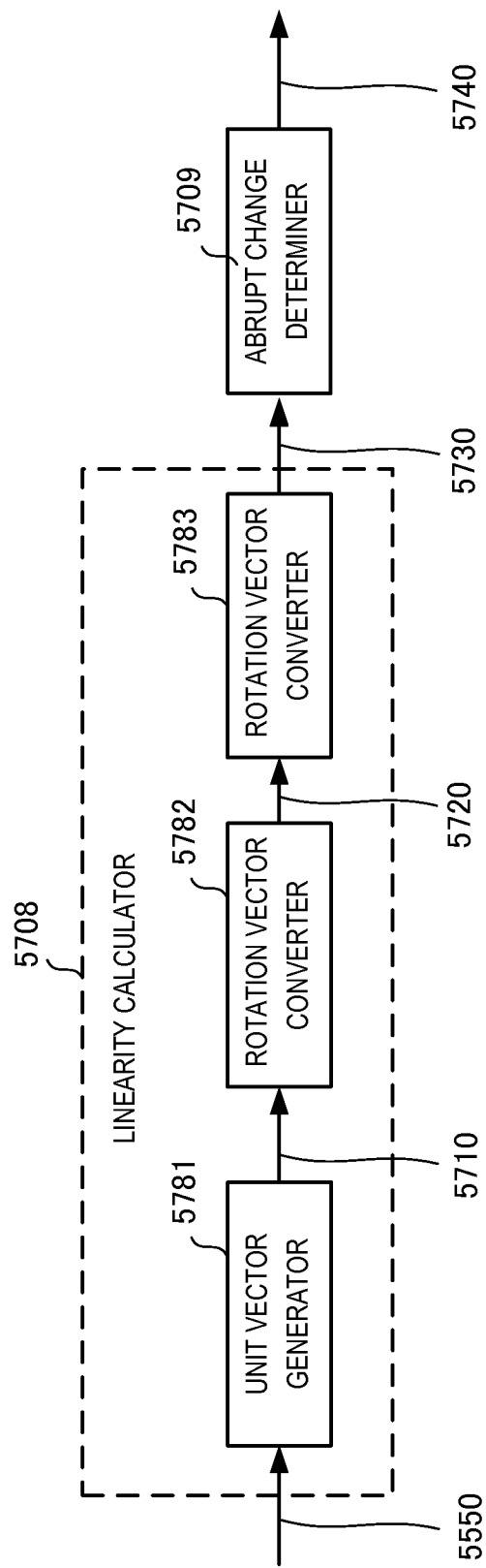
FIG. 57 is a block diagram showing the arrangement of a phase controller and an amplitude controller according to the 19th embodiment of the present invention.

A noise suppression apparatus according to the 19th embodiment of the present invention will be described next with reference to FIG. 57. FIG. 57 is a block diagram for explaining the functional arrangement of a linearity detector 5708 included in the noise suppression apparatus according to this embodiment. The linearity detector 5708 according to this embodiment is different from the 18th embodiment in that a unit vector generator 5781, a rotation vector converter 5782, and a rotation vector converter 5783 are provided. The linearity detector 5708 is also different in that an abrupt change determiner 5709 determines the presence/absence or degree of an abrupt change in a signal based on a rotation vector. The rest of the components and operations is the same as in the 18th embodiment. Hence, the same reference numerals denote the same components and operations, and a detailed description thereof will be omitted.

The unit vector generator 5781 converts an input spectrum (complex vector) into unit vectors on a frequency basis using a complex signal 5550. More specifically, each of the real part and the imaginary part of the complex signal 5550 is divided by an amplitude value.

The rotation vector converter 5782 converts a unit vector 5710 into a rotation vector (first rotation vector 5720) between adjacent frequencies. The rotation amount of the rotation vector here is equivalent to the phase change amount. Multiplication to obtain the inner product of a conjugate A* of a reference vector and a vector B after rotation is performed, thereby obtaining a rotation vector RotVec given by RotVec=A*·B.

More specifically, the real parts of the reference vector are added, the imaginary parts are added, the sums are added, and one of the imaginary parts is subtracted. The rotation vector 5720 can thus be calculated.

The rotation vector converter 5783 checks the flatness measure (variation) of the first rotation vector 5720 obtained by the rotation vector converter 5782 along the frequency axis. If the phase change amount along the frequency axis is constant, the variation in the rotation vector becomes small. Hence, the change amount of the first rotation vector 5720 is obtained along the frequency axis. More specifically, a rotation vector (second rotation vector 5730) between adjacent frequencies is obtained for the first rotation vector 5720. This is equivalent to differentiating the first rotation vector.

The abrupt change determiner 5709 recognizes the real part of the second rotation vector 5730 as a flatness measure.

Since the second rotation vector 5730 is a unit vector as well, the real part takes a value of −1 to 1. The more linearly the phase changes, the smaller the angle change amount of the first rotation vector is (the smaller the variation in the rotation vector is). The smaller the change amount of the first rotation vector is (the smaller the variation in the rotation vector is), the larger the real part of the second rotation vector is, that is, the smaller the angle of the second rotation vector is. In this case as well, one flatness measure may be obtained in correspondence with each frequency, each band (band formed by dividing the frequency into arbitrary widths), or all frequencies.

The abrupt change determiner 5709 regards the real part of the second rotation vector 5730 as the presence probability of an abrupt change, and determines the presence or degree of an abrupt change depending on whether the real part exceeds a threshold (for example, 0.7 or 0.8) close to +1. The abrupt change determiner 5709 outputs presence probability (1 to 0) of an impulsive sound as a determination result 5740. Likelihood of impulsive sound inclusion can thus be obtained.

Figure 58:
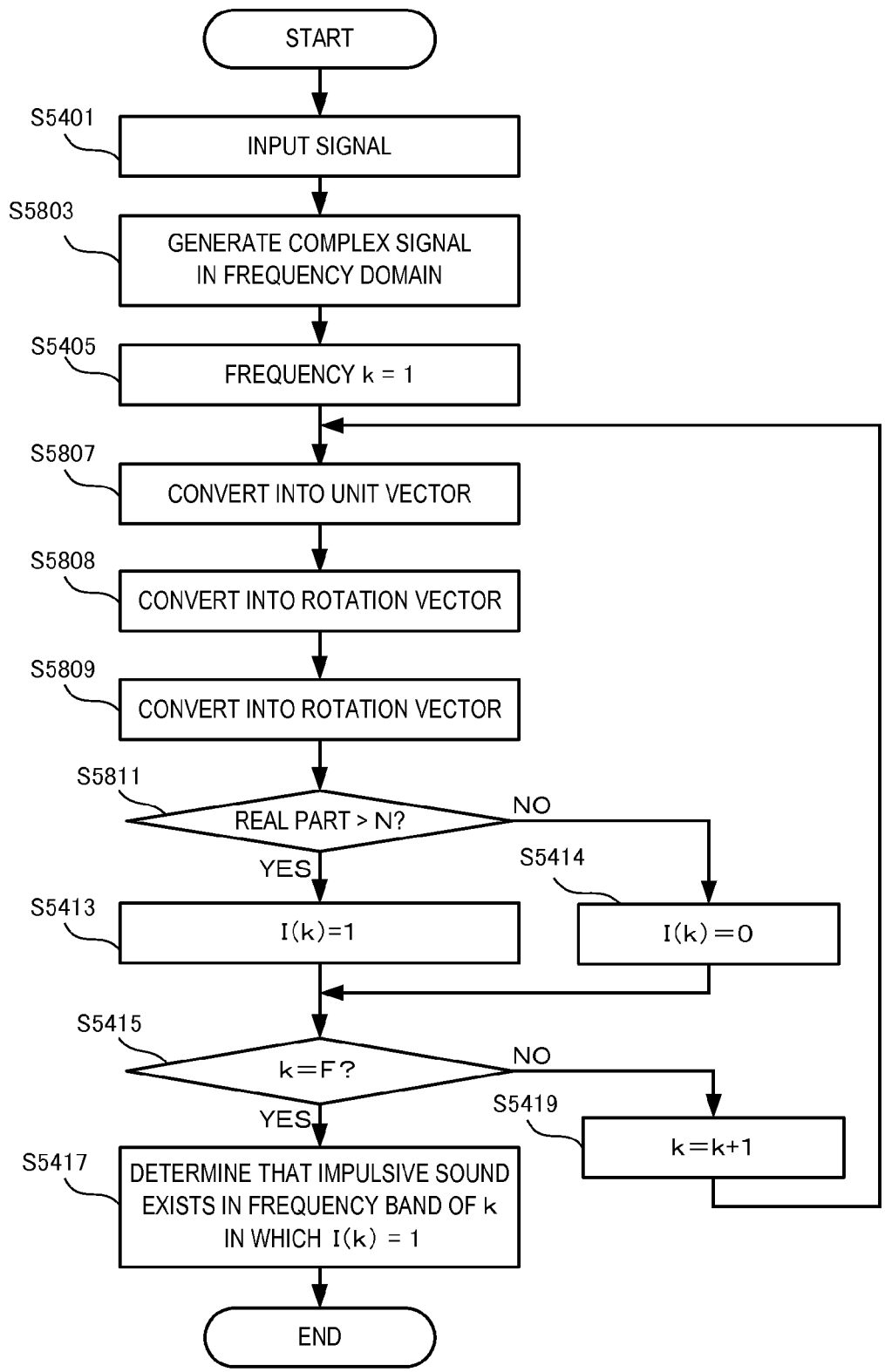
FIG. 58 is a flowchart for explaining the procedure of processing of a noise suppression apparatus according to the 19th embodiment of the present invention.

FIG. 58 is a flowchart for explaining the procedure of processing by a noise suppression program according to this embodiment. When a speech signal is input from a speech input unit 5362 in step S5401, the process advances to step S5803. In step S5803, a converter 5501 generates a complex signal from the input signal in the frequency domain. In step S5405, a discrete frequency k is set to 1, and processing in the frequency space is sequentially started. When the process advances to step S5807, the complex signal is converted into a unit vector for the set frequency. In step S5808, the unit vector of an adjacent frequency component is converted into the first rotation vector. In step S5809, the first rotation vector of the adjacent frequency component is converted into the second rotation vector. In step S5811, the real part of the second rotation vector is regarded as the presence probability of an abrupt signal change and compared with a threshold N. If the real part exceeds the predetermined threshold N, it is determined that the phase changes flatly, and the linearity is high. In step S5413, I(k)=1 is set. On the other hand, if the real part is equal to or less than the predetermined threshold N, it is determined that the phase change is not flat, and the linearity is low. In step S5414, I(k)=0 is set. Steps S5807 to S5414 are repeated until k=F (F is the number of frequency components in the entire frame). Finally in step S5417, it is determined that an abrupt signal change exists at the frequency k when I(k)=1, and the determination result is supplied to a noise suppressor 4705 and a phase controller 4702.

As described above, according to this embodiment, it is possible to detect the linearity from the rotation vector of the rotation vector of the phase using a complex signal. Note that although a unit vector is generated to use the real part of a rotation vector in flatness measure determination, the present invention is not limited to this. In addition, not the real part of the second rotation vector but the angle of the second rotation vector may be compared with the threshold, and if the angle is larger than the threshold, it may be determined that an abrupt signal change exists.

20th Embodiment

Note that in the 12th to 19th embodiments, a case where an abrupt signal change detection method is applied to a noise suppression apparatus aiming at suppressing an abrupt signal change has been described. However, the present invention is not limited to this. The abrupt signal change detection method is usable in various apparatuses, systems, and situations aiming at detecting an impulsive sound. In addition, the detection target is not limited to an impulsive sound (a speech signal that abruptly rises and immediately falls). A signal that abruptly rises (or falls) and remains intact can also be detected as an abrupt change.

For example, a present audio encoding method (for example, encoder of MPEG AAC) employs a different information compression method at an abrupt signal change called an attack. At the abrupt signal change, the analysis window length is changed, and preceding noise called a pre-echo is suppressed. Hence, the abrupt signal change needs to be detected. As compared to a method of doing detection using a change in the amplitude or entropy, it is possible to accurately detect an abrupt change and effectively compress information.

Figure 59:
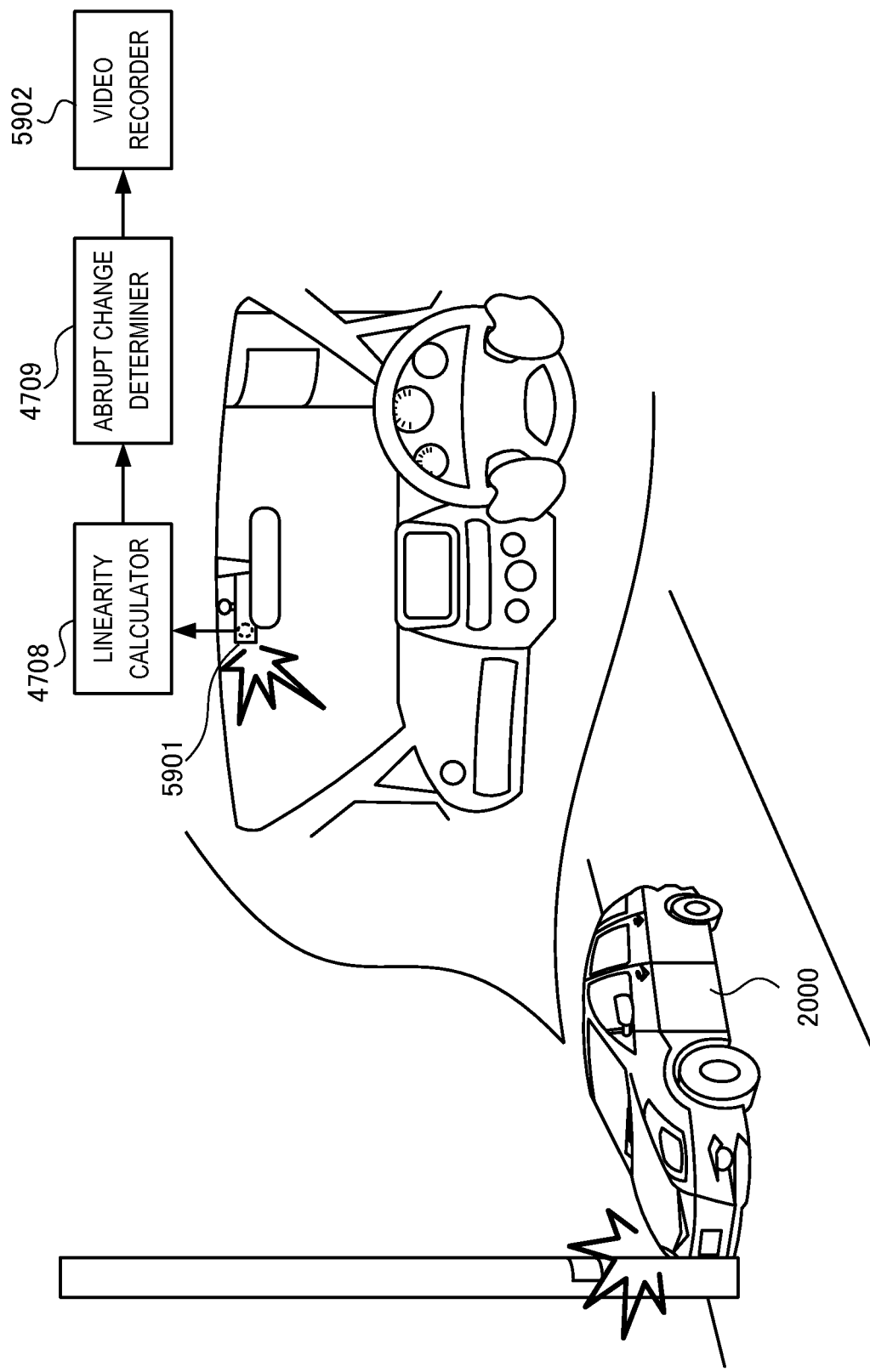
FIG. 59 is a view for explaining an application example according to the 20th embodiment of the present invention.

It is also possible to assume an application example in which a microphone 5901, a linearity calculator 4708, an abrupt change determiner 4709, and a video recorder 5902 are provided aboard a vehicle 5900, as shown in FIG. 59. Triggered by impulsive sound detection, the video recorder 5902 prohibits an image shot by a camera from being overwritten and saved, thereby leaving the record of an accident situation. At this time, overwrite saving may be prohibited after a delay of a predetermined time from impulsive sound detection. Unlike a case where an impulsive sound itself is used as a trigger, an accident situation can automatically be recorded even when the impact is small, or another vehicle is involved in an accident.

Also assume an application example in which the calculator 4708, the abrupt change determiner 4709, and an alarm unit 6001 are connected to an electrocardiograph 6000, as shown in FIG. 60. It is possible to more correctly and effectively detect an abnormal heartbeat in an electrocardiogram. In particular, this configuration is effective in a case where much noise is included. This method is also applicable to monitor the echo of an embryo. In some cases, a heart sound cannot correctly be monitored due to disturbance of noise. This technique is effective in such a case. That is, the technique is widely applicable to detect an abrupt change in a biomedical signal.

21st Embodiment

Figure 62:
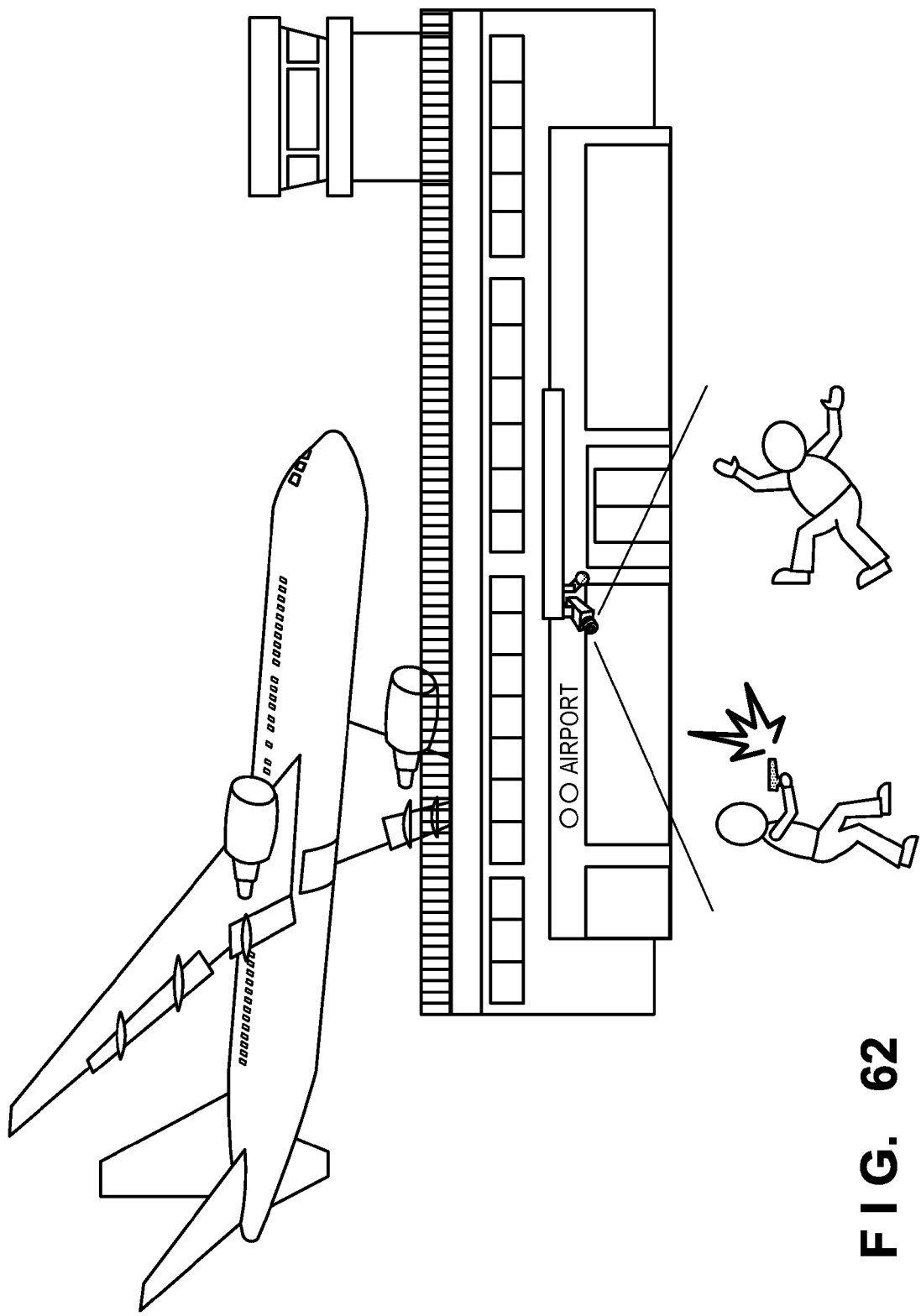
FIG. 62 is a view for explaining an application example according to the 21st embodiment of the present invention.

Similarly, in the above embodiments, impulsive sound detection according to the present invention may be used to detect an abnormality in a hard disk drive 6100, as shown in FIG. 61. The present invention may also be used to detect a gunshot or explosion sound in a situation with loud noise, for example, in an airport, as shown in FIG. 62.

Other Embodiments

While the present invention has been described with reference to exemplary embodiments, it is to be understood that the invention is not limited to the disclosed exemplary embodiments. The arrangement and details of the present invention can variously be modified without departing from the spirit and scope thereof, as will be understood by those skilled in the art. The present invention also incorporates a system or apparatus that combines different features included in the embodiments in any form.

The present invention is applicable to a system including a plurality of devices or a single apparatus. The present invention is also applicable even when an information processing program for implementing the functions of the embodiments is supplied to the system or apparatus directly or from a remote site. Hence, the present invention also incorporates the program installed in a computer to implement the functions of the present invention by the computer, a medium storing the program, and a WWW (World Wide Web) server that causes a user to download the program. In particular, the present invention incorporates a non-transitory computer readable medium.

Note that in the above embodiments, the characteristic arrangements of a signal processing apparatus, a signal processing method, and a signal processing program to be described below are shown (the arrangements are not limited to those to be described below).

(Supplementary Note 1)

There is provided a signal processing apparatus comprising:

a converter that converts an input signal into a phase component signal and an amplitude component signal in a frequency domain;

a calculator that calculates feature amounts of the phase component signal and the amplitude component signal; and a determiner that determines presence probability of an abrupt change in the input signal based on the feature amounts calculated by the calculator.

(Supplementary Note 2)

There is provided the signal processing apparatus according to supplementary note 1, wherein the calculator calculates a flatness measure of a change in the phase component signal as the feature amount.

(Supplementary Note 3)

There is provided the signal processing apparatus according to supplementary note 1 or 2, wherein the calculator calculates a flatness measure of the amplitude component signal as the feature amount.

(Supplementary Note 4)

There is provided the signal processing apparatus according to supplementary note 1, 2, or 3, wherein the determiner determines the presence probability of the abrupt change in the signal based on a value obtained by a weighted sum of changes in the phase component signal and the change in the amplitude component signal.

(Supplementary Note 5)

There is provided the signal processing apparatus according to supplementary note 1, 2, or 3, wherein the determiner determines the presence probability of the abrupt change in the signal based on a value obtained by averaging the change in the phase component signal and the change in the amplitude component signal.

(Supplementary Note 6)

There is provided the signal processing apparatus according to supplementary note 1, 2, or 3, wherein the determiner determines the presence probability of the abrupt change in the signal based on a value obtained by nonlinearly combining the change in the phase component signal and the change in the amplitude component signal.

(Supplementary Note 7)

There is provided the signal processing apparatus according to any one of supplementary notes 1 to 5, wherein the calculator calculates a flatness measure of a differential value of the phase component signal in the frequency domain, and the determiner determines that the presence probability of the abrupt change in the input signal is high if the flatness measure of the differential value is high, and the flatness measure of the amplitude component signal is high.

(Supplementary Note 8)

There is provided the signal processing apparatus according to any one of supplementary notes 1 to 7, wherein the calculator obtains a phase change ($\phi_n = \phi_n - \phi_{n-1}$) at each frequency from the phase component signal, and obtains, as the feature amount, a magnitude of a rotation vector cos($\phi_n - \phi_{n-1}$)+j sin($\phi_n - \phi_{n-1}$) having a difference ($\phi_n - \phi_{n-1}$) of the phase change as a rotation angle.

(Supplementary Note 9)

There is provided the signal processing apparatus according to any one of supplementary notes 1 to 8, wherein the converter outputs a complex signal including the phase component signal and the amplitude component signal, the calculator comprises:

a normalizer that normalizes the complex signal at each frequency to a unit vector;

a first calculator that calculates a first rotation vector from a ratio of the unit vectors at adjacent frequencies; and a second calculator that calculates a second rotation vector from a ratio of the first rotation vectors at adjacent frequencies, and the determiner determines the presence probability of the abrupt change in the input signal based on a magnitude of a real part of the second rotation vector.

(Supplementary Note 10)

There is provided the signal processing apparatus according to any one of supplementary notes 1 to 8, wherein the converter outputs a complex signal including the phase component signal and the amplitude component signal, the calculator comprises:

a normalizer that normalizes the complex signal at each frequency to a unit vector;

a first calculator that calculates a first rotation vector from a ratio of the unit vectors at adjacent frequencies; and a second calculator that calculates a second rotation vector from a ratio of the first rotation vectors at adjacent frequencies, and the determiner detects the abrupt change in the input signal based on a magnitude of an angle of the second rotation vector.

(Supplementary Note 11)

There is provided the signal processing apparatus according to any one of supplementary notes 1 to 10, further comprising an amplitude controller that suppresses an amplitude with a degree corresponding to the presence probability of the abrupt change obtained by the determiner.

(Supplementary Note 12)

There is provided the signal processing apparatus according to any one of supplementary notes 1 to 11, further comprising a phase controller that changes a phase of the input signal for a frame determined by the determiner to include the abrupt change.

(Supplementary Note 13)

There is provided a signal processing apparatus comprising:

a converter that converts an input signal into a phase component signal in a frequency domain;

a first calculator that calculates a first phase gradient based on a position of a sudden increase of the input signal;

a second calculator that calculates a second phase gradient of the phase component signal in the frequency domain; and a determiner that determines presence probability of an abrupt change in the input signal based on the first phase gradient and the second phase gradient.

(Supplementary Note 14)

There is provided the signal processing apparatus according to supplementary note 13, wherein the determiner determines the presence probability of the abrupt change in the input signal based on a similarity between the first phase gradient and the second phase gradient.

(Supplementary Note 15)

There is provided the signal processing apparatus according to supplementary note 13 or 14, wherein the first calculator comprises:

a sudden increase locator that locates a position where an absolute signal value suddenly increase in a frame;

a delay time calculator that calculates a delay time from a start of the frame to the position where the sudden increase exists; and a phase converter that converts the delay time into a phase in the frequency domain.

(Supplementary Note 16)

There is provided the signal processing apparatus according to supplementary note 13, wherein the converter further calculates an amplitude component signal of the input signal in the frequency domain, and the signal processing apparatus further comprises a calculator that calculates a flatness measure of the amplitude component signal, and the determiner further determines the presence probability of the abrupt change in the input signal in consideration of the flatness measure of the amplitude component signal.

(Supplementary Note 17)

There is provided the signal processing apparatus according to any one of supplementary notes 13 to 16, wherein the determiner determines the presence probability of the abrupt change in the signal based on values obtained by weighting the similarity between the first phase gradient and the second phase gradient and the flatness measure of the amplitude component signal.

(Supplementary Note 18)

There is provided the signal processing apparatus according to any one of supplementary notes 13 to 17, further comprising an amplitude controller that suppresses an amplitude with a degree corresponding to the presence probability of the abrupt change obtained by the determiner.

(Supplementary Note 19)

There is provided the signal processing apparatus according to any one of supplementary notes 13 to 18, further comprising a phase controller that changes a phase of the input signal for a frame determined by the determiner to include the abrupt change.

(Supplementary Note 20)

There is provided a signal processing apparatus comprising:

a converter that converts an input signal into a phase component signal in a frequency domain;

a generator that generates a low correlation signal by removing, from the input signal, a component with time correlation included in the input signal; and a determiner that determines presence probability of an abrupt change included in the input signal based on the low correlation signal and the phase component signal.

(Supplementary Note 21)

There is provided the signal processing apparatus according to supplementary note 20, further comprising:

a first calculator that calculates a first phase gradient in an abrupt signal change based on a position of a sudden increase of the low correlation signal; and a second calculator that calculates a second phase gradient of the phase component signal in the frequency domain, wherein the determiner determines the presence probability of the abrupt change in the input signal based on the first phase gradient and the second phase gradient.

(Supplementary Note 22)

There is provided the signal processing apparatus according to supplementary note 21, wherein the determiner determines the presence probability of the abrupt change in the input signal based on a similarity between the first phase gradient and the second phase gradient.

(Supplementary Note 23)

There is provided the signal processing apparatus according to supplementary note 21 or 22, wherein the first calculator comprises:

a sudden increase locator that locates a position where an absolute signal value suddenly increase in a frame;

a delay time calculator that calculates a delay time from a start of the frame to the position where the sudden increase exists; and a phase converter that converts the delay time into a phase in the frequency domain.

(Supplementary Note 24)

There is provided the signal processing apparatus according to supplementary note 20, wherein the converter further calculates an amplitude component signal of the input signal in the frequency domain, and the signal processing apparatus further comprises a calculator that calculates a flatness measure of the amplitude component signal, and the determiner further determines the presence probability of the abrupt change in the input signal in consideration of the flatness measure of the amplitude component signal.

(Supplementary Note 25)

There is provided the signal processing apparatus according to any one of supplementary notes 20 to 24, further comprising an amplitude controller that suppresses an amplitude with a degree corresponding to the presence probability of the abrupt change obtained by the determiner.

(Supplementary Note 26)

There is provided the signal processing apparatus according to any one of supplementary notes 20 to 25, further comprising a phase controller that changes a phase of the input signal for a frame determined by the determiner to include the abrupt change.

(Supplementary Note 27)

There is provided a signal processing apparatus comprising:

a converter that converts an input signal into a phase component signal in a frequency domain;

a linearity calculator that calculates a linearity of the phase component signal in the frequency domain; and a determiner that calculates presence probability of an abrupt change in the input signal based on the linearity calculated by the linearity calculator.

(Supplementary Note 28)

There is provided the signal processing apparatus according to supplementary note 27, wherein the linearity calculator calculates the linearity based on a change in the phase component signal in the frequency domain.

(Supplementary Note 29)

There is provided the signal processing apparatus according to supplementary note 27 or 28, wherein the linearity calculator calculates a flatness measure of a differential value of the phase component signal in the frequency domain, and the determiner determines that the presence probability of the abrupt change in the input signal is high if the flatness measure of the differential value is high.

(Supplementary Note 30)

There is provided the signal processing apparatus according to supplementary note 27, 28, or 29, wherein the linearity calculator calculates, for each frequency, a phase component difference as a difference between phase components at adjacent frequencies, and calculates the linearity based on the difference of the phase component difference between the adjacent frequencies.

(Supplementary Note 31)

There is provided the signal processing apparatus according to supplementary note 30, wherein the linearity calculator calculates a sum of difference of the phase component difference between the adjacent frequencies for each frame as a linearity of the frame, and if the sum is not smaller than a threshold, the determiner performs correction so as to increase the difference of the phase component difference between the adjacent frequencies.

(Supplementary Note 32)

There is provided a signal processing method comprising:

converting an input signal into a phase component signal and an amplitude component signal in a frequency domain;

calculating feature amounts of the phase component signal and the amplitude component signal; and determining presence probability of an abrupt change in the input signal based on the calculated feature amounts.

(Supplementary Note 33)

There is provided a signal processing method comprising:

converting an input signal into a phase component signal in a frequency domain;

calculating a first phase gradient based on a position of a sudden increase of the input signal;

calculating a second phase gradient of the phase component signal in the frequency domain; and determining presence probability of an abrupt change in the input signal based on the first phase gradient and the second phase gradient.

(Supplementary Note 34)

There is provided a signal processing method comprising:

converting an input signal into a phase component signal in a frequency domain;

generating a low correlation signal by removing, from the input signal, a component with time correlation included in the input signal; and determining presence probability of an abrupt change included in the input signal based on the low correlation signal and the phase component signal.

(Supplementary Note 35)

There is provided a signal processing method comprising:

converting an input signal into a phase component signal in a frequency domain;

calculating a linearity of the phase component signal in the frequency domain; and calculating presence probability of an abrupt change in the input signal based on the calculated linearity.

(Supplementary Note 36)

There is provided a signal processing program for causing a computer to execute a method comprising:

converting an input signal into a phase component signal and an amplitude component signal in a frequency domain;

calculating feature amounts of the phase component signal and the amplitude component signal; and determining presence probability of an abrupt change in the input signal based on the calculated feature amounts.

(Supplementary Note 37)

There is provided a signal processing program for causing a computer to execute a method comprising:

converting an input signal into a phase component signal in a frequency domain;

calculating a first phase gradient based on a position of a sudden increase of the input signal;

calculating a second phase gradient of the phase component signal in the frequency domain; and determining presence probability of an abrupt change in the input signal based on the first phase gradient and the second phase gradient.

(Supplementary Note 38)

There is provided a signal processing program for causing a computer to execute a method comprising:

converting an input signal into a phase component signal in a frequency domain;

generating a low correlation signal by removing, from the input signal, a component with time correlation included in the input signal; and determining presence probability of an abrupt change included in the input signal based on the low correlation signal and the phase component signal.

(Supplementary Note 39)

There is provided a signal processing program for causing a computer to execute a method comprising:

converting an input signal into a phase component signal in a frequency domain;

calculating a linearity of the phase component signal in the frequency domain; and calculating presence probability of an abrupt change in the input signal based on the calculated linearity.

This application claims the benefit of Japanese Patent Application Nos. 2013-042448, 2013-042449, 2013-042450, and 2013-042451, filed on Mar. 5, 2013, which are hereby incorporated by reference in their entirety.

The invention claimed is:

1. A signal processing apparatus comprising:
a converter that converts an input signal into a phase component signal and an amplitude component signal in a frequency domain;
a calculator that calculates a plurality of feature amounts of the phase component signal and the amplitude component signal, wherein the calculator obtains:
a phase change at one or more frequencies of the phase component signal; and
at least one feature amount including a magnitude of a rotation vector, the rotation vector having a rotation angle that is a difference of the phase change; and
a determiner, implemented by one or more processors, that determines a presence probability of a change in the input signal based on the plurality of feature amounts calculated by the calculator.

2. The signal processing apparatus according to claim 1, wherein the calculator calculates a flatness of a change in the phase component signal as the feature amount.

3. The signal processing apparatus according to claim 1, wherein the calculator calculates a flatness of the amplitude component signal as the feature amount.

4. The signal processing apparatus according to claim 1, wherein the determiner determines the presence probability of the change in the signal based on a value obtained by a weighted sum of changes in the phase component signal and the amplitude component signal.

5. The signal processing apparatus according to claim 1, wherein the determiner determines the presence probability of the change in the signal based on a value obtained by averaging the change in the phase component signal and the change in the amplitude component signal.

6. The signal processing apparatus according to claim 1, wherein the determiner determines the presence probability of the change in the signal based on a value obtained by nonlinearly combining the change in the phase component signal and the change in the amplitude component signal.

7. The signal processing apparatus according to claim 1, wherein the calculator calculates a flatness of a differential value of the phase component signal in the frequency domain, and
the determiner determines that the presence probability of the change in the input signal is high if the flatness of the differential value is high, and the flatness of the amplitude component signal is high.

8. The signal processing apparatus according to claim 1, wherein the converter outputs a complex signal including the phase component signal and the amplitude component signal,
the calculator comprises:
a normalizer that normalizes the complex signal at each frequency to a unit vector;
a first calculator that calculates a first rotation vector from a ratio of the unit vectors at adjacent frequencies; and
a second calculator that calculates a second rotation vector from a ratio of the first rotation vectors at adjacent frequencies, and
the determiner determines the presence probability of the change in the input signal based on a magnitude of a real part of the second rotation vector.

9. The signal processing apparatus according to claim 1, wherein the converter outputs a complex signal including the phase component signal and the amplitude component signal, the calculator comprises:
  a normalizer that normalizes the complex signal at each frequency to a unit vector;
  a first calculator that calculates a first rotation vector from a ratio of the unit vectors at adjacent frequencies; and
  a second calculator that calculates a second rotation vector from a ratio of the first rotation vectors at adjacent frequencies, and
  the determiner detects the change in the input signal based on the angle of the second rotation vector.

10. The signal processing apparatus according to claim 1, further comprising an amplitude controller that suppresses an amplitude based on the presence probability of the change obtained by the determiner.

11. The signal processing apparatus according to claim 1, further comprising a phase controller that changes a phase of the input signal for a frame determined by the determiner to include the change of the input signal.

12. A signal processing apparatus comprising:
  a converter, implemented by one or more processors, that converts an input signal into a phase component signal and an amplitude component signal in a frequency domain;
    a first calculator that calculates a first phase gradient based on a position of an increase of the input signal, the first calculator comprising:
    a locator, implemented by one or more processors, that locates a position of the input signal at which an absolute value of the magnitude of the input signal increases above a threshold in a frame;
    a delay time calculator that calculates a delay time from a start of the frame to the located position; and
    a phase converter that converts the delay time into a phase in the frequency domain;
  a second calculator that calculates a second phase gradient of the phase component signal in the frequency domain; and
  a determiner, implemented by one or more processors, that determines a presence probability of change in the input signal based on the first phase gradient and the second phase gradient.

13. The signal processing apparatus according to claim 12, wherein the determiner determines the presence probability of the change in the input signal based on a similarity of the first phase gradient and the second phase gradient.

14. The signal processing apparatus according to claim 12, further comprising a third calculator that calculates a flatness of the amplitude component signal,
  wherein the converter calculates the amplitude component signal of the input signal in the frequency domain, and the determiner determines the presence probability of the change in the input signal further based on the flatness of the amplitude component signal.

15. The signal processing apparatus according to claim 12, wherein the determiner determines the presence probability of the change in the input signal based on values obtained by weighting a similarity of the first phase gradient and the second phase gradient and the flatness of the amplitude component signal.

16. The signal processing apparatus according to claim 12, further comprising an amplitude controller that suppresses an amplitude based on the presence probability of the change obtained by the determiner.

17. The signal processing apparatus according to claim 12, further comprising a phase controller that changes a phase of the input signal for a frame determined by the determiner to include the change of the input signal.

18. A signal processing apparatus comprising:
  a converter that converts an input signal into a phase component signal in a frequency domain;
  a generator that generates a low correlation signal by removing, from the input signal, a component with time correlation included in the input signal; and
  a determiner, implemented by one or more processors, that determines a presence probability of a change in the input signal based on the low correlation signal and the phase component signal.

19. The signal processing apparatus according to claim 18, further comprising:
  a first calculator that calculates a first phase gradient at a position of a change in the input signal based on a position of an increase of the low correlation signal; and
  a second calculator that calculates a second phase gradient of the phase component signal in the frequency domain,
  wherein the determiner determines the presence probability of the change in the input signal based on the first phase gradient and the second phase gradient.

20. The signal processing apparatus according to claim 19, wherein the determiner determines the presence probability of the change in the input signal based on a similarity between the first phase gradient and the second phase gradient.

21. The signal processing apparatus according to claim 19, wherein the first calculator comprises:
  of an increase position locator, implemented by one or more processors, that locates a position where an absolute signal value increases above a threshold in a frame;
  a delay time calculator that calculates a delay time from a start of the frame to the located position; and
  a phase converter that converts the delay time into a phase in the frequency domain.

22. The signal processing apparatus according to claim 18, further comprising a calculator that calculates a flatness of the amplitude component signal,
  wherein the converter calculates the amplitude component signal of the input signal in the frequency domain, and the determiner determines the presence probability of the change in the input signal further based on the flatness of the amplitude component signal.

23. The signal processing apparatus according to claim 18, further comprising an amplitude controller that suppresses an based on the presence probability of the change in the input signal.

24. The signal processing apparatus according to claim 18, further comprising a phase controller that changes a phase of the input signal for a frame determined by the determiner to include the change of the input signal.

25. A signal processing method comprising:
  converting an input signal into a phase component signal and an amplitude component signal in a frequency domain;
  calculating, by one or more processors, plurality of feature amounts of the phase component signal and the amplitude component signal, wherein the calculator obtains:
    a phase change at one or more frequencies of the phase component signal; and at least one feature amount including a magnitude of a rotation vector, the rotation vector having a rotation angle that is a difference of the phase change; and determining, by one or more processors, a presence probability of a change in the input signal based on the plurality of calculated feature amounts.

26. A signal processing method comprising:
converting an input signal into a phase component signal in a frequency domain;
calculating, by one or more processors, a first phase gradient based on a position of an increase of the input signal;
locating a position of the input signal at which an absolute value of the magnitude of the input signal increases above a threshold in a frame;
calculating a delay time from a start of the frame to the located position;
converting the delay time into a phase in the frequency domain;
calculating, by one or more processors, a second phase gradient of the phase component signal in the frequency domain; and
determining, by one or more processors, a presence probability of a change in the input signal based on the first phase gradient and the second phase gradient.

27. A signal processing method comprising:
converting an input signal into a phase component signal in a frequency domain;
generating a low correlation signal by removing, from the input signal, a component with time correlation included in the input signal; and
determining, by one or more processors, a presence probability of a change in the input signal based on the low correlation signal and the phase component signal.

28. A non-transitory computer readable medium storing a signal processing program for causing a computer to execute a method comprising:
converting an input signal into a phase component signal and an amplitude component signal in a frequency domain;
calculating a plurality of feature amounts of the phase component signal and the amplitude component signal, wherein the calculator obtains:
a phase change at one or more frequencies of the phase component signal; and
at least one feature amount including a magnitude of a rotation vector, the rotation vector having a rotation angle that is a difference of the phase change; and
determining a presence probability of a change in the input signal based on the plurality of calculated feature amounts.

29. A non-transitory computer readable medium storing a signal processing program for causing a computer to execute a method comprising:
converting an input signal into a phase component signal in a frequency domain;
calculating a first phase gradient based on a position of an increase of the input signal;
locating a position of the input signal at which an absolute value of the magnitude of the input signal increases above a threshold in a frame;
calculating a delay time from a start of the frame to the located position;
converting the delay time into a phase in the frequency domain;
calculating a second phase gradient of the phase component signal in the frequency domain; and
determining a presence probability of a change in the input signal based on the first phase gradient and the second phase gradient.

30. A non-transitory computer readable medium storing a signal processing program for causing a computer to execute a method comprising:
converting an input signal into a phase component signal in a frequency domain;
generating a low correlation signal by removing, from the input signal, a component with time correlation included in the input signal; and
determining a presence probability of a change in the input signal based on the low correlation signal and the phase component signal.

* * * * *